US009505728B2

(12) United States Patent
Stock et al.

(10) Patent No.: US 9,505,728 B2
(45) Date of Patent: Nov. 29, 2016

(54) TRIAZOLONE COMPOUNDS AND USES THEREOF

(71) Applicant: INCEPTION 2, INC., San Diego, CA (US)

(72) Inventors: Nicholas Simon Stock, Encinitas, CA (US); Austin Chih-Yu Chen, San Marcos, CA (US); Yalda Mostofi Bravo, San Diego, CA (US); Jason Duarte Jacintho, San Diego, CA (US); Jill Melissa Baccei, Poway, CA (US); Brian Andrew Stearns, Encinitas, CA (US); Ryan Christopher Clark, San Diego, CA (US); Yen Pham Truong, San Diego, CA (US)

(73) Assignee: Inception 2, Inc., San Diego, CA (US)

( * ) Notice: Subject to any disclaimer, the term of this patent is extended or adjusted under 35 U.S.C. 154(b) by 0 days.

(21) Appl. No.: 14/383,096

(22) PCT Filed: Mar. 7, 2013

(86) PCT No.: PCT/US2013/029713
§ 371 (c)(1),
(2) Date: Sep. 4, 2014

(87) PCT Pub. No.: WO2013/134562
PCT Pub. Date: Sep. 12, 2013

(65) Prior Publication Data
US 2015/0080412 A1   Mar. 19, 2015

Related U.S. Application Data

(60) Provisional application No. 61/608,961, filed on Mar. 9, 2012.

(51) Int. Cl.
| *A61K 31/4196* | (2006.01) |
| *A61K 31/4439* | (2006.01) |
| *C07D 249/12* | (2006.01) |
| *C07D 401/10* | (2006.01) |
| *C07D 401/14* | (2006.01) |
| *C07D 405/14* | (2006.01) |
| *C07D 401/06* | (2006.01) |
| *C07D 403/10* | (2006.01) |
| *C07D 405/10* | (2006.01) |
| *C07D 409/10* | (2006.01) |
| *C07D 413/10* | (2006.01) |
| *C07D 417/14* | (2006.01) |
| *C07D 401/12* | (2006.01) |
| *C07D 409/06* | (2006.01) |
| *C07D 417/10* | (2006.01) |

(52) U.S. Cl.
CPC ......... *C07D 249/12* (2013.01); *A61K 31/4196* (2013.01); *A61K 31/4439* (2013.01); *C07D 401/06* (2013.01); *C07D 401/10* (2013.01); *C07D 401/12* (2013.01); *C07D 401/14* (2013.01); *C07D 403/10* (2013.01); *C07D 405/10* (2013.01); *C07D 405/14* (2013.01); *C07D 409/06* (2013.01); *C07D 409/10* (2013.01); *C07D 413/10* (2013.01); *C07D 417/10* (2013.01); *C07D 417/14* (2013.01)

(58) Field of Classification Search
None
See application file for complete search history.

(56) References Cited

U.S. PATENT DOCUMENTS

| 4,487,773 A | 12/1984 | Temple, Jr. et al. |
| 5,284,957 A | 2/1994 | Huff |
| 5,294,596 A | 3/1994 | Haas et al. |
| 5,550,244 A | 8/1996 | Kluth et al. |

(Continued)

FOREIGN PATENT DOCUMENTS

| AT | 455547 | 2/2010 |
| AU | 2003300031 | 5/2004 |

(Continued)

OTHER PUBLICATIONS

Ammazzalorso et al., Bioorg. Med. Chem. Lett. 21:4869-4872 (2011).

(Continued)

*Primary Examiner* — Samantha Shterengarts
(74) *Attorney, Agent, or Firm* — Knobbe Martens Olson & Bear LLP

(57) ABSTRACT

The invention disclosed herein is directed to compounds of Formula (I) and pharmaceutically acceptable salts thereof, which are useful in the treatment of prostate, breast, colon, pancreatic, human chronic lymphocytic leukemia, melanoma and other cancers. The invention also comprises pharmaceutical compositions comprising a therapeutically effective amount of compound of Formula (I), or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to methods of treating prostate, breast, colon, pancreatic, chronic lymphocytic leukemia, melanoma and other cancers comprising administration of a of a therapeutically effective amount of a selective PPARα antagonist. The compounds and pharmaceutical compositions of the invention are also useful in the treatment of viral infections, such as HCV infections and HIV infections. The invention disclosed herein is also directed to a methods of preventing the onset of and/or recurrence of acute and chronic myeloid leukemia, as well as other cancers, comprising administration of a of a therapeutically effective amount of a selective PPARα antagonist.

25 Claims, 1 Drawing Sheet

(56) References Cited

U.S. PATENT DOCUMENTS

| | | | |
|---|---|---|---|
| 5,629,311 A | 5/1997 | Hemmerle et al. |
| 5,856,495 A | 1/1999 | Weckbecker et al. |
| 7,816,522 B2 | 10/2010 | Clark |
| 7,816,822 B2 | 10/2010 | Nashiki |
| 7,915,267 B2 | 3/2011 | Nara et al. |
| 2002/0052510 A1 | 5/2002 | Hamilton et al. |
| 2004/0116491 A1 | 6/2004 | King et al. |
| 2005/0043181 A1 | 2/2005 | Feucht et al. |
| 2007/0032488 A1 | 2/2007 | Botyanszki et al. |
| 2009/0137603 A1 | 5/2009 | Nara et al. |
| 2009/0306397 A1 | 12/2009 | Bruns et al. |
| 2010/0022540 A1 | 1/2010 | Eggenweiler et al. |
| 2010/0331397 A1 | 12/2010 | Beigelman et al. |
| 2011/0195993 A1 | 8/2011 | Masson et al. |
| 2011/0319458 A1 | 12/2011 | Jin et al. |
| 2012/0208852 A1 | 8/2012 | Fuerstner et al. |

FOREIGN PATENT DOCUMENTS

| | | |
|---|---|---|
| BE | 894856 | 2/1983 |
| CA | 1263114 | 11/1989 |
| CN | 1629142 | 6/2005 |
| DE | 160447 | 8/1983 |
| DE | 3238590 | 4/1984 |
| DE | 19521162 | 12/1996 |
| DE | 19601189 | 7/1997 |
| EP | 0 067 508 | 12/1982 |
| EP | 0060697 | 12/1986 |
| EP | 0 273 310 | 7/1988 |
| EP | 0422469 | 4/1991 |
| EP | 0 513 766 | 11/1992 |
| EP | 0 540 318 | 5/1993 |
| EP | 0 665 227 | 8/1995 |
| EP | 1834953 | 9/2007 |
| FR | 2535168 | 5/1984 |
| GB | 2293169 | 3/1996 |
| GB | 2435827 | 9/1997 |
| GB | 2435828 | 9/1997 |
| GB | 2435829 | 9/1997 |
| IN | 183333 | 11/1999 |
| JP | 60-215675 | 10/1985 |
| JP | 2012-106996 | 6/2012 |
| KR | 20110088737 | 8/2011 |
| NL | 8204109 | 5/1984 |
| WO | WO 92/04346 | 3/1992 |
| WO | WO 93/21181 | 10/1993 |
| WO | WO94/11357 | 5/1994 |
| WO | WO 95/25443 | 9/1995 |
| WO | WO 96/11196 | 4/1996 |
| WO | WO 96/13264 | 5/1996 |
| WO | WO 96/34851 | 11/1996 |
| WO | WO 96/37492 | 11/1996 |
| WO | WO 97/01553 | 1/1997 |
| WO | WO 97/01554 | 1/1997 |
| WO | WO 97/40017 | 10/1997 |
| WO | WO 98/04135 | 2/1998 |
| WO | WO 98/15277 | 4/1998 |
| WO | WO98/18496 | 5/1998 |
| WO | WO 98/43962 | 10/1998 |
| WO | WO 99/03835 | 1/1999 |
| WO | WO99/26945 | 6/1999 |
| WO | WO 99/62880 | 12/1999 |
| WO | WO 99/62888 | 12/1999 |
| WO | WO 00/09102 | 2/2000 |
| WO | WO 00/09103 | 2/2000 |
| WO | WO 00/09125 | 2/2000 |
| WO | WO 00/12489 | 3/2000 |
| WO | WO 00/29386 | 5/2000 |
| WO | WO 00/32588 | 6/2000 |
| WO | WO 00/71118 | 11/2000 |
| WO | WO 01/46167 | 6/2001 |
| WO | WO 01/90102 | 11/2001 |
| WO | WO 02/02555 | 1/2002 |
| WO | WO 02/20489 | 3/2002 |
| WO | WO 02/20501 | 3/2002 |
| WO | WO 02/38553 | 5/2002 |
| WO | WO 03/000682 | 1/2003 |
| WO | WO03/051315 | 6/2003 |
| WO | WO03/066050 | 8/2003 |
| WO | WO 03/084948 | 10/2003 |
| WO | WO03/106448 | 12/2003 |
| WO | WO2004/032840 | 4/2004 |
| WO | WO 2004/074257 | 9/2004 |
| WO | WO2004/089306 | 10/2004 |
| WO | WO 2004/089380 | 10/2004 |
| WO | WO 2005/054179 | 6/2005 |
| WO | WO 2005/058848 | 6/2005 |
| WO | WO2005/077178 | 8/2005 |
| WO | WO2005/077345 | 8/2005 |
| WO | WO2005/080379 | 9/2005 |
| WO | WO 2005/095362 | 10/2005 |
| WO | WO 2006/044732 | 4/2006 |
| WO | WO 2006/047195 | 5/2006 |
| WO | WO 2006/068199 | 6/2006 |
| WO | WO 2006/074984 | 7/2006 |
| WO | WO 2006/078698 | 7/2006 |
| WO | WO 2006/083645 | 8/2006 |
| WO | WO2006/109056 | 10/2006 |
| WO | WO 2007/064797 | 6/2007 |
| WO | WO 2007/085349 | 8/2007 |
| WO | WO 2007/107758 | 9/2007 |
| WO | WO2008/006499 | 1/2008 |
| WO | WO2008/017594 | 2/2008 |
| WO | WO 2008/103574 | 8/2008 |
| WO | WO 2008/119662 | 10/2008 |
| WO | WO2008/127349 | 10/2008 |
| WO | WO 2008/128335 | 10/2008 |
| WO | WO2009/014910 | 1/2009 |
| WO | WO2009/017863 | 2/2009 |
| WO | WO 2009/019472 | 2/2009 |
| WO | WO 2009/023402 | 2/2009 |
| WO | WO 2009/052078 | 4/2009 |
| WO | WO 2009/074782 | 6/2009 |
| WO | WO2009/126863 | 10/2009 |
| WO | WO2009/151529 | 12/2009 |
| WO | WO 2010/015212 | 2/2010 |
| WO | WO 2010/023946 | 3/2010 |
| WO | WO 2010/048207 | 4/2010 |
| WO | WO 2010/098600 | 9/2010 |
| WO | WO2010/139966 | 12/2010 |
| WO | WO 2011/058478 | 5/2011 |
| WO | WO 2011/103546 | 8/2011 |
| WO | WO 2011/107530 | 9/2011 |
| WO | WO2011/120926 | 10/2011 |
| WO | WO 2011/126903 | 10/2011 |
| WO | WO 2011/128316 | 10/2011 |
| WO | WO 2011/082400 | 11/2011 |
| WO | WO 2012/021455 | 2/2012 |
| WO | WO 2012/037299 | 3/2012 |
| WO | WO 2012/058531 | 5/2012 |
| WO | WO2013/134562 | 9/2013 |

OTHER PUBLICATIONS

Argentine et al., The Role of New Technologies in Defining a Manufacturing Process for PPARα Agonist LY518674, Organic Process Research & Development, 13(2):131-143 (2009).

Braden et al., A Convergent Kilogram-Scale Synthesis of the PPARα Agonist LY518674: Discovery of a Novel Acid-Mediated Triazolone Synthesis, Organic Process Research & Development, 11(3):431-440 (2007).

Kuo et al., The synthesis of three isotopomers of 2-methyl-2-(4-[3-[1-(4-methylbenzyl)-5-oxo-4,5-dihydro-1H-[1,2,4]triazol-3-yl]propyl]phenoxy)propionic acid, a potent and selective peroxisome proliferator-activated receptor alpha agonist, Journal of Labelled Compounds and Radiopharmaceuticals, 50(8):693-701 (2007).

Girard, Tautomeric oxotriazoles and hydroxytriazoles. A new method for the preparation of hydroxy-1,2,4-triazoles, Compt rend. 212:547-549 (1941).

Hanif et al., 4-(3-Methoxyphenyl)-3-[2-(4-methoxyphenyl)ethyl]-1H-1,2,4-triazol-5(4H)-one, Acta Crystallographica, Section E: Structure Reports Online, 2009, E65(2), o387.

(56) References Cited

OTHER PUBLICATIONS

Hanif et al., 4-(4-Methoxyphenyl)-3-[2-(2-methoxyphenyl)ethyl]-1H-1,2,4-triazol-5(4H)-one, Acta Crystallographica, Section E: Structure Reports Online, 2009, E65(2), o429.

Hanif et al., 5-(3-Methoxyphenethyl)-4-(2-methoxyphenyl)-4H-1,2,4-triazol-3-ol, Acta Crystallographica, Section E: Structure Reports Online, 2008, E64(11), o2180, o2180/1-o2180/9.

Millar et al., Potent and selective PPAR-α agonist LY518674 upregulates both ApoA-I production and catabolism in human subjects with the metabolic syndrome, Arteriosclerosis, Thrombosis, and Vascular Biology, 29(1):140-146 (2009).

Rao et al., Synthesis of substituted 2,4-dihydro[1,2,4]-triazol-3-ones, Indian Journal of Heterocyclic Chemistry 20(1):9-12 (2010).

Tumosiene et al., Synthesis of azole derivatives from 3-phenylaminopropanohydrazide and evaluation of their antimicrobial efficacy, Heterocycles, 78(1):59-70 (2009).

Tumosiene et al., Synthesis of azoles from 3,3'-[(4-alkoxyphenyl)imino]bis(propanoic acid hydrazides), Monatshefte fuer Chemie, 140(12):1523-1528 (2009).

Tutoveanu et al., New semi- and thiosemicarbazides and cyclization products, Revistade Chimie (Bucharest, Romania) 24(3):155-158 (1973).

Xu et al., Journal of Medicinal Chemistry 46:5121-5124 (2003).

Etgen et al., 2003, PPAR ligands for metabolic disorders, Current Topics in Medicinal Chemistry, 3:1649-1661.

Moenes et al., Feb. 1996, Synthesis and antimicrobial activity of certain pyridazines, Alex. J. Pharm. Sci., 10(1):35-38.

Soliman et al., 2007, Heterocyclic synthesis with biologically active S-(6-aryl pyridazin 3-yl) thioglycollic acid hydrazides, Egypt. J. Chem. 50(4):443-453.

Extended European Search report dated Jul. 16, 2015 in patent application No. 13758171.6.

Deng et al. A novel and efficient synthesis of 2,5-substituted 1,2,4-triazol-3-ones. Tetrahedron Letters 46(46):7993-7996 (2005).

Goldin et al. Synthesis of triazolones and c-aminotriazoles by thermal condensation of carbamidoamidrazones. Chemistry of Heterocyclic Compounds 10(4):489-490 (1974).

PCT/US2013/029713 International Preliminary Report on Patentability dated Sep. 9, 2014.

PCT/US2013/029713 International Search Report dated Jun. 28, 2013.

Rashad et al. Synthesis of new quinoline derivatives as inhibitors of human tumor cells growth. Archiv der Pharmazie (Weinheim, Germany) 343(8):440-448 (2010).

Tumosiene et al. Synthesis of azoles from 3,3'-(arylimino)bis[propanoyl hydrazides]. Chemistry of Heterocyclic Compounds (New York, NY, United States) 43(9):1148-1153 (2007).

Zakaria et al. Synthesis of some new 3-mercapto-5-substituted-1,2,4-triazine-s-triazoles for evaluation as antimicrobial agents. Journal of Chemical Technology and Biotechnology 63(2):135-140 (1995).

Bravo et al., Identification of the first potent, selective and bioavailable PPARα antagonist, Bioorg. Med. Chem. Lett. 24:2267-2272 (2014).

Messmer et al., Abstract of Papers, 54th Meeting of the American Society of Hematology, Atlanta, GA, 2012; Abstract 3879.

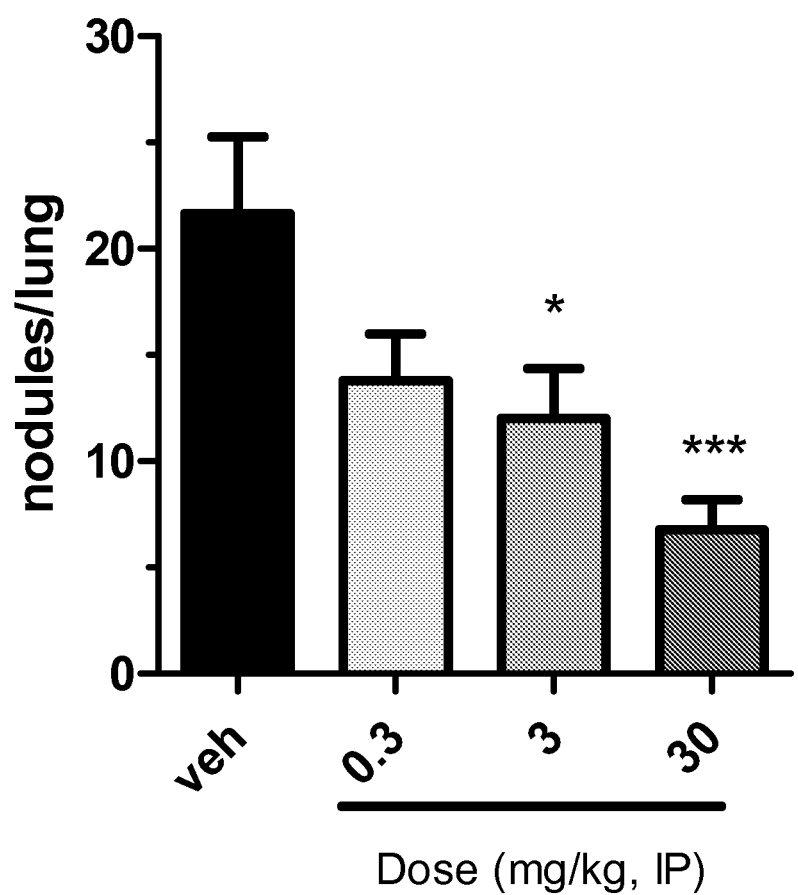

TRIAZOLONE COMPOUNDS AND USES THEREOF

RELATED APPLICATIONS

This application is filed pursuant to 35 U.S.C. §371 as a United States National Phase Application of International Application No. PCT/US2013/029713, entitled "TRIAZOLONE COMPOUNDS AND USES THEREOF", filed Mar. 7, 2013, which claims the benefit of U.S. provisional patent application No. 61/608,961 entitled "TRIAZOLONES COMPOUNDS AND USES THEREOF" filed on Mar. 9, 2012, each of which is incorporated by reference in its entirety.

FIELD OF THE INVENTION

This invention is directed to novel triazolones, or pharmaceutically acceptable salts thereof, useful in the treatment of prostate, breast, colon, pancreatic, human chronic lymphocytic leukemia, melanoma and other cancers. The invention disclosed herein is further directed to methods of treating prostate, breast, ovarian, liver, kidney, colon, pancreatic, human chronic lymphocytic leukemia, melanoma and other cancers comprising administration of selective PPARα antagonists. The compounds and pharmaceutical compositions of the invention are also useful in the treatment of viral infections, such as HCV infections and HIV infections.

BACKGROUND OF THE INVENTION

While tremendous strides have been made in the treatment of various cancers, in many cases, cancer treatment continues to be a matter of administering one or more anti-cancer agents that are marginally less chemotoxic to healthy cells than they are to the cancer in question. In recognition of this problem, there has been substantial research effort aimed at identifying, understanding and taking advantage of phenotypical behavior peculiar to certain cancer cells. It has long been observed that most cancer cell types generate energy for cellular processes through aerobic glycolysis rather than through oxidative phosphorylation as found in the normal cell. This process, which became known as the "Warburg effect", is highly energy inefficient and requires cancer cell mitochondria to resort to glucose fermentation to make up the energy deficit. Since perhaps the mid-1990's researchers have sought to identify methods of treating cancer that take advantage of the "Warburg effect" and associated aspects of cancer cell mitochondrial metabolism. See, for example, Wang, et. al., Small mitochondrial-targeting molecules as anti-cancer agents, Mol. Aspects Med. 2010 February; 31(1): 75-92.

Samudio, et. al., J. Clin. Invest. 120: 142-156 (2010), disclosed that in certain leukemia cell lines "mitochondrial uncoupling—the continuing reduction of oxygen without ATP synthesis—has recently been shown in leukemic cells to circumvent the ability of oxygen to inhibit glycolysis, and may promote the metabolic preference for glycolysis by shifting from pyruvate oxidation to fatty acid oxidation (FAO)." Samudio, et. al., also provided data indicating that inhibition of FAO could sensitize human leukemia cells to apoptosis, and further that inhibition of FAO may prove useful in the treatment of leukemia.

PPARα is known to be an important regulator of fatty acid oxidation. See Pyper, et. al., Nucl. Recept. Signal. 8:e002, e002 (2010). It has been reported that expression of the PPARα gene can be higher in human chronic lymphocytic leukemia (CLL) making this cancer type sensitive to therapies aimed at reducing FAO (Samudio et al., J. Clin. Invest. 120:142-156 (2010)). This effect may generalize to several cancer types. For example, ovarian cancer and breast cancer (Linher-Melville et al., 2011, BMC, 4; 11:56), thrive in an adipose rich environment and as a result can be negatively impacted by targeted therapies that reduce fatty acid metabolism (Nieman et al., 2011, Nat Med. 2011 Oct. 30; 17(11):1498-503). Still other cancers that rely on FAO include prostate cancer (Liu, Prostate Cancer Prostatic Dis., 2006; 9(3):230-4), colon cancer (Holla et al., 2011, JCB 286(34):30003-30009), pancreatic cancer (Khasawneh et al., 2009, PNAS, 106(9):3354-3359) and lung cancer (Zaugg et al., 2011, Genes and Development, 25:1041-1051).

GW6471 (Xu, et. al., Nature 415, 813-817 (2002)) and MK-866 (Kehrer, et. al., Biochem. J. 356, 899-906 (2001)) have been identified as antagonists of PPARα. Moreover, MK-866, whose primary activity is as an inhibitor of FLAP, has been disclosed to induce apoptosis in a human chronic lymphocytic leukemia cell line in a FLAP-independent manner; and has also been disclosed to induce apoptosis in prostate and glioblastoma cell lines.

It is our belief that in cancers that rely heavily on FAO, antagonism of PPARα by small molecules provides a panoply of anti-cancer treatment opportunities to: reduce or halt proliferation; decrease or reverse immunosuppression; enhance apoptosis; and increase susceptibility to other anti-cancer agents. These cancers include prostate, breast, colon and pancreatic cancer, among others.

Chronic myeloid leukemia (CML) is model of hematopoietic stem cell (HSC) disease. In 2008, Ito et al, disclosed evidence linking the loss of promyelocytic leukemia (PML) gene expression with favorable outcomes in CML (Nature, 2008 Jun. 19; 453 (7198) 1072-1078). More recently Ito et al., disclosed that in the PML pathway, loss of PPARδ and accompanying inhibition of mitochondrial FAO induced loss of hematopoietic stem cell (HSC) maintenance (Nature Medicine, doi:10.1038/nm.2882). Moreover, Carracedo et al., disclosed that whereas PML expression allowed luminal filling in 3D basement membrane breast cancer, the effect was reversed by inhibition of FAO (J. Clin. Invest. 2012; 122(9):3088-3100). This and other evidence support our view that inhibition of fatty acid oxidation, via antagonism of PPAR's (including PPARα), will prove effective in inhibiting leukemia stem cell differential, and therefore, prove effective in preventing the onset of and/or recurrence of acute and chronic myeloid leukemia, as well as other cancers.

PPARα antagonists have also been shown to inhibit HCV replication and thereby prove useful in the treatment of HCV infection (Rakic, B. et. al., Chem. & Biol. 13, 23-30 (January 2006)). In some embodiments, PPAR modulators have been shown to inhibit viral transcription and replication and thereby prove useful in the treatment of viral diseases (Capeau et al., PPAR Research Volume 2009, Article ID 393408, 2 pages). In some embodiments, PPARα antagonists are useful in the treatment of HIV infection. PPARα antagonists have also been disclosed to be useful in the treatment of metabolic disorders (WO2012/027482A2). Metabolic disorders include, but are not limited to diabetes, obesity, metabolic syndrome, impaired glucose tolerance, syndrome X, and cardiovascular disease.

SUMMARY OF THE INVENTION

The invention disclosed herein is directed to compounds of Formula I

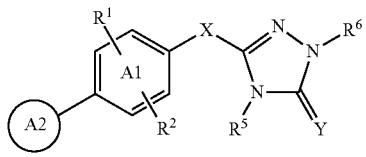

and pharmaceutically acceptable salts thereof, which are useful in the treatment of prostate, breast, colon, pancreatic, human chronic lymphocytic leukemia, melanoma and other cancers. The invention also comprises pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to methods of treating prostate, breast, ovarian, liver, kidney, colon, pancreatic, human chronic lymphocytic leukemia, melanoma and other cancers comprising administration of a therapeutically effective amount of a selective PPARα antagonist. The compounds and pharmaceutical compositions of the invention are also useful in the treatment of viral infections, such as HCV infections and HIV infections.

BRIEF DESCRIPTION OF THE DRAWINGS

FIG. 1 shows the ability of N-(6-(4-(3-(1-(4-(tert-butyl)benzyl)-4-ethyl-5-oxo-4,5-dihydro-1H-1,2,4-triazol-3-yl)propyl)phenyl)pyridin-3-yl)benzenesulfonamide (Example 10) to inhibit the metastasis of B16F10 melanoma cells to the lung.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

In a first aspect the invention is directed to a compound of Formula I

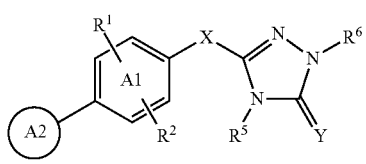

or a pharmaceutical acceptable salt thereof wherein:
A1 is phenyl or a 6-membered heteroaromatic ring having 1, 2 or 3 N in the heteroaromatic ring;

A2 is selected from A2a or A2b

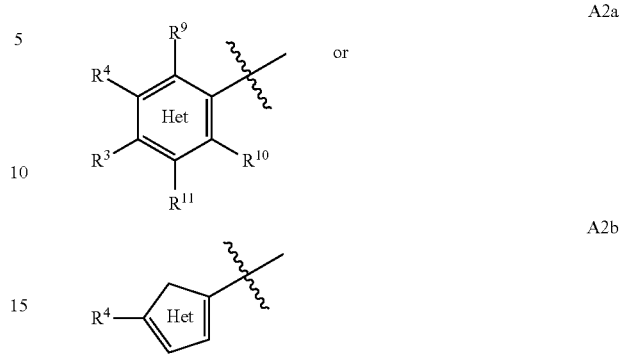

wherein A2a is phenyl or a 6-membered heteroaromatic ring having 1, 2 or 3 N in the heteroaromatic ring, and
A2b is a 5-membered heteroaromatic ring having 1, 2 or 3 heteroatoms independently selected from O, S and N;
X is selected from the group consisting of —$(CH_2)_m$—, —$(CH_2)_m$—O—$(CH_2)_n$—, —$(CH_2)_m$—NH—$(CH_2)_n$—, —$(CH_2)_m$—S(=O)$_o$—$(CH_2)_n$—, optionally mono- or di-substituted with halogen, wherein m and n are independently 0, 1, 2, 3 or 4, and each o is independently 0, 1 or 2;
Y is O or S;
$R^1$ and $R^2$ are each independently selected from the group consisting of:
(a) hydrogen,
(b) halogen,
(c) CN,
(d) —$CF_3$,
(e) —$C_{1-6}$alkyl,
(f) —$C_{1-6}$alkyl-C(=O)OH,
(g) —O—($R^7$),
(h) —S(=O)$_o R^7$,
(i) —N($R^7$)($R^8$),
(j) —N($R^7$)—C(=O)—($R^8$),
(k) —N($R^7$)—C(=O)—O—($R^8$),
(l) —N($R^7$)S(=O)$_2$($R^8$),
(m) —$C_{3-6}$cycloalkyl,
(n) —C(=O)($R^7$),
(o) aryl,
(p) heteroaryl,
(q) —OC(=O)N($R^7$)($R^8$),
(r) —S(=O)$_2$N($R^7$)($R^8$),
(s) —C(=O)N($R^7$)($R^8$), and
(t) —C($R^7$)($R^8$)OH,
wherein the alkyl portion of choices (e) and (f), and the cycloalkyl portion of choice (m) are optionally substituted with halogen, and
wherein the aryl of choice (o) and the heteroaryl of choice (p) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_n C_{1-6}$alkyl, —S(=O)$_n C_{3-6}$cycloalkyl, and CN;
$R^3$ is selected from the group consisting of:
(a) hydrogen,
(b) halogen,
(c) CN,
(d) —$CF_3$,
(e) —$C_{1-6}$alkyl,
(f) —$C_{1-6}$alkyl-C(=O)OH, (g) —O—($R^7$),
(h) —S(=O)$_o$$R^7$,
(i) —N($R^7$)($R^8$),
(j) —N($R^7$)—C(=O)—($R^8$),
(k) —N($R^7$)—C(=O)—O—($R^8$),
(l) —N($R^7$)S(=O)$_2$($R^8$),
(m) —C$_{3-6}$cycloalkyl,
(n) —C(=O)($R^7$),
(o) aryl,
(p) heteroaryl,
(q) —OC(=O)N($R^7$)($R^8$),
(r) —S(=O)$_2$N($R^7$)($R^8$),
(s) —C(=O)N($R^7$)($R^8$),
(t) —C($R^7$)($R^8$)OH,
(u) —C$_{1-6}$alkyl-S(=O)$_2$N($R^7$)($R^8$),
(v) —C$_{3-6}$cycloalkyl-S(=O)$_2$N($R^7$)($R^8$),
(w) —C$_{3-6}$cycloalkyl-C(=O)OH,
(x) heterocycle,
(y) —C$_{1-6}$alkyl-C(=O)—N($R^7$)($R^8$),
(z) —C$_{3-6}$cycloalkyl-C(=O)—N($R^7$)($R^8$),
(aa) —C(=O)OH,
(bb) —C$_{1-6}$alkyl-($R^7$),
(cc) —C$_{3-6}$cycloalkyl-($R^7$),
(dd) —N($R^7$)—C(=O)—NH($R^8$), and
(ee) —N($R^7$)—C(=O)N($R^7$)—S(=O)$_2$($R^8$),
wherein the alkyl portion of choices (e), (f), (u), (y) and (bb), and the cycloalkyl portion of choices (m), (v), (w), (z) and (cc) are optionally substituted with halogen, oxo or hydroxyl, and
wherein the aryl of choice (o), heteroaryl of choice (p), and heterocycle of choice (x) are optionally mono- or di-substituted with substituents selected from the group consisting of halogen, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_n$ C$_{1-6}$alkyl, —S(=O)$_n$C$_{3-6}$cycloalkyl, hydroxyl and CN;
$R^4$ is selected from the group consisting of:
(a) hydrogen,
(b) —N($R^7$)($R^8$),
(c) —N($R^7$)S(=O)$_2$$R^8$,
(d) —N($R^7$)—C(=O)$R^8$,
(e) —N($R^7$)C(=O)O$R^8$,
(f) —S(=O)$_o$$R^7$,
(g) —S(=O)$_2$N($R^7$)($R^8$),
(h) —C(=O)$R^7$,
(i) —C(=O)N($R^7$)($R^8$),
(j) —OC(=O)N($R^7$)($R^8$),
(k) —O—$R^7$,
(l) —C($R^7$)($R^8$)OH,
(m) —C$_{1-4}$alkyl-C(=O)NHS(=O)$_2$$R^7$,
(n) —C$_{1-4}$alkyl-S(=O)$_2$NHC(=O)$R_7$,
(o) —C$_{1-4}$alkyl-C(=O)—N($R^7$)($R^8$),
(p) —C$_{1-4}$alkyl-N($R^7$)C(=O)($R^8$),
(q) —C$_{1-4}$alkyl-N($R^7$)S(=O)$_2$($R^8$),
(r) —C$_{1-4}$alkyl-S(=O)$_2$N($R^7$)($R^8$),
(s) —C$_{1-4}$alkyl-N($R^7$)C(=O)O($R^8$),
(t) —C$_{1-4}$alkyl-O—C(=O)N($R^7$)($R^8$),
(u) —C$_{1-4}$alkyl-C(=O)($R^7$),
(v) —C$_{1-4}$alkyl-C($R^7$)($R^8$)OH,
(w) —C$_{1-4}$alkylO($R^7$),
(x) —C$_{1-6}$alkyl-C(=O)OH,
(y) —C$_{2-6}$alkenyl-C(=O)OH,
(z) —C$_{3-6}$cycloalkyl-C(=O)OH,
(aa) —C$_{3-6}$cycloalkyl-C(=O)NHS(=O)$_2$$R^7$,
(bb) —C$_{3-6}$cycloalkyl-S(=O)$_2$NHC(=O)$R^7$,
(cc) —C$_{3-6}$cycloalkyl-C(=O)—N($R^7$)($R^8$),
(dd) —C$_{3-6}$cycloalkyl-N($R^7$)C(=O)($R^8$),
(ee) —C$_{3-6}$cycloalkyl-N($R^7$)S(=O)$_2$($R^8$),
(ff) —C$_{3-6}$cycloalkyl-S(=O)$_2$N($R^7$)($R^8$),
(gg) —C$_{3-6}$cycloalkyl-N($R^7$)C(=O)O($R^8$),
(hh) —C$_{3-6}$cycloalkyl-O—C(=O)N($R^7$)($R^8$),
(ii) —C$_{3-6}$cycloalkyl-C(=O)($R^7$),
(jj) —C$_{3-6}$cycloalkyl-C($R^7$)($R^8$)OH,
(kk) —C$_{3-6}$cycloalkylO($R^7$),
(ll) —C(=O)OH,
(mm) aryl,
(nn) heteroaryl,
(oo) —C(=O)N($R^7$)S(=O)$_2$($R^8$),
(pp) —S(=O)$_2$N($R^7$)C(=O)($R^8$),
(qq) —C$_{1-4}$alkyl-$R^7$,
(rr) —C$_{3-6}$cycloalkyl-$R^7$
(ss) —N($R^7$)S(=O)$_2$N($R^8$)$_2$,
(tt) —N($R^7$)—C(=O)N($R^7$)—S(=O)$_2$($R^8$),
(uu) —N($R^7$)C(=O)NH($R^8$), and
(vv) heterocycle,
wherein the alkyl portion of choices (m), (n), (o), (p), (q), (r), (s), (t), (u), (v), (w), (x), and (qq), the alkenyl portion of choice (y), and the cycloalkyl portion of choices (z), (aa), (bb), (cc), (dd), (ee), (ff), (gg), (hh), (ii), (jj), (kk), and (rr) are optionally mono or di-substituted with halogen, —C$_{1-6}$alkyl, —C$_{3-6}$cycloalkyl, —C$_{1-6}$alkoxy, —C$_{3-6}$cycloalkoxy, aryl, —C$_{1-6}$alkylaryl, hydroxyl or oxo, and
wherein the aryl of choice (mm), the heteroaryl of choice (nn) and the heterocycle of choice (vv) are optionally mono- or di-substituted with substituents selected from the group consisting of halogen, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_n$C$_{1-6}$alkyl, S(=O)$_n$C$_{3-6}$cycloalkyl, hydroxyl and CN, or
wherein $R^3$ and $R^4$ are joined together to form a 5- or 6-membered heterocyclic ring, said ring having one heteroatom selected from O and N, wherein said ring is optionally substituted with —C(=O)OH or —C$_{1-6}$alkyl-C(=O)OH, with the proviso that at least one of $R^3$ and $R^4$ is other than hydrogen; $R^5$ is selected from the group consisting of:
(a) hydrogen,
(b) —C$_{1-6}$alkyl,
(c) —C$_{1-4}$alkyl($R^7$),
(d) —C$_{1-4}$alkylCN,
(e) —C$_{1-4}$alkylO($R^7$),
(f) aryl,
(g) heteroaryl,
(h) —C$_{3-6}$cycloalkyl,
(i) —C$_{3-6}$cycloalkylCN,
(j) —C$_{3-6}$cycloalkyl($R^7$),
(k) —C$_{3-6}$cycloalkylO($R^7$), and
(l) C$_{2-6}$alkenyl,
wherein the alkyl portion of choices (b), (c), (d) and (e), the cycloalkyl portion of choices (h), (i), (j) and (k), and the alkenyl portion of choice (l), are optionally substituted with halogen or C$_{1-4}$alkyl, and wherein the aryl of choice (f) and the heteroaryl of choice (g), are optionally mono- or di-substituted with substituents selected from the group consisting of halogen, nitro, C$_{1-6}$alkyl, CF$_3$, C$_{1-6}$alkoxy, halo C$_{1-6}$alkyl, aryl, heteroaryl, C$_{3-6}$cycloalkyl, C$_{3-6}$cycloalkoxy, and CN;
$R^6$ is selected from the group consisting of:
(a) hydrogen,
(b) —C$_{1-6}$alkyl,
(c) —C$_{1-6}$alkylaryl,
(d) —C$_{1-6}$alkylheteroaryl,
(e) —S(=O)$_o$C$_{1-6}$alkyl($R^7$),
(f) —C(=O)C$_{1-6}$alkyl($R^7$), (g) —$C_{3-6}$cycloalkyl,
(h) aryl,
(i) heteroaryl,
(j) —C(=O)$C_{3-6}$cycloalkyl($R^7$),
(k) —S(=O)$_o$$C_{3-6}$cycloalkyl($R^7$), and
(l) —$C_{1-6}$alkyl($R^7$), wherein the alkyl portion of choices (b), (c), (d), (e), (f), and (l), and the cycloalkyl portion of choices (g), (j), and (k), are optionally substituted with halogen or —$C_{1-4}$alkyl, and wherein the aryl of choices (c) and (h), and the heteroaryl of choices (d) and (i), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$ alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, (heterocyclyl optionally substituted with hydroxyl or halogen), and CN;

$R^7$ and $R^8$ are each independently selected from the following:
(a) hydrogen,
(b) —$C_{1-6}$alkyl,
(c) —$C_{3-6}$cycloalkyl,
(d) aryl,
(e) heteroaryl,
(f) —$C_{1-6}$alkylaryl,
(g) —$C_{1-6}$alkylheteroaryl,
(h) cyano,
(i) -aryl-aryl,
(j) -aryl-heteroaryl,
(k) —$NH_2$,
(l) —NH($C_1$-$C_3$alkyl), and
(m) —N($C_1$-$C_3$alkyl)$_2$, wherein the alkyl of choices (b), (f), (g), (l) and (m), and the cycloalkyl portion of (c), are each optionally mono-, di- or tri-substituted with halogen, hydroxyl, $C_{1-6}$alkyl, $C_{1-6}$alkoxy, $C_{3-6}$cycloalkyl or $C_{3-6}$cycloalkoxy, and wherein the aryl portion of choices (d), (f), (i) and (j), and the heteroaryl portion of choices (e), (g) and (j), are each optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o$$C_{1-4}$alkyl, —S(=O)$_o$$C_{3-6}$cycloalkyl, —C(=O)$C_{1-4}$alkyl, aryl, heteroaryl, —O-heteroaryl-$CF_3$, hydroxyl, —(C=O)OH, and CN;

$R^9$, $R^{10}$ and $R^{11}$ are each independently selected from the following:
(a) hydrogen,
(b) —$C_{1-6}$alkyl,
(c) —$C_{3-6}$cycloalkyl,
(d) halogen, and
(e) —O—($R^7$), wherein the alkyl of choice (b) and the cycloalkyl of choice (c) are each optionally mono-, di- or tri-substituted with halogen.

In a second aspect the invention is directed to a compound of Formula I

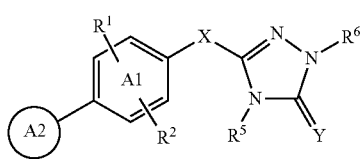

Formula I or a pharmaceutical acceptable salt thereof wherein:
A1 is phenyl or a 6-membered heteroaromatic ring having 1, 2 or 3 N in the heteroaromatic ring;
A2 is selected from A2a or A2b

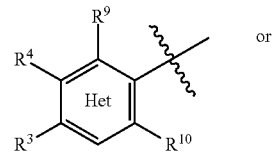

A2a

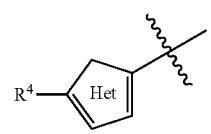

A2b wherein A2a is phenyl or a 6-membered heteroaromatic ring having 1, 2 or 3 N in the heteroaromatic ring, and
A2b is a 5-membered heteroaromatic ring having 1, 2 or 3 heteroatoms independently selected from O, S and N;
X is selected from the group consisting of —$(CH_2)_m$—, —$(CH_2)_m$—O—$(CH_2)_n$—, —$(CH_2)_m$—NH—$(CH_2)_n$—, —$(CH_2)_m$—S(=O)$_o$—$(CH_2)_n$— wherein m and n are independently 0, 1, 2, 3 or 4, and o is independently 0, 1 or 2;
Y is O or S;

$R^1$ and $R^2$ are each independently selected from the group consisting of:
(a) hydrogen,
(b) halogen,
(c) CN,
(d) —$CF_3$,
(e) —$C_{1-6}$alkyl,
(f) —$C_{1-6}$alkyl-C(=O)OH,
(g) —O—($R^7$),
(h) —S(=O)$_o$$R^7$,
(i) —N($R^7$)($R^8$),
(j) —N($R^7$)—C(=O)—($R^8$),
(k) —N($R^7$)—C(=O)—O—($R^8$),
(l) —N($R^7$)S(=O)$_2$($R^8$),
(m) —$C_{3-6}$cycloalkyl,
(n) —C(=O)($R^7$),
(o) aryl,
(p) heteroaryl,
(r) —OC(=O)N($R^7$)($R^8$),
(q) —S(=O)$_2$N($R^7$)($R^8$),
(s) —C(=O)N($R^7$)($R^8$), and
(t) —C($R^7$)($R^8$)OH, wherein the alkyl portion of choices (e) and (f), and the cycloalkyl portion of choice (m), are optionally substituted with halogen, and
wherein the aryl of choices (o) and heteroaryl of choice (p) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_n$$C_{1-6}$alkyl, —S(=O)$_n$$C_{3-6}$cycloalkyl and CN;

$R^3$ is selected from the group consisting of:
(a) hydrogen,
(b) halogen,
(c) CN,
(d) —$CF_3$,
(e) —$C_{1-6}$alkyl, (f) —$C_{1-6}$alkyl-C(=O)OH,
(g) —O—($R^7$),
(h) —S(=O)$_o$$R^7$,
(i) —N($R^7$)($R^8$),
(j) —N($R^7$)—C(=O)—($R^8$),
(k) —N($R^7$)—C(=O)—O—($R^8$),
(l) —N($R^7$)S(=O)$_2$($R^8$),
(m) —$C_{3-6}$cycloalkyl,
(n) —C(=O)($R^7$),
(o) aryl,
(p) heteroaryl,
(q) —OC(=O)N($R^7$)($R^8$),
(r) —S(=O)$_2$N($R^7$)($R^8$),
(s) —C(=O)N($R^7$)($R^8$), and
(t) —C($R^7$)($R^8$)OH, wherein the alkyl portion of choices (e) and (f), and the cycloalkyl portion of choice (m), are optionally substituted with halogen, and
wherein the aryl of choice (o) and heteroaryl of choice (p) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_n$$C_{1-6}$alkyl, —S(=O)$_n$$C_{3-6}$cycloalkyl and CN;

$R^4$ is selected from the group consisting of:
(a) hydrogen,
(b) —N($R^7$)($R^8$),
(c) —N($R^7$)S(=O)$_2$$R^8$,
(d) —N($R^7$)—C(=O)$R^8$,
(e) —N($R^7$)C(=O)O$R^8$,
(f) —S(=O)$_o$$R^7$,
(g) —S(=O)$_2$N($R^7$)($R^8$),
(h) —C(=O)$R^7$,
(i) —C(=O)N($R^7$)($R^8$),
(j) —OC(=O)N($R^7$)($R^8$),
(k) —O—$R^7$,
(l) —C($R^7$)($R^8$)OH,
(m) —$C_{1-4}$alkyl-C(=O)NHS(=O)$_2$$R^7$,
(n) —$C_{1-4}$alkyl-S(=O)$_2$NHC(=O)$R_7$,
(o) —$C_{1-4}$alkyl-C(=O)—N($R^7$)($R^8$),
(p) —$C_{1-4}$alkyl-N($R^7$)C(=O)($R^8$),
(q) —$C_{1-4}$alkyl-N($R^7$)S(=O)$_2$($R^8$),
(r) —$C_{1-4}$alkyl-S(=O)$_2$N($R^7$)($R^8$),
(s) —$C_{1-4}$alkyl-N($R^7$)C(=O)O($R^8$),
(t) —$C_{1-4}$alkyl-O—C(=O)N($R^7$)($R^8$),
(u) —$C_{1-4}$alkyl-C(=O)($R^7$),
(v) —$C_{1-4}$alkyl-C($R^7$)($R^8$)OH,
(w) —$C_{1-4}$alkylO($R^7$),
(x) —$C_{1-6}$alkyl-C(=O)OH,
(y) —$C_{2-6}$alkenyl-C(=O)OH,
(z) —$C_{3-6}$cycloalkyl-C(=O)OH,
(aa) —$C_{3-6}$cycloalkyl-C(=O)NHS(=O)$_2$$R^7$,
(bb) —$C_{3-6}$cycloalkyl-S(=O)$_2$NHC(=O)$R^7$,
(cc) —$C_{3-6}$cycloalkyl-C(=O)—N($R^7$)($R^8$),
(dd) —$C_{3-6}$cycloalkyl-N($R^7$)C(=O)($R^8$)
(ee) —$C_{3-6}$cycloalkyl-N($R^7$)S(=O)$_2$($R^8$),
(ff) —$C_{3-6}$cycloalkyl-S(=O)$_2$N($R^7$)($R^8$),
(gg) —$C_{3-6}$cycloalkyl-N($R^7$)C(=O)O($R^8$)
(hh) —$C_{3-6}$cycloalkyl-O—C(=O)N($R^7$)($R^8$)
(ii) —$C_{3-6}$cycloalkyl-C(=O)($R^7$),
(jj) —$C_{3-6}$cycloalkyl-C($R^7$)($R^8$)OH,
(kk) —$C_{3-6}$cycloalkylO($R^7$),
(ll) —C(=O)OH,
(mm) aryl,
(nn) heteroaryl,
(oo) —C(=O)N($R^7$)S(=O)$_2$($R^8$), and
(pp) —S(=O)$_2$N($R^7$)C(=O)($R^8$), wherein the alkyl portion of choices (m), (n), (o), (p), (q), (r), (s), (t), (u), (v), (w) and (x), the alkenyl portion of choice (y), and the cycloalkyl portion of choices (z), (aa), (bb), (cc), (dd), (ee), (ff), (gg), (hh), (ii), (jj) and (kk), are optionally mono- or di-substituted with halo, $C_{1-6}$alkyl, $C_{3-6}$cycloalkyl, $C_{1-6}$alkoxy, or $C_{3-6}$cycloalkoxy, and
wherein the aryl of choice (mm) and the heteroaryl of choice (nn) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_n$$C_{1-6}$alkyl, —S(=O)$_n$$C_{3-6}$cycloalkyl and CN;
with the proviso that at least one of $R^3$ and $R^4$ is other than hydrogen;

$R^5$ is selected from the group consisting of:
(a) hydrogen,
(b) —$C_{1-6}$alkyl,
(c) —$C_{1-4}$alkyl($R^7$),
(d) —$C_{1-4}$alkylCN,
(e) —$C_{1-4}$alkylO($R^7$),
(f) aryl,
(g) heteroaryl,
(h) —$C_{3-6}$cycloalkyl,
(i) —$C_{3-6}$cycloalkylCN,
(j) —$C_{3-6}$cycloalkyl($R^7$), and
(k) —$C_{3-6}$cycloalkylO($R^7$), wherein the alkyl portion of choices (b), (c), (d) and (e), and the cycloalkyl portion of choices (h), (i), (j) and (k), are optionally substituted with halogen or $C_{1-4}$alkyl, and
wherein the aryl of choice (f) and the heteroaryl of choice (g), are optionally mono- or di-substituted with substituents selected from the group consisting of halogen, nitro, $C_{1-6}$alkyl, $CF_3$, $C_{1-6}$alkoxy, halo $C_{1-6}$alkyl, aryl, heteroaryl, $C_{3-6}$cycloalkyl, $C_{3-6}$cycloalkoxy, and CN;

$R^6$ is selected from the group consisting of:
(a) hydrogen,
(b) —$C_{1-6}$alkyl,
(c) —$C_{1-6}$alkylaryl,
(d) —$C_{1-6}$alkylheteroaryl,
(e) —S(=O)$_o$$C_{1-6}$alkyl($R^7$),
(f) —C(=O)$C_{1-6}$alkyl($R^7$),
(g) —$C_{3-6}$cycloalkyl,
(h) aryl,
(i) heteroaryl,
(j) —C(O)$C_{3-6}$cycloalkyl($R^7$),
(k) —S(=O)$_o$$C_{3-6}$cycloalkyl($R^7$), and
(l) —$C_{1-6}$alkyl($R^7$), wherein the alkyl portion of choices (b), (c), (d), (e), (f), and (l), and the cycloalkyl portion of choices (g), (j), and (k), are optionally substituted with halogen or $C_{1-4}$alkyl, and
wherein the aryl of choices (c) and (h), and the heteroaryl of choices (d) and (i), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$ alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, and CN;

$R^7$ and $R^8$ are each independently selected from the following:
(a) hydrogen,
(b) —$C_{1-6}$alkyl,
(c) —$C_{3-6}$ cycloalkyl,
(d) aryl,
(e) heteroaryl, (f) —$C_{1-6}$alkylaryl, and
(g) —$C_{1-6}$alkylheteroaryl,
wherein the alkyl of choices (b), (f) and (g), and the cycloalkyl portion of (c), are each optionally mono-, di- or tri-substituted with halogen, and
wherein the aryl portion of choices (d) and (f), and the heteroaryl portion of choices (e) and (g), are each optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o C_{1-4}$alkyl, —S(=O)$_o C_{3-6}$cycloalkyl, aryl, heteroaryl, hydroxyl and CN;
$R^9$ and $R^{10}$ are each independently selected from the group consisting of:
  (a) hydrogen,
  (b) —$C_{1-6}$alkyl,
  (c) —$C_{3-6}$ cycloalkyl, and
  (d) halogen,
wherein the alkyl of choice (b) and the cycloalkyl of choice (c), are each optionally mono-, di- or tri-substituted with halogen.

Within the first and second aspect there is a genus wherein X is selected from the group consisting of —(CH$_2$)$_m$—, and —(CH$_2$)$_m$—S(=O)$_o$—(CH$_2$)$_n$—, where m+n is 2, 3 or 4 and wherein o is 0, 1 or 2.

Within this genus there is a subgenus wherein X is —CH$_2$CH$_2$CH$_2$—.

Within first and second aspect there is a genus wherein A1 is a substituted phenyl or substituted pyridine.

Within the first and second aspect there is a genus wherein A2 is A2a.

Within this genus there is a subgenus wherein A2a is a substituted phenyl, or substituted pyridine.

Within the first and second aspect there is a genus wherein Y is O.

Within the first and second aspect there is a genus wherein $R^1$ and $R^2$ are each independently selected from the group consisting of:
  (a) hydrogen,
  (b) halogen,
  (c) CN,
  (d) CF$_3$,
  (e) $C_{1-6}$alkyl,
  (g) —O—($R^7$), and
  (h) N($R^7$)($R^8$),
wherein the alkyl portion of choice (e), is optionally substituted with halogen.

Within this genus there is a subgenus wherein $R^1$ and $R^2$ are each hydrogen.

Within the first and second aspect there is a genus wherein $R^3$ is selected from the group consisting of:
  (a) —O—($R^7$),
  (b) —N($R^7$)—C(=O)—O—($R^8$),
  (c) —N($R^7$)S(=O)$_2$($R^8$),
  (d) —C(=O)($R^7$),
  (e) aryl,
  (f) heteroaryl,
  (g) —OC(=O)N($R^7$)($R^8$),
  (h) —C($R^7$)($R^8$)OH, and
  (i) hydrogen
wherein the aryl of choice (e) and the heteroaryl of choice (f) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o C_{1-6}$alkyl, —S(=O)$_o C_{3-6}$cycloalkyl, and CN.

Within this genus there is a subgenus wherein $R^3$ is selected from the group consisting of:
  (a) hydrogen
  (b) —O—($R^7$), and
  (c) —N($R^7$)S(=O)$_2$($R^8$).

Within the second aspect there is a genus wherein $R^3$ is selected from the group consisting of:
  (a) —O—($R^7$),
  (b) —N($R^7$)—C(=O)—O—($R^8$),
  (c) —N($R^7$)S(=O)$_2$($R^8$),
  (d) —C(=O)($R^7$),
  (e) aryl,
  (f) heteroaryl,
  (g) —OC(=O)N($R^7$)($R^8$), and
  (h) —C($R^7$)($R^8$)OH,
wherein the aryl of choice (e) and the heteroaryl of choice (f) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o C_{1-6}$alkyl, —S(=O)$_o C_{3-6}$cycloalkyl, and CN.

Within the first and second aspect there is a genus wherein $R^4$ is selected from the group consisting of:
  (a) hydrogen,
  (b) —N($R^7$)($R^8$),
  (c) N($R^7$)S(=O)$_2 R^8$,
  (d) —S(=O)$_2$N($R^7$)($R^8$),
  (e) —C(=O)N($R^7$)($R^8$),
  (f) —$C_{1-4}$alkyl-C(=O)NHS(=O)$_2 R^7$,
  (g) —$C_{1-4}$alkyl-S(=O)$_2$NHC(=O)$R^7$,
  (h) —$C_{1-4}$alkyl-C(=O)—N($R^7$)($R^8$),
  (i) —$C_{1-4}$alkyl-N($R^7$)S(=O)$_2$($R^8$),
  (j) —$C_{1-4}$alkyl-S(=O)$_2$N($R^7$)($R^8$),
  (k) —$C_{1-6}$alkyl-C(=O)OH,
  (l) —$C_{3-6}$cycloalkyl-C(=O)OH,
  (m) —$C_{3-6}$cycloalkyl-C(=O)NHS(=O)$_2 R^7$,
  (n) —$C_{3-6}$cycloalkyl-S(=O)$_2$NHC(=O)$R^7$,
  (o) —$C_{3-6}$cycloalkyl-C(=O)—N($R^7$)($R^8$),
  (p) —$C_{3-6}$cycloalkyl-N($R^7$)C(=O)($R^8$),
  (q) —$C_{3-6}$cycloalkyl-N($R^7$)S(=O)$_2$($R^8$),
  (r) —$C_{3-6}$cycloalkyl-S(=O)$_2$N($R^7$)($R^8$),
  (s) —C(=O)OH,
  (t) —C(=O)N$R^7$S(=O)$_2$($R^8$),
  (u) —$C_{1-4}$alkyl-N($R^7$)—C(=O)$R^8$, and
  (v) —S(=O)$_2$N($R^7$)C(=O)$R^8$,
wherein the alkyl portion of choices (f), (g), (h), (i), (j), (k) and (u), and the cycloalkyl portion of choices (l), (m), (n), (o), (p), (q) and (r), are optionally mono- or di-substituted with halogen, $C_{1-6}$alkyl, $C_{3-6}$cycloalkyl, $C_{1-6}$alkoxy, or $C_{3-6}$cycloalkoxy.

Within this genus there is a subgenus wherein $R^4$ is selected from the group consisting of:
  (a) hydrogen,
  (b) —N($R^7$)S(=O)$_2 R^8$,
  (c) —$C_{1-6}$alkyl-C(=O)OH,
  (d) —$C_{3-6}$cycloalkyl-C(=O)OH,
  (e) —C(=O)OH,
  (f) —C(=O)N($R^7$)S(=O)$_2$($R^8$), and
  (g) —S(=O)$_2$N($R^7$)C(=O)$R^8$,
wherein the alkyl portion of choice (c) and the cycloalkyl portion of choice (d), are optionally mono- or di-substituted with halogen, $C_{1-6}$alkyl, $C_{3-6}$cycloalkyl, $C_{1-6}$alkoxy, or $C_{3-6}$cycloalkoxy.

Within the first and second aspect there is a genus wherein $R^5$ is $C_{1-6}$alkyl, optionally substituted with halogen or $C_{1-4}$alkyl.

Within the first and second aspect there is a genus wherein $R^6$ is selected from the group consisting of:
(a) —$C_{1-6}$alkylaryl,
(b) —$C_{1-6}$alkylheteroaryl, and
(c) —$C_{3-6}$ cycloalkyl,
wherein the alkyl portion of choices (a) and (b), and the cycloalkyl portion of choice (c), are optionally substituted with halogen or $C_{1-4}$alkyl, and the aryl portion of choice (a) and the heteroaryl portion of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN.

Within this genus there is a subgenus wherein $R^6$ is selected from the group consisting of:
(a) —$C_{1-6}$alkylaryl, and
(b) —$C_{1-6}$alkylheteroaryl,
wherein the alkyl portion of choices (a) and (b), is optionally substituted with halogen or $C_{1-4}$alkyl, and the aryl portion of choice (a) and the heteroaryl portion of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN.

Within the first and second aspect there is a genus wherein $R^7$ is selected from hydrogen and $C_{1-4}$alkyl optionally substituted with halogen; and $R^8$ is selected from hydrogen, $C_{1-4}$alkyl optionally substituted with halogen, and aryl optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$ alkyl)$_2$, —N($C_{3-6}$cycloalkyl)$_2$, —S(=O)$_o$$C_{1-4}$alkyl, —S(=O)$_o$$C_{3-6}$cycloalkyl, aryl, heteroaryl, hydroxyl and CN.

Within the first and second aspect there is a genus wherein $R^9$ and $R^{10}$ are each independently hydrogen or F.

Within this genus there is a subgenus wherein X is selected from the group consisting of —(CH$_2$)$_m$—, and —(CH$_2$)$_m$—S(=O)$_o$—(CH$_2$)$_n$—, where m+n is 2, 3 or 4 and wherein o is 0, 1 or 2;
Y is O or S; A1 is a substituted phenyl or substituted pyridine;
A2 is A2a;
$R^1$ and $R^2$ are each independently selected from the group consisting of:
(a) hydrogen,
(b) halogen,
(c) CN,
(d) $CF_3$,
(e) $C_{1-6}$alkyl,
(g) —O—($R^7$), and
(h) —N($R^7$)($R^8$),
wherein the alkyl portion of choice (e) is optionally substituted with halogen;
$R^3$ is selected from the group consisting of:
(a) —O—($R^7$),
(b) —N($R^7$)—C(=O)—O—($R^8$),
(c) —N($R^7$)S(=O)$_2$($R^8$),
(d) —C(=O)($R^7$),
(e) aryl,
(f) heteroaryl,
(g) —OC(=O)N($R^7$)($R^8$),
(h) —C($R^7$)($R^8$)OH, and
(i) hydrogen
wherein aryl of choice (e) and heteroaryl of choice (f) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN;
$R^4$ is selected from the group consisting of:
(a) hydrogen,
(b) —N($R^7$)($R^8$),
(c) —N($R^7$)S(=O)$_2$$R^8$,
(d) —S(=O)$_2$N($R^7$)($R^8$),
(e) —C(=O)N($R^7$)($R^8$),
(f) —$C_{1-4}$alkyl-C(=O)NHS(=O)$_2$$R^7$,
(g) —$C_{1-4}$alkyl-S(=O)$_2$NHC(=O)$R^7$,
(h) —$C_{1-4}$alkyl-C(=O)—N($R^7$)($R^8$),
(i) —$C_{1-4}$alkyl-N($R^7$)S(=O)$_2$($R^8$),
(j) —$C_{1-4}$alkyl-S(=O)$_2$N($R^7$)($R^8$),
(k) —$C_{1-6}$alkyl-C(=O)OH,
(l) —$C_{3-6}$cycloalkyl-C(=O)OH,
(m) —$C_{3-6}$cycloalkyl-C(=O)NHS(=O)$_2$$R^7$,
(n) —$C_{3-6}$cycloalkyl-S(=O)$_2$NHC(=O)$R^7$,
(o) —$C_{3-6}$cycloalkyl-C(=O)—N($R^7$)($R^8$),
(p) —$C_{3-6}$cycloalkyl-N($R^7$)C(=O)($R^8$),
(q) —$C_{3-6}$cycloalkyl-N($R^7$) S(=O)$_2$($R^8$),
(r) —$C_{3-6}$cycloalkyl-S(=O)$_2$N($R^7$)($R^8$),
(s) —C(=O)OH,
(t) —C(=O)N($R^7$) S(=O)$_2$ ($R^8$),
(u) —$C_{1-4}$alkyl-N($R^7$)—C(=O)$R^8$, and
(v) —S(=O)$_2$N($R^7$)C(=O)$R^8$,
wherein the alkyl portion of choices (f), (g), (h), (i), (j), (k) and (u), and the cycloalkyl portion of choices (l), (m), (n), (o), (p), (q) and (r), are optionally mono- or di-substituted with halogen, $C_{1-6}$alkyl, $C_{3-6}$cycloalkyl, $C_{1-6}$alkoxy, or $C_{3-6}$cycloalkoxy;
$R^5$ is $C_{1-6}$alkyl, optionally substituted with halogen or $C_{1-4}$alkyl;
$R^6$ is selected from the group consisting of:
(a) —$C_{1-6}$alkylaryl,
(b) —$C_{1-6}$alkylheteroaryl, and
(c) —$C_{3-6}$ cycloalkyl,
wherein the alkyl portion of choices (a) and (b), and the cycloalkyl portion of choice (c), are optionally substituted with halogen or $C_{1-4}$alkyl, and the aryl portion of choice (a) and the heteroaryl portion of choice (b), is optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, S(=O)$_o$$C_{3-6}$cycloalkyl and CN;
$R^7$ is selected from hydrogen and $C_{1-4}$alkyl optionally substituted with halogen;
$R^8$ is selected from hydrogen, $C_{1-4}$alkyl optionally substituted with halogen, and aryl optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o$ $C_{1-4}$alkyl, —S(=O)$_o$$C_{3-6}$cycloalkyl, aryl, heteroaryl, hydroxyl and CN; and
$R^9$ and $R^{10}$ are each independently hydrogen or F.

Within this subgenus there is a class wherein
X is —CH$_2$CH$_2$CH$_2$—;
Y is O;
A1 is a substituted phenyl or substituted pyridine;
A2 is A2a, and A2a is a substituted phenyl, or substituted pyridine;
Wand R$^2$ are each hydrogen;
R$^3$ is selected from the group consisting of:
  (a) hydrogen,
  (b) —O—(R$^7$), and
  (c) —N(R$^7$)S(=O)$_2$(R$^8$);
R$^4$ is selected from the group consisting of:
  (a) hydrogen,
  (b) —N(R$^7$)S(=O)$_2$R$^8$,
  (c) —C$_{1-6}$alkyl-C(=O)OH,
  (d) —C$_{3-6}$cycloalkyl-C(=O)OH,
  (e) —C(=O)OH,
  (f) —C(=O)N(R$^7$)S(=O)$_2$(R$^8$), and
  (g) —S(=O)$_2$N(R$^7$)C(=O)R$^8$,
wherein the alkyl portion of choice (c) and the cycloalkyl portion of choice (d), are optionally mono- or di-substituted with halogen, C$_{1-6}$alkyl, C$_{3-6}$cycloalkyl, C$_{1-6}$alkoxy, or C$_{3-6}$cycloalkoxy;
R$^5$ is C$_{1-6}$alkyl, optionally substituted with halogen or C$_{1-4}$alkyl;
R$^6$ is selected from the group consisting of:
  (a) —C$_{1-6}$alkylaryl, and
  (b) —C$_{1-6}$alkylheteroaryl,
wherein the alkyl portion of choices (a) and (b) are optionally substituted with halogen or C$_{1-4}$alkyl, and the aryl portion of choice (a) and the heteroaryl portion of choice (b), are optionally mono- or di-substituted with substituents selected from the group consisting of halogen, nitro, CF$_3$, C$_{1-6}$alkyl, C$_{1-6}$alkoxy, halo C$_{1-6}$alkyl, C$_{3-6}$cycloalkyl, C$_{3-6}$cycloalkoxy, aryl, heteroaryl, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl and CN;
R$^7$ is selected from hydrogen and C$_{1-4}$alkyl optionally substituted with halogen;
R$^8$ is selected from hydrogen, C$_{1-4}$alkyl optionally substituted with halogen, and aryl optionally mono- or di-substituted with substituents selected from the group consisting of halogen, nitro, C$_{1-6}$alkyl, C$_{1-6}$alkoxy, haloC$_{1-6}$alkyl, C$_{3-6}$cycloalkyl, C$_{3-6}$cycloalkoxy, —NH(C$_{1-3}$alkyl), —NH(C$_{3-6}$cycloalkyl), —N(C$_{1-3}$alkyl)$_2$, —N(C$_{3-6}$cycloalkyl)$_2$, —S(=O)$_o$ C$_{1-4}$alkyl, —S(=O)$_o$C$_{3-6}$cycloalkyl, aryl, heteroaryl, hydroxyl and CN;
and
R$^9$ and R$^{10}$ are each independently hydrogen or F.

Within the first and second aspect there is a genus of compounds of Formula 1a or 1b

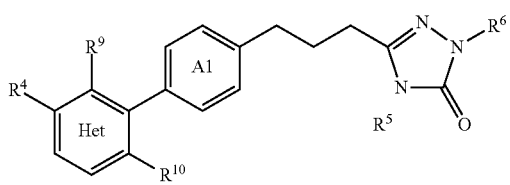

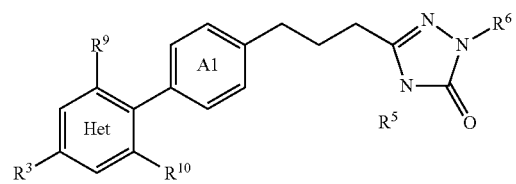

or a pharmaceutically acceptable salt thereof.

Within the first and second aspect there is a genus of compounds of Formula 1c

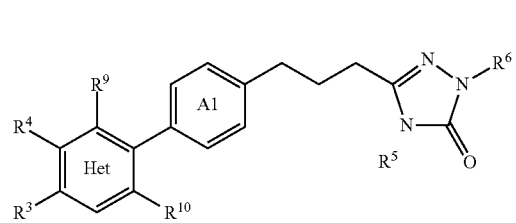

or a pharmaceutically acceptable salt thereof.

Within this genus there is a first subgenus wherein A1 is a substituted phenyl or substituted pyridine;
Het is A2a, where A2a is phenyl or substituted pyridine;
R$^3$ is selected from the group consisting of:
  (a) —O—(R$^7$),
  (b) —N(R$^7$)—C(=O)—O—(R$^8$),
  (c) —N(R$^7$)S(=O)$_2$(R$^8$),
  (d) —C(=O)(R$^7$),
  (e) aryl,
  (f) heteroaryl,
  (g) —OC(=O)N(R$^7$)(R$^8$),
  (h) —C(R$^7$)(R$^8$)OH, and
  (i) hydrogen,
wherein aryl of choice (e) and heteroaryl of choice (f) are optionally mono- or di-substituted with substituents selected from the group consisting of halogen, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl wherein and CN;
R$^4$ is selected from the group consisting of:
  (a) hydrogen,
  (b) —N(R$^7$)(R$^8$),
  (c) —N(R$^7$)S(=O)$_2$R$^8$,
  (d) —S(=O)$_2$N(R$^7$)(R$^8$),
  (e) —C(=O)N(R$^7$)(R$^8$),
  (f) —C$_{1-4}$alkyl-C(=O)NHS(=O)$_2$R$^7$,
  (g) —C$_{1-4}$alkyl-S(=O)$_2$NHC(=O)R$^7$,
  (h) —C$_{1-4}$alkyl-C(=O)—N(R$^7$)(R$^8$),
  (i) —C$_{1-4}$alkyl-N(R$^7$)—C(=O)R$^8$,
  (j) —C$_{1-4}$alkyl-N(R$_7$)S(=O)$_2$(R$^8$),
  (k) —C$_{1-4}$alkyl-S(=O)$_2$N(R$^7$)(R$^8$),
  (l) —C$_{1-6}$alkyl-C(=O)OH,
  (m) —C$_{3-6}$cycloalkyl-C(=O)OH,
  (n) —C$_{3-6}$cycloalkyl-C(=O)NHS(=O)$_2$R$^7$,
  (o) —C$_{3-6}$cycloalkyl-S(=O)$_2$NHC(=O)R$^7$,
  (p) —C$_{3-6}$cycloalkyl-C(=O)—N(R$^7$)(R$^8$),
  (q) —C$_{3-6}$cycloalkyl-N(R$^7$)C(=O)(R$^8$),
  (r) —C$_{3-6}$cycloalkyl-N(R$^7$) S(=O)$_2$ (R$^8$),
  (s) —C$_{3-6}$cycloalkyl-S(=O)$_2$N(R$^7$)(R$^8$), (t) —C(=O)OH,
(u) —C(=O)N($R^7$)S(=O)$_2$($R^8$), and
(v) —S(O)$_2$N($R^7$)C(=O)$R^8$,
wherein the alkyl portion of choices (f), (g), (h), (i), (j), (k) and (l), and the cycloalkyl portion of choices (m), (n), (o), (p), (q), (r) and (s), are optionally mono- or di-substituted with halogen, $C_{1-6}$alkyl, $C_{3-6}$cycloalkyl, $C_{1-6}$alkoxy, or $C_{3-6}$cycloalkoxy;

$R^5$ is $C_{1-6}$alkyl, optionally substituted with halogen or $C_{1-4}$alkyl;

$R^6$ is selected from the group consisting of:
(a) —$C_{1-6}$alkylaryl,
(b) —$C_{1-6}$alkylheteroaryl, and
(c) —$C_{3-6}$ cycloalkyl,
wherein the alkyl portion of choices (a) and (b), and the cycloalkyl portion of choice (c), are optionally substituted with halogen or $C_{1-4}$alkyl, and the aryl portion of choice (a) and the heteroaryl of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN;

$R^7$ is selected from hydrogen and $C_{1-4}$alkyl optionally substituted with halogen;

$R^8$ is selected from hydrogen, $C_{1-4}$alkyl optionally substituted with halogen, and aryl optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$ alkyl), —NH($C_{3-6}$cycloalkyl), —N($C_{1-3}$ alkyl)$_2$, —N($C_{3-6}$cycloalkyl)$_2$, —S(=O)$_o$$C_{1-4}$alkyl, —S(=O)$_o$$C_{3-6}$cycloalkyl, aryl, heteroaryl, hydroxyl and CN; and $R^9$ and $R^{10}$ are each independently hydrogen or F.

Within this genus there is a second subgenus wherein A1 is a substituted phenyl or substituted pyridine;
Het is A2a, where A2a is phenyl or substituted pyridine;
$R^3$ is selected from the group consisting of:
(a) —O—($R^7$),
(b) —N($R^7$)—C(=O)—O—($R^8$),
(c) —N($R^7$)S(=O)$_2$($R^8$),
(d) —C(=O)($R^7$),
(e) aryl,
(f) heteroaryl,
(g) —OC(=O)N($R^7$)($R^8$), and
(h) —C($R^7$)($R^8$)OH,
wherein aryl of choice (e) and heteroaryl of choice (f) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl wherein and CN;

$R^4$ is selected from the group consisting of:
(a) hydrogen,
(b) —N($R^7$)($R^8$),
(c) —N($R^7$)S(=O)$_2$$R^8$,
(d) —S(=O)$_2$N($R^7$)($R^8$),
(e) —C(=O)N($R^7$)($R^8$),
(f) —$C_{1-4}$alkyl-C(=O)NHS(=O)$_2$$R^7$,
(g) —$C_{1-4}$alkyl-S(=O)$_2$NHC(=O)$R^7$,
(h) —$C_{1-4}$alkyl-C(=O)—N($R^7$)($R^8$),
(i) —$C_{1-4}$alkyl-N($R^7$)—C(=O)$R^8$,
(j) —$C_{1-4}$alkyl-N($R_7$)S(=O)$_2$($R^8$),
(k) —$C_{1-4}$alkyl-S(=O)$_2$N($R^7$)($R^8$),
(l) —$C_{1-6}$alkyl-C(=O)OH,
(m) —$C_{3-6}$cycloalkyl-C(=O)OH,
(n) —$C_{3-6}$cycloalkyl-C(=O)NHS(=O)$_2$$R^7$,
(o) —$C_{3-6}$cycloalkyl-S(=O)$_2$NHC(=O)$R^7$,
(p) —$C_{3-6}$cycloalkyl-C(=O)—N($R^7$)($R^8$),
(q) —$C_{3-6}$cycloalkyl-N($R^7$)C(=O)($R^8$),
(r) —$C_{3-6}$cycloalkyl-N($R^7$)S(=O)$_2$($R^8$),
(s) —$C_{3-6}$cycloalkyl-S(=O)$_2$N($R^7$)($R^8$),
(t) —C(=O)OH,
(u) —C(=O)N($R^7$)S(=O)$_2$($R^8$), and
(v) —S(O)$_2$N($R^7$)C(=O)$R^8$,
wherein the alkyl portion of choices (f), (g), (h), (i), (j), (k) and (l), and the cycloalkyl portion of choices (m), (n), (o), (p), (q), (r) and (s), are optionally mono- or di-substituted with halogen, $C_{1-6}$alkyl, $C_{3-6}$cycloalkyl, $C_{1-6}$alkoxy, or $C_{3-6}$cycloalkoxy;

$R^5$ is $C_{1-6}$alkyl, optionally substituted with halogen or $C_{1-4}$alkyl;

$R^6$ is selected from the group consisting of:
(a) —$C_{1-6}$alkylaryl,
(b) —$C_{1-6}$alkylheteroaryl, and
(c) —$C_{3-6}$ cycloalkyl,
wherein the alkyl portion of choices (a) and (b), and the cycloalkyl portion of choice (c), are optionally substituted with halogen or $C_{1-4}$alkyl, and the aryl portion of choice (a) and the heteroaryl of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN;

$R^7$ is selected from hydrogen and $C_{1-4}$alkyl optionally substituted with halogen;

$R^8$ is selected from hydrogen, $C_{1-4}$alkyl optionally substituted with halogen, and aryl optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o$ $C_{1-4}$alkyl, —S(=O)$_o$$C_{3-6}$cycloalkyl, aryl, heteroaryl, hydroxyl and CN; and $R^9$ and $R^{10}$ are each independently hydrogen or F.

Within this first and second subgenus there is a class wherein
A1 is a substituted phenyl or substituted pyridine;
Het is A2a, and A2a is a substituted phenyl, or substituted pyridine.
W and $R^2$ are each hydrogen;
$R^3$ is selected from the group consisting of:
(a) hydrogen,
(b) —O—($R^7$), and
(c) —N($R^7$)S(=O)$_2$($R^8$);
$R^4$ is selected from the group consisting of:
(a) hydrogen,
(b) —N($R^7$)S(=O)$_2$$R^8$,
(c) —$C_{1-6}$alkyl-C(=O)OH,
(d) —$C_{3-6}$cycloalkyl-C(=O)OH,
(e) —C(=O)OH,
(f) —C(=O)N($R^7$)S(=O)$_2$($R^8$), and
(g) —S(=O)$_2$N($R^7$)C(=O)$R^8$,
wherein the alkyl portion of choice (c) and the cycloalkyl portion of choice (d), are optionally mono- or di-substituted with halogen, $C_{1-6}$alkyl, $C_{3-6}$cycloalkyl, $C_{1-6}$alkoxy, or $C_{3-6}$cycloalkoxy;

$R^5$ is $C_{1-6}$alkyl, optionally substituted with halogen or $C_{1-4}$alkyl;

$R^6$ is selected from the group consisting of:
(a) —$C_{1-6}$alkylaryl, and
(b) —$C_{1-6}$alkylheteroaryl, wherein the alkyl portion of choices (a) and (b) are optionally substituted with halogen or $C_{1-4}$alkyl, and the aryl portion of choice (a) and the heteroaryl portion of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN;

$R^7$ is selected from hydrogen and $C_{1-4}$alkyl optionally substituted with halogen;

$R^8$ is selected from hydrogen, $C_{1-4}$alkyl optionally substituted with halogen, and aryl optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$ alkyl), —NH($C_{3-6}$cycloalkyl), —N($C_{1-3}$ alkyl)$_2$, —N($C_{3-6}$cycloalkyl)$_2$, —S(=O)$_o$$C_{1-4}$alkyl, —S(=O)$_o$$C_{3-6}$cycloalkyl, aryl, heteroaryl, hydroxyl and CN;
and $R^9$ and $R^{10}$ are each independently hydrogen or F.

In some embodiments, $R^3$ is not hydrogen. In some embodiments, $R^4$ is not hydrogen. In some embodiments, $R^3$ is not hydrogen; and $R^4$ is not hydrogen.

In some embodiments, the compound of Formula I is a compound in the following table:

| Example no. | Compound name |
|---|---|
| 1 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)acetic acid |
| 2 | 4'-(3-(1-(4-(tert-Butyl)benzyl)-4-ethyl-5-oxo-4,5-dihydro-1H-1,2,4-triazol-3-yl)propyl)-[1,1'-biphenyl]-3-carboxylic acid |
| 3 | 3-(3-(4-(6-Aminopyridin-2-yl)phenyl)propyl)-1-(4-(tert-butyl)benzyl)-4-ethyl-1H-1,2,4-triazol-5(4H)-one |
| 4 | N-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)benzenesulfonamide |
| 5 | 3-(3-(4-(5-Aminopyridin-2-yl)phenyl)propyl)-1-(4-(tert-butyl)benzyl)-4-ethyl-1H-1,2,4-triazol-5(4H)-one |
| 6 | 3-(3-(3'-Amino-[1,1'-biphenyl]-4-yl)propyl)-1-(4-(tert-butyl)benzyl)-4-ethyl-1H-1,2,4-triazol-5(4H)-one |
| 7 | N-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-4-methylbenzenesulfonamide |
| 8 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-(phenylsulfonyl)acetamide |
| 9 | 4'-(3-(1-(4-(tert-Butyl)benzyl)-4-ethyl-5-oxo-4,5-dihydro-1H-1,2,4-triazol-3-yl)propyl)-N-(phenylsulfonyl)-[1,1'-biphenyl]-3-carboxamide |
| 10 | N-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)benzenesulfonamide |
| 11 | 3-(3-(4-(4-Aminopyridin-2-yl)phenyl)propyl)-1-(4-(tert-butyl)benzyl)-4-ethyl-1H-1,2,4-triazol-5(4H)-one |
| 12 | N-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)methanesulfonamide |
| 13 | 1-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)cyclopropanecarboxylic acid |
| 14 | 1-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)cyclopropanecarboxamide |
| 15 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-2-methylpropanamide |
| 16 | N-(2-(4-(3-(1-(4-(tert-Butyl)benzyl)-4-ethyl-5-oxo-4,5-dihydro-1H-1,2,4-triazol-3-yl)propyl)phenyl)pyridin-4-yl)benzenesulfonamide |
| 17 | N-(6-(4-(3-(1-(4-(tert-Butyl)benzyl)-4-ethyl-5-oxo-4,5-dihydro-1H-1,2,4-triazol-3-yl)propyl)phenyl)pyridin-4-yl)methanesulfonamide |
| 18 | 2-(4'-(3-(1-(4-(tert-Butyl)benzyl)-4-ethyl-5-oxo-4,5-dihydro-1H-1,2,4-triazol-3-yl)propyl)-2-fluoro-[1,1'-biphenyl]-3-yl)acetic acid |
| 19 | 2-(4'-(3-(1-(4-(tert-Butyl)benzyl)-4-ethyl-5-oxo-4,5-dihydro-1H-1,2,4-triazol-3-yl)propyl)-6-fluoro-[1,1'-biphenyl]-3-yl)acetic acid |
| 20 | 2-(4'-(3-(1-(4-(tert-Butyl)benzyl)-4-ethyl-5-oxo-4,5-dihydro-1H-1,2,4-triazol-3-yl)propyl)-6-methoxy-[1,1'-biphenyl]-3-yl)acetic acid |
| 21 | 2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)acetic acid |
| 22 | 2-(4'-(3-(1-(4-Cyclopropylbenzyl)-4-ethyl-5-oxo-4,5-dihydro-1H-1,2,4-triazol-3-yl)propyl)-[1,1'-biphenyl]-3-yl)acetic acid |
| 23 | 2-(4'-(3-(1-Benzyl-4-ethyl-5-oxo-4,5-dihydro-1H-1,2,4-triazol-3-yl)propyl)-[1,1'-biphenyl]-3-yl)acetic acid |
| 24 | 2-(4'-(3-(4-Ethyl-5-oxo-1-(4-(trifluoromethyl)benzyl)-4,5-dihydro-1H-1,2,4-triazol-3-yl)propyl)-[1,1'-biphenyl]-3-yl)acetic acid |
| 25 | tert-Butyl (2-(4-(3-(1-(4-(tert-butyl)benzyl)-4-ethyl-5-oxo-4,5-dihydro-1H-1,2,4-triazol-3-yl)propyl)phenyl)oxazol-4-yl)carbamate |
| 26 | 2-(4'-(3-(1-(4-Cyclohexylbenzyl)-4-ethyl-5-oxo-4,5-dihydro-1H-1,2,4-triazol-3-yl)propyl)-[1,1'-biphenyl]-3-yl)acetic acid |
| 27 | 2-(4'(((1-(4-(tert-Butyl)benzyl)-4-ethyl-5-oxo-4,5-dihydro-1H-1,2,4-triazol-3-yl)methoxy)methyl)-[1,1'-biphenyl]-3-yl)acetic acid |
| 28 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-2,2-difluoroacetic acid |
| 29 | 3-(3-(3'-(1H-Tetrazol-5-yl)-[1,1'-biphenyl]-4-yl)propyl)-1-(4-(tert-butyl)benzyl)-4-ethyl-1H-1,2,4-triazol-5(4H)-one |

-continued

| Example no. | Compound name |
|---|---|
| 30 | 2-(4'-(2-((1-(4-(tert-butyl)benzyl)-4-ethyl-5-oxo-4,5-dihydro-1H-1,2,4-triazol-3-yl)methyl)cyclopropyl)-[1,1'-biphenyl]-3-yl)acetic acid |
| 31 | 2-(4'-(3-(1-(4-(tert-Butyl)benzyl)-4-isopropyl-5-oxo-4,5-dihydro-1H-1,2,4-triazol-3-yl)propyl)-[1,1'-biphenyl]-3-yl)acetic acid |
| 32 | 2-(4'-(3-(1-(4-(tert-Butyl)benzyl)-5-oxo-4-phenyl-4,5-dihydro-1H-1,2,4-triazol-3-yl)propyl)-[1,1'-biphenyl]-3-yl)acetic acid; |
| 33 | 2-(4'-(3-(1-(4-(tert-Butyl)benzyl)-4-ethyl-5-oxo-4,5-dihydro-1H-1,2,4-triazol-3-yl)propyl)-4-fluoro-[1,1'-biphenyl]-3-yl)acetic acid |
| 34 | 3-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)acrylic acid |
| 35 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)cyclopropanecarboxylic acid |
| 36 | 3-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)propanoic acid |
| 37 | 2-(4'-(3-(1-(4-Bromobenzyl)-4-ethyl-5-oxo-4,5-dihydro-1H-1,2,4-triazol-3-yl)propyl)-[1,1'-biphenyl]-3-yl)acetic acid |
| 38 | 2-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)acetic acid |
| 39 | 2-(4-(4-(3-(1-(4-(tert-Butyl)benzyl)-4-ethyl-5-oxo-4,5-dihydro-1H-1,2,4-triazol-3-yl)propyl)phenyl)thiophen-2-yl)acetic acid |
| 40 | 1-{[4-(tert-Butyl)phenyl]methyl}-4-ethyl-3-[3-(4-{4-[(methylsulfonyl)amino](2-pyridyl)}phenyl)propyl]-1,2,4-triazolin-5-one |
| 41 | 4'-(3-(1-(4-(tert-Butyl)benzyl)-4-ethyl-5-oxo-4,5-dihydro-1H-1,2,4-triazol-3-yl)propyl)-5-(trifluoromethyl)-[1,1'-biphenyl]-3-carboxylic acid |
| 42 | 1-{[4-(tert-Butyl)phenyl]methyl}-3-[3-(4-{6-[(cyclopropylsulfonyl)amino](2-pyridyl)}phenyl) propyl]-4-ethyl-1,2,4-triazolin-5-one |
| 43 | 2-(5-{4-[3-(1-{[4-(tert-Butyl)phenyl]methyl}-4-ethyl-5-oxo-1,2,4-triazolin-3-yl)propyl]phenyl}-2-pyridyl)acetic acid |
| 44 | 2-(3-{4-[3-(1-{[4-(tert-Butyl)phenyl]methyl}-4-ethyl-5-oxo-1,2,4-triazolin-3-yl)propyl]phenyl} phenyl)propanoic acid |
| 45 | 2-(2-{4-[3-(1-{[4-(tert-Butyl)phenyl]methyl}-4-ethyl-5-oxo-1,2,4-triazolin-3-yl)propyl]phenyl}-4-pyridyl)acetic acid |
| 46 | 2-(3-{4-[3-(1-{[4-(tert-Butyl)phenyl]methyl}-4-ethyl-5-oxo-1,2,4-triazolin-3-yl)propyl]phenyl} phenyl)butanoic acid |
| 47 | 2-(3-{4-[3-(1-{[4-(tert-Butyl)phenyl]methyl}-4-ethyl-5-oxo(1,2,4-triazolin-3-yl))propyl]phenyl} phenyl)-3-phenylpropanoic acid |
| 48 | 2-(6-{4-[3-(1-{[4-(tert-Butyl)phenyl]methyl}-4-ethyl-5-oxo(1,2,4-triazolin-3-yl))propyl]phenyl}-4-(trifluoromethyl)-2-pyridyl)acetic acid |
| 49 | 2-(4'-(3-(1-(4-(tert-Butyl)benzyl)-4-ethyl-5-oxo-4,5-dihydro-1H-1,2,4-triazol-3-yl)propyl)-4-(cyclopropylmethoxy)-[1,1'-biphenyl]-3-yl)acetic acid |
| 50 | 2-(6-{4-[3-(1-{[4-(tert-Butyl)phenyl]methyl}-4-ethyl-5-oxo-1,2,4-triazolin-3-yl)propyl]phenyl}-2-pyridyl)acetic acid |
| 51 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)-N-cyclopropyl-2-hydroxyacetamide |
| 52 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)-N-cyclopropyl-2-oxoacetamide |
| 53 | 2-(4'-(3-(1-(4-(tert-Butyl)benzyl)-4-(cyclopropylmethyl)-5-oxo-4,5-dihydro-1H-1,2,4-triazol-3-yl)propyl)-[1,1'-biphenyl]-3-yl)acetic acid |
| 54 | 2-(4'-(3-(1-((5-(tert-Butyl)thiophen-2-yl)methyl)-4-ethyl-5-oxo-4,5-dihydro-1H-1,2,4-triazol-3-yl)propyl)-[1,1'-biphenyl]-3-yl)acetic acid |
| 55 | 2-(4'-(3-(1-(4-(tert-Butyl)benzyl)-5-oxo-4-(2,2,2-trifluoroethyl)-4,5-dihydro-1H-1,2,4-triazol-3-yl)propyl)-4-methoxy-[1,1'-biphenyl]-3-yl)acetic acid |
| 56 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-cyclopropyl-2-hydroxyacetamide |
| 57 | 2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-cyclopropyl-2-oxoacetamide |
| 58 | 3-{3-[4-(6-Amino-5-methoxy(2-pyridyl))phenyl]propyl}-1-{[4-(tert-butyl)phenyl]methyl}-4-ethyl-1,2,4-triazolin-5-one |
| 59 | 1-{[4-(tert-Butyl)phenyl]methyl}-4-ethyl-3-[3-(4-{5-methoxy-6-[(phenylsulfonyl)amino](2-pyridyl)}phenyl)propyl]-1,2,4-triazolin-5-one |
| 60 | 3-{3-[4-(6-Amino-5-ethoxy(2-pyridyl))phenyl]propyl}-1-{[4-(tert-butyl)phenyl]methyl}-4-ethyl-1,2,4-triazolin-5-one |
| 61 | 2-(5-{4-[3-(1-{[4-(tert-Butyl)phenyl]methyl}-4-ethyl-5-oxo(1,2,4-triazolin-3-yl))propyl]phenyl}-2-ethylthiophenyl)acetic acid |
| 62 | 1-{[4-(tert-Butyl)phenyl]methyl}-3-[3-(4-{5-ethoxy-6-[(phenylsulfonyl)amino](2-pyridyl)}phenyl)propyl]-4-ethyl-1,2,4-triazolin-5-one |
| 63 | 2-(4'-(3-(4-Ethyl-1-(4-(3-fluorooxetan-3-yl)benzyl)-5-oxo-4,5-dihydro-1H-1,2,4-triazol-3-yl)propyl)-[1,1'-biphenyl]-3-yl)acetic acid |
| 64 | 2-(5-{4-[3-(1-{[4-(tert-Butyl)phenyl]methyl}-4-ethyl-5-oxo(1,2,4-triazolin-3-yl))propyl]phenyl}-2-methylthiophenyl)acetic acid |
| 65 | 4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-carboxylic acid |
| 66 | 4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-carboxylic acid |
| 67 | 2-(4'-(3-(1-(3-Bromo-4-(tert-butyl)benzyl)-4-ethyl-5-oxo-4,5-dihydro-1H-1,2,4-triazol-3-yl)propyl)-[1,1'-biphenyl]-3-yl)acetic acid |

-continued

| Example no. | Compound name |
|---|---|
| 68 | 2-(4'-(3-(1-(4-(tert-Butyl)benzyl)-5-oxo-4-propyl-4,5-dihydro-1H-1,2,4-triazol-3-yl)propyl)-4-ethoxy-[1,1'-biphenyl]-3-yl)acetic acid |
| 69 | 2-(4'-(3-(4-Butyl-1-(4-(tert-butyl)benzyl)-5-oxo-4,5-dihydro-1H-1,2,4-triazol-3-yl)propyl)-4-ethoxy-[1,1'-biphenyl]-3-yl)acetic acid |
| 70 | 5-(4-(3-(1-(4-(tert-Butyl)benzyl)-4-ethyl-5-oxo-4,5-dihydro-1H-1,2,4-triazol-3-yl)propyl)phenyl)-1H-indole-3-carboxylic acid |
| 71 | 1-{[4-(tert-Butyl)phenyl]methyl}-4-ethyl-3-{3-[4-(5-{[(4-propylphenyl)sulfonyl]amino}(2-pyridyl))phenyl]propyl}-1,2,4-triazolin-5-one |
| 72 | 1-{[4-(tert-Butyl)phenyl]methyl}-4-ethyl-3-{3-[4-(6-{[(4-propylphenyl)sulfonyl]amino}(2-pyridyl))phenyl]propyl}-1,2,4-triazolin-5-one |
| 73 | 1-{[4-(tert-Butyl)phenyl]methyl}-4-ethyl-3-(3-{4-[6-({[4-(4-methylphenyl)phenyl]sulfonyl}amino)(2-pyridyl)]phenyl}propyl)-1,2,4-triazolin-5-one |
| 74 | 1-{[4-(tert-Butyl)phenyl]methyl}-4-ethyl-3-(3-{4-[6-({[4-(4-methoxyphenyl)phenyl]sulfonyl}amino)(2-pyridyl)]phenyl}propyl)-1,2,4-triazolin-5-one |
| 75 | 1-Acetyl-5-{[(6-{4-[3-(1-{[4-(tert-butyl)phenyl]methyl}-4-ethyl-5-oxo(1,2,4-triazolin-3-yl))propyl]phenyl}(3-pyridyl))amino]sulfonyl}indoline |
| 76 | 2-(4'-(3-(4-Allyl-1-(4-(tert-butyl)benzyl)-5-oxo-4,5-dihydro-1H-1,2,4-triazol-3-yl)propyl)-4-methoxy-[1,1'-biphenyl]-3-yl)acetic acid |
| 77 | 1-{[4-(tert-Butyl)phenyl]methyl}-4-ethyl-3-[3-(4-{5-[({4-[5-(trifluoromethyl)(2-pyridyloxy)]phenyl}sulfonyl)amino](2-pyridyl)}phenyl)propyl]-1,2,4-triazolin-5-one |
| 78 | 1-{[4-(tert-Butyl)phenyl]methyl}-4-ethyl-3-{3-[4-(6-{[benzylsulfonyl]amino}(2-pyridyl))phenyl]propyl}-1,2,4-triazolin-5-one |
| 79 | 1-{[4-(tert-Butyl)phenyl]methyl}-4-ethyl-3-{3-[4-(5-{[benzylsulfonyl]amino}(2-pyridyl))phenyl]propyl}-1,2,4-triazolin-5-one |
| 80 | 2-(4'-(3-(1-(4-(tert-Butyl)benzyl)-5-oxo-4-propyl-4,5-dihydro-1H-1,2,4-triazol-3-yl)propyl)-4-methoxy-[1,1'-biphenyl]-3-yl)acetic acid |
| 81 | N-(2-(4-(3-(1-(4-(tert-Butyl)benzyl)-4-ethyl-5-oxo-4,5-dihydro-1H-1,2,4-triazol-3-yl)propyl)phenyl)pyrimidin-4-yl)benzenesulfonamide |
| 82 | 1-{[4-(tert-Butyl)phenyl]methyl}-4-ethyl-3-(3-{4-[6-({[4-(trifluoromethyl)phenyl]sulfonyl}amino)(2-pyridyl)]phenyl}propyl)-1,2,4-triazolin-5-one |
| 83 | 1-{[4-(tert-Butyl)phenyl]methyl}-3-{3-[4-(6-{[(4-chlorophenyl)sulfonyl]amino}(2-pyridyl))phenyl]propyl}-4-ethyl-1,2,4-triazolin-5-one |
| 84 | 1-{[4-(tert-Butyl)phenyl]methyl}-4-ethyl-3-{3-[4-(6-{[(4-methoxyphenyl)sulfonyl]amino}(2-pyridyl))phenyl]propyl}-1,2,4-triazolin-5-one |
| 85 | 2-(4'-(3-(1-(3-Cyclopropyl-4-(tert-butyl)benzyl)-4-ethyl-5-oxo-4,5-dihydro-1H-1,2,4-triazol-3-yl)propyl)-[1,1'-biphenyl]-3-yl)acetic acid |
| 86 | 1-{[4-(tert-Butyl)phenyl]methyl}-4-ethyl-3-(3-{4-[5-({[4-(trifluoromethyl)phenyl]sulfonyl}amino)(2-pyridyl)]phenyl}propyl)-1,2,4-triazolin-5-one |
| 87 | 1-{[4-(tert-Butyl)phenyl]methyl}-4-ethyl-3-{3-[4-(5-methoxy-6-{[benzylsulfonyl]amino}(2-pyridyl))phenyl]propyl}-1,2,4-triazolin-5-one |
| 88 | 1-{[4-(tert-Butyl)phenyl]methyl}-4-ethyl-3-(3-{4-[5-methoxy-6-({[4-(trifluoromethyl)phenyl]sulfonyl}amino)(2-pyridyl)]phenyl}propyl)-1,2,4-triazolin-5-one |
| 89 | 5-(4-(3-(1-(4-(tert-Butyl)benzyl)-4-ethyl-5-oxo-4,5-dihydro-1H-1,2,4-triazol-3-yl)propyl)phenyl)benzofuran-3-carboxylic acid |
| 90 | 1-{[4-(tert-Butyl)phenyl]methyl}-3-{3-[4-(5-{[(4-chlorophenyl)sulfonyl]amino}(2-pyridyl))phenyl]propyl}-4-ethyl-1,2,4-triazolin-5-one |
| 91 | 1-{[4-(tert-Butyl)phenyl]methyl}-4-ethyl-3-{3-[4-(5-{[(4-methoxyphenyl)sulfonyl]amino}(2-pyridyl))phenyl]propyl}-1,2,4-triazolin-5-one |
| 92 | 1-{[4-(tert-Butyl)phenyl]methyl}-3-{3-[4-(6-{[(4-chlorophenyl)sulfonyl]amino}-5-methoxy(2-pyridyl))phenyl]propyl}-4-ethyl-1,2,4-triazolin-5-one |
| 93 | 1-{[4-(tert-Butyl)phenyl]methyl}-4-ethyl-3-{3-[4-(5-methoxy-6-{[(4-methoxyphenyl)sulfonyl] amino}(2-pyridyl))phenyl]propyl}-1,2,4-triazolin-5-one |
| 94 | 2-(4'-(3-(1-(4-(tert-Butyl)benzyl)-4-ethyl-5-oxo-4,5-dihydro-1H-1,2,4-triazol-3-yl)propyl)-4-propoxy-[1,1'-biphenyl]-3-yl)acetic acid |
| 95 | 2-(4'-(3-(1-(4-(tert-Butyl)benzyl)-4-methyl-5-oxo-4,5-dihydro-1H-1,2,4-triazol-3-yl)propyl)-4-ethoxy-[1,1'-biphenyl]-3-yl)acetic acid |
| 96 | (rac)-5-(4-(3-(1-(4-(tert-Butyl)benzyl)-4-ethyl-5-oxo-4,5-dihydro-1H-1,2,4-triazol-3-yl)propyl)phenyl)-2,3-dihydrobenzofuran-3-carboxylic acid |
| 97 | N-(6-{4-[3-(1-{[4-(tert-Butyl)phenyl]methyl}-4-ethyl-5-oxo(1,2,4-triazolin-3-yl))propyl]phenyl}(2-pyridyl))benzamide |
| 98 | 1-{[4-(tert-Butyl)phenyl]methyl}-4-ethyl-3-[3-(4-{6-methoxy-5-[(phenylsulfonyl)amino](2-pyridyl)}phenyl)propyl]-1,2,4-triazolin-5-one |
| 99 | N-benzyl-4'-(3-(1-(4-(tert-butyl)benzyl)-4-ethyl-5-oxo-4,5-dihydro-1H-1,2,4-triazol-3-yl)propyl)-[1,1'-biphenyl]-4-sulfonamide |
| 100 | N-(6-{4-[3-(1-{[4-(tert-Butyl)phenyl]methyl}-4-ethyl-5-oxo-1,2,4-triazolin-3-yl)propyl]phenyl}-2-pyridyl)butanamide |
| 101 | N-(6-{4-[3-(1-{[4-(tert-Butyl)phenyl]methyl}-4-ethyl-5-oxo(1,2,4-triazolin-3-yl))propyl]phenyl}(2-pyridyl))-2-phenylacetamide |
| 102 | N-(6-{4-[3-(1-{[4-(tert-Butyl)phenyl]methyl}-4-ethyl-5-oxo(1,2,4-triazolin-3-yl))propyl]phenyl}(2-pyridyl))cyclopropylcarboxamide |
| 103 | N-((4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)sulfonyl)propionamide |
| 104 | N-Benzyl-1-(4'-(3-(1-(4-(tert-butyl)benzyl)-4-ethyl-5-oxo-4,5-dihydro-1H-1,2,4-triazol-3-yl)propyl)-[1,1'-biphenyl]-4-yl)methanesulfonamide |
| 105 | N-Benzyl-1-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)methanesulfonamide |

| Example no. | Compound name |
|---|---|
| 106 | 2-(4'-(3-(1-(4-(tert-Butyl)benzyl)-4-methyl-5-oxo-4,5-dihydro-1H-1,2,4-triazol-3-yl)propyl)-4-methoxy-[1,1'-biphenyl]-3-yl)acetic acid |
| 107 | 3-{3-[4-(3-{[(Dimethylamino)sulfonyl]amino}phenyl)phenyl]propyl}-1-{[4-(tert-butyl)phenyl]methyl}-4-ethyl-1,2,4-triazolin-5-one |
| 108 | N-(2-(4-(3-(1-(4-(tert-Butyl)benzyl)-4-ethyl-5-oxo-4,5-dihydro-1H-1,2,4-triazol-3-yl)propyl)phenyl)pyrimidin-5-yl)benzenesulfonamide |
| 109 | 3-(3-(4-(5-Aminopyridin-3-yl)phenyl)propyl)-1-(4-(tert-butyl)benzyl)-4-ethyl-1H-1,2,4-triazol-5(4H)-one |
| 110 | 1-{[4-(tert-Butyl)phenyl]methyl}-4-ethyl-3-[3-(4-{5-methoxy-6-[N-methyl(phenylsulfonyl)amino](2-pyridyl)}phenyl)propyl]-1,2,4-triazolin-5-one |
| 111 | 3-{3-[4-(5-Amino-4-methoxy(2-pyridyl))phenyl]propyl}-1-{[4-(tert-butyl)phenyl]methyl}-4-ethyl-1,2,4-triazolin-5-one |
| 112 | 1-{[4-(tert-Butyl)phenyl]methyl}-4-ethyl-3-[3-(4-{4-methoxy-5-[(phenylsulfonyl)amino](2-pyridyl)}phenyl)propyl]-1,2,4-triazolin-5-one |
| 113 | 1-{[4-(tert-Butyl)phenyl]methyl}-3-{3-[4-(6-{[(6-chloro(3-pyridyl))sulfonyl]amino}-5-methoxy(2-pyridyl))phenyl]propyl}-4-ethyl-1,2,4-triazolin-5-one |
| 114 | 1-{[4-(tert-Butyl)phenyl]methyl}-4-ethyl-3-{3-[4-(5-methoxy-6-{[(6-methoxy(3-pyridyl))sulfonyl]amino}(2-pyridyl))phenyl]propyl}-1,2,4-triazolin-5-one |
| 115 | 2-(4'-(3-(1-(3-Methyl-4-(tert-butyl)benzyl)-4-ethyl-5-oxo-4,5-dihydro-1H-1,2,4-triazol-3-yl)propyl)-[1,1'-biphenyl]-3-yl)acetic acid |
| 116 | N-(((4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)methyl)sulfonyl)propionamide |
| 117 | N-(5-(4-(3-(1-(4-(tert-Butyl)benzyl)-4-ethyl-5-oxo-4,5-dihydro-1H-1,2,4-triazol-3-yl)propyl)phenyl)pyridin-3-yl)benzenesulfonamide |
| 118 | N-(5-(4-(3-(1-(4-(tert-Butyl)benzyl)-4-ethyl-5-oxo-4,5-dihydro-1H-1,2,4-triazol-3-yl)propyl)phenyl)pyrazin-2-yl)benzenesulfonamide |
| 119 | N-(5-(4-(3-(1-(4-(tert-Butyl)benzyl)-4-ethyl-5-oxo-4,5-dihydro-1H-1,2,4-triazol-3-yl)propyl)phenyl)pyrazin-2-yl)-1-phenylmethanesulfonamide |
| 120 | 1-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)cyclopropanecarbonitrile |
| 121 | 4'-(3-(1-(4-(tert-Butyl)benzyl)-4-ethyl-5-oxo-4,5-dihydro-1H-1,2,4-triazol-3-yl)propyl)-4-(difluoromethoxy)-[1,1'-biphenyl]-3-carboxylic acid |
| 122 | 1-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)cyclopropanecarboxylic acid |
| 123 | 4'-(3-(1-(4-(tert-Butyl)benzyl)-4-ethyl-5-oxo-4,5-dihydro-1H-1,2,4-triazol-3-yl)propyl)-4-methoxy-N-(pyridin-2-yl)-[1,1'-biphenyl]-3-sulfonamide |
| 124 | 1-{[4-(tert-Butyl)phenyl]methyl}-4-ethyl-3-[3-(4-{6-methyl-5-[(phenylsulfonyl)amino](2-pyridyl)}phenyl)propyl]-1,2,4-triazolin-5-one |
| 125 | 1-{[4-(tert-Butyl)phenyl]methyl}-4-ethyl-3-{3-[4-(6-methyl-5-{[benzylsulfonyl]amino}(2-pyridyl))phenyl]propyl}-1,2,4-triazolin-5-one |
| 126 | 1-{[4-(tert-Butyl)phenyl]methyl}-4-ethyl-3-[3-(4-{4-methyl-5-[(phenylsulfonyl)amino](2-pyridyl)}phenyl)propyl]-1,2,4-triazolin-5-one |
| 127 | 1-{[4-(tert-Butyl)phenyl]methyl}-4-ethyl-3-{3-[4-(4-methyl-5-{[benzylsulfonyl]amino}(2-pyridyl))phenyl]propyl}-1,2,4-triazolin-5-one |
| 128 | 1-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)cyclopropanecarboxylic acid |
| 129 | N-(6-(4-(3-(1-(4-(tert-Butyl)benzyl)-4-ethyl-5-oxo-4,5-dihydro-1H-1,2,4-triazol-3-yl)propyl)phenyl)pyrazin-2-yl)benzenesulfonamide |
| 130 | 2-(4'-(3-(1-(4-(tert-Butyl)benzyl)-4-ethyl-5-oxo-4,5-dihydro-1H-1,2,4-triazol-3-yl)propyl)-4-(trifluoromethoxy)-[1,1'-biphenyl]-3-yl)acetic acid |
| 131 | 4'-(3-(1-(4-(tert-Butyl)benzyl)-4-ethyl-5-oxo-4,5-dihydro-1H-1,2,4-triazol-3-yl)propyl)-4-(trifluoromethoxy)-[1,1'-biphenyl]-3-carboxylic acid |
| 132 | 4'-(3-(1-(4-(tert-Butyl)benzyl)-4-ethyl-5-oxo-4,5-dihydro-1H-1,2,4-triazol-3-yl)propyl)-4-methyl-[1,1'-biphenyl]-3-carboxylic acid |
| 133 | 1-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)cyclobutanecarboxylic acid |
| 134 | 4'-(3-(1-(4-(tert-Butyl)benzyl)-4-ethyl-5-oxo-4,5-dihydro-1H-1,2,4-triazol-3-yl)propyl)-4-(trifluoromethyl)-[1,1'-biphenyl]-3-carboxylic acid |
| 135 | 2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)-N-(methylsulfonyl)acetamide |
| 136 | 2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)-N-(phenylsulfonyl)acetamide |
| 137 | 1-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)cyclopropanecarboxylic acid |
| 138 | N-(4-(4-(3-(1-(4-(tert-Butyl)benzyl)-4-ethyl-5-oxo-4,5-dihydro-1H-1,2,4-triazol-3-yl)propyl)phenyl)pyrimidin-2-yl)benzenesulfonamide |
| 139 | 6-(4-(3-(1-(4-(tert-Butyl)benzyl)-4-ethyl-5-oxo-4,5-dihydro-1H-1,2,4-triazol-3-yl)propyl)phenyl)-3-methoxypicolinic acid |
| 140 | 2-(4-(3-(1-(4-(tert-Butyl)benzyl)-4-ethyl-5-oxo-4,5-dihydro-1H-1,2,4-triazol-3-yl)propyl)phenyl)-5-methoxyisonicotinic acid |
| 141 | (R)-2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)propanoic acid |
| 142 | (S)-2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)propanoic acid |
| 143 | 1-(4-(tert-Butyl)benzyl)-4-ethyl-3-(3-(4'-(3-fluorooxetan-3-yl)-[1,1'-biphenyl]-4-yl)propyl)-1H-1,2,4-triazol-5(4H)-one |

-continued

| Example no. | Compound name |
|---|---|
| 144 | 2-(6-(4-(3-(1-(4-(tert-Butyl)benzyl)-4-ethyl-5-oxo-4,5-dihydro-1H-1,2,4-triazol-3-yl)propyl)phenyl)-3-methoxypyridin-2-yl)acetic acid |
| 145 | 2-(4'-(3-(1-(4-(tert-Butyl)benzyl)-4-ethyl-5-oxo-4,5-dihydro-1H-1,2,4-triazol-3-yl)propyl)-2'-hydroxy-4-methoxy-[1,1'-biphenyl]-3-yl)acetic acid |
| 146 | 2-(4'-(3-(1-(4-(tert-Butyl)benzyl)-4-ethyl-5-oxo-4,5-dihydro-1H-1,2,4-triazol-3-yl)propyl)-3'-hydroxy-4-methoxy-[1,1'-biphenyl]-3-yl)acetic acid |
| 147 | 3-(3-(3'-Amino-4'-methoxy-[1,1'-biphenyl]-4-yl)propyl)-1-(4-(tert-butyl)benzyl)-4-ethyl-1H-1,2,4-triazol-5(4H)-one |
| 148 | 3-(3-(3'-Amino-4'-(trifluoromethyl)-[1,1'-biphenyl]-4-yl)propyl)-1-(4-(tert-butyl)benzyl)-4-ethyl-1H-1,2,4-triazol-5(4H)-one |
| 149 | 3-(3-(3'-Amino-4'-methyl-[1,1'-biphenyl]-4-yl)propyl)-1-(4-(tert-butyl)benzyl)-4-ethyl-1H-1,2,4-triazol-5(4H)-one |
| 150 | 2-(4'-(3-(1-(4-(tert-Butyl)benzyl)-4-ethyl-5-oxo-4,5-dihydro-1H-1,2,4-triazol-3-yl)propyl)-4-methoxy-2'-(trifluoromethyl)-[1,1'-biphenyl]-3-yl)acetic acid |
| 151 | 1-{[4-(tert-Butyl)phenyl]methyl}-4-ethyl-3-[3-(4-{4-methoxy-3-[(phenylsulfonyl)amino]phenyl}phenyl)propyl]-1,2,4-triazolin-5-one |
| 152 | 1-{[4-(tert-Butyl)phenyl]methyl}-4-ethyl-3-[3-(4-{4-methyl-3-[(phenylsulfonyl)amino]phenyl}phenyl)propyl]-1,2,4-triazolin-5-one |
| 153 | 1-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)-3-phenylurea |
| 154 | N-((6-(4-(3-(1-(4-(tert-Butyl)benzyl)-4-ethyl-5-oxo-4,5-dihydro-1H-1,2,4-triazol-3-yl)propyl)phenyl)pyridin-2-yl)carbamoyl)benzenesulfonamide |
| 155 | 1-Benzyl-3-(6-(4-(3-(1-(4-(tert-butyl)benzyl)-4-ethyl-5-oxo-4,5-dihydro-1H-1,2,4-triazol-3-yl)propyl)phenyl)pyridin-2yl)urea |
| 156 | 3-(3-{4-[5-Amino-3-(trifluoromethyl)(2-pyridyl)]phenyl}propyl)-1-{[4-(tert-butyl)phenyl]methyl}-4-ethyl-1,2,4-triazolin-5-one |
| 157 | 2-(4'-(3-(1-(4-(tert-Butyl)benzyl)-4-ethyl-5-oxo-4,5-dihydro-1H-1,2,4-triazol-3-yl)propyl)-4-methoxy-2'-methyl-[1,1'-biphenyl]-3-yl)acetic acid |
| 158 | 2-(4'-(3-(1-(4-(tert-Butyl)benzyl)-4-ethyl-5-oxo-4,5-dihydro-1H-1,2,4-triazol-3-yl)propyl)-3',4-dimethoxy-[1,1'-biphenyl]-3-yl)acetic acid |
| 159 | 2-(4'-(3-(1-(4-(tert-Butyl)benzyl)-4-ethyl-5-oxo-4,5-dihydro-1H-1,2,4-triazol-3-yl)propyl)-2',4-dimethoxy-[1,1'-biphenyl]-3-yl)acetic acid |
| 160 | N-((6-(4-(3-(1-(4-(tert-Butyl)benzyl)-4-ethyl-5-oxo-4,5-dihydro-1H-1,2,4-triazol-3-yl)propyl)phenyl)pyridin-3-yl)carbamoyl)benzenesulfonamide |
| 161 | 3-(3-{4-[6-Amino-5-(trifluoromethyl)(2-pyridyl)]phenyl}propyl)-1-{[4-(tert-butyl)phenyl]methyl}-4-ethyl-1,2,4-triazolin-5-one |
| 162 | 6-(4-(3-(1-(4-(tert-Butyl)benzyl)-4-ethyl-5-oxo-4,5-dihydro-1H-1,2,4-triazol-3-yl)propyl)phenyl)-3-methoxypyrazine-2-carboxylic acid |
| 163 | 2-(4'-(3-(1-(4-(tert-Butyl)benzyl)-4-ethyl-5-oxo-4,5-dihydro-1H-1,2,4-triazol-3-yl)-1,1-difluoropropyl)-4-methoxy-[1,1'-biphenyl]-3-yl)acetic acid |
| 164 | 1-{[4-(tert-Butyl)phenyl]methyl}-4-ethyl-3-[3-(4-{6-[(phenylsulfonyl)amino]-5-(trifluoromethyl)(2-pyridyl)}phenyl)propyl]-1,2,4-triazolin-5-one |
| 165 | 6-(4-(3-(1-(4-(tert-Butyl)benzyl)-4-ethyl-5-oxo-4,5-dihydro-1H-1,2,4-triazol-3-yl)propyl)phenyl)-3-methylpicolinic acid |
| 166 | 1-(4-(tert-Butyl)benzyl)-4-ethyl-3-(3-(4-(6-(3-fluorooxetan-3-yl)pyridine-3-yl)phenyl)propyl)-1H-1,2,4-triazol-5(4H)-one |
| 167 | 1-(4-(tert-Butyl)benzyl)--3-(3-(4'-(3-hydroxyoxetan-3-yl)-[1,1'-biphenyl]-4-yl)propyl)-1H-1,2,4-triazol-5(4H)-one |
| 168 | 4'-(3-(1-(4-(tert-Butyl)benzyl)-4-ethyl-5-oxo-4,5-dihydro-1H-1,2,4-triazol-3-yl)propyl)-4-propoxy-[1,1'-biphenyl]-3-carboxylic acid |
| 169 | 1-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)-3-ethylurea |
| 170 | 1-(4-(tert-Butyl)benzyl)-4-ethyl-3-(3-(4-(2-(3-fluorooxetan-3-yl)pyrimidin-5-yl)phenyl)propyl)-1H-1,2,4-triazol-5(4H)-one |
| 171 | 1-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)-3-ethylurea |
| 172 | 3-(3-{4-[3-(Aminomethyl)phenyl]phenyl}propyl)-1-{[4-(tert-butyl)phenyl]methyl}-4-ethyl-1,2,4-triazolin-5-one |
| 173 | 1-(4-(tert-Butyl)benzyl)-4-ethyl-3-(3-(4-(2-(3-hydroxyoxetan-3-yl)pyrimidin-5-yl)phenyl)propyl)-1H-1,2,4-triazol-5(4H)-one |
| 174 | 1-(4-(tert-Butyl)benzyl)-4-ethyl-3-(3-(4'-(3-hydroxyoxetan-3-yl)-[1,1'-biphenyl]-4-yl)propyl)-1H-1,2,4-triazol-5(4H)-one |
| 176 | 1-(4-(tert-Butyl)benzyl)-4-ethyl-3-(3-(4'-(1-hydroxycyclobutyl)-[1,1'-biphenyl]-4-yl)propyl)-1H-1,2,4-triazol-5(4H)-one |
| 177 | 1-{[4-(tert-Butyl)phenyl]methyl}-4-ethyl-3-{3-[4-(3-{[(phenylsulfonyl)amino]methyl}phenyl)phenyl]propyl}-1,2,4-triazolin-5-one |
| 178 | 1-{[4-(tert-Butyl)phenyl]methyl}-4-ethyl-3-{3-[4-(3-{[(methylsulfonyl)amino]methyl}phenyl)phenyl]propyl}-1,2,4-triazolin-5-one |
| 179 | 3-(5-{4-[3-(1-{[4-(tert-Butyl)phenyl]methyl}-4-ethyl-5-oxo(1,2,4-triazolin-3-yl))propyl]phenyl}-2-methoxyphenyl)propanoic acid |
| 180 | 1-{[4-(tert-Butyl)phenyl]methyl}-4-ethyl-3-[3-(4-{methoxy-3-[(methylamino)methyl]phenyl} phenyl)propyl]-1,2,4-triazolin-5-one |
| 181 | 2-(4-(3-(1-(4-(tert-Butyl)benzyl)-4-ethyl-5-oxo-4,5-dihydro-1H-1,2,4-triazol-3-yl)propyl)phenyl)-5-methoxypyrimidine-4-carboxylic acid |
| 182 | 1-{[4-(tert-Butyl)phenyl]methyl}-4-ethyl-3-{3-[4-(4-methoxy-3-{2-[(phenylsulfonyl)amino]ethyl}phenyl)phenyl]propyl}-1,2,4-triazolin-5-one |

-continued

| Example no. | Compound name |
|---|---|
| 183 | 1-{[4-(tert-Butyl)phenyl]methyl}-4-ethyl-3-{3-[4-(4-methoxy-3-{2-[(methylsulfonyl)amino]ethyl}phenyl)phenyl]propyl}-1,2,4-triazolin-5-one |
| 184 | 3-(3-{4-[3-(Aminomethyl)-4-methoxyphenyl]phenyl}propyl)-1-{[4-(tert-butyl)phenyl]methyl}-4-ethyl-1,2,4-triazolin-5-one |
| 185 | 1-{[4-(tert-Butyl)phenyl]methyl}-4-ethyl-3-{3-[4-(4-methoxy-3-{[(phenylsulfonyl)amino]methyl}phenyl)phenyl]propyl}-1,2,4-triazolin-5-one |
| 186 | 1-{[4-(tert-Butyl)phenyl]methyl}-4-ethyl-3-{3-[4-(4-methoxy-3-{[(methylsulfonyl)amino]methyl}phenyl)phenyl]propyl}-1,2,4-triazolin-5-one |
| 187 | 1-(4-(tert-Butyl)benzyl)-4-ethyl-3-(3-(4'-(4-hydroxytetrahydro-2H-pyran-4-yl)-[1,1'-biphenyl]-4-yl)propyl)-1H-1,2,4-triazol-5(4H)-one |
| 188 | 1-{[4-(tert-Butyl)phenyl]methyl}-4-ethyl-3-(3-{4-[4-methoxy-3-({[benzylsulfonyl]amino}methyl)phenyl]phenyl}propyl)-1,2,4-triazolin-5-one |
| 189 | 1-{[4-(tert-Butyl)phenyl]methyl}-4-ethyl-3-[3-(4-{6-[(ethylsulfonyl)amino]-5-methoxy(2-pyridyl)}phenyl)propyl]-1,2,4-triazolin-5-one |
| 190 | 1-{[4-(tert-Butyl)phenyl]methyl}-4-ethyl-3-[3-(4-{6-[(cyclopropylsulfonyl)amino]-5-methoxy(2-pyridyl)}phenyl)propyl]-1,2,4-triazolin-5-one |
| 191 | 1-(4-(tert-Butyl)benzyl)-4-ethyl-3-(3-(4-(5-(3-fluorooxetan-3-yl)pyridine-2-yl)phenyl)propyl)-1H-1,2,4-triazol-5(4H)-one |
| 192 | 1-{[4-(tert-Butyl)phenyl]methyl}-4-ethyl-3-[3-(4-{6-[(cyclohexylsulfonyl)amino]-5-methoxy(2-pyridyl)}phenyl)propyl]-1,2,4-triazolin-5-one |
| 193 | 3-{4-[3-(1-{[4-(tert-Butyl)phenyl]methyl}-4-ethyl-5-oxo(1,2,4-triazolin-3-yl))propyl]phenyl}-5-methoxybenzoic acid |
| 194 | 2-(3-{4-[3-(1-{[4-(tert-Butyl)phenyl]methyl}-4-ethyl-5-oxo(1,2,4-triazolin-3-yl))propyl]phenyl}-5-methoxyphenyl)acetic acid |
| 195 | 1-(4-(tert-Butyl)benzyl)-3-(3,3-difluoro-3-(4-(5-(3-fluorooxetan-3-yl)pyridine-2-yl)phenyl)propyl)-4-ethyl-1H-1,2,4-triazol-5(4H)-one |
| 196 | 1-(4-(tert-Butyl)benzyl)-3-(3,3-difluoro-3-(4'-(3-hydroxyoxetan-3-yl)-[1,1'-biphenyl]-4-yl)propyl)-4-ethyl-1H-1,2,4-triazol-5(4H)-one |
| 197 | 1-(4-(tert-Butyl)benzyl)-4-ethyl-3-(3-(4-(5-(3-hydroxyoxetan-3-yl)pyridine-2-yl)phenyl)propyl)-1H-1,2,4-triazol-5(4H)-one |
| 198 | 2-(5-(6-(3-(1-(4-(tert-Butyl)benzyl)-4-ethyl-5-oxo-4,5-dihydro-1H-1,2,4-triazol-3-yl)propyl)pyridin-3-yl)-2-methoxyphenyl)acetic acid |
| 199 | 2-(4'-(3-(1-(4-(tert-Butyl)benzyl)-4-ethyl-5-oxo-4,5-dihydro-1H-1,2,4-triazol-3-yl)propyl)-3-methoxy-[1,1'-biphenyl]-4-yl)acetic acid |
| 200 | 2-(4'-(3-(1-(4-(tert-Butyl)benzyl)-4-ethyl-5-oxo-4,5-dihydro-1H-1,2,4-triazol-3-yl)propyl)-4-isopropoxy-[1,1'-biphenyl]-3-yl)acetic acid |
| 201 | 1-(4-(tert-Butyl)benzyl)-4-ethyl-3-(3-(4-(2-(3-fluorooxetan-3-yl)thiazol-4-yl)phenyl)propyl)-1H-1,2,4-triazol-5(4H)-one |
| 202 | 1-(4-(tert-Butyl)benzyl)-4-ethyl-3-(3-(4-(2-(3-fluorooxetan-3-yl)thiazol-5-yl)phenyl)propyl)-1H-1,2,4-triazol-5(4H)-one |
| 203 | 1-(4-(tert-Butyl)benzyl)-4-ethyl-3-(3-(4-(2-(3-hydroxyoxetan-3-yl)thiazol-4-yl)phenyl)propyl)-1H-1,2,4-triazol-5(4H)-one |
| 204 | 1-(4-(tert-Butyl)benzyl)-4-ethyl-3-(3-(4-(2-(3-hydroxyoxetan-3-yl)thiazol-5-yl)phenyl)propyl)-1H-1,2,4-triazol-5(4H)-one | or a pharmaceutically acceptable salt thereof.

In another aspect the invention is directed to a pharmaceutical composition comprising a compound of Formula I, or a pharmaceutically acceptable salt thereof, and a pharmaceutically acceptable carrier.

In another aspect the invention is directed to a method of treating a cancer which is negatively impacted by diminution in its metabolism of fatty acid oxidation via the administration of a therapeutically effective amount of a compound of Formula I, or a pharmaceutically acceptable salt thereof.

Within this aspect there is a genus wherein the cancer is selected from prostate, breast, ovarian, liver, kidney, colon, pancreatic, human chronic lymphocytic leukemia, and melanoma.

In another aspect the invention is directed to a method of treating cancer comprising the administration of a therapeutically effective amount of a compound of Formula I, or a pharmaceutically acceptable salt thereof.

In another aspect the invention is directed to a method of preventing the onset of and/or recurrence of acute and chronic myeloid leukemia, as well as other cancers, through the administration of a therapeutically effective amount of a compound of Formula I, or a pharmaceutically acceptable salt thereof.

DEFINITIONS

The term "patient" includes mammals such as mice, rats, cows, sheep, pigs, rabbits, goats, horses, monkeys, dogs, cats, and humans.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, $C_{1-6}$alkyl indicates that the group may have from 1 to 6 (inclusive) carbon atoms in it. Any atom can be optionally substituted, e.g., by one or more substitutents. Examples of alkyl groups include without limitation methyl, ethyl, n-propyl, isopropyl, n-butyl, sec-butyl and tert-butyl.

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O-(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S-(alkyl). The terms "haloalkoxy" and "thioalkoxy" refer to —O-(haloalkyl) and —S-(haloalkyl), respectively. The term "sulfhydryl" refers to —SH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl.

The term "heterocycle" or "heterocyclic", as used herein except where noted, represents a stable 4-, 5-, 6- or 7-membered monocyclic- or stable 6-, 7-, 8-, 9-, 10-, 11-, or 12-membered fused bicyclic heterocyclic ring system which comprises at least one non-aromatic (i.e. saturated or partially unsaturated) ring which consists of carbon atoms and from one to four heteroatoms selected from the group consisting of N, O and S, wherein the nitrogen and sulfur heteroatoms may optionally be oxidized, and wherein the nitrogen heteroatom may optionally be quaternized. In the case of a "heterocycle" which is a bicyclic group, the second ring may also be a non-aromatic ring which consists of carbon atoms and from one to four heteroatoms selected from the group consisting of N, O and S, as defined above, or the second ring may be a benzene ring, or a "cycloalkyl", or a "cycloalkenyl", as defined immediately below. Examples of such heterocyclic groups include, but are not limited to, azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, pyran, pyrazolidine, pyrazoline, pyrrolidine, pyrroline, tetrahydrofuran, tetrahydropyran, thiamorpholine, thiazoline, thiazolidine, thiomorpholine, and N-oxides thereof.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclopentenyl, cyclohexenyl, cyclohexadienyl, or norbornenyl.

The term "cycloalkylene", as used herein, refers to a divalent monocyclic cycloalkyl group having the indicated number of ring atoms.

The term "heterocycloalkylene", as used herein, refers to a divalent monocyclic heterocyclyl group having the indicated number of ring atoms.

The term "aryl" as used herein, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, or biphenyl.

The term "heteroaryl", as used herein except where noted, represents a stable 5-, 6- or 7-membered monocyclic- or stable 9 or 10-membered fused bicyclic ring system which comprises at least one aromatic ring, —which consists of carbon atoms and from one to three heteroatoms selected from the group consisting of N, O and S wherein the nitrogen and sulfur heteroatoms may optionally be oxidized, and the nitrogen heteroatom may optionally be quaternized. In the instance where nitrogen is the only heteroatom, there may be four nitrogens. In the case of a "heteroaryl" which is a bicyclic group, the second ring need not be aromatic and need not comprise a heteroatom. Accordingly, "heteroaryl" includes, for example, a stable 5-, 6- or 7-membered monocyclic aromatic ring consisting of carbon atoms and from one to four heteroatoms, as defined immediately above, fused to a benzene ring, or fused to a "heterocycle", a "cycloalkyl", or a "cycloalkenyl", as defined above. Examples of such heteroaryl groups include, but are not limited to, benzimidazole, benzisothiazole, benzisoxazole, benzofuran, isobenzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "acyl", as used herein, refers to those groups derived from an organic acid by removal of the hydroxy portion of the acid. Accordingly, acyl is meant to include, for example, acetyl, propionyl, butyryl, decanoyl, pivaloyl, benzoyl and the like.

Compound Forms and Salts

The compounds of this invention may contain one or more asymmetric centers and thus occur as racemates and racemic mixtures, enantiomerically enriched mixtures, single enantiomers, individual diastereomers and diastereomeric mixtures. The compounds of this invention may also be represented in multiple tautomeric forms, in such instances, the invention expressly includes all tautomeric forms of the compounds described herein, even though only a single tautomeric form may be represented. All such isomeric forms of such compounds are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids.

When the compound of the present invention is acidic, salts may be prepared from pharmaceutically acceptable non-toxic bases, including inorganic and organic acids. Such salts that may be prepared include lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use. A Handbook"; Wermuth, C. G. and Stahl, P. H. (eds.) Verlag Helvetica Chimica Acta, Zurich, 2002 [ISBN 3-906390-26-8] each of which is incorporated herein by reference in their entireties.

The compounds may be radiolabeled with radioactive isotopes, such as for example tritium, iodine-125 or carbon-14. All isotopic variations of the compounds of the invention, whether radioactive or not, are intended to be encompassed within the scope of the invention.

In some embodiments, hydrogen atoms of the compounds described herein may be replaced with deuterium atoms.

In some embodiments, compounds of Formula I are prepared as prodrugs. Prodrugs are generally drug precursors that, following administration to a subject and subsequent absorption, are converted to an active, or a more active species via some process, such as conversion by a metabolic pathway. Examples of prodrugs include $C_{1-6}$ alkyl esters of carboxylic acid groups, which, upon administration to a subject, are capable of providing active compounds.

Pharmaceutical Compositions

The term "pharmaceutically acceptable carrier" refers to a carrier or an adjuvant that may be administered to a patient, together with a compound of this invention, or a pharmaceutically acceptable salt thereof, and which does not destroy the pharmacological activity thereof and is nontoxic when administered in doses sufficient to deliver a therapeutic amount of the compound.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. For convenience, the total daily dosage may be divided and administered in portions during the day if desired.

Uses

In one aspect the invention disclosed herein is directed to compounds of Formula I and pharmaceutically acceptable salts thereof, which are useful in the treatment of prostate, breast, ovarian, liver, kidney, colon, pancreatic, human chronic lymphocytic leukemia, melanoma and other cancers. In another aspect, the invention is directed to a method of preventing the onset of and/or recurrence of acute and chronic myeloid leukemia, as well as other cancers. The invention also includes pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, melanoma and other cancers. The invention disclosed herein is further directed to methods of treating prostate, breast, colon, pancreatic, human chronic lymphocytic leukemia, melanoma and other cancers comprising administration of a therapeutically effective amount of a selective PPARα antagonist. The methods include administering to the subject an effective amount of a compound of Formula (I) (and/or a compound of any of the other formulae described herein) or a salt (e.g., a pharmaceutically acceptable salt) thereof as defined anywhere herein to the patient. In another aspect, the use of a compound of Formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, alleviating, or slowing the progression of) or prevention (e.g., delaying the onset of or reducing the risk of developing) of one or more diseases, disorders, or conditions caused by, or associated with, prostate, breast, ovarian, liver, kidney, colon, pancreatic, human chronic lymphocytic leukemia, melanoma and other cancers.

In one aspect the invention is directed a method of treating a cancer which is negatively impacted by diminution in its metabolism via fatty acid oxidation, comprising administration of a therapeutically effective amount of a compound of Formula I (and/or a compound of any of the other formulae described herein) or a salt (e.g., a pharmaceutically acceptable salt) there of. In another aspect, the invention is directed to a method of treating a cancer having a metabolism that is reliant on fatty acid oxidation, comprising administration of a therapeutically effective amount of a compound of Formula I (and/or a compound of any of the other formulae described herein), or a pharmaceutically acceptable salt thereof.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

In one aspect the compounds of the invention may be co-administered with one or more additional anti-cancer agents. The additional anti-cancer agents include, but are not limited to alkylating agents such as cyclophosphamide, chlorambucil, mecloreethamine, ifosfamide, or melphalan; antimetabolites such as methotrexate, cytarabine, fludarabine, 6-mercaptopurine, azathioprene, pyrimidines, or 5-fluorouracil; antimitotic agents such as vincristine, paclitaxel, vinorelbine or docetaxaxel; a topoisomerase inhibitors such as doxorubicin or irinotecan; platinum derivatives such as cisplatin, carboplatin or oxaliplatin; hormone therapeutics such as tamoxifen; aromatase inhibitors such as bicalutamide, anastrozole, exemestane or letrozole; signaling inhibitors such as imatinib, gefitinib or erlotinib; monoclonal antibodies such as rituximab, trastuzumab, gemtuzumab or ozogamicin; differentiating agents such as tretinoin or arsenic trioxide; antiangiogenic agents such as bevacizumab, sorafinib or sunitinib; biologic response modifiers such as interferon-alpha; topoisomerase inhibitors such as camptothecins (including irinotecan and topotecan), amsacrine, etoposide, etoposide phosphate, or teniposide; cytotoxic antibiotics such as actinomycin, anthracyclines including doxorubicin, daunorubicin, valrubicin, idarubicin, epirubicin, bleomycin, plicamycin or mitomycin; vinca alkaloids such as vincristine, vinblastine, viorelbine or vindesine; podophyllotoxins such as etoposide and teniposide; or mTOR inhibitors such as rapamycin, temsirolimus and everolimus.

Other anti-cancer agents for use in combination with the compounds include one or more of the following: abiraterone; adriamycin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; everolimus; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rapamycin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; temsirolimus; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In certain embodiments, the additional agents may be administered separately (e.g., sequentially; on different overlapping schedules), as part of a multiple dose regimen, from the compounds of this invention (e.g., one or more compounds of Formula (I) and/or a compound of any of the other formulae, including any subgenera or specific compounds thereof). In other embodiments, these agents may be part of a single dosage form, mixed together with the compounds of this invention in a single composition. In still another embodiment, these agents can be given as a separate dose that is administered at about the same time as that of one or more compounds of Formula (I) (and/or a compound of any of the other formulae, including any subgenera or specific compounds thereof) are administered (e.g., simultaneously with the administration of one or more compounds of Formula (I) (and/or a compound of any of the other formulae, including any subgenera or specific compounds thereof)). When the compositions of this invention include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase and then combined with emulsifying and/or suspending agents. If desired, certain sweetening and/or flavoring and/or coloring agents may be added.

Biological Function

The utility of the invention can be demonstrated by one or more of the following methods or other methods known in the art:

Human PPARα Reporter Assay

The screening of test compounds for agonist or antagonist activities against human PPARα receptors was performed using a commercial kit, Human PPARα Reporter Assay System (Indigo Biosciences, Cat. #IB00111).

This nuclear receptor assay system utilizes proprietary non-human mammalian cells engineered to provide constitutive, high-level expression of Human PPARα. Because these cells incorporate a PPARα-responsive luciferase reporter gene, quantifying expressed luciferase activity provides a sensitive surrogate measure of PPARα activity in the treated cells. The primary application of this reporter assay system is in the screening of test samples to quantify any functional activity, either agonist or antagonist, that they may exert against human PPARα.

While this assay may be used to measure agonism, each of the Examples, vide infra, exhibits antagonism rather than agonism. Briefly, reporter cells are dispensed into wells of the assay plate and then immediately dosed with test compounds. Following an overnight incubation, the treatment media is discarded and Luciferase Detection Reagent (LDR) is added. The intensity of light emission from the ensuing luciferase reaction provides a sensitive measure that is directly proportional to the relative level of PPARα activation in the reporter cells.

| Example | Luciferase IC$_{50}$ (nM) | MS* (ESI) |
| --- | --- | --- |
| 1 | 95 | 512 (+H) |
| 2 | 57 | 598 (+H) |
| 3 | 271 | 470 (+H) |
| 4 | 40 | 610 (+H) |
| 5 | 43 | 470 (+H) |
| 6 | 255 | 469 (+H) |
| 7 | 471 | 623 (+H) |
| 8 | 304 | 651 (+H) |
| 9 | 363 | 637 (+H) |
| 10 | 67 | 610 (+H) |
| 11 | 157 | 470 (+H) |
| 12 | 63 | 548 (+H) |
| 13 | 268 | 538 (+H) |
| 14 | 284 | 537 (+H) |

-continued

| Example | Luciferase IC$_{50}$ (nM) | MS* (ESI) |
|---|---|---|
| 15 | 519 | 539 (+H) |
| 16 | 90 | 610 (+H) |
| 17 | 407 | 548 (+H) |
| 18 | 1420 | 530 (+H) |
| 19 | 796 | 530 (+H) |
| 20 | 1832 | 542 (+H) |
| 21 | 25 | 542 (+H) |
| 22 | 612 | 496 (+H) |
| 23 | 7312 | 456 (+H) |
| 24 | 579 | 524 (+H) |
| 25 | 184 | 560 (+H) |
| 26 | 4112 | 538 (+H) |
| 27 | 2170 | 514 (+H) |
| 28 | 1983 | 546 (−H) |
| 29 | 1189 | 520 (−H) |
| 30 | 1280 | 524 (+H) |
| 31 | 1962 | 526 (+H) |
| 32 | 2986 | 560 (+H) |
| 33 | 427 | 530 (+H) |
| 34 | 1451 | 522 (−H) |
| 35 | 1117 | 536 (−H) |
| 36 | 2759 | 526 (+H) |
| 37 | 1958 | 535 (+H) |
| 38 | 10 | 556 (+H) |
| 39 | 707 | 518 (+H) |
| 40 | 408 | 548 (+H) |
| 41 | 510 | 566 (+H) |
| 42 | 488 | 574 (+H) |
| 43 | 898 | 513 (+H) |
| 44 | 652 | 526 (+H) |
| 45 | 306 | 513 (+H) |
| 46 | 699 | 540 (+H) |
| 47 | 685 | 602 (+H) |
| 48 | 426 | 581 (+H) |
| 49 | 69 | 582 (+H) |
| 50 | 568 | 513 (+H) |
| 51 | 292 | 567 (+H) |
| 52 | 440 | 565 (+H) |
| 53 | 363 | 538 (+H) |
| 54 | 499 | 518 (+H) |
| 55 | 250 | 596 (+H) |
| 56 | 330 | 567 (+H) |
| 57 | 175 | 565 (+H) |
| 58 | 71 | 500 (+H) |
| 59 | 3 | 640 (+H) |
| 60 | 63 | 514 (+H) |
| 61 | 20 | 572 (+H) |
| 62 | 5 | 654 (+H) |
| 63 | 562 | 560 (+H) |
| 64 | 38 | 559 (+H) |
| 65 | 6 | 528 (+H) |
| 66 | 3 | 542 (+H) |
| 67 | 88 | 591 (+H) |
| 68 | 32 | 570 (+H) |
| 69 | 24 | 584 (+H) |
| 70 | 270 | 537 (+H) |
| 71 | 865 | 652 (+H) |
| 72 | 208 | 652 (+H) |
| 73 | 62 | 700 (+H) |
| 74 | 945 | 716 (+H) |
| 75 | 207 | 693 (+H) |
| 76 | 261 | 554 (+H) |
| 77 | 703 | 771 (+H) |
| 78 | 37 | 624 (+H) |
| 79 | 263 | 624 (+H) |
| 80 | 22 | 556 (+H) |
| 81 | 127 | 611 (+H) |
| 82 | 181 | 678 (+H) |
| 83 | 60 | 645 (+H) |
| 84 | 208 | 640 (+H) |
| 85 | 662 | 552 (+H) |
| 86 | 971 | 678 (+H) |
| 87 | 10 | 654 (+H) |
| 88 | 24 | 708 (+H) |
| 89 | 251 | 538 (+H) |
| 90 | 487 | 645 (+H) |
| 91 | 136 | 640 (+H) |

-continued

| Example | Luciferase IC$_{50}$ (nM) | MS* (ESI) |
|---|---|---|
| 92 | 5 | 675 (+H) |
| 93 | 3 | 670 (+H) |
| 94 | 16 | 570 (+H) |
| 95 | 15 | 542 (+H) |
| 96 | 272 | 540 (+H) |
| 97 | 745 | 574 (+H) |
| 98 | 264 | 640 (+H) |
| 99 | 524 | 623 (+H) |
| 100 | 712 | 540 (+H) |
| 101 | 402 | 588 (+H) |
| 102 | 695 | 538 (+H) |
| 103 | 436 | 589 (+H) |
| 104 | 591 | 637 (+H) |
| 105 | 985 | 637 (+H) |
| 106 | 26 | 528 (+H) |
| 107 | 683 | 576 (+H) |
| 108 | 165 | 611 (+H) |
| 109 | 590 | 470 (+H) |
| 110 | 534 | 654 (+H) |
| 111 | 641 | 500 (+H) |
| 112 | 816 | 640 (+H) |
| 113 | 8 | 676 (+H) |
| 114 | 7 | 671 (+H) |
| 115 | 116 | 526 (+H) |
| 116 | 987 | 603 (+H) |
| 117 | 799 | 610 (+H) |
| 118 | 446 | 611 (+H) |
| 119 | 941 | 625 (+H) |
| 120 | 604 | 563 (+H) |
| 121 | 39 | 564 (+H) |
| 122 | 188 | 582 (+H) |
| 123 | 186 | 640 (+H) |
| 124 | 290 | 624 (+H) |
| 125 | 356 | 638 (+H) |
| 126 | 201 | 624 (+H) |
| 127 | 445 | 638 (+H) |
| 128 | 281 | 568 (+H) |
| 129 | 36 | 611 (+H) |
| 130 | 11 | 596 (+H) |
| 131 | 15 | 582 (+H) |
| 132 | 12 | 512 (+H) |
| 133 | 597 | 582 (+H) |
| 134 | 109 | 566 (+H) |
| 135 | 192 | 619 (+H) |
| 136 | 41 | 681 (+H) |
| 137 | 676 | 538 (+H) |
| 138 | 33 | 611 (+H) |
| 139 | 89 | 529 (+H) |
| 140 | 396 | 529 (+H) |
| 141 | 29 | 556 (+H) |
| 142 | 272 | 556 (+H) |
| 143 | 101 | 528 (+H) |
| 144 | 114 | 543 (+H) |
| 145 | 692 | 558 (+H) |
| 146 | 98 | 558 (+H) |
| 147 | 85 | 499 (+H) |
| 148 | 241 | 537 (+H) |
| 149 | 161 | 483 (+H) |
| 150 | 126 | 610 (+H) |
| 151 | 61 | 639 (+H) |
| 152 | 160 | 623 (+H) |
| 153 | 947 | 589 (+H) |
| 154 | 241 | 653 (+H) |
| 155 | 362 | 603 (+H) |
| 156 | 684 | 538 (+H) |
| 157 | 94 | 556 (+H) |
| 158 | 184 | 572 (+H) |
| 159 | 410 | 572 (+H) |
| 160 | 429 | 653 (+H) |
| 161 | 638 | 538 (+H) |
| 162 | 630 | 530 (+H) |
| 163 | 15 | 578 (+H) |
| 164 | 20 | 678 (+H) |
| 165 | 202 | 513 (+H) |
| 166 | 91 | 529 (+H) |
| 167 | 454 | 498 (+H) |
| 168 | 9 | 556 (+H) |

| Example | Luciferase IC$_{50}$ (nM) | MS* (ESI) |
|---|---|---|
| 169 | 535 | 541 (+H) |
| 170 | 41 | 530 (+H) |
| 171 | 816 | 541 (+H) |
| 172 | 647 | 484 (+H) |
| 173 | 126 | 528 (+H) |
| 174 | 144 | 526 (+H) |
| 176 | 78 | 524 (+H) |
| 177 | 419 | 624 (+H) |
| 178 | 417 | 562 (+H) |
| 179 | 121 | 556 (+H) |
| 180 | 640 | 527 (+H) |
| 181 | 846 | 530 (+H) |
| 182 | 414 | 667 (+H) |
| 183 | 440 | 605 (+H) |
| 184 | 534 | 513 (+H) |
| 185 | 423 | 653 (+H) |
| 186 | 587 | 591 (+H) |
| 187 | 607 | 554 (+H) |
| 188 | 430 | 667 (+H) |
| 189 | 36 | 592 (+H) |
| 190 | 12 | 604 (+H) |
| 191 | 41 | 529 (+H) |
| 192 | 12 | 646 (+H) |
| 193 | 21 | 528 (+H) |
| 194 | 83 | 542 (+H) |
| 195 | 49 | 563 (+H) |
| 196 | 110 | 562 (+H) |
| 197 | 106 | 527 (+H) |
| 198 | 623 | 543 (+H) |
| 199 | 292 | 542 (+H) |
| 200 | 13 | 570 (+H) |
| 201 | 533 | 535 (+H) |
| 202 | 51 | 535 (+H) |
| 203 | 873 | 533 (+H) |
| 204 | 50 | 533 (+H) |

*mass spectroscopic data

Target Selectivity Assays

To determine species selectivity, a Mouse PPARα Reporter Assay System was used (Indigo Biosciences, Cat. #M00111). Activity of test compounds to antagonize or agonize other isoforms of human PPAR, for example β/δ and γ, were assessed using the corresponding kits from Indigo Biosciences (Cat. #IB00121 and #IB00101, respectively). In addition to PPAR activity, compounds were also screened for activity against other nuclear hormone receptors including Estrogen Receptor β, Glucocorticoid Receptor and Thyroid Receptor β using commercially available kits (Indigo Biosciences, Cat. #IB00411, IB00201 and IB01101, respectively). Each assay system from Indigo Biosciences uses technology analogous to the human PPARα kit, with the variance being that the cells used for each assay were engineered to over-express the receptor of interest. In addition, the appropriate receptor agonist (included with each kit) was used at ~EC$_{80}$ for assays in which antagonist potency was being assessed.

| Target Selectivity - Counterscreen Assay Results | | | | | | |
|---|---|---|---|---|---|---|
| Example | PPAR alpha IC$_{50}$ (nM) | PPAR beta/delta IC$_{50}$ (nM) | PPAR gamma IC$_{50}$ (nM) | Thyroid Receptor β IC$_{50}$ | Glucocorticoid Receptor IC$_{50}$ | Estrogen Receptor β IC$_{50}$ |
| 10 | 67 | 2600 | 2900 | >10 μM | 36.5 μM | 11.4 μM |
| 23 | 25 | >50000 | >50000 | >10 μM | >10 μM | 17.5 μM |

Measuring Fatty Acid Oxidation Using $^3$H Palmitate

Fatty acid oxidation is measured using $^3$H palmitate metabolism into $^3$H$_2$O as described previously (Nieman et al., 2011). Briefly, cells (e.g. HepG2, PC3 and CLL) are plated in growth media and allowed to adhere overnight. Cells are then treated with compound or 40 μM etomoxir (an inhibitor of fatty acid oxidation) as control. After treatment, cells are washed with DPBS followed by incubation in assay buffer (growth media, $^3$H palmitate and compound). After incubation, media is collected and proteins precipitated with 5% trichloroacetic acid. The precipitate is pelleted by centrifugation and the supernatant collected. Any remaining $^3$H palmitate in the supernatant is then removed by purification over a Dowex anion exchange column $^3$H$_2$O is then measured by scintillation counting.

Measurement of Cell Viability

Purified CLL cells were cultured at 2×10$^5$ cells/200 μL of RPMI1640 supplemented with 10% FCS in 96-well plates under various treatment conditions. Determination of CLL cell viability was based on the analysis of mitochondrial transmembrane potential (ΔΨm) using 3,3'-dihexyloxacarbocyanine iodide (DiOC6) (Invitrogen) and cell membrane permeability to propidium iodide (PI) (Sigma). For viability assays, 100 μL of the cell culture was collected at the indicated time points and transferred to polypropylene tubes containing 100 μL of 40 μM DiOC6 and 10 μg/mL PI in culture media. The cells were then incubated at 37° C. for 15 min and analyzed within 30 min by flow cytometry using an Accuri C6 flow cytometer. The percentage of viable cells was determined by gating on PI negative and DiOC6 bright cells.

In Vivo PD Model: PPAR Alpha Agonist-Induced Changes in Liver Gene Expression

CD-1 mice were treated with test compound 1-2 hours prior to oral gavage with the PPAR alpha agonist WY14,643 (3 mg/kg). For the 1 day pharmacodynamic model, animals were euthanized 6 hours after agonist treatment. For the 3 day pharmacodynamic model, mice were dosed again with antagonist and WY14,643 on day 2 and day 3. In this case, mice were euthanized 6 hours following WY14,643 on day 3. Upon termination, blood was collected for DMPK analysis. Liver was collected, placed into Trizol and stored at −80° C. until processing. RNA was extracted from thawed and homogenized tissue using standard Trizol RNA isolation methods. RT-PCR was performed on the extracted RNA using primers specific for PPAR alpha regulated genes. Quantitative PCR was performed on the resulting cDNA and expression was normalized to β-actin.

In Vivo Cancer Model: B16F10 Model of Pulmonary Metastasis

B16F10 cells were cultured in standard growth media, harvested when approximately 50% confluent and injected into C57BL6 mice via the tail vein (50,000 cells per mouse in 200 μL). Mice were then treated daily with test compound. On day 21, mice were euthanized. Lungs were harvested and placed into Fekete's solution overnight to facilitate visualization of the tumors. Black nodules were enumerated.

FIG. 1 shows inhibition of metastasis of B16F10 melanoma cells to the lung following intraperitoneal doses of N-(6-(4-(3-(1-(4-(tert-Butyl)benzyl)-4-ethyl-5-oxo-4,5-dihydro-1H-1,2,4-triazol-3-yl)propyl)phenyl) pyridin-3-yl) benzenesulfonamide (Example 10) at 0.3, 3 and 30 mg/kg. Statistics were performed by ANOVA with Dunnett's Multiple Comparison Test post-hoc to determine statistical differences from vehicle treatment group (* denotes P<0.05 while *** denotes P<0.001).

Synthesis

The starting materials used for the synthesis are either synthesized or obtained from commercial sources, such as, but not limited to, Sigma-Aldrich, Fluka, Acros Organics, Alfa Aesar, VWR Scientific, and the like. General methods for the preparation of compounds can be modified by the use of appropriate reagents and conditions for the introduction of the various moieties found in the structures as provided herein.

In some embodiments, compounds described herein are prepared as outlined in the following general synthetic scheme. Generally, a commercially available carboxylic acid, such as 4-(4-bromophenyl)butanoic acid, is first converted into the corresponding hydrazide with hydrazine under typical coupling conditions (e.g. CDI, EDCI, HATU, etc.). The hydrazide thus obtained is then reacted with an alkyl isocyanate, which are commercially available or otherwise readily available. Subsequent cyclization of the resulting acyl hydrazine carboxamide is carried out in the presence of base (e.g. NaOH, KOH, etc.), acid (e.g. camphorsulfonic acid, methanesulfonic acid, etc.) or buffered lewis acid (e.g. TMSOTf with TEA, TMSOTf with Hunig's base, etc), to provide the requisite triazolone. At this junction, one could choose to functionalize first the NH of the triazolone using standard N-alkylation (e.g. $Cs_2CO_3$ with $R^2$-Hal, $K_2CO_3$ with $R^2$-Hal, etc.) or N-arylation (e.g. CuI, L-proline, $K_2CO_3$, $R^2$—I; $Cu(OAc)_2$, trans-diaminecyclohexane, $K_2CO_3$, $R^2$I, etc.) conditions, before one elaborates the aryl bromide under standard metal-catalyzed conditions (e.g. Suzuki coupling with $Pd(PPh_3)_4$, aq. $Na_2CO_3$, $R^3$—B(OH)$_2$; Stille coupling with $Pd(PPh_3)_4$, KF, $R^3$—SnBu$_3$; Negishi coupling with $Pd(PPh_3)_4$, $R^3$—Zn—Br; etc.). Alternatively, one could instead choose to elaborate the aryl bromide under more specialized metal-catalyzed conditions (e.g. $Pd_2(dba)_3$, S-Phos, aq. $Na_2CO_3$, $R^4$—B(OH)$_2$) before one functionalize the NH of the triazolone via standard N-alkylation or N-arylation conditions. The latter sequence would allow one to deploy metal-mediated cross-coupling conditions to further decorate the newly installed triazolone substituent without cross-reactivity issues. For examples where the starting carboxylic acid is not commercially available, one could instead synthesize these requisite acids using a two-step sequence where the commercially available aldehyde is allowed to react with acrylonitrile under standard Stetter conditions (e.g. KCN, NaCN, etc.), followed by deoxygenation-hydrolysis under standard Wolf-Kisner conditions (e.g. NH$_2$NH$_2$, KOH). If appropriate, one could also deoxyfluorinate the intermediate ketone nitrile obtained from the Stetter condensation using commercially available reagents such as DAST or deoxyfluor before carrying out the nitrile hydrolysis. Regardless of the synthetic approach employed, Compound I thus accessed can optionally itself be further functionalized, depending on what other existing functionalities are present, using standard elaborative transformations known to those skilled in the art such as sulfonylation, amide coupling, hydrolysis, alkylation, oxidation, reduction, hydrogenation, de-alkylation, etc. or combinations thereof.

General Synthetic Scheme for Exemplary Compounds

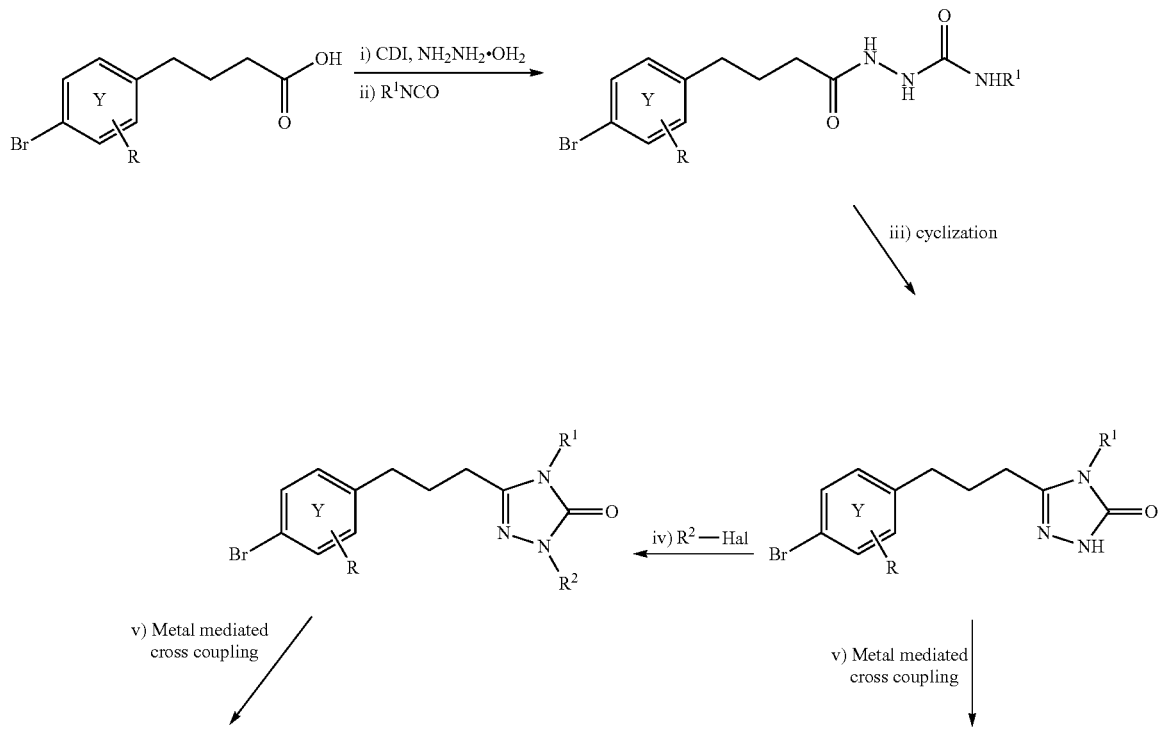

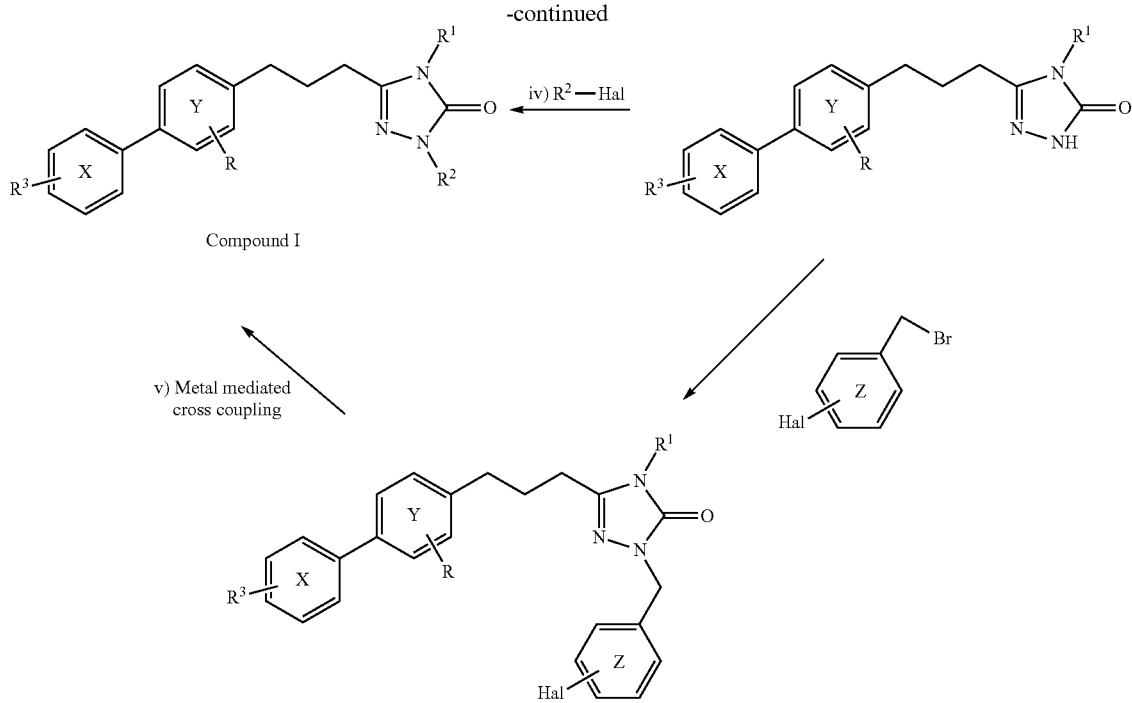

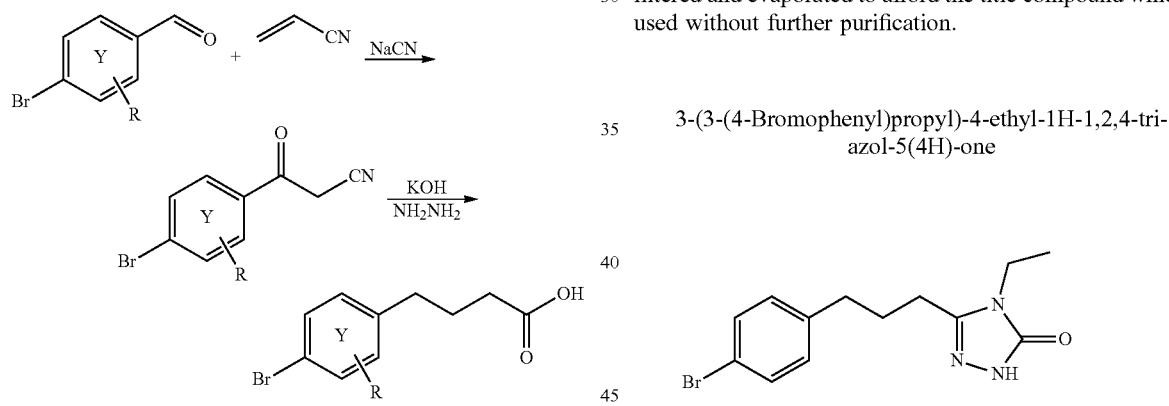

Preparation of Intermediates

4-(4-Bromophenyl)butanehydrazide

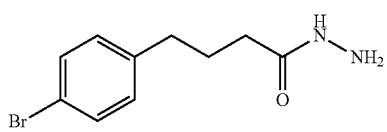 [SMILES: NNC(=O)CCCc1ccc(Br)cc1]

To a solution of 4-(4-bromophenyl)butanoic acid (10.2 g, 41.9 mmol) in THF (175 mL) was added carbonyldiimidazole (7.47 g, 46.1 mmol) and stirred at room temperature for 2 hrs. Hydrazine hydrate (8.5 mL; ~4 eq) was added in one portion and stirring maintained for a period of 1 hr. The solvent was evaporated, the residue partitioned between EtOAc and water, extracted with EtOAc, dried (MgSO$_4$), filtered and evaporated to afford the title compound which is used without further purification.

3-(3-(4-Bromophenyl)propyl)-4-ethyl-1H-1,2,4-triazol-5(4H)-one

Step 1:

To a solution of 4-(4-bromophenyl)butanehydrazide (5.3 g, 20.6 mmol) in THF (100 mL) was added ethyl isocyanate (2 mL, 24.7 mmol) dropwise. After stirring at room temperature for 2 hrs, a precipitate had formed. The solvent was then removed in vacuo and the product thus obtained was used in the next step without further purification.

Step 2:

The isolated material from the prior reaction was dissolved in MeOH (200 mL) and added potassium hydroxide (11 g). The resulting solution was heated to reflux for 12 hrs. The solvent was then removed in vacuo and the residue diluted with DCM (200 mL) and acidified with 1N HCl until an aqueous pH of ~2 was achieved. The organic layer was separated and the aqueous phase was extracted with DCM. The combined organic phases were then dried (MgSO$_4$), filtered and evaporated to dryness to afford the crude title compound as a colorless solid.

3-(3-(4-Bromophenyl)propyl)-4-isopropyl-1H-1,2,4-triazol-5(4H)-one

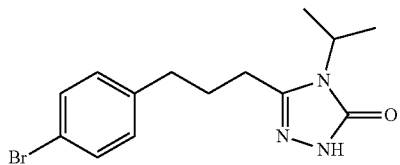 [SMILES: CC(C)n1c(CCCc2ccc(Br)cc2)n[nH]c1=O]

Prepared in an analogous fashion to the prior ethyl derivative but using isopropyl isocyanate instead.

3-(3-(4-Bromophenyl)propyl)-4-phenyl-1H-1,2,4-triazol-5(4H)-one

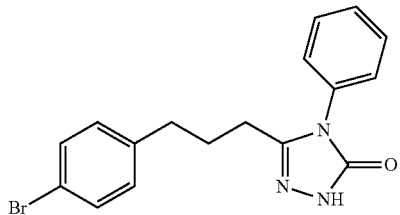 [SMILES: O=c1[nH]nc(CCCc2ccc(Br)cc2)n1-c1ccccc1]

Prepared in an analogous fashion to the ethyl derivative but using phenyl isocyanate instead.

3-(3-(4-Bromophenyl)propyl)-4-propyl-1H-1,2,4-triazol-5(4H)-one

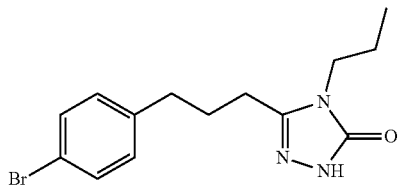 [SMILES: CCCn1c(CCCc2ccc(Br)cc2)n[nH]c1=O]

Prepared in an analogous fashion to the ethyl derivative but using n-propyl isocyanate instead.

3-(3-(4-Bromophenyl)propyl)-4-butyl-1H-1,2,4-triazol-5(4H)-one

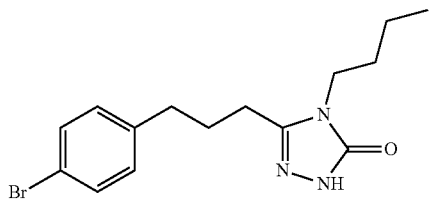 [SMILES: CCCCn1c(CCCc2ccc(Br)cc2)n[nH]c1=O]

Prepared in an analogous fashion to the ethyl derivative but using n-butyl isocyanate instead.

3-(3-(4-Bromophenyl)propyl)-1-(4-(tert-butyl)benzyl)-4-ethyl-1H-1,2,4-triazol-5(4H)-one

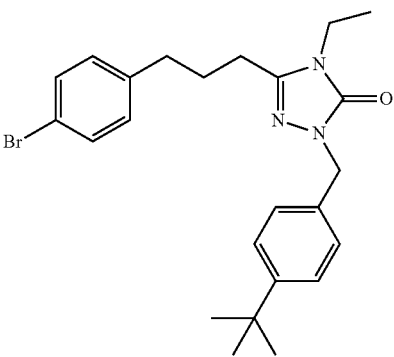 [SMILES: CCn1c(CCCc2ccc(Br)cc2)nn(Cc2ccc(C(C)(C)C)cc2)c1=O]

To a solution of 3-(3-(4-bromophenyl)propyl)-4-ethyl-1H-1,2,4-triazol-5(4H)-one (6.05 g, 19.6 mmol) in DMF (40 mL) was added potassium carbonate (10.8 g, 80 mmol) and 4-(tert-butyl)benzyl bromide (4.3 mL, 21.6 mmol). The resulting suspension was then heated at 45° C. until complete reaction as judged by LCMS analysis (~2 hrs). The reaction was allowed to cool to room temperature and partitioned between EtOAc and water. The organic phase was separated, the aqueous phase was back extracted with EtOAc. The combined organic phases was washed with water (×2), dried (MgSO$_4$), filtered and the filtrate concentrated in vacuo. The residue thus obtained was purified on silica gel eluting with a solvent gradient of 0 to 50% EtOAc in hexanes to afford the title compound as a colorless oil.

3-(3-(4-Bromophenyl)propyl)-1-(4-(tert-butyl)benzyl)-4-isopropyl-1H-1,2,4-triazol-5(4H)-one

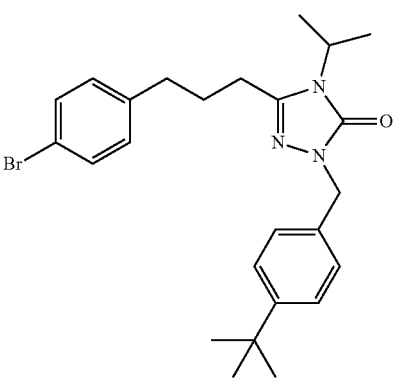 [SMILES: CC(C)n1c(CCCc2ccc(Br)cc2)nn(Cc2ccc(C(C)(C)C)cc2)c1=O]

Prepared in an analogous fashion to the prior ethyl derivative.

3-(3-(4-Bromophenyl)propyl)-1-(4-(tert-butyl)benzyl)-4-phenyl-1H-1,2,4-triazol-5(4H)-one

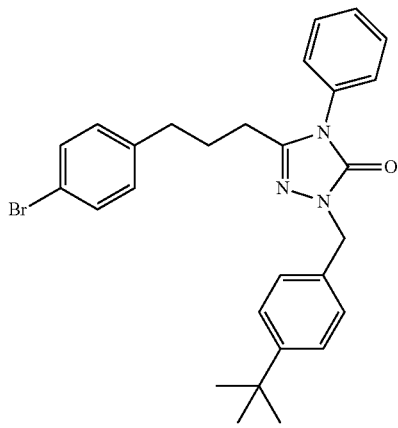 [SMILES: CC(C)(C)c1ccc(Cn2nc(CCCc3ccc(Br)cc3)n(-c3ccccc3)c2=O)cc1]

Prepared in an analogous manner to the prior ethyl derivative.

3-(3-(4-Bromophenyl)propyl)-1-(4-(tert-butyl)benzyl)-4-propyl-1H-1,2,4-triazol-5(4H)-one

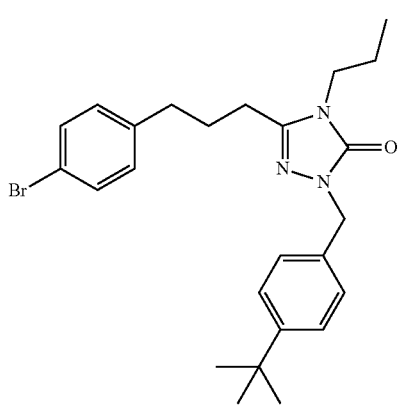 [SMILES: CCCn1c(CCCc2ccc(Br)cc2)nn(Cc2ccc(C(C)(C)C)cc2)c1=O]

Prepared in analogous fashion to the prior ethyl derivative.

3-(3-(4-Bromophenyl)propyl)-4-butyl-1-(4-(tert-butyl)benzyl)-1H-1,2,4-triazol-5(4H)-one

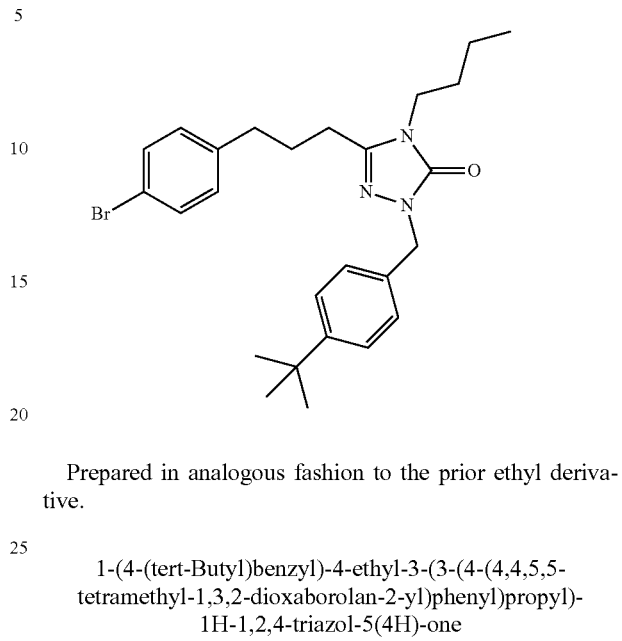

Prepared in analogous fashion to the prior ethyl derivative.

1-(4-(tert-Butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one

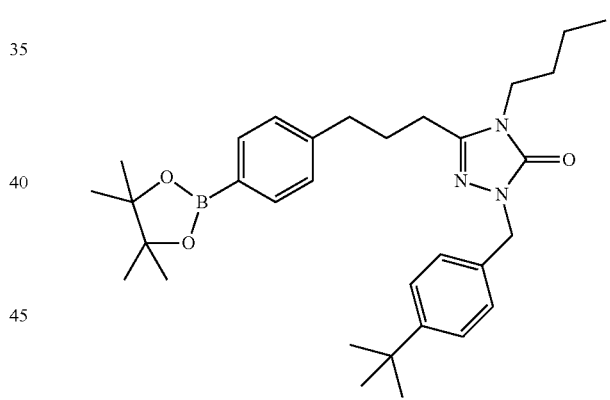

To a solution of 3-(3-(4-bromophenyl)propyl)-1-(4-(tert-butyl)benzyl)-4-ethyl-1H-1,2,4-triazol-5(4H)-one (10.0 g, 21.9 mmol) in p-dioxane (150 mL) was added potassium acetate (6.5 g, 66.2 mmol), bis(pinacolato)diboron (7.2 g, 28.4 mmol) and [1,1'-bis(diphenylphosphino)ferrocene]dichloropalladium(II) (750 mg). The solution was degassed by sparging with nitrogen gas for 10 minutes and then heated at 85° C. under a nitrogen atmosphere for 12 hrs. The solvent was evaporated in vacuo and the residue thus obtained was partitioned between EtOAc and water. The organic phase was then separated, washed with water, dried (MgSO$_4$), filtered and the filtrate concentrated in vacuo. The resulting residue was purified using silica gel chromatography eluting with a gradient of 0 to 60% EtOAc in hexanes to afford the title compound as an oily solid.

Methyl 2-(5-bromo-2-hydroxyphenyl)acetate

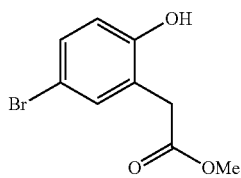 [SMILES: COC(=O)Cc1cc(Br)ccc1O]

To a solution of 2-(2-hydroxyphenyl)acetic acid (15.6 g, 103 mmol) in MeOH (350 mL) was added tetrabutylammonium tribromide (50 g, 103 mmol) in small portions over a 10 minute period. After stirring at ambient temperature for 24 hrs, the solvent was evaporated and the residue taken up in EtOAc and 1N aq. HCl. The aqueous wash was separated and back-extracted with EtOAc. The combined organic phases were then dried (MgSO$_4$), filtered and the filtrate concentrated in vacuo. The resulting residue was purified on silica gel eluting with a gradient of 30% EtOAc in hexanes to afford the title compound as a colorless solid.

Methyl 2-(5-bromo-2-ethoxyphenyl)acetate

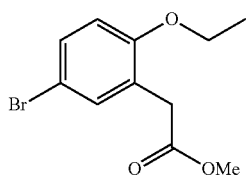

To a solution of methyl 2-(5-bromo-2-hydroxyphenyl)acetate (1.0 g, 4.1 mmol) in DMF (8 mL) was added cesium carbonate (2.66 g, 8.2 mmol) and iodoethane (392 µL, 4.9 mmol). After 2 hrs of stirring at rt, the reaction mixture was partitioned between EtOAc and water. The organic phase was then separated, washed with water, dried (MgSO$_4$), filtered and the filtrate concentrated in vacuo. The resulting residue was purified on silica gel eluting with a gradient of 0 to 10% EtOAc in hexanes to afford the title compound as a colorless oil.

Methyl 2-(5-bromo-2-methoxyphenyl)acetate

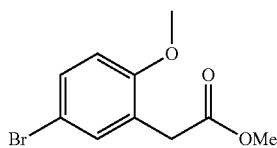

Prepared in an analogous fashion to the aforementioned ethyl derivative using instead methyl iodide as the electrophile.

Methyl 2-(5-bromo-2-(cyclopropylmethoxy)phenyl)acetate

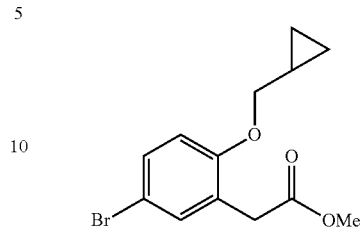

Prepared in analogous fashion to the aforementioned ethyl derivative using (bromomethyl)cyclopropane as the electrophile.

Methyl 2-(5-bromo-2-propoxyphenyl)acetate

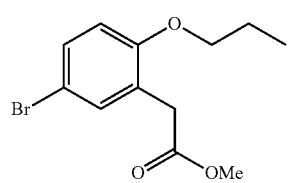 [SMILES: CCCOc1ccc(Br)cc1CC(=O)OC]

Prepared in analogous fashion to the aforementioned ethyl derivative using 1-bromopropane as the electrophile.

Ethyl 5-bromo-2-methoxybenzoate

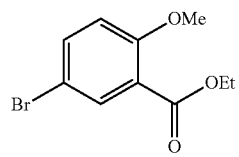 [SMILES: CCOC(=O)c1cc(Br)ccc1OC]

To a solution of ethyl 5-bromo-2-hydroxybenzoate (2.0 g, 8.66 mmol) in DMF (15 mL) was added cesium carbonate (5.64 g, 17.3 mmol) and iodomethane (600 µL, 9.63 mmol). After 2 hrs of stirring at rt, the reaction mixture was partitioned between EtOAc and water. The organic phase was then separated, washed with water, dried (MgSO$_4$), filtered and the filtrate concentrated in vacuo. The resulting residue was purified on silica gel eluting with a gradient of 0 to 20% EtOAc in hexanes to afford the title compound as a colorless oil.

Ethyl 5-bromo-2-ethoxybenzoate

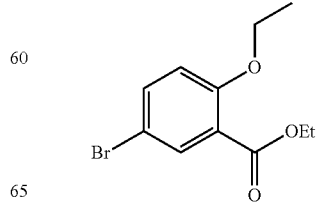

Prepared in an analogous fashion to the aforementioned methyl derivative with iodoethane as the electrophile.

Methyl 5-bromo-2-propoxybenzoate

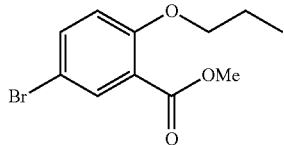

Prepared in an analogous fashion to the aforementioned methyl derivative with 1-bromopropane as the electrophile and methyl 5-bromo-2-hydroxybenzoate as the nucleophile.

Methyl 2-(2-ethoxy-5-(4,4,5,5-tetramethyl-1,3,2-dioxaborolan-2-yl)phenyl)acetate

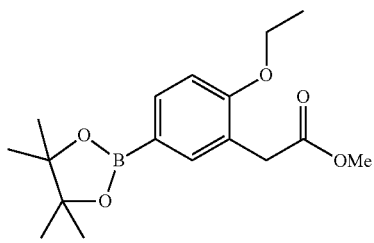 [SMILES: CCOc1ccc(B2OC(C)(C)C(C)(C)O2)cc1CC(=O)OC]

To a solution of methyl 2-(5-bromo-2-ethoxyphenyl)acetate (1.42 g, 5.2 mmol) in p-dioxane (35 mL) was added potassium acetate (1.53 g, 15.6 mmol), bis(pinacolato)diboron (1.6 g, 6.3 mmol) and Pd(dppf)Cl$_2$ (100 mg). The solution as degassed via sub-surface purging with dry nitrogen gas for 10 minutes, then heated at 85° C. under a nitrogen atmosphere for 12 hrs. After complete reaction, the suspension was allowed to cool, evaporated, the residue partitioned between EtOAc and water and the organic phase separated, dried (MgSO$_4$), filtered and evaporated in vacuo. The residue was purified on silica gel eluting with a gradient of 0 to 20% EtOAc in hexanes to afford the title compound as a colorless oil which solidified upon standing.

Methyl 2-(2-methoxy-5-(4,4,5,5-tetramethyl-1,3,2-dioxaborolan-2-yl)phenyl)acetate

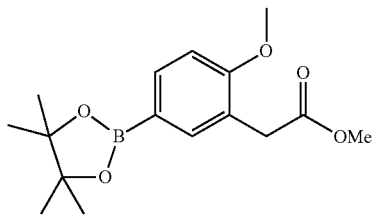 [SMILES: COC(=O)Cc1cc(B2OC(C)(C)C(C)(C)O2)ccc1OC]

Prepared in an analogous fashion to the aforementioned ethyl derivative with methyl 2-(5-bromo-2-methoxyphenyl)acetate as the aryl bromide.

Methyl 5-bromo-1H-indole-3-carboxylate

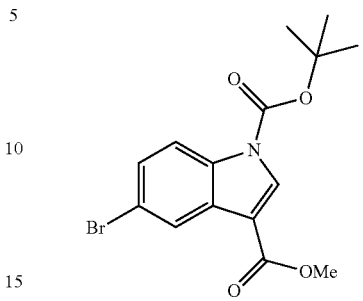

To a solution of methyl 1H-indole-3-carboxylate (1.0 g, 3.94 mmol) in MeCN (20 mL) was added di-tert-butyldicarbonate (1.0 g, 4.58 mmol) and DMAP (cat.) and the solution allowed to stir for 16 hrs. The solvent was evaporated to dryness and the residue partitioned between EtOAc and water. The organic phase was separated, dried (MgSO$_4$), filtered and evaporated to afford the title compound. This was used without further purification.

Methyl 5-bromobenzofuran-3-carboxylate

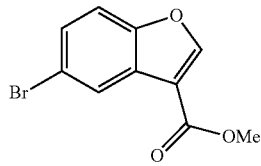 [SMILES: COC(=O)c1coc2ccc(Br)cc12]

To a solution of 5-bromobenzofuran-3(2H)-one (1.0 g, 4.7 mmol) in CH$_2$Cl$_2$ (20 mL) cooled to 0° C. was added diisopropylethylamine (1.64 mL, 9.4 mmol) and dropwise addition of trifluoromethanesulfonic anhydride (909 µL, 5.4 mmol). After 10 minutes, the reaction mixture was diluted with CH$_2$Cl$_2$, washed with water, the organic phase separated, dried (MgSO$_4$), filtered and evaporated. The residue was filtered through a plug if silica eluting with EtOAc/hexanes (1:1) to afford the intermediate triflate used without further analysis. The triflate was dissolved in MeOH (15 mL) and triethylamine (5 mL) to which was added Pd(OAc)$_2$ (105 mg, 0.47 mmol) and 1,3-bis(diphenylphosphino)propane (194 mg, 0.47 mmol) and the solution sparged with CO gas via sub-surface purge. The resulting solution was heated to 80° C. under an atmosphere of CO for 16 hrs after which the solution was evaporated, the residue partitioned between EtOAc and water, the organic phase separated, dried (MgSO$_4$), filtered and evaporated in vacuo. Purification of the residue on silica gel eluting with a gradient of EtOAc in hexanes (0 to 15%) afforded the title compound.

(rac)-Methyl 5-bromo-2,3-dihydrobenzofuran-3-carboxylate

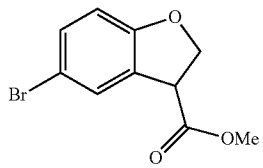 [SMILES: COC(=O)C1COc2ccc(Br)cc21]

To a solution of the previously synthesized methyl 5-bromobenzofuran-3-carboxylate (120 mg, 0.47 mmol) in MeOH (5 mL) was added magnesium turnings (~100 mg) and the solution stirred vigorously for 6 hrs after which TLC analysis indicated complete reduction. 1N aq. HCl was carefully added to the solution and after complete dissolution of the magnesium metal the resulting mixture was partitioned between EtOAc and water. The organic phase was separated, dried ($MgSO_4$), filtered and evaporated to give the title compound in quantitative yield.

1-(5-Bromo-2-ethoxyphenyl)cyclopropanecarbonitrile

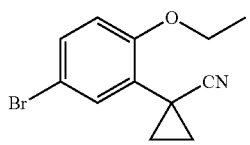

Step 1:

To a solution of 4-bromo-2-methylphenol (5.0 g, 26.7 mmol) in DMF (20 mL) was added cesium carbonate (13.0 g, 39.9 mmol) and iodoethane (2.6 mL, 32.5 mmol) and the suspension stirred vigorously for 12 hrs. The resulting mixture was partitioned between EtOAc and water. The organic phase was then separated, washed further with water, dried ($MgSO_4$), and filtered. Evaporation of the filtrate in vacuo afforded 4-bromo-1-ethoxy-2-methylbenzene which could be used without further purification.

Step 2:

To the previously synthesized ether (4.97 g, 23.1 mmol) in carbon tetrachloride (80 mL) was added N-bromosuccinimide (4.93 g, 27.6 mmol) and benzoyl peroxide (100 mg). The resulting solution was heated to reflux for 3 hrs, allowed to cool, partially evaporated and then filtered. The filtrate was evaporated in vacuo to afford 4-bromo-2-(bromomethyl)-1-ethoxybenzene which could be used without further purification.

Step 3:

To a solution of the aforementioned bromide (6.8 g, 23.1 mmol) in DMF (20 mL) was added potassium cyanide (2.26 g, 34.7 mmol) and the resulting suspension stirred for 48 hrs. The reaction mixture was diluted with EtOAc. The organic layer was separated, washed further with water, dried ($MgSO_4$), and the filtrate concentrated in vacuo. The crude residue thus obtained was purified on silica gel eluting with a gradient of EtOAc in hexanes (0 to 10%) to afford 2-(5-bromo-2-ethoxyphenyl)acetonitrile (2.5 g, 45%) over 3 steps.

Step 4:

In a sealable vial was placed 2-(5-bromo-2-ethoxyphenyl)acetonitrile (1.0 g, 4.16 mmol), potassium hydroxide (50% aq. soln; 2 mL), 1,2-dibromoethane (541 μL, 6.25 mmol) and tetrabutylammonium bromide (200 mg). The mixture was heated at 50° C. with vigorous stirring for 4 hrs after which the solution was diluted in EtOAc and then acidified with 1N aq. HCl. The organic phase was separated, dried ($MgSO_4$), filtered and evaporated to afford the title compound.

1-(5-Bromo-2-methoxyphenyl)cyclopropanecarbonitrile

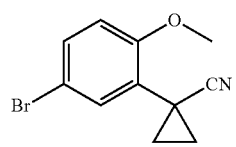

Prepared in an analogous fashion to the aforementioned ethyl derivative with iodomethane as the electrophile in step 1.

1-(5-Bromo-2-methoxyphenyl)cyclobutanecarbonitrile

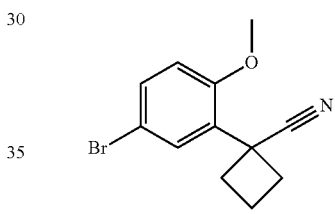

Prepared in an analogous fashion to the aforementioned ethyl derivative with iodomethane as the electrophile in step 1 and 1,3-dibromopropane as the electrophile in step 4.

2-(5-Bromo-2-isopropoxyphenyl)acetonitrile

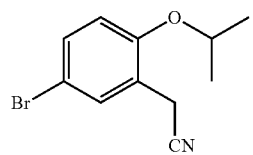

Prepared in an analogous fashion to the aforementioned ethyl derivative with 2-iodopropane as the electrophile in step 1 and omitting the cyclopropanation step (i.e. step 4).

2-(4-Bromo-2-methoxyphenyl)acetonitrile

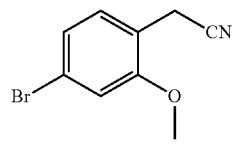

Prepared in an analogous fashion to 2-(5-bromo-2-isopropoxyphenyl)acetonitrile, but with iodomethane as the electrophile and 5-bromo-2-methylphenol as the nucleophile in step 1.

Example 1

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)acetic acid

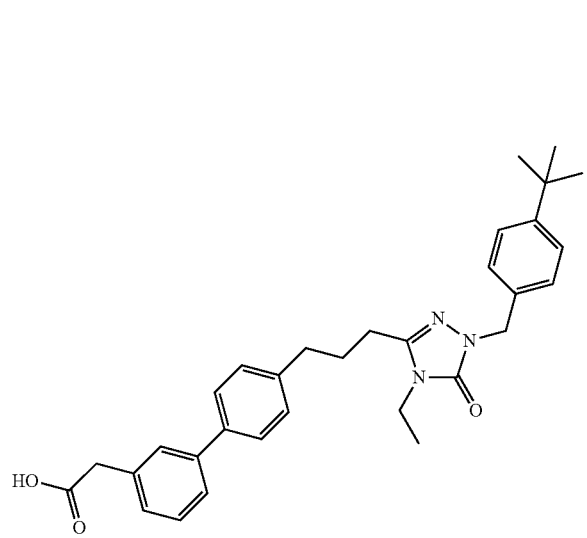 [SMILES: CCn1c(CCCc2ccc(-c3cccc(CC(=O)O)c3)cc2)nn(Cc2ccc(C(C)(C)C)cc2)c1=O]

Step 1:

To a solution of 3-(3-(4-bromophenyl)propyl)-1-(4-(tert-butyl)benzyl)-4-ethyl-1H-1,2,4-triazol-5(4H)-one (275 mg, 0.6 mmol) in DME (4 mL) and water (1.5 mL) was added potassium carbonate (208 mg, 1.5 mmol) and ethyl 2-(3-(4,4,5,5-tetramethyl-1,3,2-dioxaborolan-2-yl)phenyl)acetate (210 mg, 0.72 mmol). The resulting suspension was sparged with nitrogen for 10 minutes before tetrakis(triphenylphosphine)palladium (0) (30 mg) was added. The reaction vessel was then sealed and heated at 80° C. for 3 hrs. After cooling, the solution was partitioned between EtOAc and water. The organic phase was separated, dried (MgSO$_4$), filtered and the filtrate concentrated in vacuo. The resulting residue was purified using silica gel chromatography (0 to 50% EtOAc in hexanes) to afford ethyl 2-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)acetate.

Step 2:

To the isolated ester (270 mg, 5 mmol) in a mixture of THF:MeOH:H$_2$O (6:1.5:1.5 mL) was added lithium hydroxide monohydrate (60 mg). The resulting mixture was then stirred at room temperature until reaction completion as judged by LCMS analysis. At this time, the reaction mixture was diluted with EtOAc and water, and then added solid citric acid added to an aqueous pH of ~4. The organic phase was separated, washed further with H$_2$O, dried (MgSO$_4$), and filtered. Concentration of the resulting filtrate in vacuo afforded the title compound as a colorless foam. LC-MS 512 (M+H)$^+$.

Example 2

4'-(3-(1-(4-(tert-Butyl)benzyl)-4-ethyl-5-oxo-4,5-dihydro-1H-1,2,4-triazol-3-yl)propyl)-[1,1'-biphenyl]-3-carboxylic acid Prepared in an analogous manner to example 1 using ethyl 3-(4,4,5,5-tetramethyl-1,3,2-dioxaborolan-2-yl)benzoate as the coupling partner in step 1. LC-MS 498 (M+H)$^+$.

Example 3

3-(3-(4-(6-Aminopyridin-2-yl)phenyl)propyl)-1-(4-(tert-butyl)benzyl)-4-ethyl-1H-1,2,4-triazol-5(4H)-one

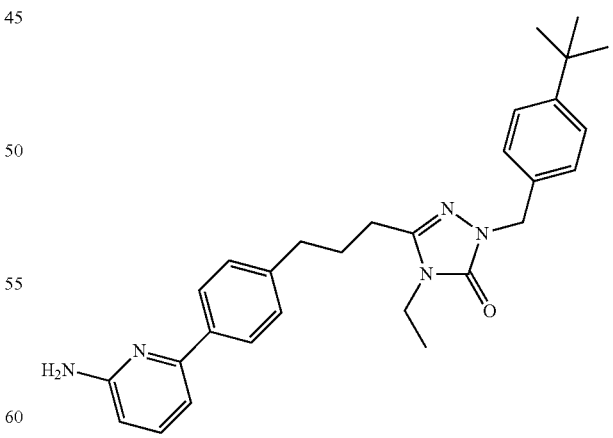

A mixture of 1-(4-(tert-butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one (98 mg, 0.194 mmol), 2-amino-6-bromopyridine (40 mg, 0.233 mmol, 1.2 eq) and potassium carbonate (80 mg, 0.582 mmol, 3 eq) were taken up in DME (2 mL) and water (1 mL). To this was added tetrakis(triphenylphosphine)palladium(0) (22 mg, 0.0194 mmol, 0.1 eq) and the resulting mixture was stirred at 85° C. under an atmosphere of $N_2$ for 24 hrs. The reaction mixture was then cooled to room temperature and the solvent was removed in vacuo. The crude material thus obtained was partitioned between water and EtOAc. The aqueous layer was back-extracted with EtOAc (3×20 mL) and the combined organic extracts were dried over anhydrous $Na_2SO_4$ and filtered. The filtrate thus obtained was then evaporated in vacuo to afford the crude product that could be purified further by flash column chromatography (silica gel, 0-10% MeOH/DCM) to afford the title compound as a white foam (75.5 mg, 83%). LC-MS: 470 $(M+H)^+$.

Example 4

N-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)benzenesulfonamide

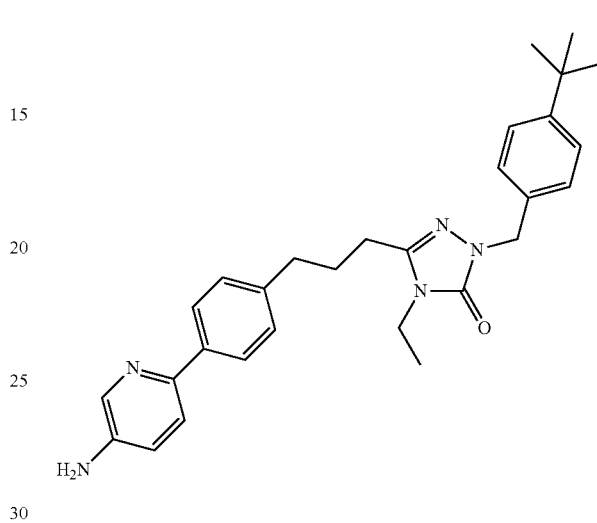

A mixture of 3-(3-(4-(6-aminopyridin-2-yl)phenyl)propyl)-1-(4-(tert-butyl)benzyl)-4-ethyl-1H-1,2,4-triazol-5(4H)-one (126 mg, 0.268 mmol) and benzene sulfonylchloride (38 μL, 0.295 mmol, 1.1 eq) was stirred in pyridine (1.5 mL) at room temperature for 24 hrs. The mixture thus obtained was poured onto dichloromethane (40 mL) and washed with saturated $CuSO_4$, water, and brine. The organic extract was then dried over anhydrous $Na_2SO_4$, filtered and the filtrate concentrated in vacuo. The crude product thus obtained was then purified by flash column chromatography (silica gel, 0-90% EtOAc/Hexanes) to afford the title compound as a white solid (115.6 mg, 71%). LC-MS: 610 $(M+H)^+$.

Example 5

3-(3-(4-(5-Aminopyridin-2-yl)phenyl)propyl)-1-(4-(tert-butyl)benzyl)-4-ethyl-1H-1,2,4-triazol-5(4H)-one

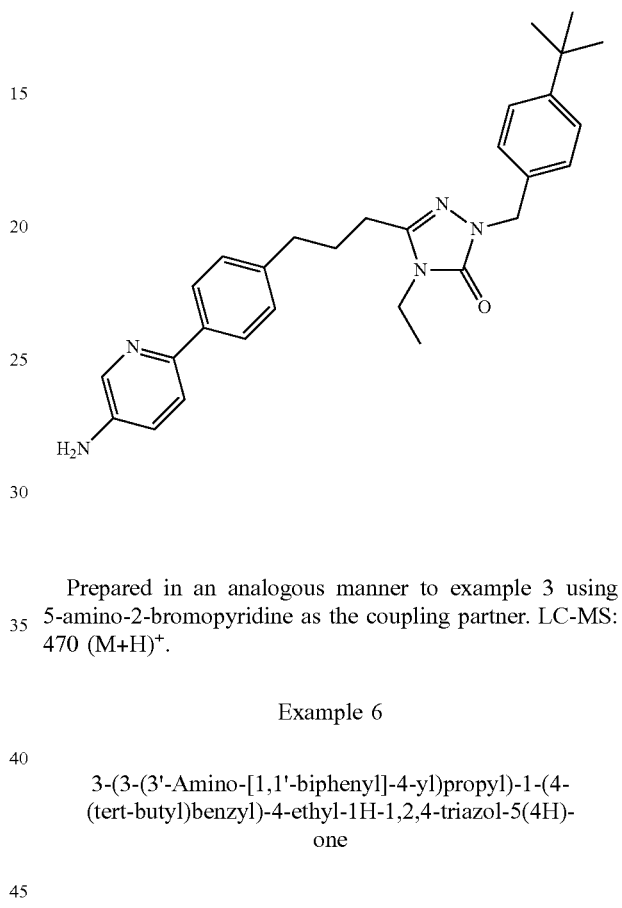

Prepared in an analogous manner to example 3 using 5-amino-2-bromopyridine as the coupling partner. LC-MS: 470 $(M+H)^+$.

Example 6

3-(3-(3'-Amino-[1,1'-biphenyl]-4-yl)propyl)-1-(4-(tert-butyl)benzyl)-4-ethyl-1H-1,2,4-triazol-5(4H)-one

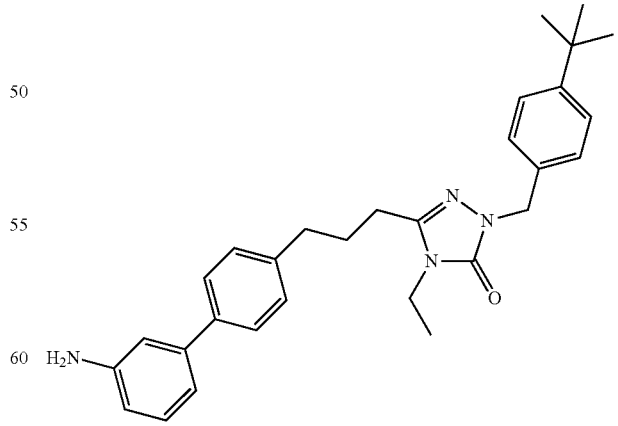

Prepared in an analogous manner to example 1 using 3-(4,4,5,5-tetramethyl-1,3,2-dioxaborolan-2-yl)aniline as the coupling partner in step 1. LC-MS: 469 $(M+H)^+$.

Example 7

N-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-4-methylbenzenesulfonamide

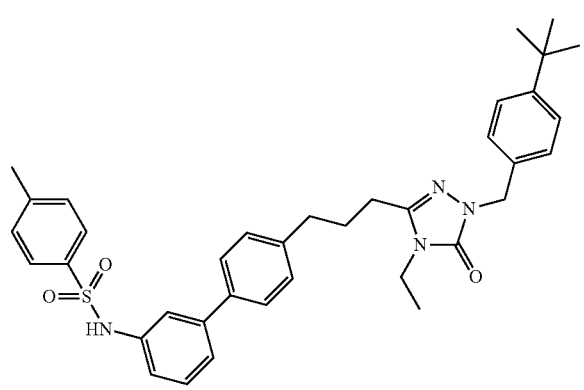 [SMILES: CCn1c(CCCc2ccc(-c3cccc(NS(=O)(=O)c4ccc(C)cc4)c3)cc2)nn(Cc2ccc(C(C)(C)C)cc2)c1=O]

Prepared in an analogous manner to example 1 using (3-(4-methylphenylsulfonamido)phenyl)boronic acid as the coupling partner in step 1. LC-MS: 623 (M+H)⁺.

Example 8

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-(phenylsulfonyl) acetamide To a solution of 2-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)acetic acid (100 mg, 0.195 mmol) in THF (1.5 mL) was added carbonyldiimidazole (41 mg, 0.253 mmol) and catalytic amount of DMAP. The resulting solution was stirred at ambient temperature for 3 hrs after which benzenesulfonamide (46 mg, 0.3 mmol) was added and the reaction heated at 50° C. for 16 hrs. The reaction as allowed to cool to RT, diluted with EtOAc and washed with 1N HCl. The organic phase was separated, dried (MgSO₄), filtered and the filtrate evaporated in vacuo. The residue thus obtained was purified using silica gel chromatography (0 to 5% MeOH in DCM) to afford the title compound. LC-MS: 651 (M+H)⁺.

Example 9

4'-(3-(1-(4-(tert-Butyl)benzyl)-4-ethyl-5-oxo-4,5-dihydro-1H-1,2,4-triazol-3-yl)propyl)-N-(phenylsulfonyl)-[1,1'-biphenyl]-3-carboxamide

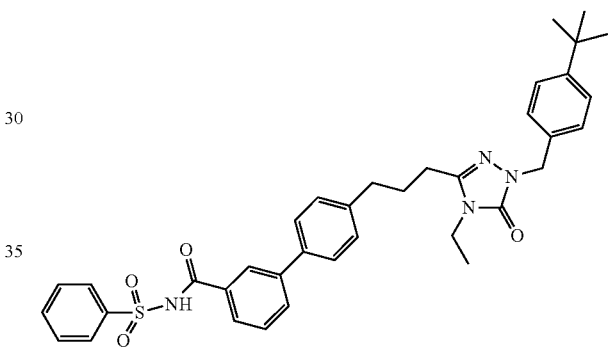

Prepared in an analogous manner to example 8 using 4'-(3-(1-(4-(tert-butyl)benzyl)-4-ethyl-5-oxo-4,5-dihydro-1H-1,2,4-triazol-3-yl)propyl)-[1,1'-biphenyl]-3-carboxylic acid as the starting material. LC-MS 637 (M+H)⁺.

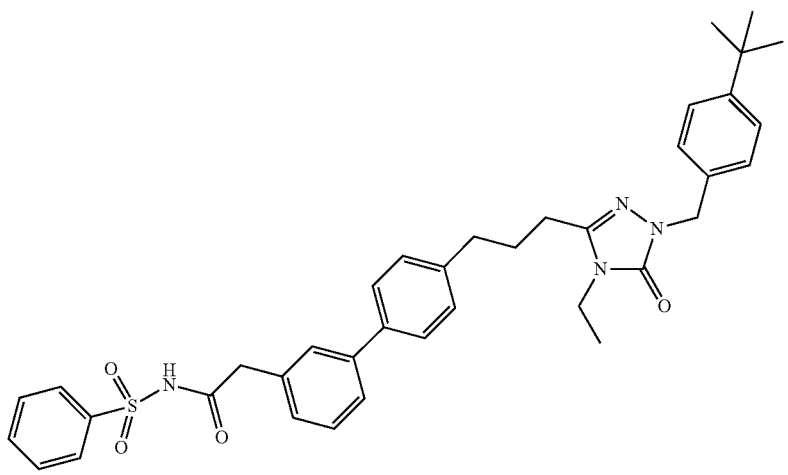 [SMILES: CCn1c(CCCc2ccc(-c3cccc(CC(=O)NS(=O)(=O)c4ccccc4)c3)cc2)nn(Cc2ccc(C(C)(C)C)cc2)c1=O]

Example 10

N-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)benzenesulfonamide

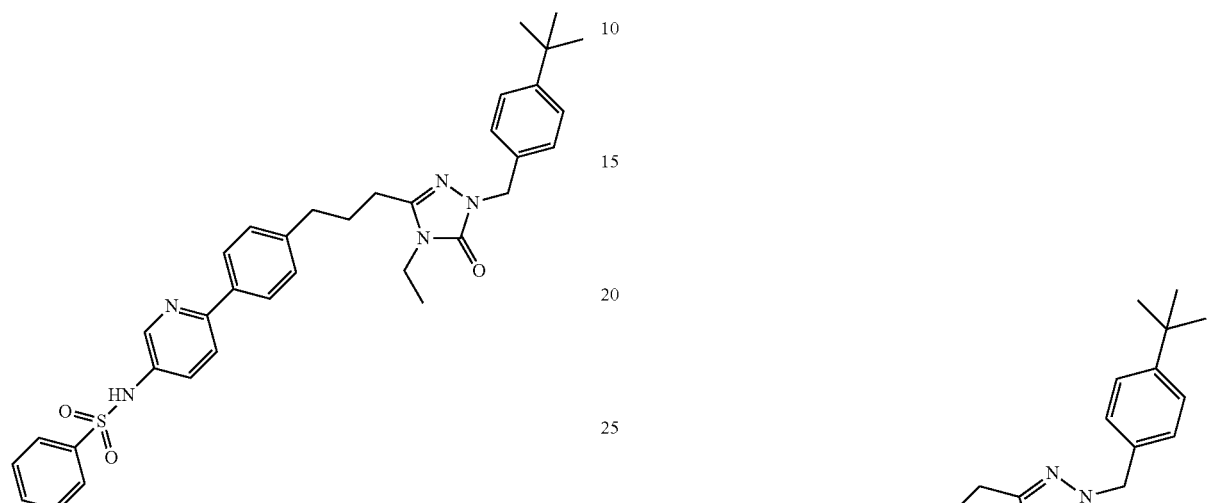

Prepared in an analogous manner to example 4 using 3-(3-(4-(5-aminopyridin-2-yl)phenyl)propyl)-1-(4-(tert-butyl)benzyl)-4-ethyl-1H-1,2,4-triazol-5(4H)-one as the starting material. LC-MS: 610 (M+H)+.

Example 11

3-(3-(4-(4-Aminopyridin-2-yl)phenyl)propyl)-1-(4-(tert-butyl)benzyl)-4-ethyl-1H-1,2,4-triazol-5(4H)-one

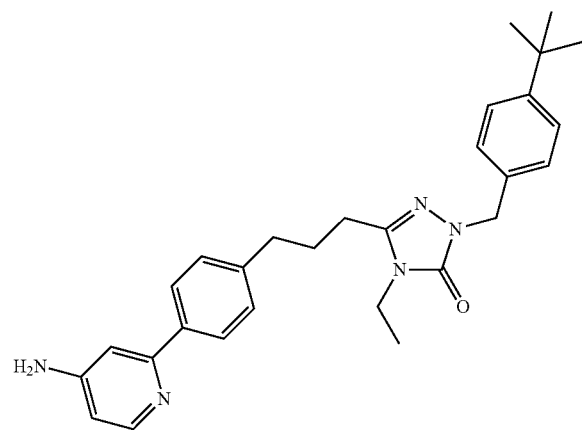 [SMILES: CCn1c(CCCc2ccc(-c3cc(N)ccn3)cc2)nn(Cc2ccc(C(C)(C)C)cc2)c1=O]

Prepared in an analogous manner to example 3 using 4-amino-2-chloropyridine as the coupling partner. LC-MS: 470 (M+H)+.

Example 12

N-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)methanesulfonamide A mixture of 3-(3-(4-(5-aminopyridin-2-yl)phenyl)propyl)-1-(4-(tert-butyl)benzyl)-4-ethyl-1H-1,2,4-triazol-5(4H)-one (44 mg, 0.094 mmol, methane sulfonylchloride (8 µL, 0.094 mmol, 1 eq), 4-dimethylaminopyridine (12 mg, 94 µmol, 1 eq), and 1,8-diazabicycloundec-7-ene (28 µL, 187 µmol, 2 eq.) was stirred in 1,2-dichloroethane (2 mL) at 50° C. for 18 hrs. The reaction mixture was cooled to room temperature and the solvent was then removed in vacuo. The crude material thus obtained was partitioned between water and ethyl acetate. The aqueous layer was extracted with ethyl acetate (2×20 mL) and the combined organic extracts were dried over anhydrous $Na_2SO_4$, filtered and the filtrate concentrated in vacuo. The crude product thus obtained was then purified on reverse phase HPLC to afford a the title compound as a white solid (20.2 mg, 40%). LC-MS: 548 (M+H)+.

Examples 13

1-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)cyclopropanecarboxylic acid and 14; 1-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)cyclopropanecarboxamide

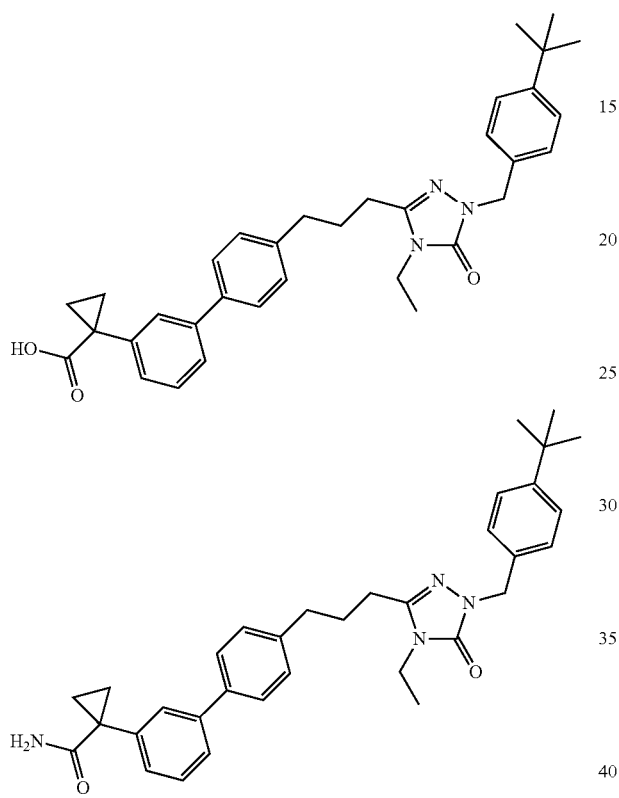

Step 1;
To a solution of 1-(4-(tert-butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one (270 mg, 0.54 mmol) in DME (5 mL) and $H_2O$ (1.5 mL) was added 1-(3-bromophenyl)cyclopropanecarbonitrile (143 mg, 0.64 mmol) and potassium carbonate (186 mg, 1.34 mmol). The resulting mixture was sparged with nitrogen gas for 10 minutes before tetrakis(triphenylphosphine)palladium (0) (20 mg) was added. The reaction vessel was then sealed and heated at 85° C. for 10 hrs. The reaction mixture was allowed to cool to RT and partitioned between EtOAc and water. The organic phase was separated, dried ($MgSO_4$), filtered and the filtrate concentrated in vacuo. The residue thus obtained was purified using silica gel chromatography (0 to 70% EtOAc in hexanes) to afford 1-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)cyclopropanecarbonitrite.

Step 2;
To the isolated nitrile (200 mg, 0.39 mmol) in p-dioxane (4 mL) and water (4 mL) was added potassium hydroxide (750 mg). The reaction vessel was then sealed and heated at 120° C. for 24 hrs. After cooling to RT, the mixture was partitioned between EtOAc and 1N HCl (to pH 2). The organic phase was separated, dried ($MgSO_4$), filtered and the filtrate concentrated in vacuo. The residue thus obtained was purified on reverse phase HPLC to afford the two title compounds. Example 13: LC-MS: 538 $(M+H)^+$, example 14: LC-MS: 537 $(M+H)^+$.

Example 15

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-2-methylpropanamide

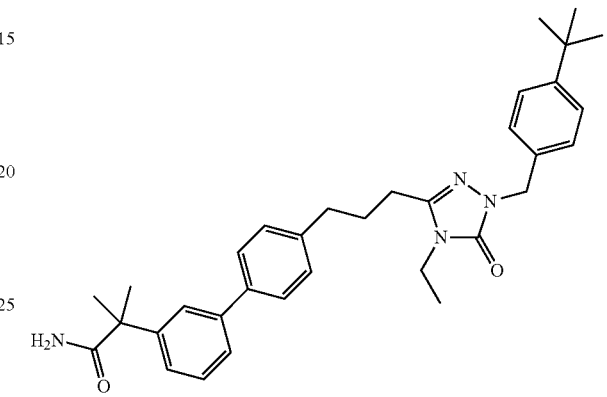

Prepared in an analogous manner to example 14 using 2-(3-bromophenyl)-2-methylpropanenitrile as the coupling partner. LC-MS: 539 $(M+H)^+$.

Example 16

N-(2-(4-(3-(1-(4-(tert-Butyl)benzyl)-4-ethyl-5-oxo-4,5-dihydro-1H-1,2,4-triazol-3-yl)propyl)phenyl)pyridin-4-yl)benzenesulfonamide

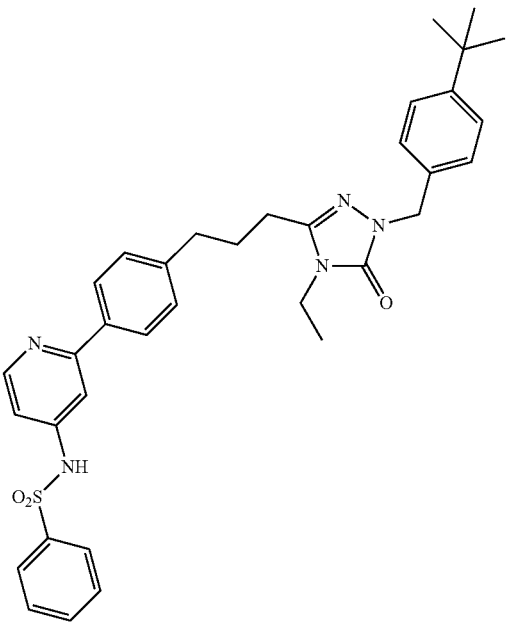 [SMILES: CCn1c(CCCc2ccc(-c3cc(NS(=O)(=O)c4ccccc4)ccn3)cc2)nn(Cc2ccc(C(C)(C)C)cc2)c1=O]

Prepared in an analogous manner to example 4 using 3-(3-(4-(4-aminopyridin-2-yl)phenyl)propyl)-1-(4-(tert-butyl)benzyl)-4-ethyl-1H-1,2,4-triazol-5(4H)-one as the starting material. LC-MS: 610 (M+H)+.

Example 17

N-(6-(4-(3-(1-(4-(tert-Butyl)benzyl)-4-ethyl-5-oxo-4,5-dihydro-1H-1,2,4-triazol-3-yl)propyl)phenyl)pyridin-4-yl)methanesulfonamide

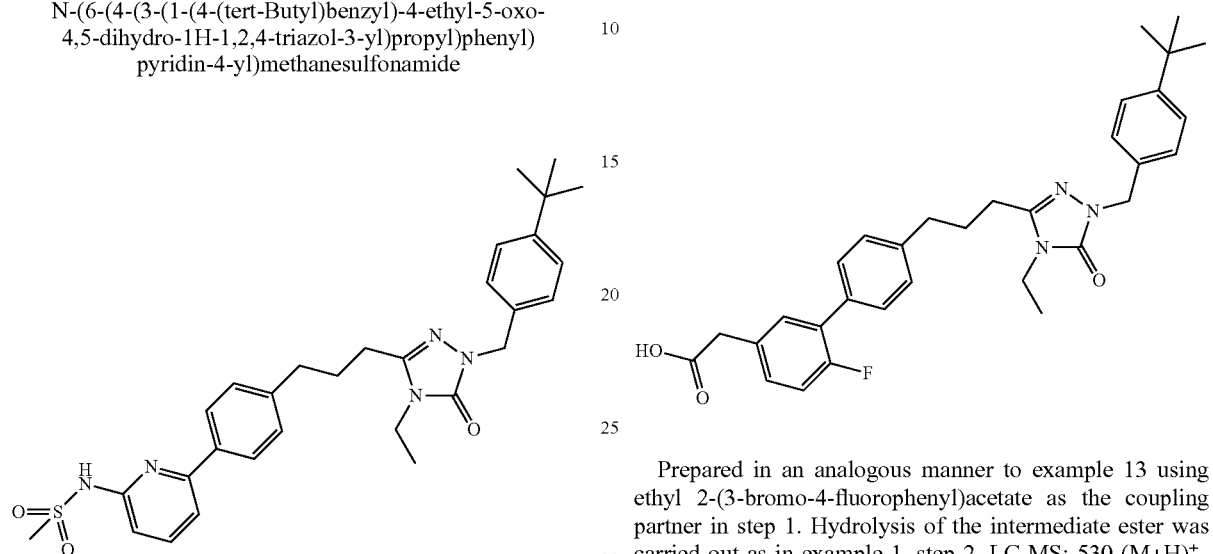

Prepared in an analogous manner to example 12 using 3-(3-(4-(4-aminopyridin-2-yl)phenyl)propyl)-1-(4-(tert-butyl)benzyl)-4-ethyl-1H-1,2,4-triazol-5(4H)-one as the starting material. LC-MS: 548 (M+H)+.

Example 18

2-(4'-(3-(1-(4-(tert-Butyl)benzyl)-4-ethyl-5-oxo-4,5-dihydro-1H-1,2,4-triazol-3-yl)propyl)-2-fluoro-[1,1'-biphenyl]-3-yl)acetic acid

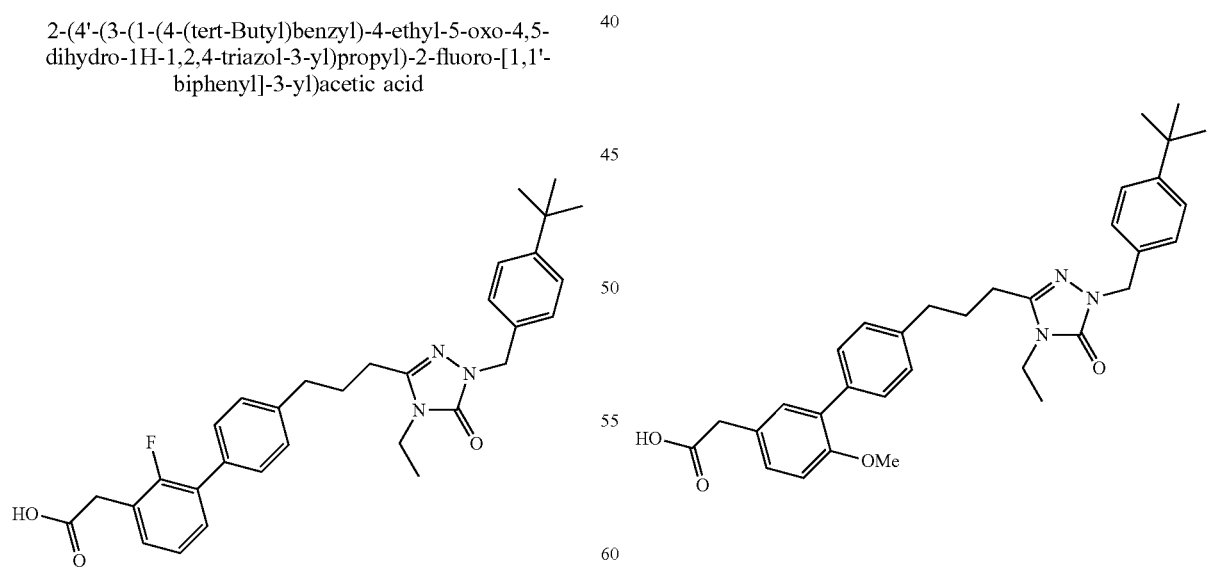

Prepared in an analogous manner to example 13 using 2-(3-bromo-2-fluorophenyl)acetonitrile as the coupling partner in step 1. Hydrolysis of the intermediate nitrile was carried out at 85° C. under similar conditions to step 2. LC-MS: 530 (M+H)+.

Example 19

2-(4'-(3-(1-(4-(tert-Butyl)benzyl)-4-ethyl-5-oxo-4,5-dihydro-1H-1,2,4-triazol-3-yl)propyl)-6-fluoro-[1,1'-biphenyl]-3-yl)acetic acid

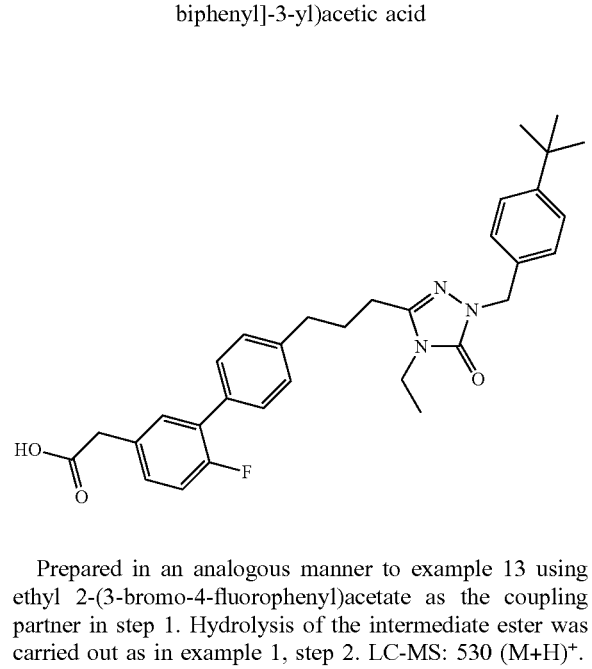

Prepared in an analogous manner to example 13 using ethyl 2-(3-bromo-4-fluorophenyl)acetate as the coupling partner in step 1. Hydrolysis of the intermediate ester was carried out as in example 1, step 2. LC-MS: 530 (M+H)+.

Example 20

2-(4'-(3-(1-(4-(tert-Butyl)benzyl)-4-ethyl-5-oxo-4,5-dihydro-1H-1,2,4-triazol-3-yl)propyl)-6-methoxy-[1,1'-biphenyl]-3-yl)acetic acid Prepared in an analogous manner to example 13 using ethyl 2-(3-bromo-4-methoxyphenyl)acetate as the coupling partner in step 1. Hydrolysis of the intermediate ester was carried out as in example 1, step 2. LC-MS: 542 (M+H)+.

Example 21

2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)acetic acid

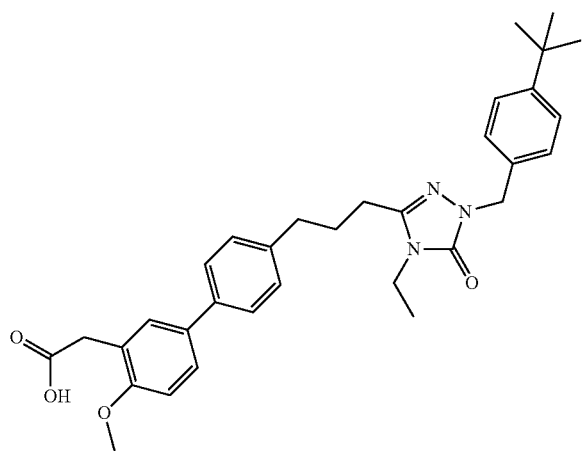 [SMILES: CCn1c(CCCc2ccc(-c3ccc(OC)c(CC(=O)O)c3)cc2)nn(Cc2ccc(C(C)(C)C)cc2)c1=O]

Prepared in an analogous manner to example 13 using ethyl 2-(5-bromo-2-methoxyphenyl)acetate as coupling partner in step 1. Hydrolysis of the intermediate ester was carried out as in example 1, step 2. LC-MS: 542 (M+H)$^+$.

Example 22

2-(4'-(3-(1-(4-Cyclopropylbenzyl)-4-ethyl-5-oxo-4,5-dihydro-1H-1,2,4-triazol-3-yl)propyl)-[1,1'-biphenyl]-3-yl)acetic acid

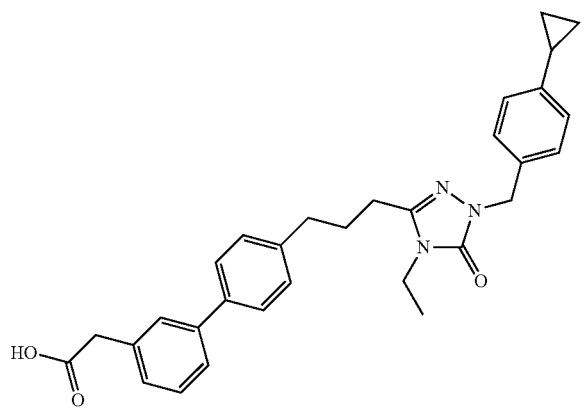 [SMILES: CCn1c(CCCc2ccc(-c3cccc(CC(=O)O)c3)cc2)nn(Cc2ccc(C3CC3)cc2)c1=O]

Step 1;

Under a nitrogen atmosphere, 3-(3-(4-bromophenyl)propyl)-4-ethyl-1H-1,2,4-triazol-5(4H)-one (0.20 g, 0.65 mmol), Pd(PPh)$_4$ (0.056 g, 0.065 mmol), KF (0.17 g, 2.84 mmol), (3-(2-ethoxy-2-oxoethyl)phenyl)boronic acid (0.296 g, 1.42 mmol), toluene (4 mL) and water (4 mL) were combined and the resulting mixture was stirred under nitrogen at 100° C. for 16 hrs. The reaction mixture was then cooled to rt, diluted with EtOAc and washed with a 50% brine/50% water solution. The organic phase was separated, washed once more with brine, filtered through a Na$_2$SO$_4$/paper plug, and the filtrate concentrated in vacuo. The residue was thus obtained was purified by column chromatography using a 1%-9% gradient MeOH/DCM as eluent to afford 0.190 g of ethyl 2-(4'-(3-(4-ethyl-5-oxo-4,5-dihydro-1H-1,2,4-triazol-3-yl)propyl)-[1,1'-biphenyl]-3-yl)acetate (contaminated with unreacted starting material which coeluted). This was used as is in the next step.

Step 2;

To a solution of ethyl 2-(4'-(3-(4-ethyl-5-oxo-4,5-dihydro-1H-1,2,4-triazol-3-yl)propyl)-[1,1'-biphenyl]-3-yl)acetate (0.10 g, 0.25 mmol) in anhydrous CH$_3$CN (4 mL) and Cs$_2$CO$_3$ (0.25 g, 0.72 mmol) at rt was added 4-bromobenzyl bromide (0.076 g, 0.31 mmol). The resulting mixture was stirred at 65° C. for 16 hrs. The mixture was diluted with EtOAc and a 50% brine/50% water solution. The organic extract was separated, washed once more with brine, filtered through a Na$_2$SO$_4$/paper plug, and the filtrate concentrated in vacuo. The crude product thus obtained was used as is in the next step.

Step 3;

Under a nitrogen atmosphere, ethyl 2-(4'-(3-(1-(4-bromobenzyl)-4-ethyl-5-oxo-4,5-dihydro-1H-1,2,4-triazol-3-yl)propyl)-[1,1'-biphenyl]-3-yl)acetate (0.07 g, 0.12 mmol), P(Cy)$_3$ (0.007 g, 0.025 mmol), cyclopropylboronic acid (0.054 g, 0.62 mmol), K$_3$PO$_4$.xH$_2$O, toluene (4 mL) and water (0.4 mL) were combined. The suspension thus obtained was purged with nitrogen for 5 min after which Pd(OAc)$_2$ (0.003 g, 0.012 mmol) was added and the resulting mixture was stirred at 100° C. for 48 hrs. The reaction was cooled to rt and diluted with EtOAc and brine. The brine layer was separated and back-extracted with DCM. The combined organic extracts were concentrated in vacuo and the residue thus obtained was then purified by preparatory TLC using 5% MeOH/DCM as eluent to afford 0.050 g (76% yield) of ethyl 2-(4'-(3-(1-(4-cyclopropylbenzyl)-4-ethyl-5-oxo-4,5-dihydro-1H-1,2,4-triazol-3-yl)propyl)-[1,1'-biphenyl]-3-yl)acetate as an oil.

Step 4;

To a solution of ethyl 2-(4'-(3-(1-(4-cyclopropylbenzyl)-4-ethyl-5-oxo-4,5-dihydro-1H-1,2,4-triazol-3-yl)propyl)-[1,1'-biphenyl]-3-yl)acetate (0.050 g, 0.10 mmol) in THF (1 mL) and MeOH (1 mL) was added water (1 mL) and LiOH (0.023 g, 0.96 mmol). The resulting mixture was stirred at 60° C. for 16 hrs. The solvents were evaporated and the resulting residue was taken up in DCM and 0.5 M aq. HCl. The aqueous layer was separated and extracted once more with DCM. The combined organics were then concentrated in vacuo and the residue thus obtained was purified by preparatory TLC using 10% MeOH/DCM as eluent to afford 0.010 g (16% yield, two steps) of the title compound as a yellow foam. LC-MS: 496 (M+H)$^+$.

Example 23

2-(4'-(3-(1-Benzyl-4-ethyl-5-oxo-4,5-dihydro-1H-1,2,4-triazol-3-yl)propyl)-[1,1'-biphenyl]-3-yl)acetic acid

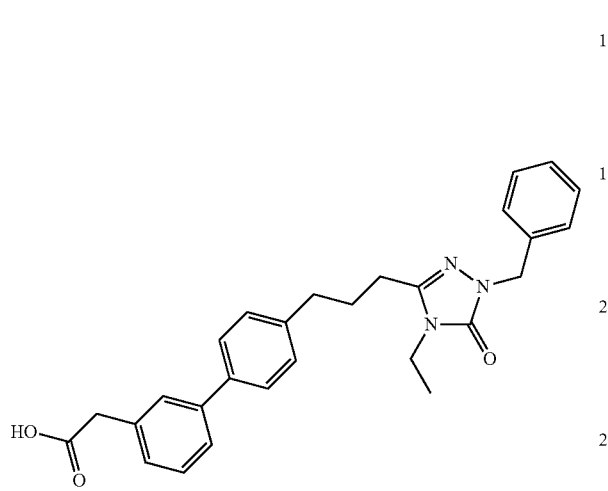

Prepared in an analogous manner to example 22 using benzyl bromide as the electrophile in step 2. LC-MS: 456 (M+H)+.

Example 24

2-(4'-(3-(4-Ethyl-5-oxo-1-(4-(trifluoromethyl)benzyl)-4,5-dihydro-1H-1,2,4-triazol-3-yl)propyl)-[1,1'-biphenyl]-3-yl)acetic acid

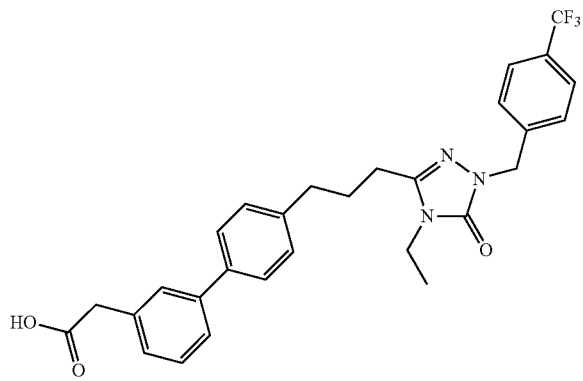 [SMILES: CCn1c(CCCc2ccc(-c3cccc(CC(=O)O)c3)cc2)nn(Cc2ccc(C(F)(F)F)cc2)c1=O]

Prepared in an analogous manner to example 22 using 4-trifluorobenzyl bromide as the electrophile in step 2. LC-MS: 524 (M+H)+.

Example 25 tert-Butyl (2-(4-(3-(1-(4-(tert-butyl)benzyl)-4-ethyl-5-oxo-4,5-dihydro-1H-1,2,4-triazol-3-yl)propyl)phenyl)oxazol-4-yl)carbamate

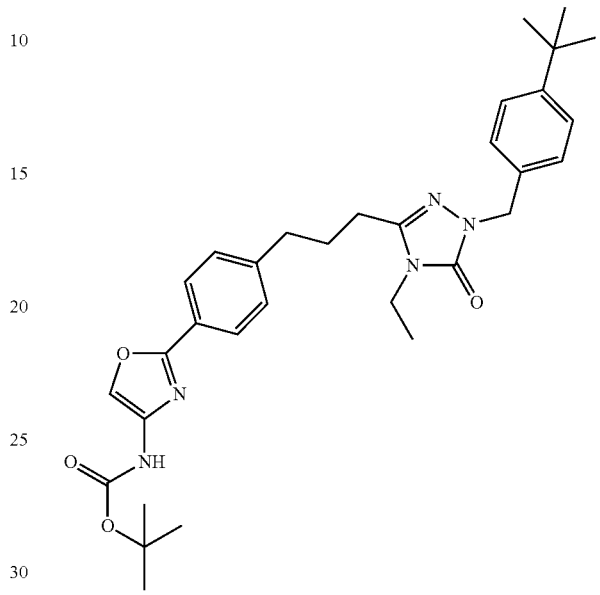

Step 1;

A mixture of 3-(3-(4-bromophenyl)propyl)-1-(4-(tert-butyl)benzyl)-4-ethyl-1H-1,2,4-triazol-5(4H)-one (2.2 g, 4.37 mmol), ethyl-2-bromooxazole-4-carboxylate (1.15 g, 5.24 mmol, 1.2 eq) and potassium carbonate (1.81 g, 13.11 mmol, 3 eqv) were dissolved in DME (12 mL) and $H_2O$ (6 mL). To this was then added tetrakis(triphenylphosphine)palladium (0) (505 mg, 0.437 mmol, 0.1 eq) and the resulting mixture was stirred at 85° C. under an atmosphere of $N_2$ for 24 hrs. The reaction mixture was cooled to room temperature and the solvent was removed in vacuo. The crude material thus obtained was then partitioned between water and ethyl acetate. The aqueous layer was separated and back-extracted with ethyl acetate (3×20 mL). The combined organic extracts were then dried over anhydrous $Na_2SO_4$, filtered and the filtrate concentrated in vacuo. The crude product thus obtained was purified on flash column chromatography (silica gel, 0-70% EtOAc/Hexanes) to afford ethyl 2-(4-(3-(1-(4-(tert-butyl)benzyl)-4-ethyl-5-oxo-4,5-dihydro-1H-1,2,4-triazol-3-yl)propyl)phenyl) oxazole-4-carboxylate (1.82 g, 82%) as a white foam.

Step 2;

To a stirred solution of ethyl 2-(4-(3-(1-(4-(tert-butyl)benzyl)-4-ethyl-5-oxo-4,5-dihydro-1H-1,2,4-triazol-3-yl)propyl)phenyl) oxazole-4-carboxylate (1.82 g, 3.48 mmol) in THF (4 mL), water (4 mL) and methanol (4 mL) was added lithium hydroxide (56 mg, 13.92 mmol, 4 eq). The resulting mixture was stirred at 60° C. for 13 hrs. After cooling to room temperature, the mixture was diluted with saturated ammonium chloride and ethyl acetate. The aqueous layer was separated and back-extracted with ethyl acetate (2×20 mL). The combined organic extracts were dried over anhydrous $Na_2SO_4$, filtered and the filtrate concentrated in vacuo. The crude product thus obtained was used directly in the next step without further purification.

Step 3;

A mixture of 2-(4-(3-(1-(4-(tert-butyl)benzyl)-4-ethyl-5-oxo-4,5-dihydro-1H-1,2,4-triazol-3-yl)propyl)phenyl)oxazole-4-carboxylic acid (1.6 g, 3.28 mmol), triethylamine (550 µL, 3.94 mmol, 1.2 eq) and diphenylphosphoryl azide (830 µL, 3.61 mmol, 1.1 eq) were dissolved in t-butanol (11 mL). The resulting mixture was stirred at reflux under an atmosphere of $N_2$ for 18 hrs. The reaction mixture was then cooled to room temperature and diluted with water and ethyl acetate. The aqueous layer was separated and back-extracted with ethyl acetate (2×30 mL). The combined organic extracts were dried over anhydrous $Na_2SO_4$, filtered and the filtrate concentrated in vacuo. The crude product thus obtained was purified further by way of flash column chromatography (silica gel, 0-80% EtOAc/Hexanes) to afford the title compound as a white solid (403 mg, 22%). LC-MS: 560 $(M+H)^+$.

Example 26

2-(4'-(3-(1-(4-Cyclohexylbenzyl)-4-ethyl-5-oxo-4,5-dihydro-1H-1,2,4-triazol-3-yl)propyl)-[1,1'-biphenyl]-3-yl)acetic acid

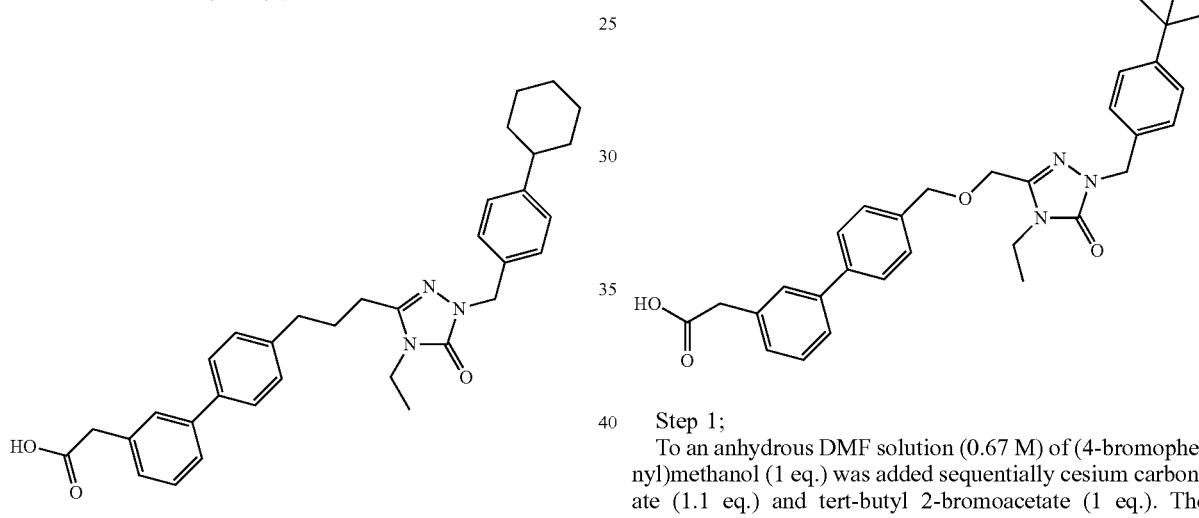

Step 1;

Under a nitrogen atmosphere, $K_2CO_3$ (0.056 g, 0.41 mmol), 2-(cyclohex-1-en-1-yl)-4,4,5,5-tetramethyl-1,3,2-dioxaborolane (0.039 g, 0.19 mmol), ethyl 2-(4'-(3-(1-(4-bromobenzyl)-4-ethyl-5-oxo-4,5-dihydro-1H-1,2,4-triazol-3-yl)propyl)-[1,1'-biphenyl]-3-yl)acetate (0.076 g, 0.14 mmol), DME (4 mL) and water (2 mL) were combined. The reaction mixture was purged with nitrogen for several minutes before $Pd(PPh)_4$ (0.016 g, 0.014 mmol) was added. The resulting mixture was stirred under nitrogen at 85° C. for 16 hrs. The solution was then cooled to rt and diluted with EtOAc and a 10% brine/90% water solution. The organic layer was separated, washed once more with water, and concentrated in vacuo. The crude ethyl 2-(4'-(3-(1-(4-(cyclohex-1-en-1-yl)benzyl))-4-ethyl-5-oxo-4,5-dihydro-1H-1,2,4-triazol-3-yl)propyl)-[1,1'-biphenyl]-3-yl)acetate (0.10 g) thus obtained was immediately taken on to the next step.

Step 2;

A solution of ethyl 2-(4'-(3-(1-(4-(cyclohex-1-en-1-yl)benzyl))-4-ethyl-5-oxo-4,5-dihydro-1H-1,2,4-triazol-3-yl)propyl)-[1,1'-biphenyl]-3-yl)acetate (0.10 g, 0.10 mmol) in EtOAc (3 mL) and MeOH (3 mL) was purged with nitrogen and then added 10% Pd/C (dry) (0.10 g, 100% wt/wt) in one rapid portion. Thereafter, the reaction vessel was purged with hydrogen gas and stirred under an atmosphere of hydrogen for 16 hrs. The reaction was quenched with DCM, filtered through a celite plug and the filtrate thus obtained was concentrated in vacuo. The residue thus obtained was dissolved in THF (2 mL) and MeOH (2 mL), to which was then added water (1 mL) and LiOH (0.043 g, 1.77 mmol). The resulting mixture was stirred at 60° C. for 16 hrs. The solvents were evaporated and the residue partitioned between DCM and 0.5 M aq. HCl. The organic phase was separated, concentrated in vacuo and the resulting residue was purified by preparatory TLC using 10% MeOH/DCM as eluent to afford 0.028 g of the title compound (39% yield) as a white foam. LC-MS: 538 $(M+H)^+$.

Example 27

2-(4'(((1-(4-(tert-Butyl)benzyl)-4-ethyl-5-oxo-4,5-dihydro-1H-1,2,4-triazol-3-yl) methoxy)methyl)-[1,1'-biphenyl]-3-yl)acetic acid

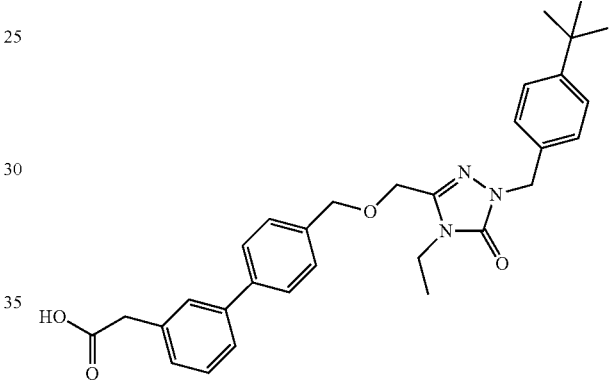

Step 1;

To an anhydrous DMF solution (0.67 M) of (4-bromophenyl)methanol (1 eq.) was added sequentially cesium carbonate (1.1 eq.) and tert-butyl 2-bromoacetate (1 eq.). The resulting suspension was allowed to stir at RT for 16 hrs. The reaction was then diluted with ether and carefully quenched with 1 N aq. HCl. The organic layer was separated and washed further with water and brine. The organic extract was then dried over sodium sulfate and filtered. Concentration of the filtrate in vacuo afforded the crude reaction product as a viscous oil. Further purification by way of column chromatography ($SiO_2$, gradient elution, Hex to 3:7 (v/v) Hex: EtOAc) afforded tert-butyl 2-((4-bromobenzyl)oxy)acetate as a colorless oil (44% yield). LC-MS: 301, 303 $(M+H)^+$.

Step 2;

To a dichloromethane solution (0.13 M) of tert-butyl 2-((4-bromobenzyl)oxy)acetate (1 eq) was added dropwise at RT trifluoroacetic acid (10 eq.). The resulting solution was stirred at RT for 18 hrs. The volatiles were then removed in vacuo and the resulting residue was triturated in 1:1 (v/v) ether: hexanes to furnish 2-((4-bromobenzyl)oxy)acetic acid as a white solid (75% yield). LC-MS: 243, 245 $(M-H)^-$.

Step 3;

2-((4-Bromobenzyl)oxy)acetic acid (1 eq), 1-(4-(tert-butyl)benzyl)-N-ethylhydrazinecarboxamide monomethanesulfonate (1.2 eq., prepared according to published procedure found in Braden, T. M. et al., *Org. Process Res. Dev.*

2007, 11, p. 431-440) and 2-(7-aza-1H-benzotriazole-1-yl)-1,1,3,3-tetramethyluronium hexafluorophosphate (1.3 eq.) were combined in anhydrous DMF (0.073 M). To the reaction solution was then added Hunig's base (2.6 eq.) and the resulting yellow solution was allowed to stir at RT for 14 hrs. The reaction mixture was then quenched with ether and 1 N aq. HCl. The organic extract was separated and washed further with 1 N aq. NaOH, water and brine. The organic extract was then dried over sodium sulfate and filtered. Concentration of the filtrate in vacuo afforded the crude reaction product as a white semi-solid. Further purification by way of column chromatography (SiO$_2$, gradient elution, 4:1 (v/v) Hex: EtOAc to EtOAc) afforded 2-(2-((4-bromobenzyl)oxy)acetyl)-1-(4-(tert-butyl)benzyl)-N-ethylhydrazinecarboxamide as a white solid (41% yield). LC-MS: 476, 478 (M+H)$^+$.

Step 4;

To an EtOAc solution (0.075 M) of 2-(2-((4-bromobenzyl)oxy)acetyl)-1-(4-(tert-butyl)benzyl)-N-ethylhydrazinecarboxamide (1 eq.) was added camphorsulfonic acid (1 eq.) and the resulting solution was heated at 80° C. for 16 hrs. The volatiles were then removed in vacuo and the crude product thus obtained was subjected to purification by way of column chromatography (SiO$_2$, gradient elution, 4:1 (v/v) Hex: EtOAc to EtOAc). 3-(((4-Bromobenzyl)oxy)methyl)-1-(4-(tert-butyl)benzyl)-4-ethyl-1H-1,2,4-triazol-5(4H)-one was isolated as a colorless, viscous oil (85% yield). LC-MS: 458, 460 (M+H)$^+$.

Step 5;

To a DME solution (0.1 M) of 3-((4-bromobenzyl)oxy)methyl)-1-(4-(tert-butyl)benzyl)-4-ethyl-1H-1,2,4-triazol-5(4H)-one (1 eq.) was added Pd$_2$dba$_3$ (0.025 eq.), dicyclohexyl(2',6'-dimethoxybiphenyl-2-yl)phosphine (0.2 eq.), and ethyl 2-(3-(4,4,5,5-tetramethyl-1,3,2-dioxaborolan-2-yl)phenyl acetate (1 eq.). The resulting solution was sub-surface purged with nitrogen gas for 15 min before 0.3 M aq. potassium phosphate (4 eq.) was added. The reaction vessel was sealed and heated at 110° C. for 16 hrs. The reaction mixture was then cooled to RT, diluted with EtOAc and washed sequentially with 1 N aq. HCl, water and finally brine. The organic extract was then dried over sodium sulfate and filtered. Concentration of the filtrate in vacuo afforded a yellow oil. This was then taken up in anhydrous ethanol (0.05 M) and added concentrated sulfuric acid (0.5 eq.). The resulting solution was stirred at RT for 4 hrs. The volatiles were then removed in vacuo and the resulting residue was partitioned between ether and water. The organic extract was separated and washed sequentially with sat. aq. NaHCO$_3$, water and brine. The organic extract was then dried over sodium sulfate and filtered. Concentration of the filtrate in vacuo afforded a yellow oil. Further purification by way of column chromatography (SiO$_2$, gradient elution, 9:1 (v/v) Hex: EtOAc to EtOAc) afforded ethyl 2-(4'-(((1-(4-(tert-butyl)benzyl)-4-ethyl-5-oxo-4,5-dihydro-1H-1,2,4-triazol-3-yl)methoxy)methyl)-[1,1'-biphenyl]-3-yl)acetate as a pale yellow oil (71% yield). LC-MS 542: (M+H)$^+$.

Step 6;

To a 2:1 (v/v) solution of THF and methanol (0.07 M) of ethyl 2-(4'-(1-(4-(tert-butyl)benzyl)-4-ethyl-5-oxo-4,5-dihydro-1H-1,2,4-triazol-3-yl)methoxy)methyl)-[1,1'-biphenyl]-3-yl)acetate (1 eq.) was added 2 N aq. lithium hydroxide (3 eq.). The resulting solution was stirred at RT for 14 hrs. The volatiles were then removed in vacuo and the resulting residue was partitioned between EtOAc and 1 N aq. HCl. The organic extract was separated and then washed sequentially with water and brine. The organic extract was then dried over sodium sulfate and filtered. Concentration of the filtrate in vacuo afforded the title compound as a white solid (71% yield). LC-MS: 514 (M+H)$^+$.

Example 28

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-2,2-difluoroacetic acid

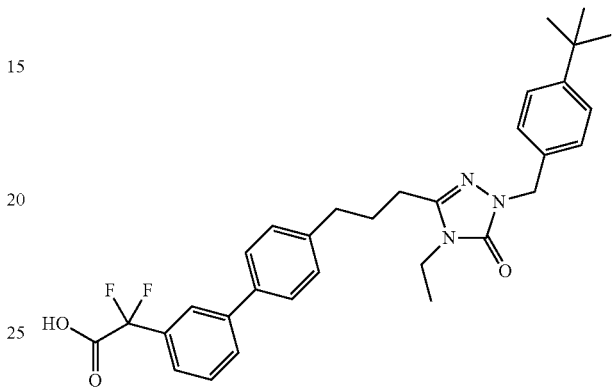

Step 1;

To an anhydrous THF solution (0.5 M) of methyl 2-(3-bromophenyl)acetate (1 eq.) was added, at −78° C., sodium hexamethyldisilazide (2.2 eq., 1 M THF solution) dropwise over a period of 5 min. The resulting pale yellow solution was stirred at −78° C. for 20 min before N-fluoro-N-(phenylsulfonyl)-benzenesulfonamide (2.2 eq., 0.5 M THF solution) was added dropwise over a period of 10 min After 3.5 hrs, the reaction mixture was quenched carefully with the dropwise addition of 1 N aq. HCl. The aqueous layer was separated and back-extracted with ether. The combined organic extracts were then washed sequentially with 10% aq. NaHCO$_3$, water and brine. The organic extract was dried over sodium sulfate and filtered. Concentration of the filtrate in vacuo afforded a pale yellow semi-solid. This was then briefly sonicated in 1:1 (v/v) hexanes and ether. The resulting suspension was then filtered through a bed of celite and the filtrate was concentrated in vacuo to afford methyl 2-(3-bromophenyl)-2,2-difluoroacetate as a yellow oil (98% yield).

Step 2:

To a DME solution (0.2 M) of 1-(4-(tert-butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one (1 eq.) was added Pd$_2$dba$_3$ (0.025 eq.), dicyclohexyl(2',6'dimethoxybiphenyl-2-yl)phosphine (0.2 eq.), and methyl 2-(3-bromophenyl)-2,2-difluoroacetate (1 eq.). The resulting solution was sub-surface purged with nitrogen gas for 15 min before 0.3 M aq. potassium phosphate (4 eq.) was added. The reaction vessel was sealed and heated at 110° C. for 16 hrs. The reaction mixture was then cooled to RT, diluted with ether and washed sequentially with 1 N aq. HCl, water and finally brine. The organic extract was then dried over sodium sulfate and filtered. Concentration of the filtrate in vacuo afforded a yellow oil. Further purification by way of column chromatography (SiO$_2$, gradient elution, 4:1 (v/v) Hex: EtOAc to EtOAc) afforded the title compound as a pale yellow foam (18% yield). LC-MS: 546 (M−H)$^−$.

Example 29

3-(3-(3'-(1H-Tetrazol-5-yl)-[1,1'-biphenyl]-4-yl)propyl)-1-(4-(tert-butyl)benzyl)-4-ethyl-1H-1,2,4-triazol-5(4H)-one

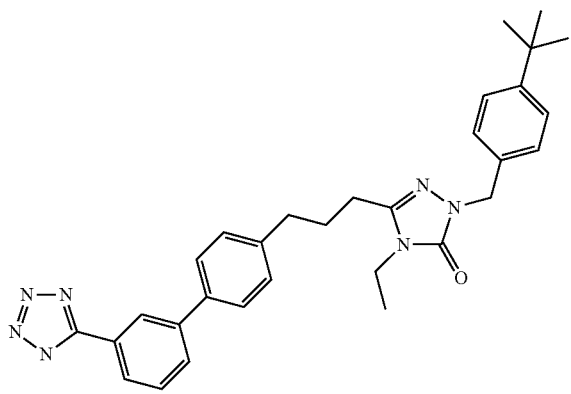 [SMILES: CCn1c(CCCc2ccc(-c3cccc(-c4nnn[nH]4)c3)cc2)nn(Cc2ccc(C(C)(C)C)cc2)c1=O]

To a DME solution (0.1 M) of 3-(3-(4-bromophenyl)propyl)-1-(4-tert-butyl)benzyl)-4-ethyl-1H-1,2,4-triazol-5 (4H)-one (1 eq.) was added Pd₂dba₃ (0.025 eq.), dicyclohexyl(2',6'dimethoxybiphenyl-2-yl)phosphine (0.2 eq.), and (3-(1H-tetrazol-5-yl)phenyl)boronic acid (1 eq.). The resulting solution was sub-surface purged with nitrogen gas for 15 min before 0.3 M aq. potassium phosphate (4 eq.) was added. The reaction vessel was sealed and heated at 110° C. for 16 h. The reaction mixture was then cooled to RT, diluted with EtOAc and washed sequentially with 1 N aq. HCl, water and finally brine. The organic extract was then dried over sodium sulfate and filtered. Concentration of the filtrate in vacuo afforded an orange solid. Further purification by way of column chromatography ($C_{18}$-reverse phase, gradient elution, 9:1 (v/v) $H_2O$: MeCN+0.1% TFA to MeCN+0.1% TFA) afforded the title compound as a white solid (11% yield). LC-MS: 520 (M–H)⁻.

Example 30

2-(4'-(2-((1-(4-(tert-butyl)benzyl)-4-ethyl-5-oxo-4,5-dihydro-1H-1,2,4-triazol-3-yl)methyl)cyclopropyl)-[1,1'-biphenyl]-3-yl)acetic acid

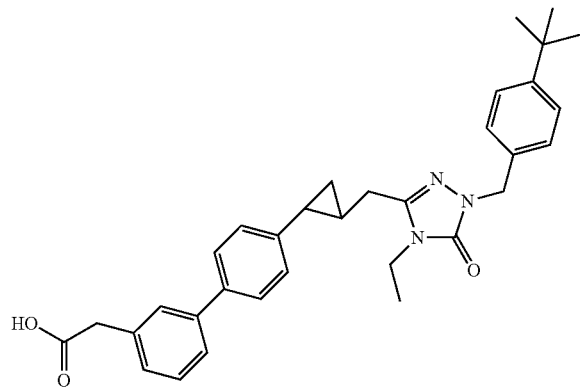 [SMILES: CCn1c(CC2CC2c2ccc(-c3cccc(CC(=O)O)c3)cc2)nn(Cc2ccc(C(C)(C)C)cc2)c1=O]

Step 1;

To a solution of (E)-ethyl 3-(4-bromophenyl)acrylate (10.0 g, 39.2 mmol) in THF (150 mL) was slowly added at –78° C. a solution of DIBAl—H (86 mL of 1M solution in hexanes, 86.0 mmol). The resulting solution was then allowed to slowly warm to 0° C., after which a further 10 mL of DIBAl—H solution was added. TLC analysis indicated complete reaction and the mixture was re-cooled to –78° C. MeOH was then slowly added to quench the remaining reducing agent and the mixture allowed to warm back to rt over 30 minutes. The resulting mixture was poured into a saturated aqueous solution of Rochelle's salt and then extracted with EtOAc. The organic phase was separated, dried (MgSO₄), filtered and the filtrate concentrated in vacuo. The crude product thus obtained was purified on silica eluting with a gradient of 0 to 35% EtOAc in hexanes to afford 6.0 g (71%) of (E)-3-(4-bromophenyl)prop-2-en-1-ol.

Step 2;

To a solution of diethylzinc (1.0M; 9.4 mL, 9.4 mmol) in anhydrous DCE (30 mL) at –23° C. was added iodochloromethane (1.37 mL, 18.7 mmol) and the resulting mixture was maintained at –23° C. for 20 minutes. (E)-3-(4-Bromophenyl)prop-2-en-1-ol (1.0 g, 4.7 mmol) was then added as a solution in DCE (20 mL) dropwise after which the reaction was allowed to stir at –23° C. for another hr. The mixture was carefully quenched with saturated ammonium chloride solution and extracted with DCM. The combined organic extracts were dried (MgSO₄), filtered and the filtrate concentrated in vacuo. The residue thus obtained was purified on silica gel eluting with a gradient of 0 to 30% EtOAc in hexanes to afford the (2-(4-bromophenyl)cyclopropyl) methanol (862 mg, 81%).

Step 3;

To an ice-cooled solution of (2-(4-bromophenyl)cyclopropyl)methanol (850 mg, 3.74 mmol) in DCM (15 mL) was added methanesulfonyl chloride (330 µL; 4.3 mmol) and Et₃N (1 mL, 7.2 mmol). After stirring at room temperature for 1 hr, the reaction mixture was diluted with DCM and washed with saturated aqueous sodium bicarbonate solution. The organic phase was separated, dried (MgSO₄), filtered and the filtrate was partially concentrated in vacuo until about 5 mL of solvent remained. To this mixture was added 7 mL of DMF before the remaining DCM was evaporated in vacuo. Finally, potassium cyanide (487 mg, 7.4 mmol) was added and the reaction solution was stirred for 12 hrs at 60° C. The mixture was diluted with EtOAc and washed with water. The organic extract was then separated, dried (MgSO₄), filtered and the filtrate concentrated in vacuo. The residue thus obtained was purified on silica gel eluting with a gradient of 0 to 20% EtOAc in hexanes to afford 2-(2-(4-bromophenyl)cyclopropyl)acetonitrile contaminated with approx 10% of the ring opened nitrile.

Step 4;

To a solution of 2-(2-(4-bromophenyl)cyclopropyl)acetonitrile (800 mg, 3.39 mmol) in EtOH (6 mL) and water (1 mL) was added potassium hydroxide (400 mg, 7.1 mmol). The reaction vessel was then sealed and heated to 85° C. until complete conversion to the acid as judged by LC-MS analysis (~24 hrs). The reaction mixture was diluted with EtOAc and acidified with 1N HCl until an aqueous pH of ~2 was attained. The organic phase was then separated, washed further with water, dried (MgSO$_4$), and filtered. Concentration of the filtrate in vacuo afforded 2-(2-(4-bromophenyl)cyclopropyl)acetic acid as a viscous oil.

Step 5;

To a solution of 2-(2-(4-bromophenyl)cyclopropyl)acetic acid (623 mg, 2.44 mmol) in THF (10 mL) was first added carbonyldiimidazole (475 mg, 2.93 mmol) and then, after stirring for 2 hrs, hydrazine monohydrate (500 µL, ~4 eq.). After another 1 hr of stirring at RT, the solvent was removed in vacuo. The residue was taken up in EtOAc, washed with water, dried (MgSO$_4$), and filtered. Concentration of the filtrate in vacuo afforded 2-(2-(4-bromophenyl)cyclopropyl) acetohydrazide as a viscous oil.

Step 6;

To a solution of 2-(2-(4-bromophenyl)cyclopropyl)acetohydrazide (2.44 mmol) in THF (10 mL) was added ethyl isocyanate (230 µL, 2.90 mmol). After 1 hr at RT, the solvent was evaporated in vacuo to afford 2-(2-(2-(4-bromophenyl) cyclopropyl)acetyl)-N-ethylhydrazinecarboxamide as a pink solid.

Step 7:

The hydrazine carboxamide from step 6 (2.44 mmol) was dissolved in MeOH (10 mL) and added potassium hydroxide (500 mg). The resulting mixture was heated at reflux for 12 hrs. After completion of reaction, the solvent was removed in vacuo and the residue thus obtained was partitioned between DCM and 1N HCl. The organic extract was then separated, dried (MgSO$_4$), filtered and filtrate concentrated in vacuo. The residue was purified on silica gel eluting with 100% EtOAc to afford 3-((2-(4-bromophenyl)cyclopropyl) methyl)-4-ethyl-1H-1,2,4-triazol-5(4H)-one as a colorless solid.

Step 8;

To a solution of 3-((2-(4-bromophenyl)cyclopropyl) methyl)-4-ethyl-1H-1,2,4-triazol-5(4H)-one (444 mg, 1.35 mmol) in DMF (3 mL) was added potassium carbonate (764 mg, 5.5 mmol) and 4-(tert-butyl)benzylbromide (280 µL, 1.52 mmol). The mixture was heated at 45° C. until the reaction was judged to be complete by LC-MS analysis (~3 hrs). The mixture was partitioned between EtOAc and water. The organic phase was separated, washed further with water, dried (MgSO$_4$), filtered and the filtrate concentrated in vacuo. The residue was purified on silica gel eluting with a gradient of 0 to 60% EtOAc in hexanes to afford 3-((2-(4-bromophenyl)cyclopropyl)methyl)-1-(4-(tert-butyl)benzyl)-4-ethyl-1H-1,2,4-triazol-5(4H)-one. This could then be coupled in an analogous fashion as example 1 to afford the title compound as a white solid. LC-MS: 524 (M+H)$^+$.

Example 31

2-(4'-(3-(1-(4-(tert-Butyl)benzyl)-4-isopropyl-5-oxo-4,5-dihydro-1H-1,2,4-triazol-3-yl)propyl)-[1,1'-biphenyl]-3-yl)acetic acid Prepared in an analogous fashion to example 1, but employing 3-(3-(4-bromophenyl)propyl)-1-(4-(tert-butyl)benzyl)-4-isopropyl-1H-1,2,4-triazol-5(4H)-one as the coupling partner in step 1. LC-MS: 526 (M+H)$^+$.

Example 32

2-(4'-(3-(1-(4-(tert-Butyl)benzyl)-5-oxo-4-phenyl-4,5-dihydro-1H-1,2,4-triazol-3-yl)propyl)-[1,1'-biphenyl]-3-yl)acetic acid Prepared in an analogous fashion to example 1, but employing 3-(3-(4-bromophenyl)propyl)-1-(4-(tert-butyl)benzyl)-4-phenyl-1H-1,2,4-triazol-5(4H)-one as the coupling partner in step 1. LC-MS: 560 (M+H)$^+$.

Example 33

2-(4'-(3-(1-(4-(tert-Butyl)benzyl)-4-ethyl-5-oxo-4,5-dihydro-1H-1,2,4-triazol-3-yl)propyl)-4-fluoro-[1,1'-biphenyl]-3-yl)acetic acid

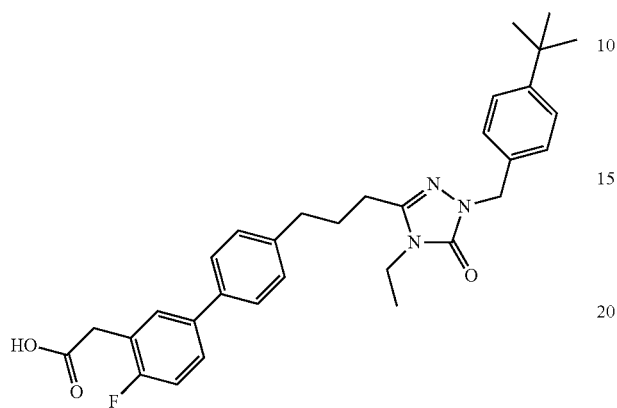

Prepared in an analogous manner to example 13, step 1 using ethyl 2-(5-bromo-2-fluorophenyl)acetate as coupling partner. Hydrolysis of the intermediate ester was carried out as in example 1, step 2. LC-MS: 530 (M+H)$^+$.

Example 34

3-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)acrylic acid

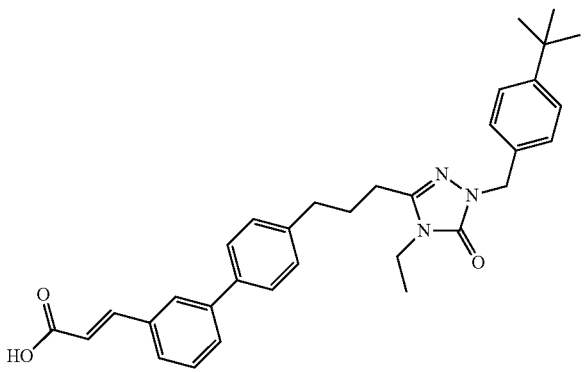 [SMILES: CCn1c(CCCc2ccc(-c3cccc(/C=C/C(=O)O)c3)cc2)nn(Cc2ccc(C(C)(C)C)cc2)c1=O]

To a DME solution (0.07 M) of 1-(4-(tert-butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one (1 eq.) was added Pd$_2$dba$_3$ (0.025 eq.), dicyclohexyl(2',6'dimethoxybiphenyl-2-yl)phosphine (0.2 eq.), and (E)-3-(3-bromophenyl) acrylic acid (1 eq.). The resulting solution was sub-surface purged with nitrogen gas for 10 min before 0.3 M aq. potassium phosphate (4 eq.) was added. The reaction vessel was sealed and heated at 110° C. for 16 h. The reaction mixture was then cooled to RT, diluted with EtOAc and washed sequentially with 1 N aq. HCl, water and finally brine. The organic extract was then dried over sodium sulfate and filtered. Concentration of the filtrate in vacuo afforded a viscous, orange oil. Further purification by way of column chromatography (C$_{18}$-reverse phase, gradient elution, 9:1 (v/v) H$_2$O: MeCN+0.1% TFA to MeCN+0.1% TFA) afforded the title compound as a pale yellow foam (73% yield). LC-MS: 522 (M−H)$^-$.

Example 35

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)cyclopropanecarboxylic acid

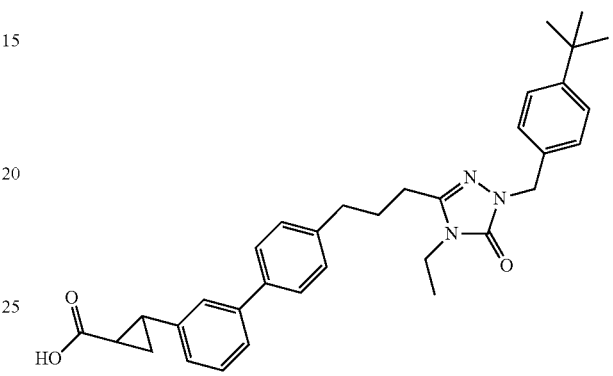

Step 1;

To an ethanol solution (0.8 M) of (E)-3-(3-bromophenyl) acrylic acid (1 eq.) was added concentrated sulfuric acid (4.7 eq.). The resulting solution was allowed to stir at RT for 6 hrs. The volatiles were then removed in vacuo and the resulting residue was partitioned between ether and 1N aq. NaOH. The organic layer was separated, washed further with water then brine, and dried over sodium sulfate. Filtration and concentration of the filtrate in vacuo furnished (E)-ethyl 3-(3-bromophenyl)acrylate as a colorless oil (53% yield).

Step 2;

To an anhydrous DMSO solution (0.3 M) of trimethylsulfoxonium iodide (1.8 eq.) was added at RT sodium hydride (1.7 eq., 60% dispersion in paraffin oil) in one rapid portion. The resulting suspension was allowed to stir at RT for 1.5 hrs during which time the reaction mixture became yellow in color. Then, (E)-ethyl 3-(3-bromophenyl)acrylate (1 eq.) was added and the resulting mixture was heated at 60° C. for 14 hrs. The now orange solution was cooled to RT and diluted with ether. This was then washed sequentially with 1 N aq. HCl, 1 N aq. NaOH, water and brine. The organic layer was dried over sodium sulfate and filtered. Concentration of the filtrate in vacuo furnished a viscous, red oil that was then subjected to purification by way of column chromatography (SiO$_2$, gradient elution, Hex to 3:7 (v/v) Hex: EtOAc). Ethyl 2-(3-bromophenyl)cyclopropanecarboxylate was isolated as a colorless oil (20% yield). LC-MS: 269, 271 (M+H)$^+$.

Step 3;

To a DME solution (0.045 M) of 1-(4-(tert-butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one (1 eq.) was added Pd$_2$dba$_3$ (0.025 eq.), dicyclohexyl(2',6'dimethoxybiphenyl-2-yl)phosphine (0.2 eq.), and ethyl 2-(3-bromophenyl)cyclopropanecarboxylate (1 eq). The resulting solution was sub-surface purged with nitrogen gas for 10 min before 0.3 M aq. potassium phosphate (4 eq.) was added. The reaction vessel was sealed and heated at 110° C. for 16 hrs. The reaction mixture was then cooled to RT, diluted with EtOAc and washed sequentially with 1N aq. HCl, water and finally brine. The organic extract was then dried over sodium sulfate and filtered. Concentration of the filtrate in vacuo afforded a golden, yellow oil. This was then taken in a 2:1 (v/v) THF and methanol solution (0.1 M) and added 2 N aq. lithium hydroxide (3 eq.). The resulting solution was stirred at RT for 4 h. The volatiles were then removed in vacuo and the resulting residue was partitioned between EtOAc and 1 N aq. HCl. The organic extract was separated and then washed sequentially with water and brine. The organic extract was then dried over sodium sulfate and filtered. Concentration of the filtrate in vacuo afforded a viscous yellow oil. Further purification by way of column chromatography (SiO$_2$, gradient elution, 9:1 (v/v) Hex: EtOAc to EtOAc) afforded the title compound as a white foam (62% yield). LC-MS: 536 (M−H)$^-$.

Example 36

3-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)propanoic acid

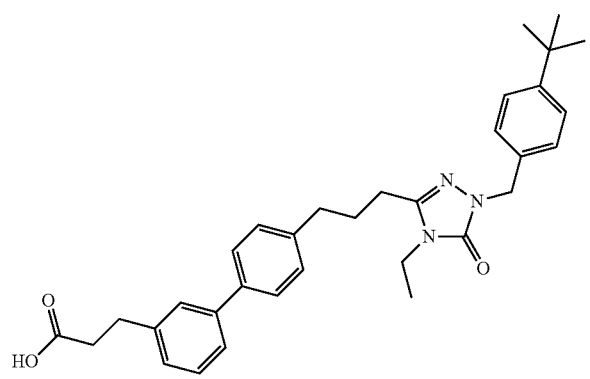

To an EtOAc solution (0.04 M) of 3-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)acrylic acid (1 eq., example 36) was added palladium over carbon (0.25 eq., 10% w/w). The reaction suspension was thrice evacuated and back-filled with nitrogen. To thus obtained deoxygenated suspension was then gently sub-surface bubbled hydrogen gas for 1.5 h. The reaction was finally quenched with the addition of dichloromethane. The suspension was then carefully filtered through a pad of dichloromethane-wetted celite and the insolubles were rinsed further with methanol, EtOAc and finally dichloromethane. Concentration of the filtrate thus obtained in vacuo afforded the title compound as a white foam (73% yield). LC-MS: 526 (M+H)$^+$.

Example 37

2-(4'-(3-(1-(4-Bromobenzyl)-4-ethyl-5-oxo-4,5-dihydro-1H-1,2,4-triazol-3-yl)propyl)-[1,1'-biphenyl]-3-yl)acetic acid

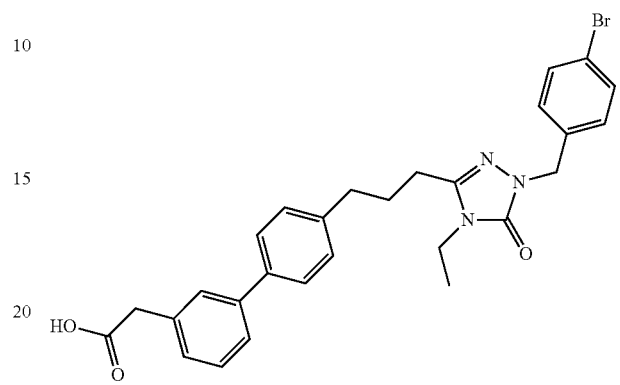

To a solution of ethyl 2-(4'-(3-(1-(4-bromobenzyl)-4-ethyl-5-oxo-4,5-dihydro-1H-1,2,4-triazol-3-yl)propyl)-[1,1'-biphenyl]-3-yl)acetate (0.143 g, 0.25 mmol, intermediate from example 24, step 2) in THF (2 mL) and MeOH (2 mL) was added water (2 mL) and LiOH (0.061 g, 2.56 mmol). The resulting mixture was stirred at 60° C. for 16 hrs. The solvents were evaporated and the residue treated with DCM and 0.25 M HCl solution. The aqueous layer was separated and back-extracted with DCM. The combined organic extracts were concentrated in vacuo and the crude material thus obtained was purified by preparatory TLC using 10% MeOH/DCM as eluent to afford 0.021 g of the title compound (15% yield) as a white foam. LC-MS: 535 (M+H)$^+$.

Example 38

2-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)acetic acid

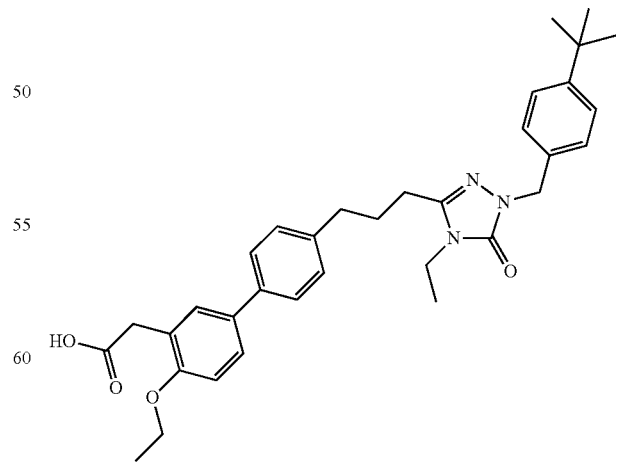

Prepared in an analogous manner to example 13, step 1 using methyl 2-(5-bromo-2-ethoxyphenyl)acetate as the

Example 39

2-(4-(4-(3-(1-(4-(tert-Butyl)benzyl)-4-ethyl-5-oxo-4,5-dihydro-1H-1,2,4-triazol-3-yl)propyl)phenyl)thiophen-2-yl)acetic acid

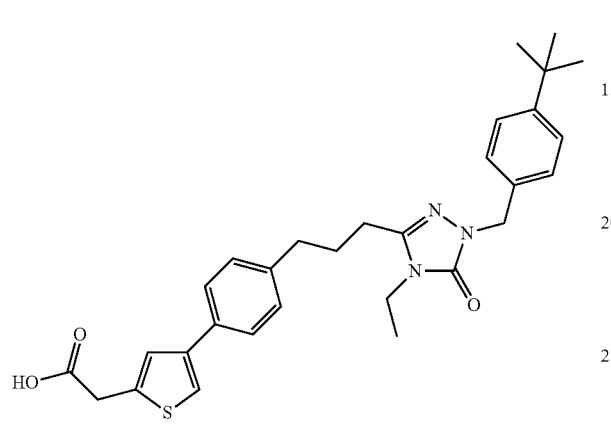

Prepared in an analogous manner to example 13, step 1 using ethyl 2-(4-bromothiophen-2-yl)acetate as the coupling partner in step 1. Hydrolysis of the intermediate ester was carried out as in example 1, step 2. LC-MS: 518 (M+H)+

Example 40

1-{[4-(tert-Butyl)phenyl]methyl}-4-ethyl-3-[3-(4-{4-[(methylsulfonyl)amino](2-pyridyl)}phenyl)propyl]-1,2,4-triazolin-5-one

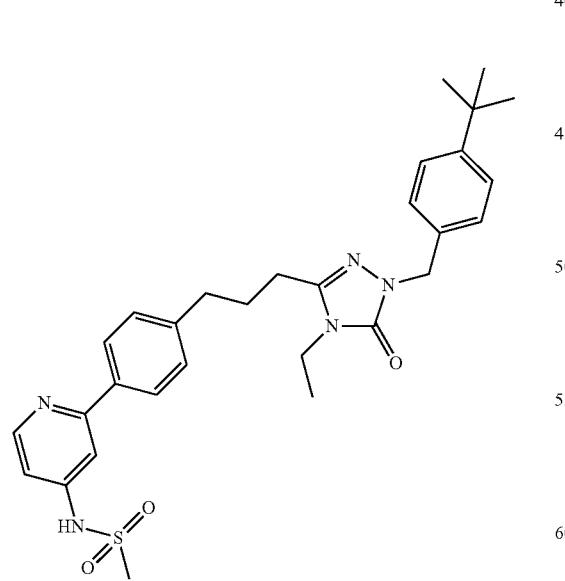

Prepared in an analogous manner to example 12, but using instead 3-(3-(4-(4-aminopyridin-2-yl)phenyl)propyl)-1-(4-(tert-butyl)benzyl)-4-ethyl-1H-1,2,4-triazol-5(4H)-one (example 11) as the starting material. LC-MS: 548 (M+H)+

Example 41

4'-(3-(1-(4-(tert-Butyl)benzyl)-4-ethyl-5-oxo-4,5-dihydro-1H-1,2,4-triazol-3-yl)propyl)-5-(trifluoromethyl)-[1,1'-biphenyl]-3-carboxylic acid

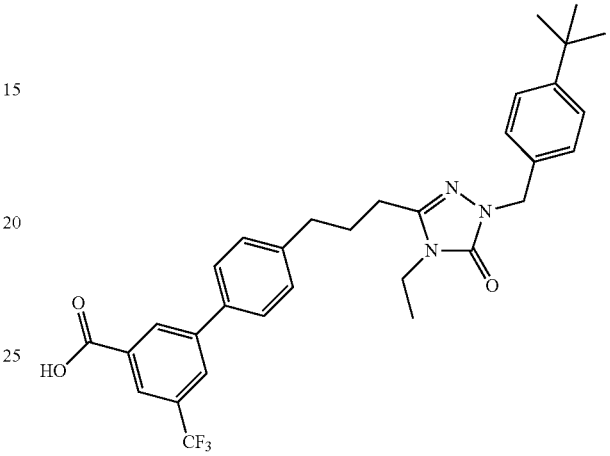

Prepared in an analogous manner to example 13 using instead ethyl 3-bromo-5-(trifluoromethyl)benzoate as the coupling partner in step 1. Hydrolysis of the intermediate ester was carried out as in example 1, step 2. LC-MS: 566 (M+H)+.

Example 42

1-{[4-(tert-Butyl)phenyl]methyl}-3-[3-(4-{6-[(cyclopropylsulfonyl)amino](2-pyridyl)}phenyl) propyl]-4-ethyl-1,2,4-triazolin-5-one

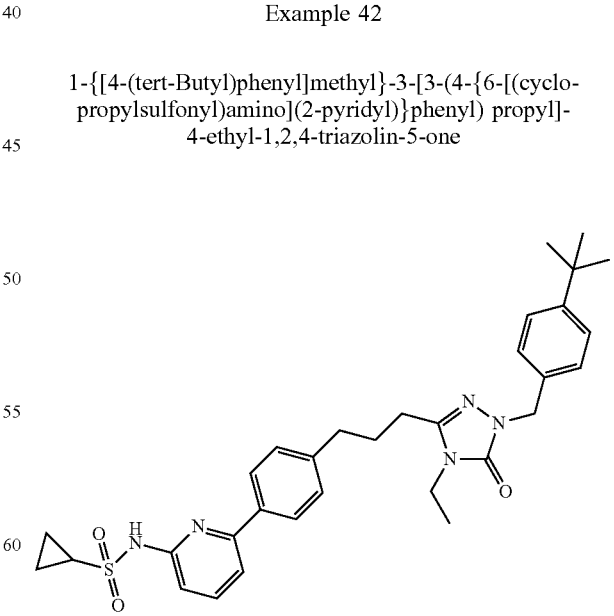

Prepared in an analogous manner to example 4 using instead cyclopropane sulfonyl chloride as the electrophile. LC-MS: 574 (M+H)+.

Example 43

2-(5-{4-[3-(1-{[4-(tert-Butyl)phenyl]methyl}-4-ethyl-5-oxo-1,2,4-triazolin-3-yl)propyl]phenyl}-2-pyridyl)acetic acid

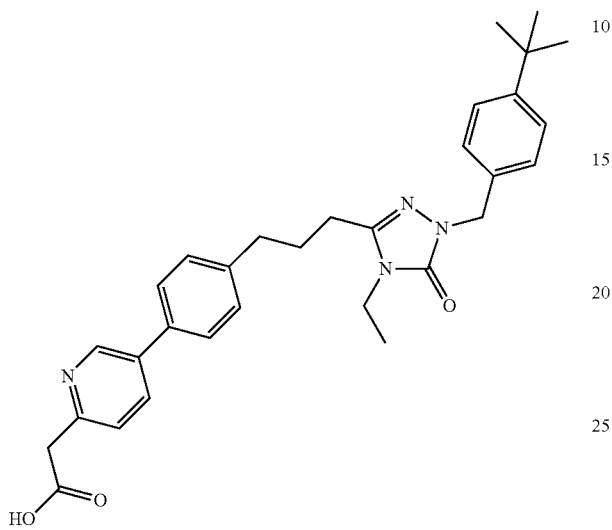

Prepared in an analogous manner to example 13 using instead ethyl 2-(5-bromopyridin-2-yl)acetate as the coupling partner in step 1. Hydrolysis of the intermediate ester was carried out as in example 1, step 2. LC-MS: 513 (M+H)$^+$.

Example 44

2-(3-{4-[3-(1-{[4-(tert-Butyl)phenyl]methyl}-4-ethyl-5-oxo-1,2,4-triazolin-3-yl)propyl]phenyl}phenyl)propanoic acid

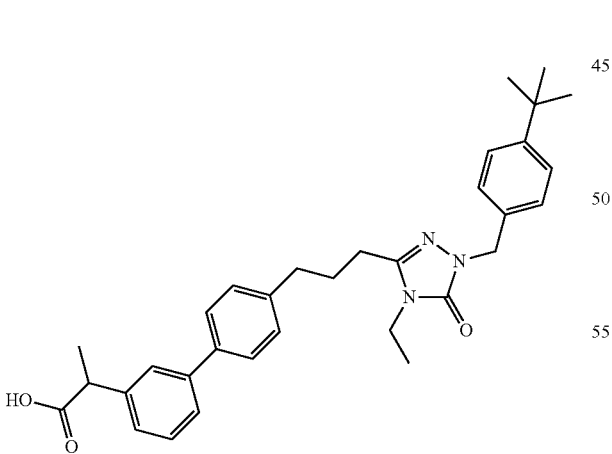

Prepared in an analogous manner to example 13 using instead ethyl 2-(3-bromophenyl)propanoate (prepared according to the procedure described in *Bioorg. Med. Chem.* 2011, 19(11), p 3299-3311) as the coupling partner in step 1. Hydrolysis of the intermediate ester was carried out as in example 1, step 2. LC-MS: 526 (M+H)$^+$.

Example 45

2-(2-{4-[3-(1-{[4-(tert-Butyl)phenyl]methyl}-4-ethyl-5-oxo-1,2,4-triazolin-3-yl)propyl]phenyl}-4-pyridyl)acetic acid

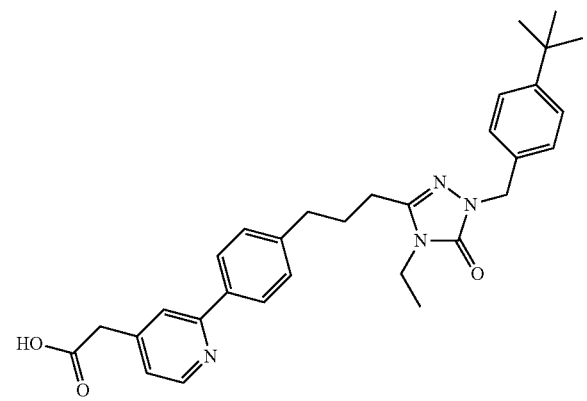

Prepared in an analogous manner to example 13 using instead ethyl 2-(2-chloropyridin-4-yl)acetate as the coupling partner in step 1. Hydrolysis of the intermediate ester was carried out as in example 1, step 2. LC-MS: 513 (M+H)$^+$.

Example 46

2-(3-{4-[3-(1-{[4-(tert-Butyl)phenyl]methyl}-4-ethyl-5-oxo-1,2,4-triazolin-3-yl)propyl]phenyl}phenyl)butanoic acid

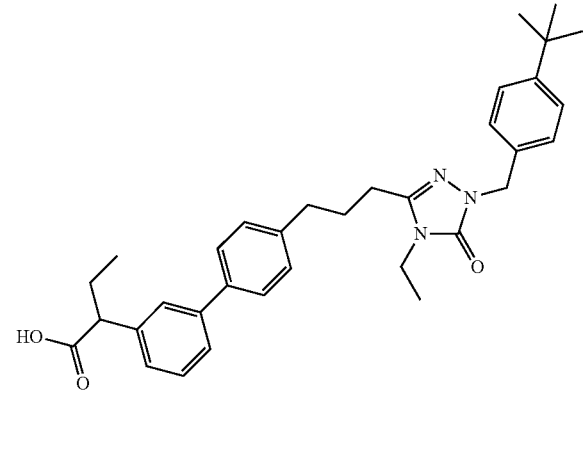 [SMILES: CCC(C(=O)O)c1cccc(-c2ccc(CCCc3nn(Cc4ccc(C(C)(C)C)cc4)c(=O)n3CC)cc2)c1]

Prepared in an analogous manner to example 13 using instead ethyl 2-(3-bromophenyl)butanoate (prepared according to the procedure described in *Bioorg. Med. Chem.* 2011, 19(11), p 3299-3311) as the coupling partner in step 1. Hydrolysis of the intermediate ester was carried out as in example 1, step 2. LC-MS: 540 (M+H)$^+$.

Example 47

2-(3-{4-[3-(1-{[4-(tert-Butyl)phenyl]methyl}-4-ethyl-5-oxo(1,2,4-triazolin-3-yl))propyl]phenyl}phenyl)-3-phenylpropanoic acid

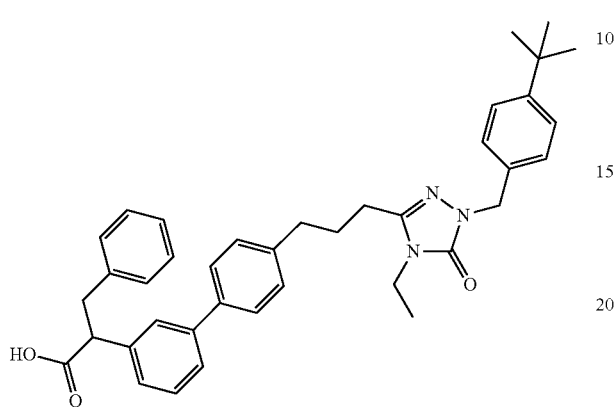

Prepared in an analogous manner to example 13 using instead ethyl 2-(3-bromophenyl)-3-phenylpropanoate (prepared according to the procedure described in *Bioorg. Med. Chem.* 2011, 19(11), p 3299-3311) as the coupling partner in step 1. Hydrolysis of the intermediate ester was carried out as in example 1, step 2. LC-MS: 602 (M+H)$^+$.

Example 48

2-(6-{4-[3-(1-{[4-(tert-Butyl)phenyl]methyl}-4-ethyl-5-oxo(1,2,4-triazolin-3-yl))propyl]phenyl}-4-(trifluoromethyl)-2-pyridyl)acetic acid

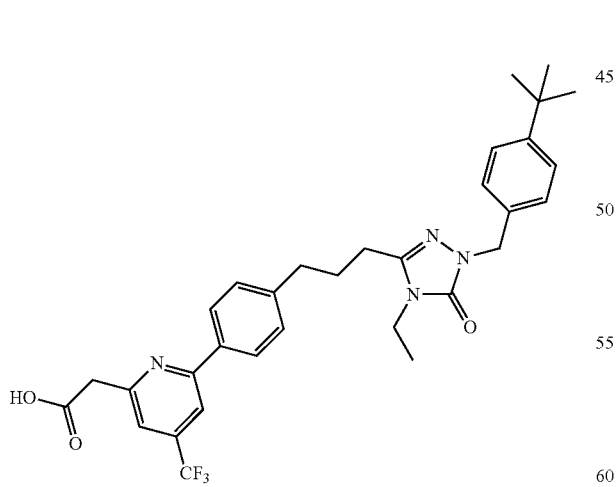

Prepared in an analogous manner to example 13 using instead ethyl 2-(6-chloro-4-(trifluoromethyl) pyridin-2-yl)acetate as the coupling partner in step 1. Hydrolysis of the intermediate ester was carried out as in example 1, step 2. LC-MS: 581 (M+H)$^+$.

Example 49

2-(4'-(3-(1-(4-(tert-Butyl)benzyl)-4-ethyl-5-oxo-4,5-dihydro-1H-1,2,4-triazol-3-yl)propyl)-4-(cyclopropylmethoxy)-[1,1'-biphenyl]-3-yl)acetic acid

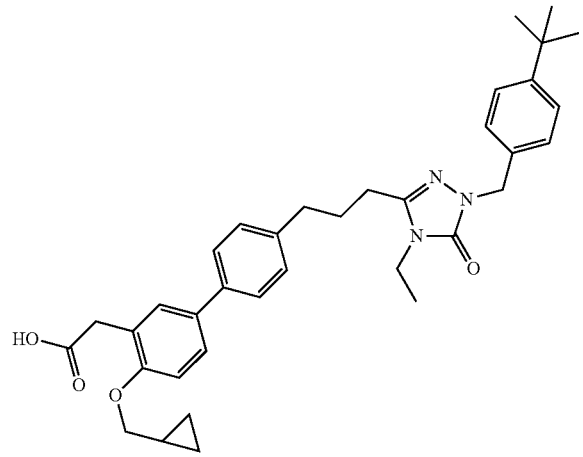 [SMILES: CCn1c(CCCc2ccc(-c3ccc(OCC4CC4)c(CC(=O)O)c3)cc2)nn(Cc2ccc(C(C)(C)C)cc2)c1=O]

Prepared in an analogous manner to example 13 using instead methyl 2-(5-bromo-2-(cyclopropylmethoxy)phenyl)acetate as coupling partner in step 1. Hydrolysis of the intermediate ester was carried out as in example 1, step 2. LC-MS: 582 (M+H)$^+$.

Example 50

2-(6-{4-[3-(1-{[4-(tert-Butyl)phenyl]methyl}-4-ethyl-5-oxo-1,2,4-triazolin-3-yl)propyl]phenyl}-2-pyridyl) acetic acid Step 1;

To a stirred a solution of diisopropylamine (5.3 mL, 37.6 mmol) in anhydrous THF (100 mL) mixture was added at −78° C. n-butyllithium (13.8 mL, 34.4 mmol, 2.5 M solution in hexanes) dropwise. The resulting mixture was stirred for 1 hr at −78° C. before 2-chloro-6-methylpyridine (3.4 mL, 31.3 mmol) and tetramethylethylenediamine (4.7 mL, 31.3 mmol) were added. The reaction mixture was then allowed to warm to 0° C. over 2 hrs. The reaction mixture was re-cooled to −78° C. before dimethyl carbonate (7.9 mL, 93.9 mmol) was added and the resulting solution was allowed to warm slowly to room temperature overnight. Reaction was quenched with the addition of saturated aq ammonium chloride and extracted with EtOAc. The combined organic extracts were washed further with water and brine, dried (Na₂SO₄), filtered and the filtrate concentrated in vacuo. The residue thus obtained was purified on silica gel eluting with a solvent gradient of 0 to 50% EtOAc in hexanes to afford methyl 2-(6-chloropyridin-2-yl)acetate.

Step 2:

Prepared in an analogous manner to example 1 using methyl 2-(6-chloropyridin-2-yl)acetate from the previous step as the coupling partner in step 1. Hydrolysis of the intermediate ester was then carried out as in example 1, step 2. LC-MS: 513 (M+H)⁺.

Example 51

2-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)-N-cyclopropyl-2-hydroxyacetamide

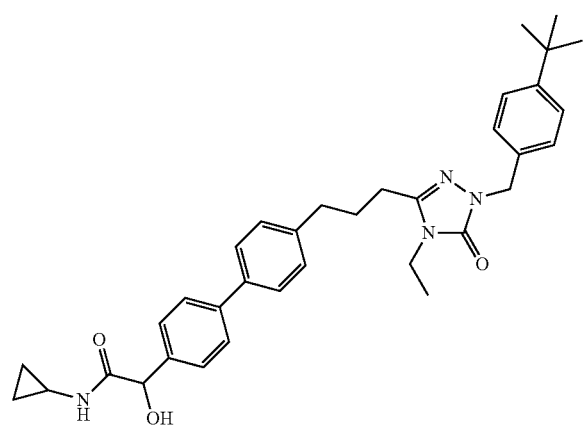 [SMILES: CCn1c(CCCc2ccc(-c3ccc(C(O)C(=O)NC4CC4)cc3)cc2)nn(Cc2ccc(C(C)(C)C)cc2)c1=O]

Step 1;

To a solution of ethyl 2-bromo-(4-bromophenyl)acetate (1 mL, 5.1 mmol) in DMF (10 mL) was added potassium acetate (750 mg, 7.6 mmol) and the resulting reaction solution was heated at 70° C. for 16 hrs. The reaction was then quenched with 10% aq. HCl and extracted with ether. The combined organic extracts were then washed further with water and brine, dried over Na₂SO₄, and filtered. Concentration of the filtrate in vacuo afforded the crude ethyl 2-acetoxy-2-(4-bromophenyl)acetate as a viscous oil.

Step 2;

To a solution of 1-(4-(tert-butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one (492 mg, 0.98 mmol) in DME (12 mL) was added Pd₂dba₃ (22 mg, 0.024 mmol), dicyclohexyl(2',6'dimethoxybiphenyl-2-yl)phosphine (80 mg, 0.196 mmol), and ethyl 2-acetoxy-2-(4-bromophenyl) acetate (441 mg, 1.47 mmol) from the previous step. The resulting solution was sub-surface purged with nitrogen gas for 10 min before 0.4 M aq. potassium phosphate (10 mL) was added. The reaction vessel was sealed and heated at 80° C. for 16 hrs. The reaction mixture was then cooled to RT, quenched with 1N aq. HCl and extracted with EtOAc. The combined organic extracts were washed further with 1N aq. HCl, water and finally brine. The organic extract was then dried over sodium sulfate, filtered and concentrated in vacuo. Purification by way of reverse-phase column chromatography (C₁₈, gradient elution, 9:1 (v/v) H₂O: MeCN+ 0.1% TFA to MeCN+0.1% TFA) afforded 2-(4'-(3-(1-(4-(tert-butyl)benzyl)-4-ethyl-5-oxo-4,5-dihydro-1H-1,2,4-triazol-3-yl)propyl)-[1,1'-biphenyl]-4-yl)-2-hydroxyacetic acid the title compound as a white foam.

Step 3:

To a solution of 2-(4'-(3-(1-(4-(tert-butyl)benzyl)-4-ethyl-5-oxo-4,5-dihydro-1H-1,2,4-triazol-3-yl)propyl)-[1,1'-biphenyl]-4-yl)-2-hydroxyacetic acid (82 mg, 0.16 mmol) in DMF (2 mL) was added cyclopropylamine (21 µL, 0.3 mmol) and HATU (75 mg, 0.2 mmol). Finally, diisopropylethylamine (52 µL, 0.3 mmol) was added and the resulting yellow solution was allowed to stir at RT for 16 hrs. The crude reaction mixture was then diluted with ether and washed sequentially with 10% aq. HCl, 1 N aq. NaOH, water and brine. The organic extract was then dried over Na₂SO₄, filtered and the filtrate concentrated in vacuo to afford the crude product as a pale yellow oil. Further purification by way of column chromatography (SiO₂, gradient elution, 9:1 (v/v) Hex: EtOAc to EtOAc) afforded the title compound as a white foam (73% yield). LC-MS: 567 (M+H)⁺.

Example 52

2-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)-N-cyclopropyl-2-oxoacetamide

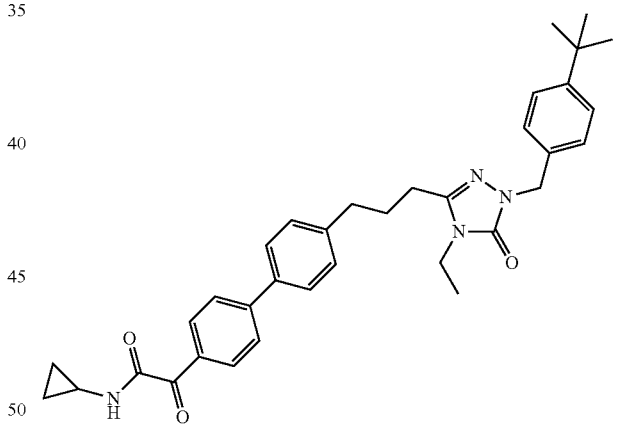

To a solution of 2-(4'-(3-(1-(4-(tert-butyl)benzyl)-4-ethyl-5-oxo-4,5-dihydro-1H-1,2,4-triazol-3-yl)propyl)-[1,1'-biphenyl]-4-yl)-N-cyclopropyl-2-hydroxyacetamide (65 mg, 0.11 mmol, example 51) was added Dess-Martin periodinane (73 mg, 0.15 mmol) in one rapid portion at 0° C. The resulting solution was first stirred at 0° C. for 30 min and then at RT for 4 h. The reaction mixture was then diluted with ether and washed sequentially with 10% aq. Na₂S₂O₃, sat. aq. NaHCO₃, water and brine. The organic extract was then dried over Na₂SO₄, filtered and the filtrate concentrated in vacuo to afford the crude product as a viscous oil. Further purification by way of column chromatography (SiO₂, gradient elution, 9:1 (v/v) Hex: EtOAc to EtOAc) afforded the title compound as a white foam (93% yield). LC-MS: 565 (M+H)⁺.

Example 53

2-(4'-(3-(1-(4-(tert-Butyl)benzyl)-4-(cyclopropylmethyl)-5-oxo-4,5-dihydro-1H-1,2,4-triazol-3-yl)propyl)-[1,1'-biphenyl]-3-yl)acetic acid

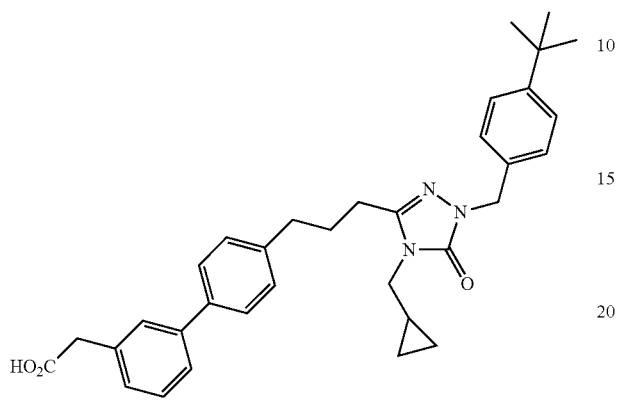

Step 1;

2-((4-Bromobenzyl)oxy)acetic acid (590 mg, 2.4 mmol), 1-(4-(tert-butyl)benzyl)hydrazinecarboxamide monomethanesulfonate (774 mg, 2.5 mmol, prepared according to published procedure found in Braden, T. M. et al., *Org. Process Res. Dev.* 2007, 11, p. 431-440) and 2-(7-aza-1H-benzotriazole-1-yl)-1,1,3,3-tetramethyluronium hexafluorophosphate (1.2 g, 3.15 mmol) were combined in anhydrous DMF (30 mL). To the reaction solution was then added Hunig's base (1.1 mL, 6.3 mmol) and the resulting yellow solution was allowed to stir at RT for 16 hrs. The reaction mixture was then quenched with EtOAc and 1 N aq. HCl. The organic extract was separated and washed further with water and brine. The organic extract was then dried over sodium sulfate and filtered. Concentration of the filtrate in vacuo afforded the crude reaction product as a white semisolid. Further purification by way of column chromatography (SiO$_2$, gradient elution, 4:1 (v/v) Hex: EtOAc to EtOAc) afforded 2-(4-(4-bromophenyl)butanoyl)-1-(4-(tert-butyl)benzyl)hydrazinecarboxamide as a white solid (778 mg, 72% yield).

Step 2;

To a solution of 2-(4-(4-bromophenyl)butanoyl)-1-(4-(tert-butyl)benzyl)hydrazinecarboxamide (778 mg, 1.74 mmol) in EtOAc (15 mL) was added camphorsulfonic acid (405 mg, 1.74 mmol) and the resulting solution was heated at 80° C. for 16 hrs. The volatiles were then removed in vacuo and the crude product thus obtained was recrystallized from ether and hexanes. 3-(3-(4-Bromophenyl)propyl)-1-(4-(tert-butyl)benzyl)-1H-1,2,4-triazol-5(4H)-one was isolated as a white solid (428 mg, 57% yield).

Step 3;

To a solution of 3-(3-(4-bromophenyl)propyl)-1-(4-(tert-butyl)benzyl)-1H-1,2,4-triazol-5(4H)-one (80 mg, 0.19 mmol) in DMF (2 mL) was added sodium hydride (60% w/w dispersion in oil, 14 mg, 0.35 mmol). The resulting suspension was allowed to stir at RT for 3 hrs before cyclopropylmethyl bromide (40 µL, 0.35 mmol) was added. After another 8 hrs of stirring at RT, the crude reaction mixture was diluted with ether and washed sequentially with 10% aq. HCl, 1 N aq. NaOH, water and brine. The organic extract was then dried over Na$_2$SO$_4$, filtered and the filtrate concentrated in vacuo. Purification by way of column chromatography (SiO$_2$, gradient elution, 8:1 (v/v) Hex: EtOAc to EtOAc) afforded 3-(3-(4-bromophenyl)propyl)-1-(4-(tert-butyl)benzyl)-4-(cyclopropylmethyl)-1H-1,2,4-triazol-5 (4H)-one as a colorless oil (77 mg, 78% yield).

Step 4;

Carried out in an analogous manner to example 1, using instead 3-(3-(4-bromophenyl)propyl)-1-(4-(tert-butyl)benzyl)-4-(cyclopropylmethyl)-1H-1,2,4-triazol-5(4H)-one prepared in the previous step as the coupling partner. LC-MS: 538 (M+H)$^+$.

Example 54

2-(4'-(3-(1-((5-(tert-Butyl)thiophen-2-yl)methyl)-4-ethyl-5-oxo-4,5-dihydro-1H-1,2,4-triazol-3-yl)propyl)-[1,1'-biphenyl]-3-yl)acetic acid

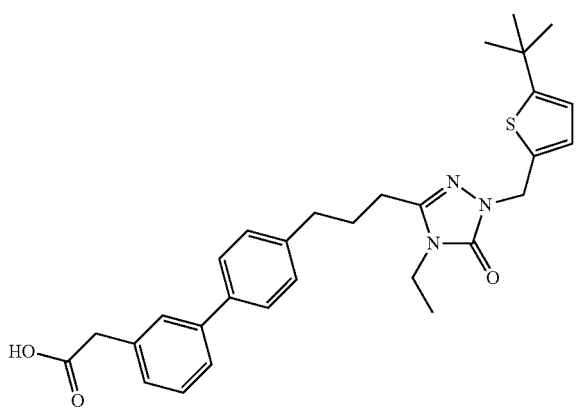 [SMILES: CCn1c(CCCc2ccc(-c3cccc(CC(=O)O)c3)cc2)nn(Cc2ccc(C(C)(C)C)s2)c1=O]

Step 1;

To a solution of 5-(tert-butyl)thiophene-2-carboxylic acid (0.20 g, 1.09 mmol) and TEA (0.33 mL, 2.39 mmol) in anhydrous THF (20 mL) at 0° C. was added ethyl chloroformate (0.12 mL, 1.19 mmol). The resulting mixture was stirred at RT for 2 hrs, the solids were filtered off, and to the filtrate was added LiBH$_4$ (5.40 mL, 10.85 mmol, 2.0 M in THF). The resulting mixture was stirred for 16 hrs at 55° C. The volatiles were then evaporated and the residue was diluted with DCM and 1:1 brine/water. The organic extract was separated, filtered through a Na$_2$SO$_4$/paper plug, and the filtrate concentrated in vacuo. Crude 1-(5-(tert-butyl)thiophen-2-yl)methanol thus obtained was used directly in the next step.

Step 2;

To a solution of 1-(5-(tert-butyl)thiophen-2-yl)methanol (0.15 g, 0.88 mmol) in DCM (20 mL) at −78° C. was added TEA (0.37 mL, 2.6 mmol), followed by methanesulfonyl chloride (0.10 mL, 1.3 mmol). The resulting mixture was stirred at RT for 1.5 hrs and the volatiles were then evaporated. The resulting residue was quenched with 20% citric acid solution (aq.) and extracted with ether. The combined organic extracts were washed further with brine, filtered through a Na$_2$SO$_4$/paper plug and concentrated in vacuo. Crude (5-(tert-butyl)thiophen-2-yl)methyl methanesulfonate thus obtained was used directly in the next step.

Step 3;

Carried out in an analogous manner to example 22, using instead (5-(tert-butyl)thiophen-2-yl)methyl methanesulfonate prepared in the electrophile in step 2. Hydrolysis of the intermediate ester was then carried out as in example 1, step 2. LC-MS: 518 (M+H)+.

Example 55

2-(4'-(3-(1-(4-(tert-Butyl)benzyl)-5-oxo-4-(2,2,2-trifluoroethyl)-4,5-dihydro-1H-1,2,4-triazol-3-yl)propyl)-4-methoxy-[1,1'-biphenyl]-3-yl)acetic acid

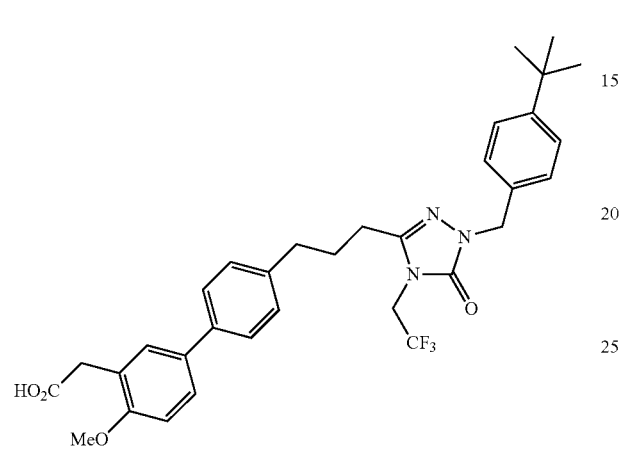

Prepared in an analogous manner to example 53, using instead 2,2,2-trifluoroethyl triflate as the electrophile in step 3 and methyl 2-(2-methoxy-5-(4,4,5,5-tetramethyl-1,3,2-dioxaborolan-2-yl)phenyl)acetate as the boronate coupling partner in step 4. LC-MS: 596 (M+H)+.

Example 56

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-cyclopropyl-2-hydroxyacetamide

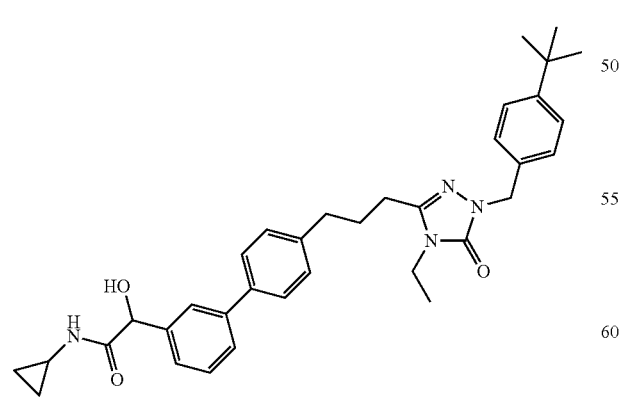

Prepared in an analogous manner to example 51, using instead ethyl 2-bromo-(3-bromophenyl)acetate as the substrate in step 1. LC-MS: 567 (M+H)+.

Example 57

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-cyclopropyl-2-oxoacetamide

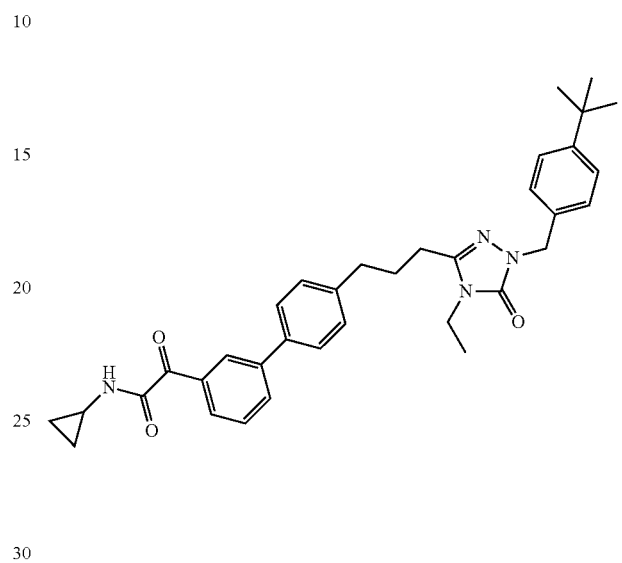

Prepared in an analogous manner to example 52, using instead 2-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)-N-cyclopropyl-2-hydroxyacetamide as the substrate in step 1. LC-MS: 565 (M+H)+.

Example 58

3-{3-[4-(6-Amino-5-methoxy(2-pyridyl))phenyl]propyl}-1-{[4-(tert-butyl)phenyl]methyl}-4-ethyl-1,2,4-triazolin-5-one

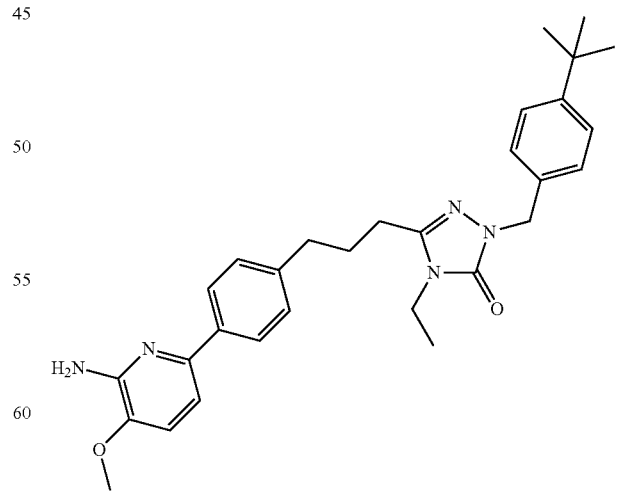

Step 1:
To a stirred solution of 3-hydroxy-2-nitropyridine (10 g, 71.4 mmol) in MeOH (200 mL) was added sodium methoxide (19.8 mL, 71.4 mmol, 3.6 M solution in MeOH) and the resulting mixture was allowed to stir at room temperature for 30 min. The reaction mixture was then cooled to 0° C. and bromine (3.7 mL, 71.4 mmol) was added slowly over a period of 30 min After the reaction was deemed to be complete by LC-MS, the mixture was quenched with glacial acetic acid (1.3 mL) and the volatiles were removed in vacuo. The crude residue thus obtained was azeotroped with heptane to afford 6-bromo-2-nitropyridin-3-ol as a brown solid.

Step 2;

To a solution of the aforementioned nitropyridine (4 g, 18.4 mmol) in acetone (50 mL) was added potassium carbonate (3 g, 22.1 mmol) and iodomethane (1.4 mL, 22.1 mmol). The resulting suspension was heated at 40° C. until the reaction was deemed to be complete by TLC. The volatiles were the removed in vacuo and the resulting residue was partitioned between water and EtOAc. The aqueous layer was separated and back-extracted with EtOAc. The combined organic extracts were dried over anhydrous Na$_2$SO$_4$, filtered and the filtrate concentrated in vacuo. Further purification by way of column chromatography (SiO$_2$, gradient elution, 9:1 (v/v) Hex: EtOAc to EtOAc).

Step 3;

A mixture of 1-(4-(tert-butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one (470 mg, 0.934 mmol), 6-bromo-3-methoxy-2-nitropyridine (266 mg, 1.12 mmol) and potassium carbonate (386 mg, 2.80 mmol) were taken up in DME (4 mL) and water (2 mL). To this was then added tetrakis(triphenylphosphine)palladium(0) (108 mg, 0.0935 mmol) and the resulting biphasic suspension was heated at 85° C. under an atmosphere of N$_2$ for 24 hrs. The reaction mixture was then cooled to room temperature and the volatiles were removed in vacuo. The crude material thus obtained was partitioned between water and EtOAc. The aqueous layer was separated and back-extracted with EtOAc. The combined organic extracts were then dried over anhydrous Na$_2$SO$_4$, filtered, and the filtrate concentrated in vacuo. Further purification by way of column chromatography (SiO$_2$, gradient elution, 9:1 (v/v) Hex: EtOAc to EtOAc) afforded 1-(4-(tert-butyl)benzyl)-4-ethyl-3-(3-(4-(5-methoxy-6-nitropyridin-2-yl)phenyl)propyl)-1H-1,2,4-triazol-5(4H)-one (356 mg, 74% yield).

Step 4;

To a solution of the aforementioned nitropyridine (356 mg, 0.673 mmol) in MeOH/EtOAc (1:1, 10 mL) was added Pd/C (10% w/w, dry, 200 mg). The suspension thus obtained was then stirred at room temperature under a balloon-maintained hydrogen atmosphere for 16 hrs. The reaction was quenched with the addition of DCM and then filtered through a pad of DCM-wetted celite, The insolubles were washed further with DCM and the filtrate thus obtained was concentrated in vacuo. Further purification by way of column chromatography (SiO$_2$, gradient elution, DCM to 95:5 (v/v) DCM: MeOH) afforded the title compound as a colorless foam. LC-MS: 500 (M+H)$^+$.

Example 59

1-{[4-(tert-Butyl)phenyl]methyl}-4-ethyl-3-[3-(4-{5-methoxy-6-[(phenylsulfonyl)amino](2-pyridyl)}phenyl)propyl]-1,2,4-triazolin-5-one

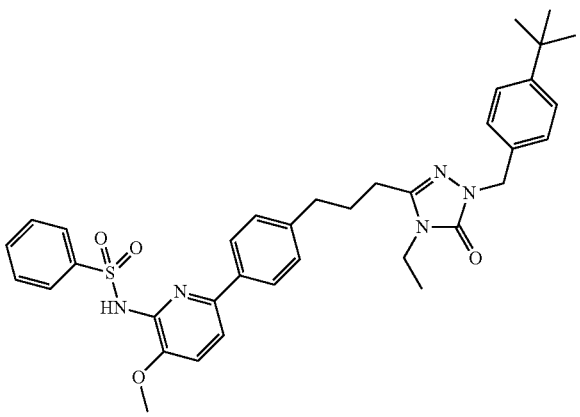 [SMILES: CCn1c(CCCc2ccc(-c3ccc(OC)c(NS(=O)(=O)c4ccccc4)n3)cc2)nn(Cc2ccc(C(C)(C)C)cc2)c1=O]

To a solution of 3-{3-[4-(6-amino-5-methoxy(2-pyridyl))phenyl]propyl}-1-{[4-(tert-butyl)phenyl]methyl}-4-ethyl-1,2,4-triazolin-5-one (247 mg, 0.494 mmol) in pyridine (1.5 mL) was added benzene sulfonylchloride (70 µL, 0.544 mmol, 1.1 eq). After 24 hrs of stirring at RT, the reaction mixture was then poured onto dichloromethane (40 mL) and washed sequentially with saturated aq. CuSO$_4$, water, and brine. The organic extract was dried over anhydrous Na$_2$SO$_4$, filtered and the filtrate concentrated in vacuo. The crude product thus obtained was then purified by flash column chromatography (SiO$_2$, gradient elution, 9:1 (v/v) Hex: EtOAc to EtOAc) to afford the title compound as a white solid (115.6 mg, 78%). LC-MS: 640 (M+H)$^+$.

Example 60

3-{3-[4-(6-Amino-5-ethoxy(2-pyridyl))phenyl]propyl}-1-{[4-(tert-butyl)phenyl]methyl}-4-ethyl-1,2,4-triazolin-5-one

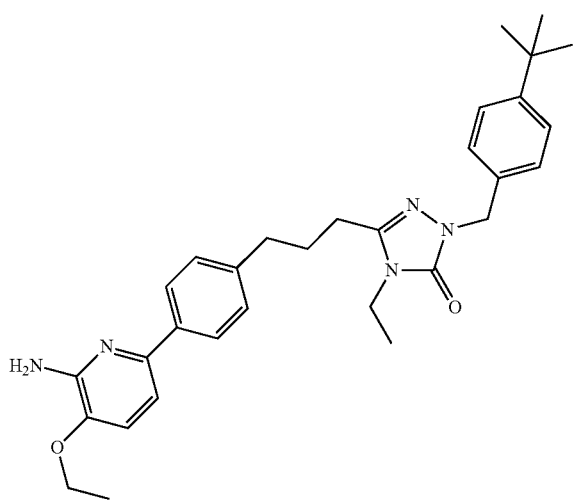 [SMILES: CCOc1ccc(-c2ccc(CCCc3nn(Cc4ccc(C(C)(C)C)cc4)c(=O)n3CC)cc2)nc1N]

Prepared in an analogous manner to example 58 but using instead ethyl iodide as the electrophile in step 2. LC-MS: 514 (M+H)+.

Example 61

2-(5-{4-[3-(1-{[4-(tert-Butyl)phenyl]methyl}-4-ethyl-5-oxo(1,2,4-triazolin-3-yl))propyl]phenyl}-2-ethylthiophenyl)acetic acid

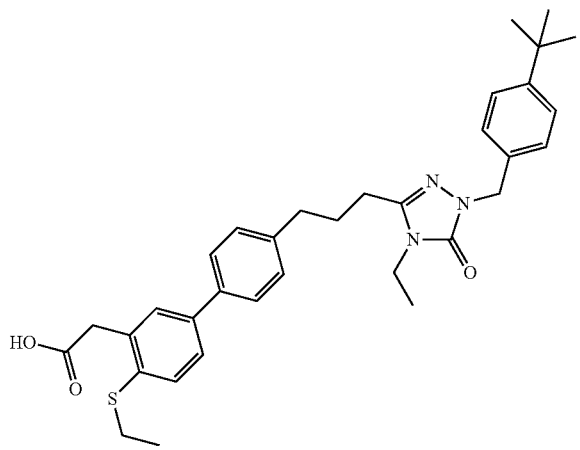 [SMILES: CCSc1ccc(-c2ccc(CCCc3nn(Cc4ccc(C(C)(C)C)cc4)c(=O)n3CC)cc2)cc1CC(=O)O]

Step 1;

To a stirred solution of 1-bromo-2-(bromomethyl)-4-iodobenzene (5 g, 13.3 mmol) in DMF (44 mL) was added potassium cyanide (1.7 g, 26.6 mmol) and the resulting mixture was stirred at room temperature for 16 hrs. This was then diluted with water and extracted with diethyl ether. The combined organic extracts were dried over anhydrous $Na_2SO_4$, filtered and the filtrate concentrated in vacuo. Further purification by way of column chromatography ($SiO_2$, gradient elution, 9:1 (v/v) Hex: EtOAc to EtOAc) afforded 2-(2-bromo-5-iodophenyl)acetonitrile as a pale yellow oil.

Step 2;

A mixture of 1-(4-(tert-butyl)benzyl)-4-ethyl-3-(3-(4-(4,4,5,5-tetramethyl-1,3,2-dioxaborolan-2-yl)phenyl)propyl)-1H-1,2,4-triazol-5(4H)-one (538 mg, 1.07 mmol), 2-(2-bromo-5-iodophenyl)acetonitrile (413 mg, 1.3 mmol) and potassium carbonate (443 mg, 3.2 mmol) were taken up in DME (4 mL) and water (2 mL). To this was then added tetrakis(triphenylphosphine)palladium(0) (124 mg, 0.107 mmol) and the resulting mixture was stirred at 85° C. under an atmosphere of $N_2$ for 24 hrs. The reaction mixture was then cooled to room temperature and the volatiles were removed in vacuo. The crude material thus obtained was then partitioned between water and EtOAc. The aqueous layer was separated and back-extracted with EtOAc. The combined organic extracts were dried over anhydrous $Na_2SO_4$, filtered and the filtrate concentrated in vacuo. Further purification by way of column chromatography ($SiO_2$, gradient elution, 9:1 (v/v) Hex: EtOAc to EtOAc) afforded 2-(4-bromo-4'-(3-(1-(4-(tert-butyl)benzyl)-4-ethyl-5-oxo-4,5-dihydro-1H-1,2,4-triazol-3-yl)propyl)-[1,1'-biphenyl]-3-yl)acetonitrile.

Step 3;

To a stirred suspension of potassium carbonate (38 mg, 0.27 mmoL) in xylene (5 mL) was added at 0° C. ethanethiol (0.040 mL, 0.54 mmol). The reaction mixture was allowed to warm slowly to room temperature over 1 hr. In a separate round bottom flask, the isolated nitrile from the previous step (246 mg, 0.431 mmol), $Pd_2(dba)_3$ (40 mg, 0.043 mmol) and Xantphos (28 mg, 0.047 mmol) were combined in deoxygenated xylenes (10 mL) and this was then added to the above thiol mixture. The reaction mixture thus obtained was then heated at reflux over night under a nitrogen atmosphere. After cooling to room temperature, the reaction mixture was diluted with EtOAc and washed with water. The organic phase was separated, dried ($MgSO_4$), filtered and the filtrate concentrated in vacuo. The crude product thus obtained was purified by way of column chromatography ($SiO_2$, gradient elution, 9:1 (v/v) Hex: EtOAc to EtOAc) to afford 2-(4'-(3-(1-(4-(tert-butyl)benzyl)-4-ethyl-5-oxo-4,5-dihydro-1H-1,2,4-triazol-3-yl)propyl)-4-(ethylthio)-[1,1'-biphenyl]-3-yl)acetonitrile.

Step 4;

To a solution of the isolated nitrile from the previous step (250 mh, 0.45 mmol) in $EtOH:H_2O$ (1:1 v/v, 4 mL) was added potassium hydroxide (300 mg, 4.5 mmol). The resulting mixture was then heated at reflux for 16 hrs. The volatiles were then removed in vacuo and the resulting residue was taken up in 1 N aq. HCl and EtOAc. The organic extract was separated, washed further with water and brine, dried ($MgSO_4$), and filtered. Concentration of the filtrate in vacuo afforded the crude product that was purified further by reverse phase HPLC. The titled compound was isolated as a white solid. LC-MS: 572 (M+H)+.

Example 62

1-{[4-(tert-Butyl)phenyl]methyl}-3-[3-(4-{5-ethoxy-6-[(phenylsulfonyl)amino](2-pyridyl)}phenyl)propyl]-4-ethyl-1,2,4-triazolin-5-one

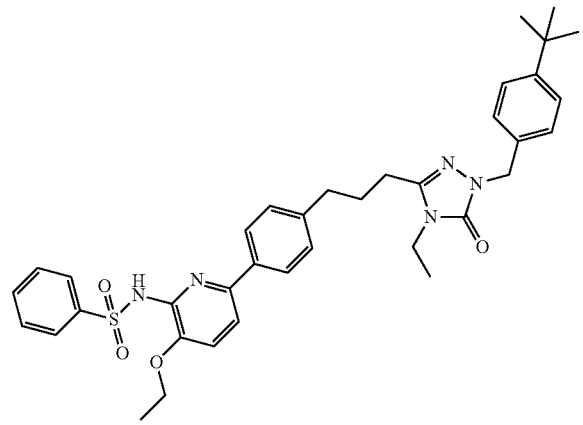 [SMILES: CCOc1ccc(-c2ccc(CCCc3nn(Cc4ccc(C(C)(C)C)cc4)c(=O)n3CC)cc2)nc1NS(=O)(=O)c1ccccc1]

Prepared in an analogous manner to example 4 but using instead 3-{3-[4-(6-amino-5-ethoxy(2-pyridyl))phenyl]propyl}-1-{[4-(tert-butyl)phenyl]methyl}-4-ethyl-1,2,4-triazolin-5-one (example 60) as the starting material. LC-MS: 654 (M+H)+.

Example 63

2-(4'-(3-(4-Ethyl-1-(4-(3-fluorooxetan-3-yl)benzyl)-5-oxo-4,5-dihydro-1H-1,2,4-triazol-3-yl)propyl)-[1,1'-biphenyl]-3-yl)acetic acid

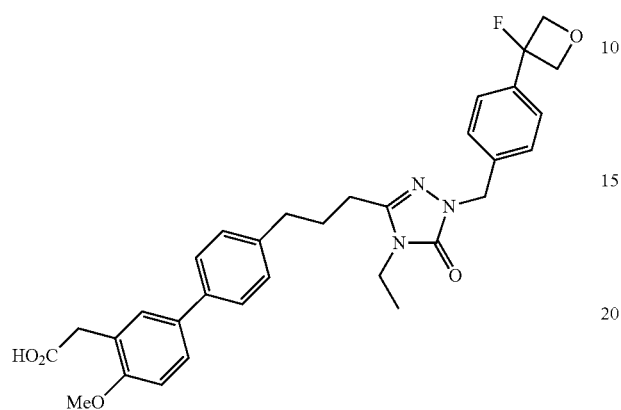

Step 1;

To a solution of 4-bromobenzyl alcohol (1.0 g, 5.3 mmol) in THF (50 mL) was added sodium hydride (0.32 g, 8 mmol, 60% w/w dispersion in oil) in one rapid portion. After 1 hr of stirring at RT, the reaction suspension was cooled to −78° C. before n-BuLi (2.1 mL, 5.3 mmol, 2.5 M solution in hexanes) was added dropwise over 12 min. The resulting yellow suspension was stirred at −78° C. for another 45 min before 3-oxetanone (310 µL, 5.3 mmol) was added neat, dropwise over a period of 10 min. The reaction mixture was then allowed to warm slowly to RT over 1 hr and stirred at RT for another 2 hrs. The reaction was quenched with the addition of saturated aq. NH$_4$Cl and then extracted with ether. The combined organic extracts were washed further with water and brine, dried over Na$_2$SO$_4$, filtered and the filtrate concentrated in vacuo. Further purification by way of column chromatography (SiO$_2$, gradient elution, 4:1 (v/v) Hex: EtOAc to EtOAc) afforded 3-(4-(hydroxymethyl)phenyl)oxetan-3-ol as a white solid (112 mg, 12% yield).

Step 2;

To a solution of 3-(4-(hydroxymethyl)phenyl)oxetan-3-ol (112 mg, 0.63 mmol) in DCM (5 mL) was added sequentially at 0° C. triethylamine (220 µL, 1.6 mmol) and methanesulfonyl chloride (62 µL, 0.8 mmol). The resulting solution was allowed to warm slowly to RT over 3 hrs before the reaction was quenched with the addition of ether and water. The organic layer was separated, washed sequentially with 10% aq. HCl, water and brine, dried over Na$_2$SO$_4$, and filtered. Concentration of the filtrate in vacuo afforded the crude 4-(3-hydroxyoxetan-3-yl)benzyl methanesulfonate as a golden, yellow oil.

Step 3;

To a solution of 4-(3-hydroxyoxetan-3-yl)benzyl methanesulfonate (163 mg, 0.63 mmol) in DCM (2 mL) was added dropwise at −78° C. neat diethylaminosulfur trifluoride (165 µL, 1.26 mmol). The resulting mixture was allowed to stir at −78° C. for 8 hrs before it was carefully quenched with sat. aq. NaHCO$_3$. The organic layer was separated, dried over Na$_2$SO$_4$, filtered and the filtrate concentrated in vacuo. Purification by way of column chromatography (SiO$_2$, gradient elution, 9:1 (v/v) Hex: EtOAc to EtOAc) afforded 4-(3-fluorooxetan-3-yl)benzyl methanesulfonate as a pale yellow oil that solidified upon standing (34 mg, 20% yield over two steps).

Step 4;

Carried out in an analogous manner to example 22 using instead 4-(3-fluorooxetan-3-yl)benzyl methanesulfonate prepared in the previous step as the electrophile. LC-MS: 560 (M+H)$^+$.

Example 64

2-(5-{4-[3-(1-{[4-(tert-Butyl)phenyl]methyl}-4-ethyl-5-oxo(1,2,4-triazolin-3-yl))propyl]phenyl}-2-methylthiophenyl)acetic acid

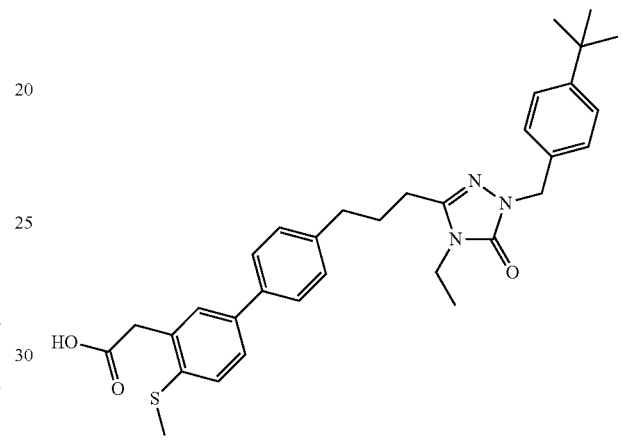

Prepared in an analogous manner to example 61 but using instead sodium thiomethoxide as the nucleophile in step 3. LC-MS: 559 (M+H)$^+$.

Example 65

4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-carboxylic acid

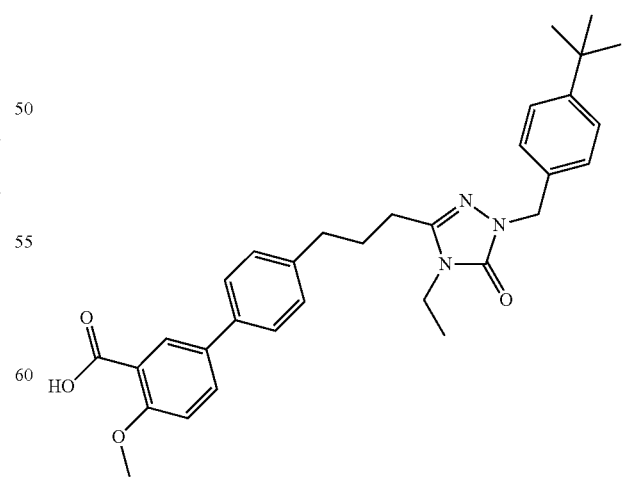

Prepared in an analogous manner to example 13 but using instead 5-bromo-2-methoxybenzoate as the coupling partner

Example 66

4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-carboxylic acid

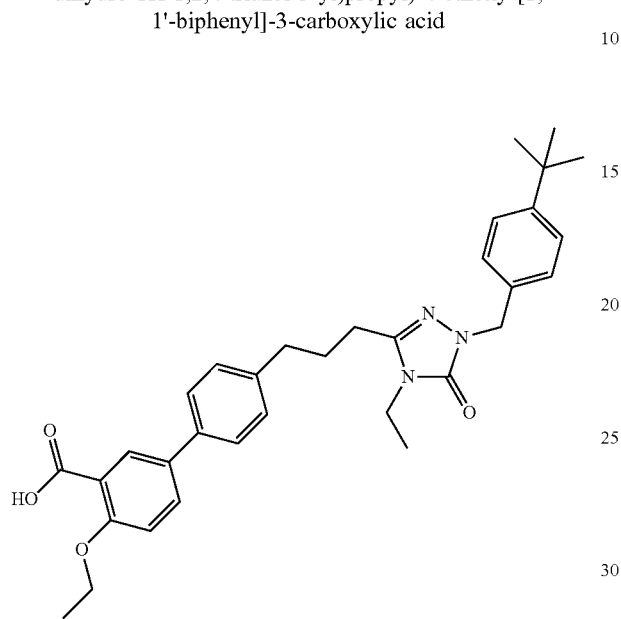

Prepared in an analogous manner to example 13 but using instead 5-bromo-2-ethoxybenzoate as the coupling partner in step 1. Hydrolysis of the intermediate ester was carried out as in example 1, step 2. LC-MS: 542 (M+H)$^+$.

Example 67

2-(4'-(3-(1-(3-Bromo-4-(tert-butyl)benzyl)-4-ethyl-5-oxo-4,5-dihydro-1H-1,2,4-triazol-3-yl)propyl)-[1,1'-biphenyl]-3-yl)acetic acid

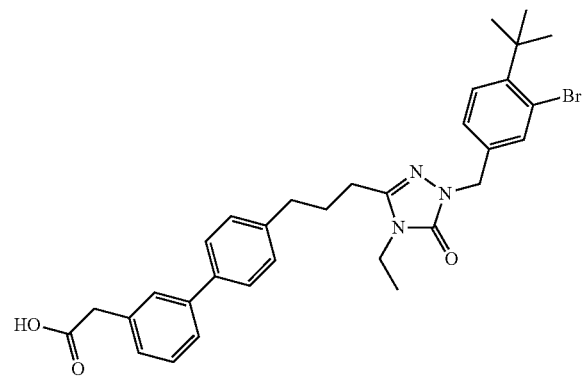 [SMILES: CCn1c(CCCc2ccc(-c3cccc(CC(=O)O)c3)cc2)nn(Cc2ccc(C(C)(C)C)c(Br)c2)c1=O]

Prepared in an analogous manner to example 54 but using instead 3-bromo-4-(tert-butyl)benzoic acid as the acid substrate in step 1. LC-MS: 591 (M+H)$^+$.

Example 68

2-(4'-(3-(1-(4-(tert-Butyl)benzyl)-5-oxo-4-propyl-4,5-dihydro-1H-1,2,4-triazol-3-yl)propyl)-4-ethoxy-[1,1'-biphenyl]-3-yl)acetic acid

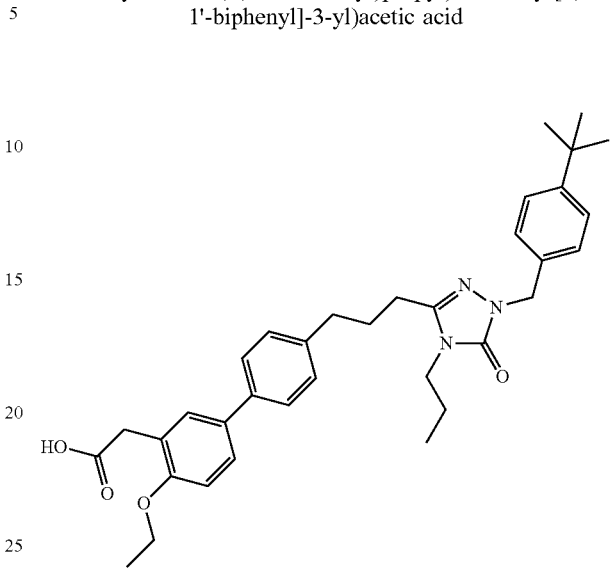

Prepared in an analogous manner to example 1 but using instead 3-(3-(4-bromophenyl)propyl)-1-(4-(tert-butyl)benzyl)-4-isopropyl-1H-1,2,4-triazol-5(4H)-one and methyl 2-(2-ethoxy-5-(4,4,5,5-tetramethyl-1,3,2-dioxaborolan-2-yl)phenyl)acetate as coupling partners in step 1. LC-MS: 570 (M+H)$^+$.

Example 69

2-(4'-(3-(4-Butyl-1-(4-(tert-butyl)benzyl)-5-oxo-4,5-dihydro-1H-1,2,4-triazol-3-yl)propyl)-4-ethoxy-[1,1'-biphenyl]-3-yl)acetic acid

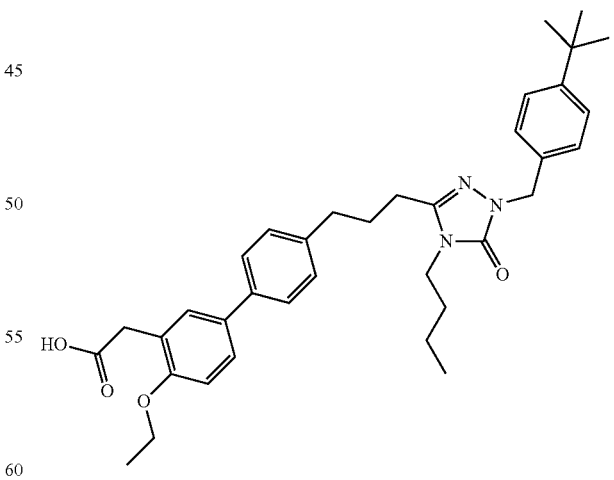

Prepared in an analogous manner to example 1 but using instead 3-(3-(4-bromophenyl)propyl)-4-butyl-1-(4-(tert-butyl)benzyl)-1H-1,2,4-triazol-5(4H)-one and methyl 2-(2-ethoxy-5-(4,4,5,5-tetramethyl-1,3,2-dioxaborolan-2-yl)phenyl)acetate as coupling partners in step 1. LC-MS: 584 (M+H)$^+$.

Example 70

5-(4-(3-(1-(4-(tert-Butyl)benzyl)-4-ethyl-5-oxo-4,5-dihydro-1H-1,2,4-triazol-3-yl)propyl)phenyl)-1H-indole-3-carboxylic acid

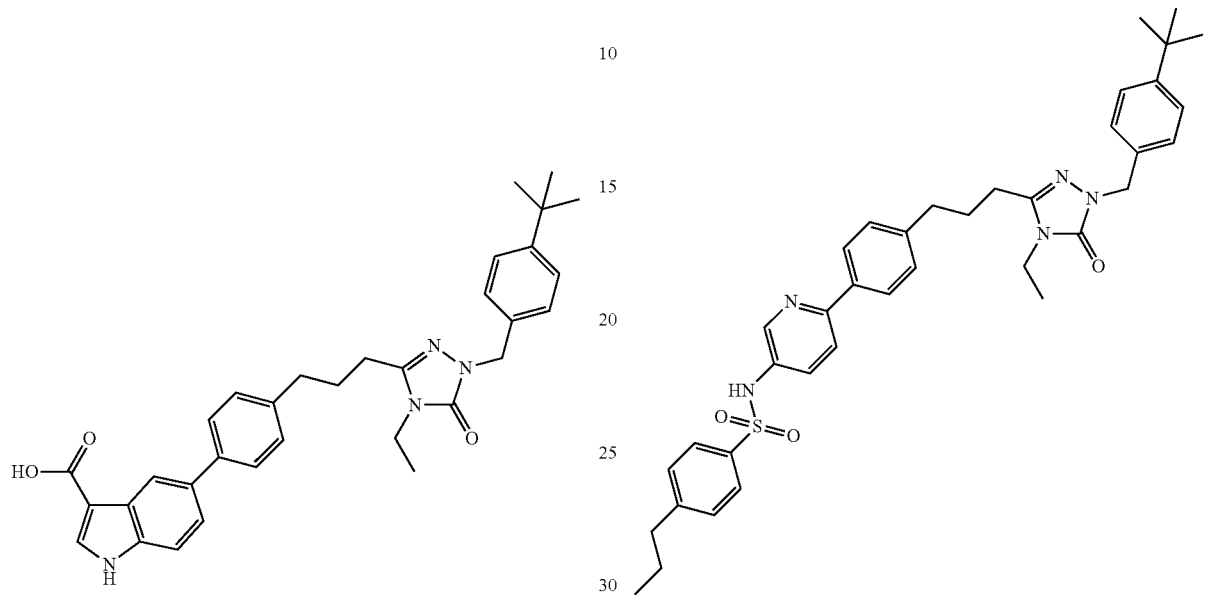

Prepared in an analogous manner to example 13 but using instead 5-bromo-1H-indole-3-carboxylate as the coupling partner in step 1. Hydrolysis of the intermediate ester was carried out as in example 1, step 2. LC-MS: 537 (M+H)+.

Example 71

1-{[4-(tert-Butyl)phenyl]methyl}-4-ethyl-3-{3-[4-(5-{[(4-propylphenyl)sulfonyl]amino}(2-pyridyl))phenyl]propyl}-1,2,4-triazolin-5-one

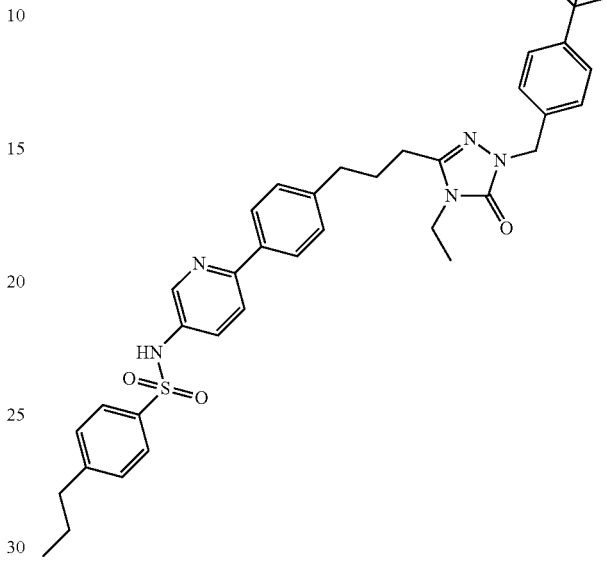

Prepared in an analogous manner to example 12 using instead 4-n-propylbenzenesulfonyl chloride as the electrophile. LC-MS: 652 (M+H)+.

Example 72

1-{[4-(tert-Butyl)phenyl]methyl}-4-ethyl-3-{3-[4-(6-{[(4-propylphenyl)sulfonyl]amino}(2-pyridyl))phenyl]propyl}-1,2,4-triazolin-5-one

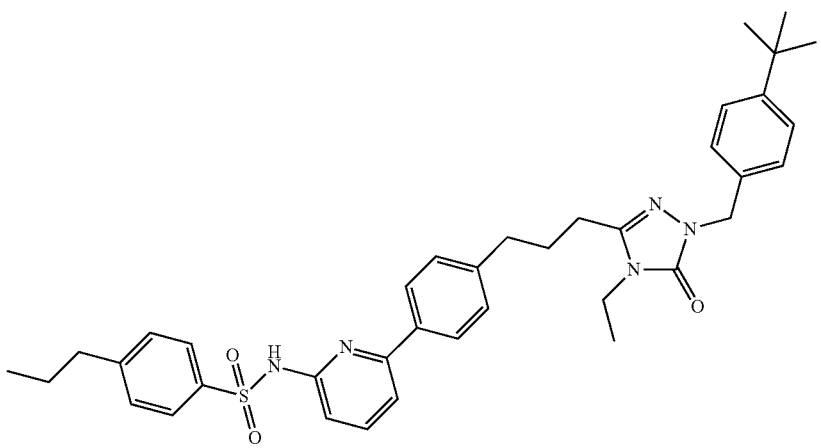 [SMILES: CCCc1ccc(S(=O)(=O)Nc2cccc(-c3ccc(CCCc4nn(Cc5ccc(C(C)(C)C)cc5)c(=O)n4CC)cc3)n2)cc1]

Prepared in an analogous manner to example 4 using instead 4-n-propylbenzenesulfonyl chloride as the electrophile. LC-MS: 652 (M+H)+.

Example 73

1-{[4-(tert-Butyl)phenyl]methyl}-4-ethyl-3-(3-{4-[6-({[4-(4-methylphenyl)phenyl]sulfonyl}amino)(2-pyridyl)]phenyl}propyl)-1,2,4-triazolin-5-one

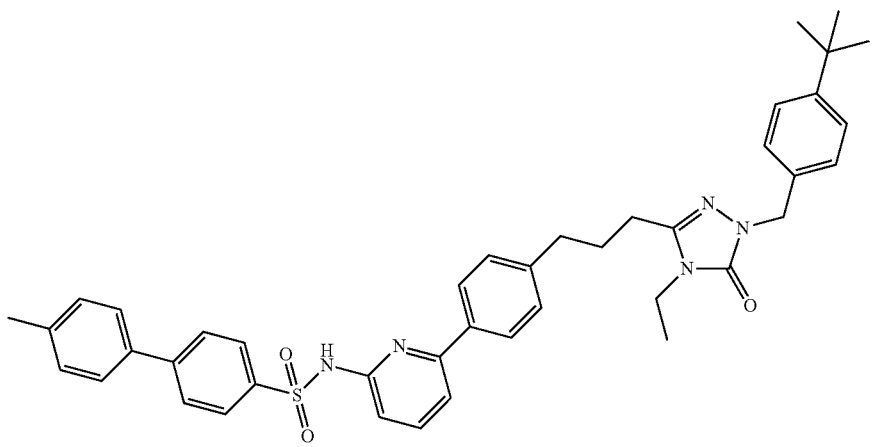 [SMILES: CCn1c(CCCc2ccc(-c3cccc(NS(=O)(=O)c4ccc(-c5ccc(C)cc5)cc4)n3)cc2)nn(Cc2ccc(C(C)(C)C)cc2)c1=O]

Prepared in an analogous manner to example 4 using instead 4-methylbiphenyl-4-sulfonyl chloride as the electrophile. LC-MS: 700 (M+H)+.

Example 74

1-{[4-(tert-Butyl)phenyl]methyl}-4-ethyl-3-(3-{4-[6-({[4-(4-methoxyphenyl)phenyl]sulfonyl}amino)(2-pyridyl)]phenyl}propyl)-1,2,4-triazolin-5-one

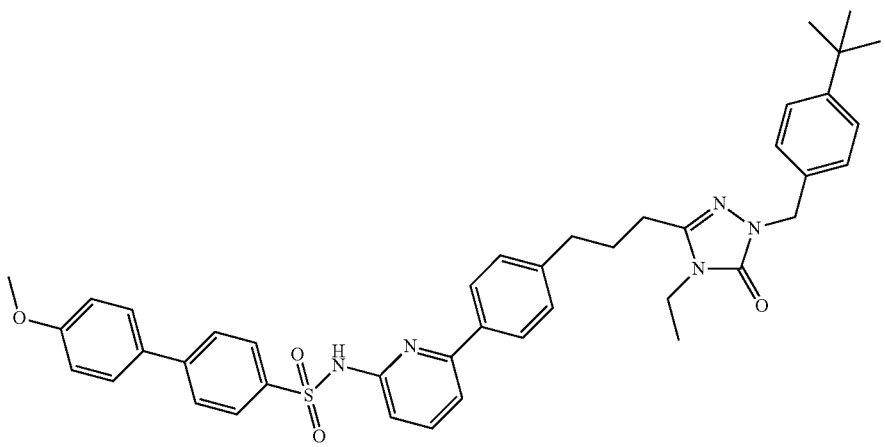 [SMILES: CCn1c(CCCc2ccc(-c3cccc(NS(=O)(=O)c4ccc(-c5ccc(OC)cc5)cc4)n3)cc2)nn(Cc2ccc(C(C)(C)C)cc2)c1=O]

Prepared in an analogous manner to example 4 using instead 4-methoxybiphenyl-4-sulfonyl chloride as the electrophile. LC-MS: 716 (M+H)+.

Example 75

1-Acetyl-5-{[(6-{4-[3-(1-{[4-(tert-butyl)phenyl]
methyl}-4-ethyl-5-oxo(1,2,4-triazolin-3-yl))propyl]
phenyl}(3-pyridyl))amino]sulfonyl}indoline

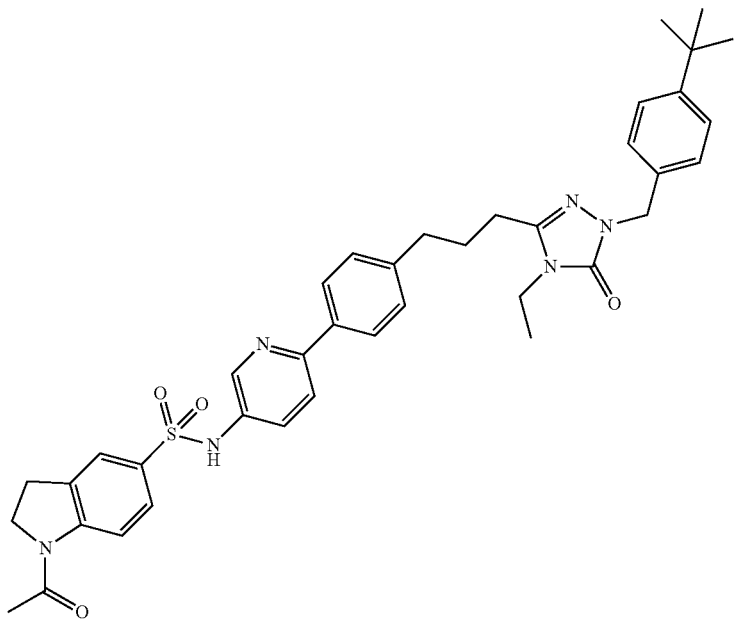 [SMILES: CCn1c(CCCc2ccc(-c3ccc(NS(=O)(=O)c4ccc5c(c4)CCN5C(C)=O)cn3)cc2)nn(Cc2ccc(C(C)(C)C)cc2)c1=O]

Prepared in an analogous manner to example 12 using instead 1-acetyl-5-indolinesulfonyl chloride as the electrophile. LC-MS: 693 (M+H)+.

Example 76

2-(4'-(3-(4-Allyl-1-(4-(tert-butyl)benzyl)-5-oxo-4,5-
dihydro-1H-1,2,4-triazol-3-yl)propyl)-4-methoxy-[1,
1'-biphenyl]-3-yl)acetic acid

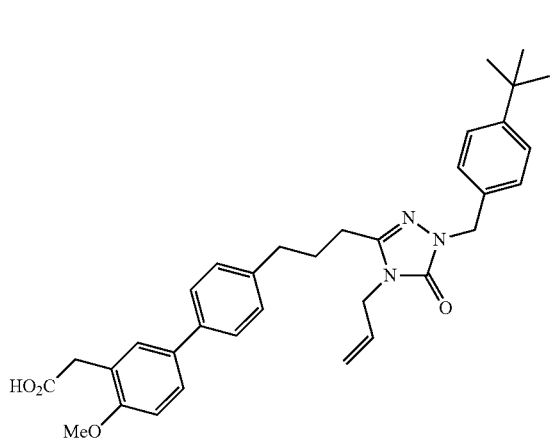 [SMILES: C=CCn1c(CCCc2ccc(-c3ccc(OC)c(CC(=O)O)c3)cc2)nn(Cc2ccc(C(C)(C)C)cc2)c1=O]

Prepared in an analogous manner to example 53, using instead allyl bromide as the electrophile in step 3 and methyl 2-(2-methoxy-5-(4,4,5,5-tetramethyl-1,3,2-dioxaborolan-2-yl)phenyl)acetate as the boronate coupling partner in step 4. LC-MS: 554 (M+H)+.

Example 77

1-{[4-(tert-Butyl)phenyl]methyl}-4-ethyl-3-[3-(4-{5-
[({4-[5-(trifluoromethyl)(2-pyridyloxy)]
phenyl}sulfonyl)amino](2-pyridyl)}phenyl)propyl]-
1,2,4-triazolin-5-one

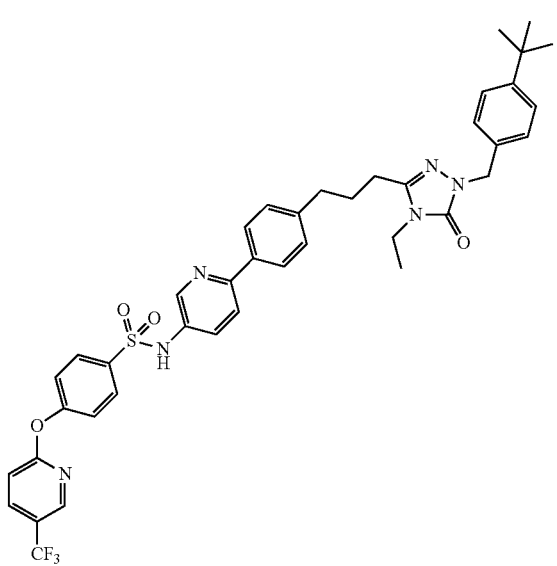 [SMILES: CCn1c(CCCc2ccc(-c3ccc(NS(=O)(=O)c4ccc(Oc5ccc(C(F)(F)F)cn5)cc4)cn3)cc2)nn(Cc2ccc(C(C)(C)C)cc2)c1=O]

Prepared in an analogous manner to example 12 using instead 4-([5-trifluoromethyl)pyridine-2-yl]oxy)benzenesulfonyl chloride as the electrophile. LC-MS: 771 (M+H)+.

Example 78

1-{[4-(tert-Butyl)phenyl]methyl}-4-ethyl-3-{3-[4-(6-{[benzylsulfonyl]amino}(2-pyridyl))phenyl]propyl}-1,2,4-triazolin-5-one

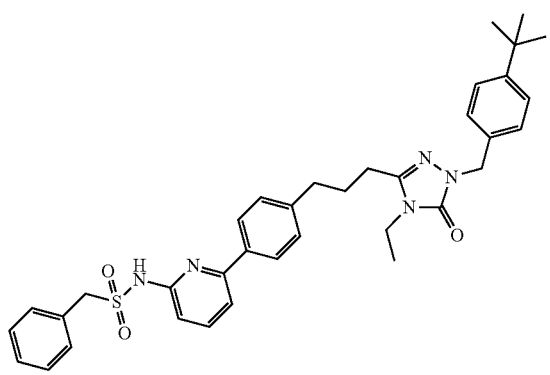 [SMILES: CCn1c(CCCc2ccc(-c3cccc(NS(=O)(=O)Cc4ccccc4)n3)cc2)nn(Cc2ccc(C(C)(C)C)cc2)c1=O]

Prepared in an analogous manner to example 4 using instead benzylsulfonyl chloride as the electrophile. LC-MS: 624 (M+H)+.

Example 79

1-{[4-(tert-Butyl)phenyl]methyl}-4-ethyl-3-{3-[4-(5-{[benzylsulfonyl]amino}(2-pyridyl))phenyl]propyl}-1,2,4-triazolin-5-one

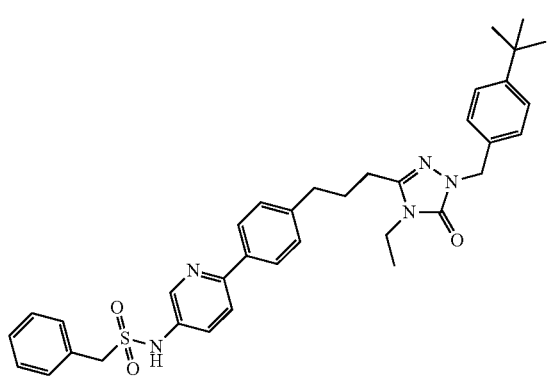 [SMILES: CCn1c(CCCc2ccc(-c3ccc(NS(=O)(=O)Cc4ccccc4)cn3)cc2)nn(Cc2ccc(C(C)(C)C)cc2)c1=O]

Prepared in an analogous manner to example 12 using instead benzylsulfonyl chloride as the electrophile. LC-MS: 624 (M+H)+.

Example 80

2-(4'-(3-(1-(4-(tert-Butyl)benzyl)-5-oxo-4-propyl-4,5-dihydro-1H-1,2,4-triazol-3-yl)propyl)-4-methoxy-[1,1'-biphenyl]-3-yl)acetic acid

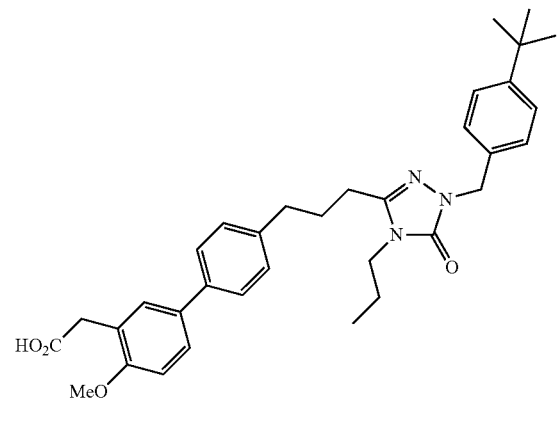 [SMILES: CCCn1c(CCCc2ccc(-c3ccc(OC)c(CC(=O)O)c3)cc2)nn(Cc2ccc(C(C)(C)C)cc2)c1=O]

Prepared in an analogous manner to example 36, using instead 2-(4'-(3-(4-allyl-1-(4-(tert-butyl)benzyl)-5-oxo-4,5-dihydro-1H-1,2,4-triazol-3-yl)propyl)-4-methoxy-[1,1'-biphenyl]-3-yl)acetic acid (example 76) as the substrate. LC-MS: 556 (M+H)+.

Example 81

N-(2-(4-(3-(1-(4-(tert-Butyl)benzyl)-4-ethyl-5-oxo-4,5-dihydro-1H-1,2,4-triazol-3-yl)propyl)phenyl)pyrimidin-4-yl)benzenesulfonamide

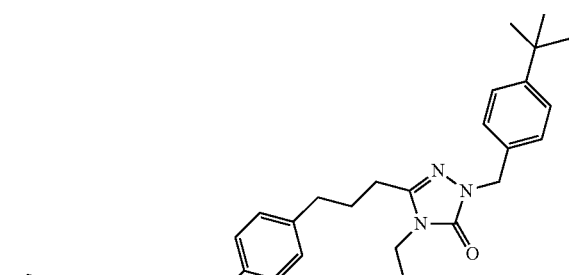

Step 1;
Carried out in an analogous manner to example 3 using instead 2-chloropyrimidin-4-amine as the coupling partner and dioxane as the reaction solvent.

Step 2;
Carried out in an analogous manner to example 4 using instead 3-(3-(4-(4-aminopyrimidin-2-yl)phenyl)propyl)-1-(4-(tert-butyl)benzyl)-4-ethyl-1H-1,2,4-triazol-5(4H)-one from the previous step as the substrate. LC-MS: 611 (M+H)+.

Example 82

1-{[4-(tert-Butyl)phenyl]methyl}-4-ethyl-3-(3-{4-[6-({[4-(trifluoromethyl)phenyl]sulfonyl}amino)(2-pyridyl)]phenyl}propyl)-1,2,4-triazolin-5-one

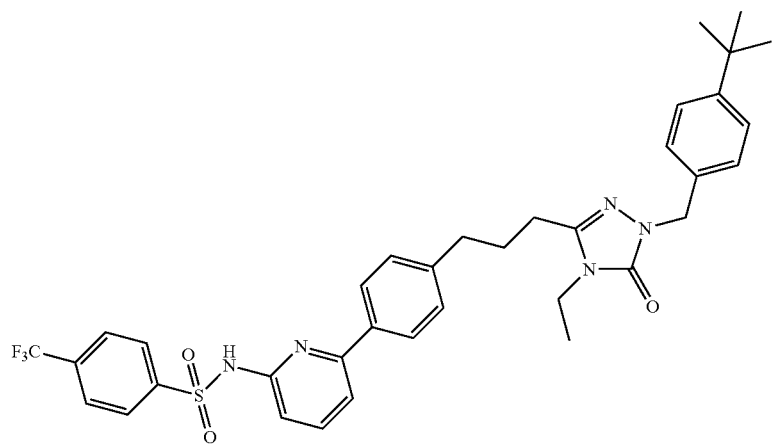 [SMILES: CCn1c(CCCc2ccc(-c3cccc(NS(=O)(=O)c4ccc(C(F)(F)F)cc4)n3)cc2)nn(Cc2ccc(C(C)(C)C)cc2)c1=O]

Prepared in an analogous manner to example 4 using instead 4-(trifluoromethyl)benzenesulfonyl chloride as the electrophile. LC-MS: 678 (M+H)$^+$.

Example 83

1-{[4-(tert-Butyl)phenyl]methyl}-3-{3-[4-(6-{[(4-chlorophenyl)sulfonyl]amino}(2-pyridyl))phenyl]propyl}-4-ethyl-1,2,4-triazolin-5-one

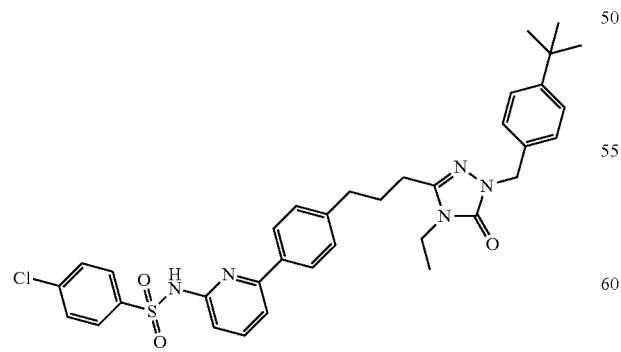

Prepared in an analogous manner to example 4 using instead 4-chlorobenzenesulfonyl chloride as the electrophile. LC-MS: 645 (M+H)$^+$.

Example 84

1-{[4-(tert-Butyl)phenyl]methyl}-4-ethyl-3-{3-[4-(6-{[(4-methoxyphenyl)sulfonyl]amino}(2-pyridyl))phenyl]propyl}-1,2,4-triazolin-5-one

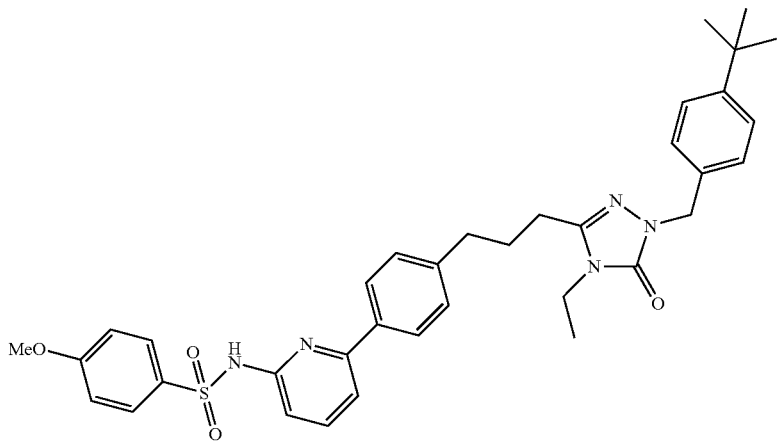 [SMILES: CCn1c(CCCc2ccc(-c3cccc(NS(=O)(=O)c4ccc(OC)cc4)n3)cc2)nn(Cc2ccc(C(C)(C)C)cc2)c1=O]

Prepared in an analogous manner to example 4 using instead 4-methoxybenzenesulfonyl chloride as the electrophile. LC-MS: 640 (M+H)$^+$.

Example 85

2-(4'-(3-(1-(3-Cyclopropyl-4-(tert-butyl)benzyl)-4-ethyl-5-oxo-4,5-dihydro-1H-1,2,4-triazol-3-yl)propyl)-[1,1'-biphenyl]-3-yl)acetic acid Prepared using the penultimate intermediate from example 67 with the coupling conditions described in example 22, step 3. Hydrolysis of the resulting ester was then carried out as in example 1, step 2 to deliver the title compound as a white foam. LC-MS: 552 (M+H)$^+$.

Example 86

1-{[4-(tert-Butyl)phenyl]methyl}-4-ethyl-3-(3-{4-[5-({[4-(trifluoromethyl)phenyl]sulfonyl}amino)(2-pyridyl)]phenyl}propyl)-1,2,4-triazolin-5-one Prepared in an analogous manner to example 12 using instead 4-(trifluoromethyl)benzenesulfonyl chloride as the electrophile. LC-MS: 678 (M+H)$^+$.

Example 87

1-{[4-(tert-Butyl)phenyl]methyl}-4-ethyl-3-{3-[4-(5-methoxy-6-{[benzylsulfonyl]amino}(2-pyridyl))phenyl]propyl}-1,2,4-triazolin-5-one

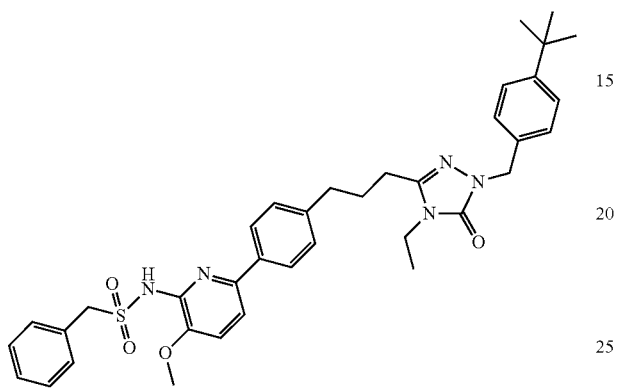

Prepared in an analogous manner to example 78 using instead 3-{3-[4-(6-amino-5-methoxy(2-pyridyl))phenyl]propyl}-1-{[4-(tert-butyl)phenyl]methyl}-4-ethyl-1,2,4-triazolin-5-one (example 58) as the nucleophile. LC-MS: 654 (M+H)$^+$.

Example 88

1-{[4-(tert-Butyl)phenyl]methyl}-4-ethyl-3-(3-{4-[5-methoxy-6-({[4-(trifluoromethyl)phenyl]sulfonyl}amino)(2-pyridyl)]phenyl}propyl)-1,2,4-triazolin-5-one Prepared in an analogous manner to example 59 using instead 4-(trifluoromethyl)benzenesulfonyl chloride as the electrophile. LC-MS: 708 (M+H)$^+$.

Example 89

5-(4-(3-(1-(4-(tert-Butyl)benzyl)-4-ethyl-5-oxo-4,5-dihydro-1H-1,2,4-triazol-3-yl)propyl)phenyl)benzofuran-3-carboxylic acid

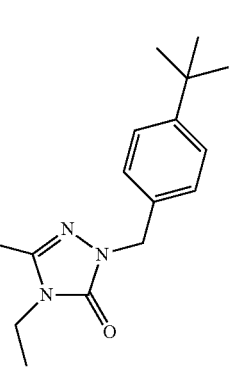

Prepared in an analogous manner to example 13 but using instead methyl 5-bromobenzofuran-3-carboxylate as the coupling partner in step 1. Hydrolysis of the intermediate ester was carried out as in example 1, step 2. LC-MS: 538 (M+H)$^+$.

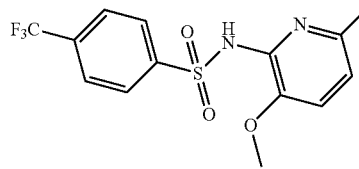

Example 90

1-{[4-(tert-Butyl)phenyl]methyl}-3-{3-[4-(5-{[(4-chlorophenyl)sulfonyl]amino}(2-pyridyl))phenyl]propyl}-4-ethyl-1,2,4-triazolin-5-one

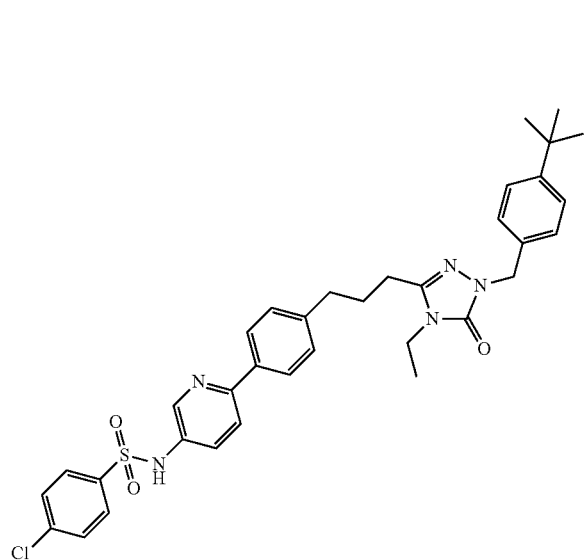 [SMILES: CCn1c(CCCc2ccc(-c3ccc(NS(=O)(=O)c4ccc(Cl)cc4)cn3)cc2)nn(Cc2ccc(C(C)(C)C)cc2)c1=O]

Prepared in an analogous manner to example 12 using instead 4-chlorobenzenesulfonyl chloride as the electrophile. LC-MS: 645 (M+H)+.

Example 91

1-{[4-(tert-Butyl)phenyl]methyl}-4-ethyl-3-{3-[4-(5-{[(4-methoxyphenyl)sulfonyl]amino}(2-pyridyl))phenyl]propyl}-1,2,4-triazolin-5-one

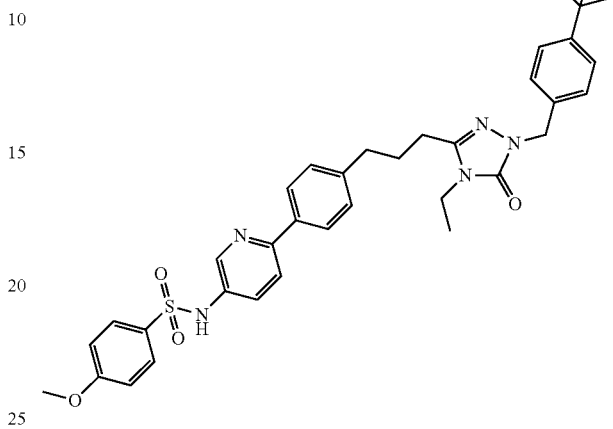

Prepared in an analogous manner to example 12 using instead 4-methoxybenzenesulfonyl chloride as the electrophile. LC-MS: 640 (M+H)+.

Example 92

1-{[4-(tert-Butyl)phenyl]methyl}-3-{3-[4-(6-{[(4-chlorophenyl)sulfonyl]amino}-5-methoxy(2-pyridyl))phenyl]propyl}-4-ethyl-1,2,4-triazolin-5-one

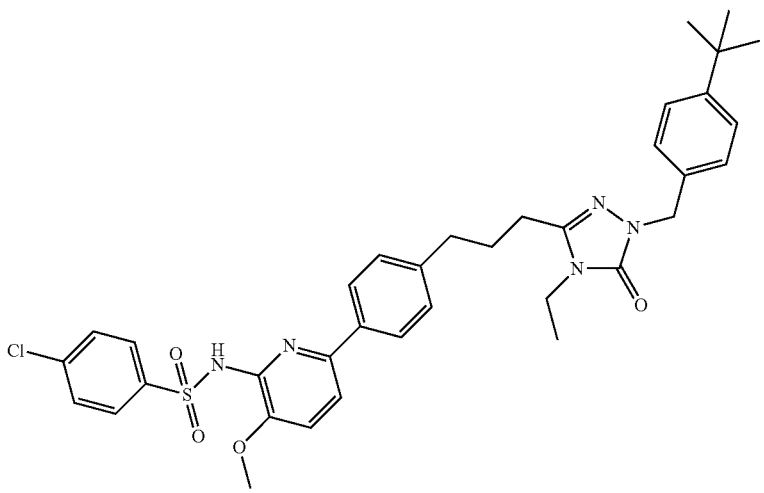 [SMILES: CCn1c(CCCc2ccc(-c3ccc(OC)c(NS(=O)(=O)c4ccc(Cl)cc4)n3)cc2)nn(Cc2ccc(C(C)(C)C)cc2)c1=O]

Prepared in an analogous manner to example 59 using instead 4-chlorobenzenesulfonyl chloride as the electrophile. LC-MS: 675 (M+H)+.

Example 93

1-{[4-(tert-Butyl)phenyl]methyl}-4-ethyl-3-{3-[4-(5-methoxy-6-{[(4-methoxyphenyl)sulfonyl]amino}(2-pyridyl))phenyl]propyl}-1,2,4-triazolin-5-one

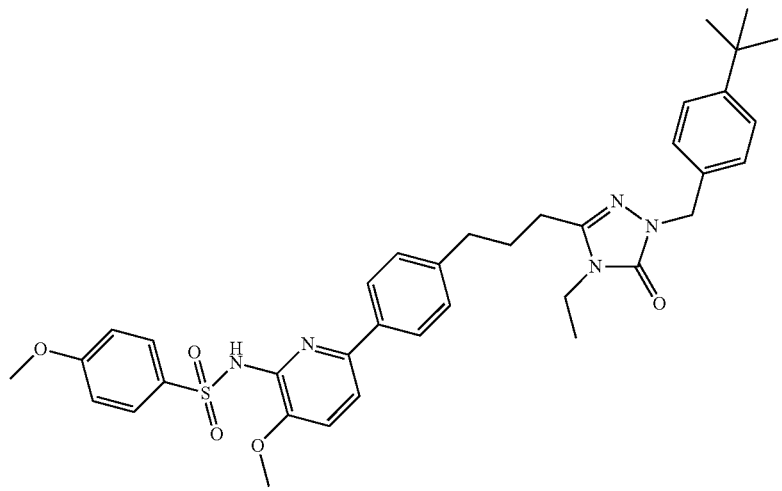 [SMILES: CCn1c(CCCc2ccc(-c3ccc(OC)c(NS(=O)(=O)c4ccc(OC)cc4)n3)cc2)nn(Cc2ccc(C(C)(C)C)cc2)c1=O]

Prepared in an analogous manner to example 59 using instead 4-methoxybenzenesulfonyl chloride as the electrophile. LC-MS: 670 (M+H)+.

Example 94

2-(4'-(3-(1-(4-(tert-Butyl)benzyl)-4-ethyl-5-oxo-4,5-dihydro-1H-1,2,4-triazol-3-yl)propyl)-4-propoxy-[1,1'-biphenyl]-3-yl)acetic acid

Example 95

2-(4'-(3-(1-(4-(tert-Butyl)benzyl)-4-methyl-5-oxo-4,5-dihydro-1H-1,2,4-triazol-3-yl)propyl)-4-ethoxy-[1,1'-biphenyl]-3-yl)acetic acid

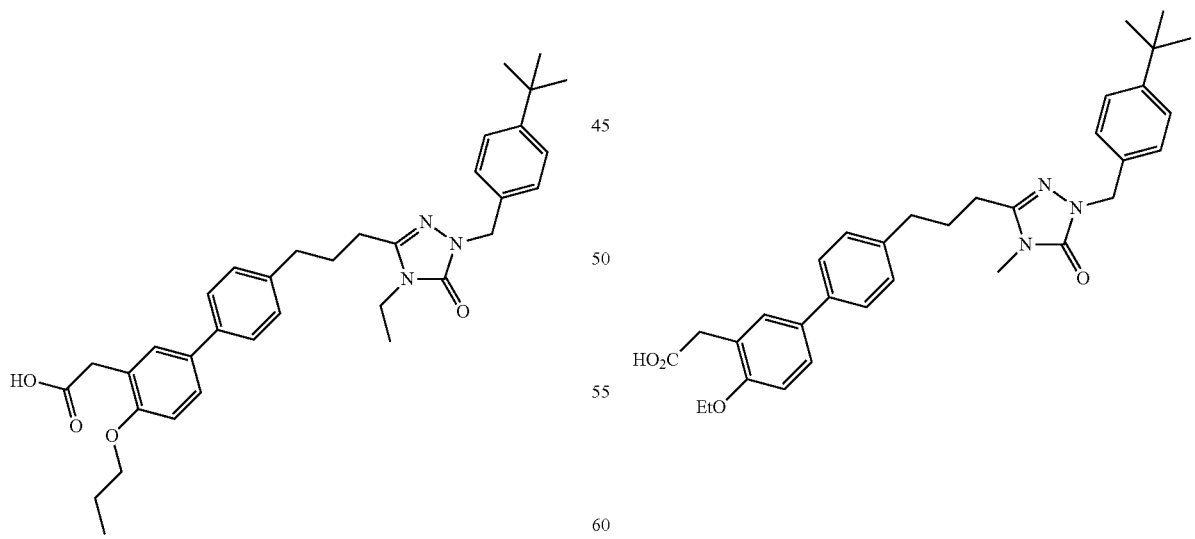

Prepared in an analogous manner to example 13 but using instead methyl 2-(5-bromo-2-propoxyphenyl)acetate as the coupling partner in step 1. Hydrolysis of the intermediate ester was carried out as in example 1, step 2. LC-MS: 570 (M+H)+.

Prepared in an analogous manner to example 53, using instead methyl iodide as the electrophile in step 3 and methyl 2-(2-ethoxy-5-(4,4,5,5-tetramethyl-1,3,2-dioxaborolan-2-yl)phenyl)acetate as the boronate coupling partner in step 4. LC-MS: 542 (M+H)+.

Example 96

(rac)-5-(4-(3-(1-(4-(tert-Butyl)benzyl)-4-ethyl-5-oxo-4,5-dihydro-1H-1,2,4-triazol-3-yl)propyl)phenyl)-2,3-dihydrobenzofuran-3-carboxylic acid

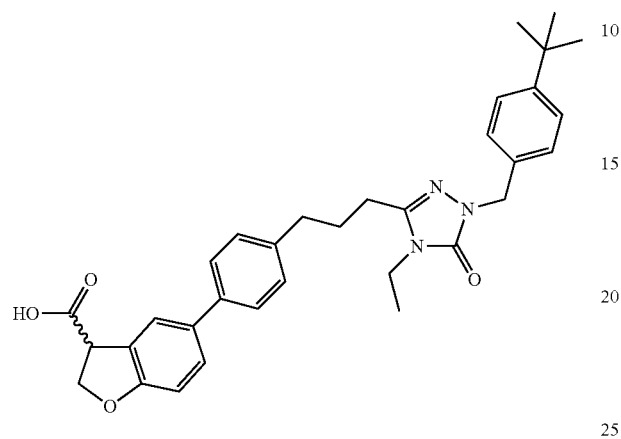

Prepared in an analogous manner to example 13 but using instead (rac)-methyl 5-bromo-2,3-dihydrobenzofuran-3-carboxylate as the coupling partner in step 1. Hydrolysis of the intermediate ester was carried out as in example 1, step 2. LC-MS: 540 (M+H)$^+$.

Example 97

N-(6-{4-[3-(1-{[4-(tert-Butyl)phenyl]methyl}-4-ethyl-5-oxo(1,2,4-triazolin-3-yl))propyl]phenyl}(2-pyridyl))benzamide

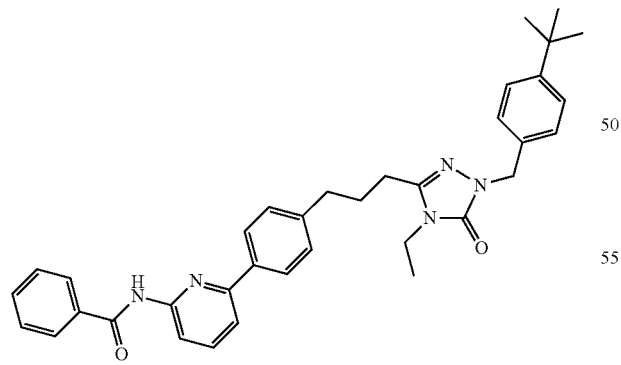

Prepared in an analogous manner to example 4 using instead benzoyl chloride as the electrophile. LC-MS: 574 (M+H)$^+$.

Example 98

1-{[4-(tert-Butyl)phenyl]methyl}-4-ethyl-3-[3-(4-{6-methoxy-5-[(phenylsulfonyl)amino](2-pyridyl)}phenyl)propyl]-1,2,4-triazolin-5-one

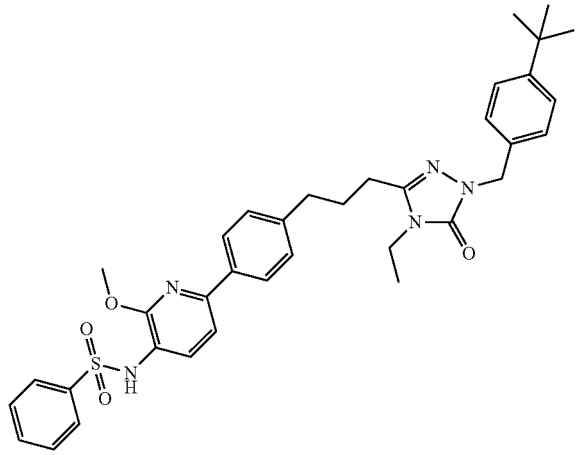 [SMILES: CCn1c(CCCc2ccc(-c3ccc(NS(=O)(=O)c4ccccc4)c(OC)n3)cc2)nn(Cc2ccc(C(C)(C)C)cc2)c1=O]

Step 1 to 3;

Carried out in an analogous manner as detailed in step 2 to 4 of example 58, using instead 6-chloro-3-nitropyridin-2-ol as the start material in step 2.

Step 4:

Carried out in an analogous manner to example 59 using instead 1-(4-(tert-butyl)benzyl)-4-ethyl-3-(3-(4-(6-methoxy-5-nitropyridin-2-yl)phenyl)propyl)-1H-1,2,4-triazol-5(4H)-one prepared in the previous step as the nucleophile. LC-MS: 640 (M+H)$^+$.

Example 99

N-benzyl-4'-(3-(1-(4-(tert-butyl)benzyl)-4-ethyl-5-oxo-4,5-dihydro-1H-1,2,4-triazol-3-yl)propyl)-[1,1'-biphenyl]-4-sulfonamide

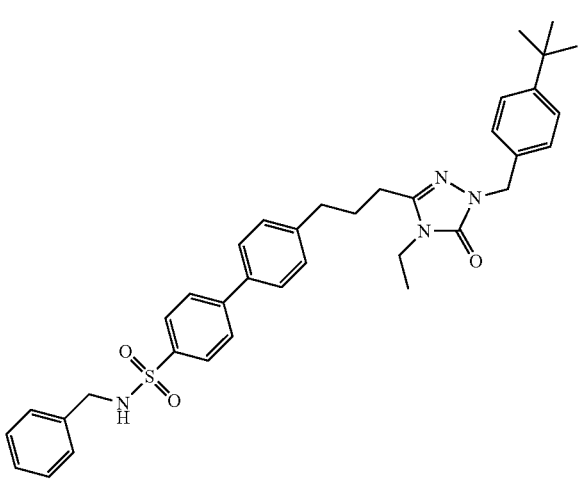 [SMILES: CCn1c(CCCc2ccc(-c3ccc(S(=O)(=O)NCc4ccccc4)cc3)cc2)nn(Cc2ccc(C(C)(C)C)cc2)c1=O]

Prepared in an analogous manner to example 28 but omitting the first step and using instead ethyl N-benzyl-4-bromobenzenesulfonamide as the coupling partner in step 2. LC-MS: 623 (M+H)+.

Example 100

N-(6-{4-[3-(1-{[4-(tert-Butyl)phenyl]methyl}-4-ethyl-5-oxo-1,2,4-triazolin-3-yl)propyl]phenyl}-2-pyridyl)butanamide Prepared in an analogous manner to example 4 using instead butyryl chloride as the electrophile. LC-MS: 540 (M+H)+.

Example 101

N-(6-{4-[3-(1-{[4-(tert-Butyl)phenyl]methyl}-4-ethyl-5-oxo(1,2,4-triazolin-3-yl))propyl]phenyl}(2-pyridyl))-2-phenylacetamide Prepared in an analogous manner to example 4 using instead phenylacetyl chloride as the electrophile. LC-MS: 588 (M+H)+.

Example 102

N-(6-{4-[3-(1-{[4-(tert-Butyl)phenyl]methyl}-4-ethyl-5-oxo(1,2,4-triazolin-3-yl))propyl]phenyl}(2-pyridyl))cyclopropylcarboxamide

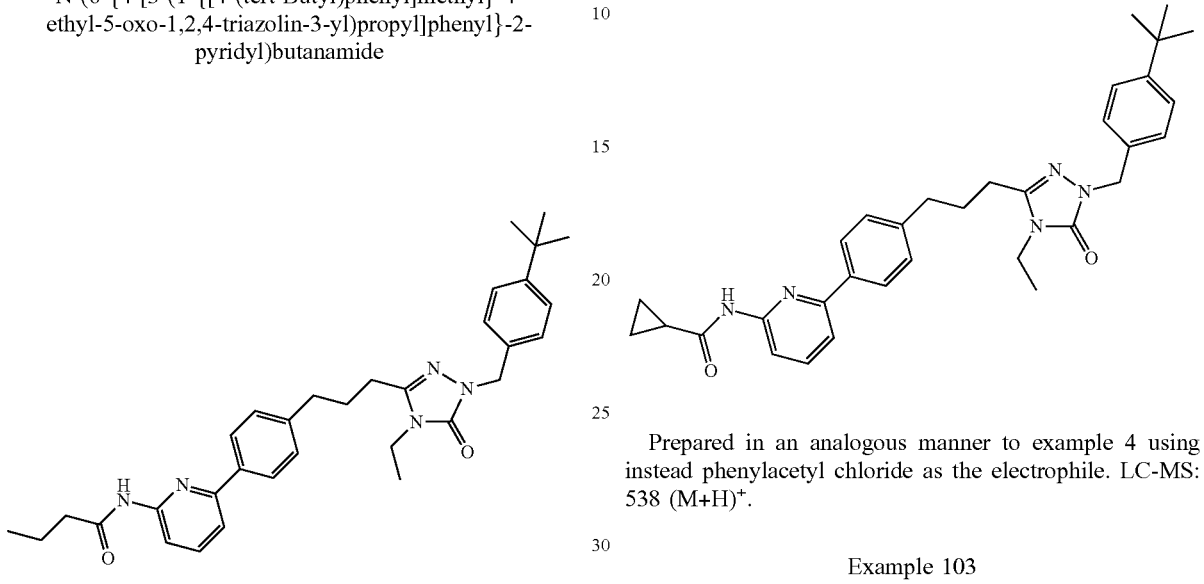

Prepared in an analogous manner to example 4 using instead phenylacetyl chloride as the electrophile. LC-MS: 538 (M+H)+.

Example 103

N-((4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)sulfonyl)propionamide

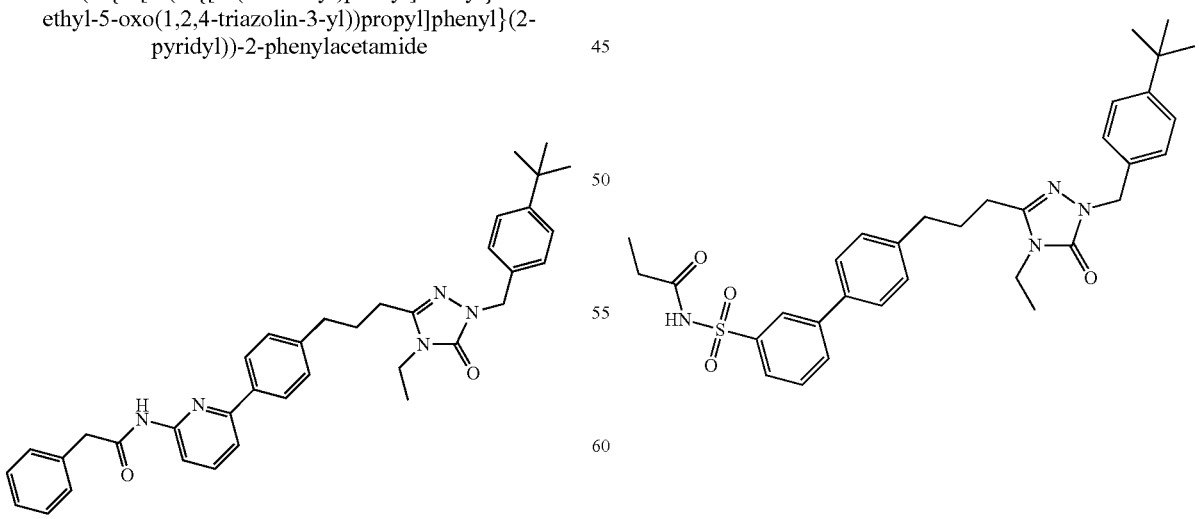

Prepared in an analogous manner to example 28 but omitting the first step and using instead N-((3-bromophenyl)sulfonyl)propionamide as the coupling partner in step 2. LC-MS: 589 (M+H)+.

Example 104

N-Benzyl-1-(4'-(3-(1-(4-(tert-butyl)benzyl)-4-ethyl-5-oxo-4,5-dihydro-1H-1,2,4-triazol-3-yl)propyl)-[1,1'-biphenyl]-4-yl)methanesulfonamide

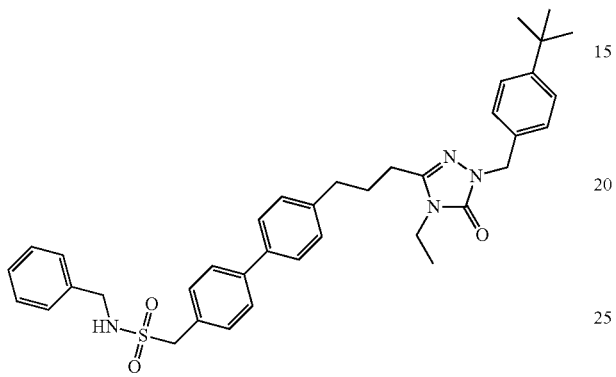

Prepared in an analogous manner to example 28 but omitting the first step and using instead N-benzyl-1-(4-bromophenyl)methanesulfonamide as the coupling partner in step 2. LC-MS: 637 (M+H)$^+$.

Example 105

N-Benzyl-1-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)methanesulfonamide

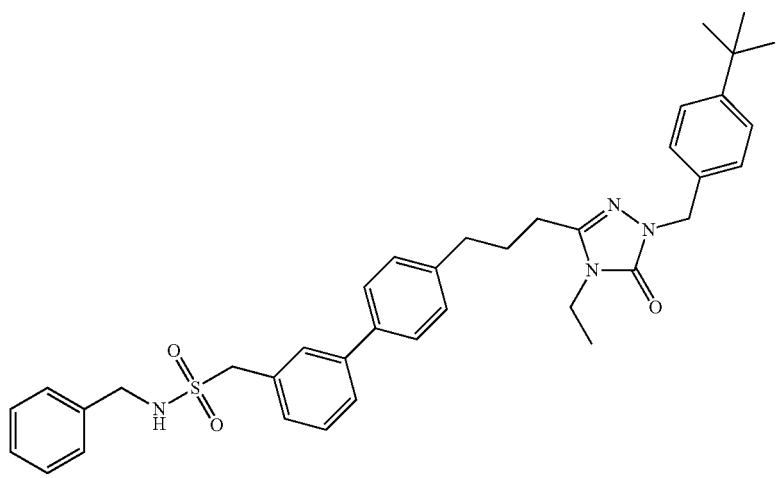 [SMILES: CCn1c(CCCc2ccc(-c3cccc(CS(=O)(=O)NCc4ccccc4)c3)cc2)nn(Cc2ccc(C(C)(C)C)cc2)c1=O]

Prepared in an analogous manner to example 28 but omitting the first step and using instead N-benzyl-1-(3-bromophenyl)methanesulfonamide as the coupling partner in step 2. LC-MS: 637 (M+H)$^+$.

Example 106

2-(4'-(3-(1-(4-(tert-Butyl)benzyl)-4-methyl-5-oxo-4,5-dihydro-1H-1,2,4-triazol-3-yl)propyl)-4-methoxy-[1,1'-biphenyl]-3-yl)acetic acid

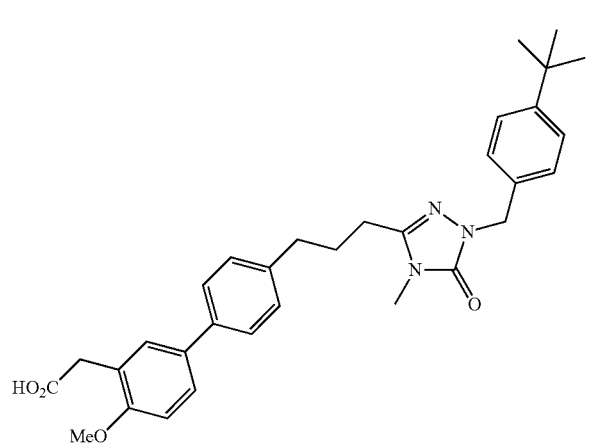 [SMILES: COc1ccc(-c2ccc(CCCc3nn(Cc4ccc(C(C)(C)C)cc4)c(=O)n3C)cc2)cc1CC(=O)O]

Prepared in an analogous manner to example 53, using instead methyl iodide as the electrophile in step 3 and methyl 2-(2-methoxy-5-(4,4,5,5-tetramethyl-1,3,2-dioxaborolan-2-yl)phenyl)acetate as the boronate coupling partner in step 4. LC-MS: 528 (M+H)$^+$.

Example 107

3-{3-[4-(3-{[(Dimethylamino)sulfonyl]amino}phenyl)phenyl]propyl}-1-{[4-(tert-butyl)phenyl]methyl}-4-ethyl-1,2,4-triazolin-5-one

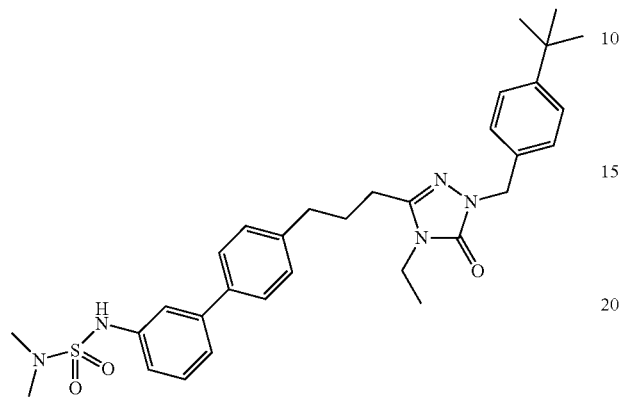

Prepared in an analogous manner to example 28 but omitting the first step and using instead 3-(N,N-dimethylsulfamoylamino)phenylboronic acid as the coupling partner in step 2. LC-MS: 576 (M+H)$^+$.

Example 108

N-(2-(4-(3-(1-(4-(tert-Butyl)benzyl)-4-ethyl-5-oxo-4,5-dihydro-1H-1,2,4-triazol-3-yl)propyl)phenyl)pyrimidin-5-yl)benzenesulfonamide

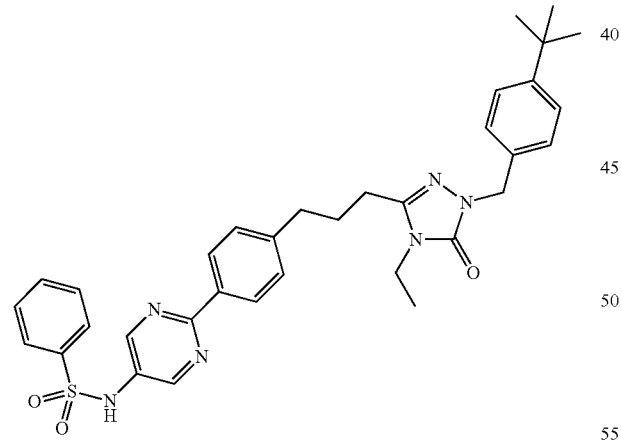

Step 1:
Carried out in an analogous manner to that detailed in example 3, using instead 2-chloropyrimidin-5-amine as the coupling partner.

Step 2:
Carried out in an analogous manner to that detailed in example 4 using 3-(3-(4-(5-aminopyrimidin-2-yl)phenyl)propyl)-1-(4-(tert-butyl)benzyl)-4-ethyl-1H-1,2,4-triazol-5(4H)-one from the previous step as the starting material. LC-MS: 611 (M+H)$^+$.

Example 109

3-(3-(4-(5-Aminopyridin-3-yl)phenyl)propyl)-1-(4-(tert-butyl)benzyl)-4-ethyl-1H-1,2,4-triazol-5(4H)-one

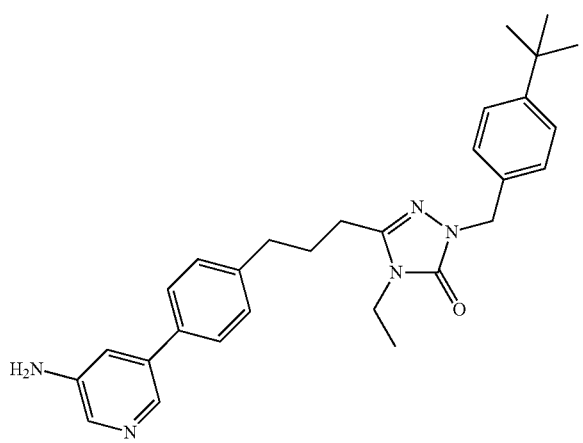 [SMILES: CCn1c(CCCc2ccc(-c3cncc(N)c3)cc2)nn(Cc2ccc(C(C)(C)C)cc2)c1=O]

Prepared in an analogous manner to example 3 but using instead 5-bromopyridin-3-amine as the coupling partner. LC-MS: 470 (M+H)$^+$.

Example 110

1-{[4-(tert-Butyl)phenyl]methyl}-4-ethyl-3-[3-(4-{5-methoxy-6-[N-methyl(phenylsulfonyl)amino](2-pyridyl)}phenyl)propyl]-1,2,4-triazolin-5-one

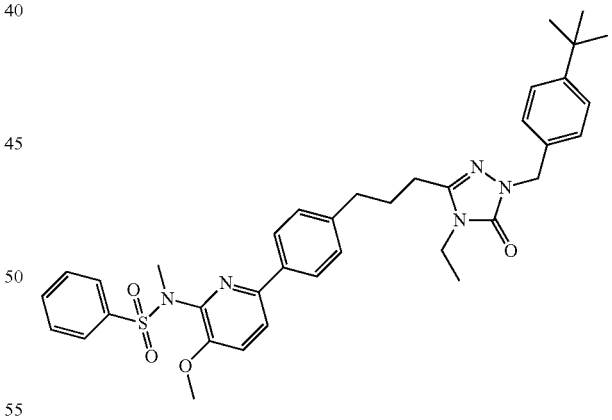

To a solution of 1-{[4-(tert-butyl)phenyl]methyl}-4-ethyl-3-[3-(4-{5-methoxy-6-[(phenylsulfonyl)amino](2-pyridyl)}phenyl)propyl]-1,2,4-triazolin-5-one (45 mg, 0.067 mmol, example 59) in DMF (3 mL) was added potassium carbonate (14 mg, 0.10 mmol) and iodomethane (6 µL, 0.080 mmol). The resulting mixture was then stirred at room temperature over night. The reaction solution was then diluted with water and back extracted with EtOAc. The combined organic extracts were dried over anhydrous Na$_2$SO$_4$, filtered and the filtrate concentrated in vacuo. The crude product thus obtained was purified further by flash column chromatography (SiO$_2$, gradient elution, Hex to 2:1 (v/v) Hex: EtOAc) to afford the titled compound (24 mg, 55%). LC-MS: 654 (M+H)$^+$.

Example 111

3-{3-[4-(5-Amino-4-methoxy(2-pyridyl))phenyl]propyl}-1-{[4-(tert-butyl)phenyl]methyl}-4-ethyl-1,2,4-triazolin-5-one

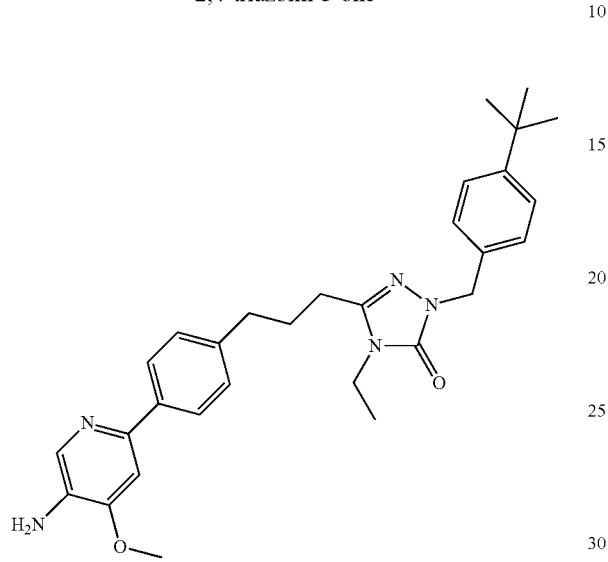

Step 1 to 3;

Carried out in an analogous manner as detailed in step 2 to 4 of example 58 but using instead 2-chloro-5-nitropyridin-4-ol (prepared according the procedure found in *J. Med. Chem. Lett.* 2007. 50, p. 2-5) as the starting material. LC-MS: 500 (M+H)$^+$.

Example 112

1-{[4-(tert-Butyl)phenyl]methyl}-4-ethyl-3-[3-(4-{4-methoxy-5-[(phenylsulfonyl)amino](2-pyridyl)}phenyl)propyl]-1,2,4-triazolin-5-one

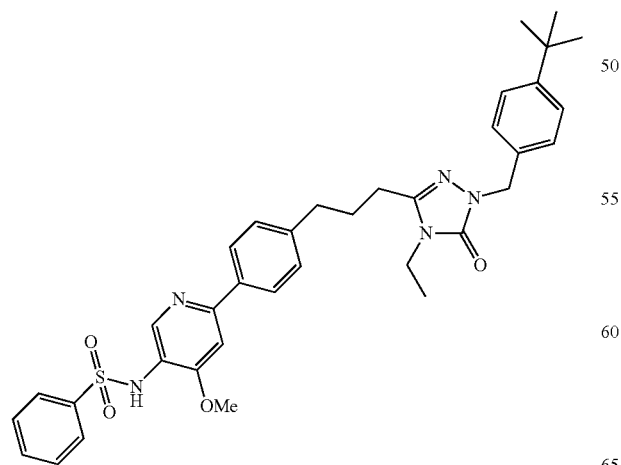

Prepared in an analogous manner to example 59 but using instead 3-{3-[4-(5-amino-4-methoxy(2-pyridyl))phenyl]propyl}-1-{[4-(tert-butyl)phenyl]methyl}-4-ethyl-1,2,4-triazolin-5-one (example 111) as the nucleophile. LC-MS: 640 (M+H)$^+$.

Example 113

1-{[4-(tert-Butyl)phenyl]methyl}-3-{3-[4-(6-{[(6-chloro(3-pyridyl))sulfonyl]amino}-5-methoxy(2-pyridyl))phenyl]propyl}-4-ethyl-1,2,4-triazolin-5-one

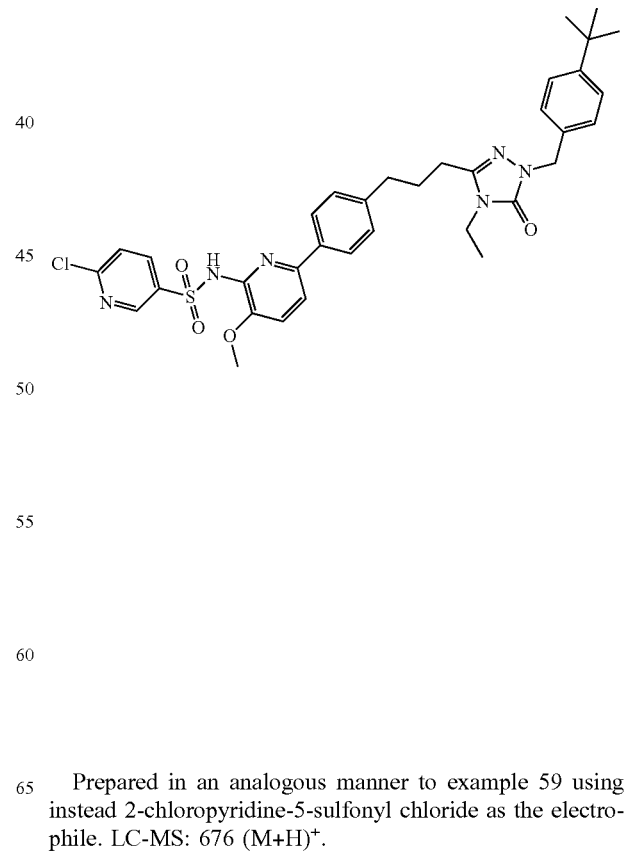

Prepared in an analogous manner to example 59 using instead 2-chloropyridine-5-sulfonyl chloride as the electrophile. LC-MS: 676 (M+H)$^+$.

Example 114

1-{[4-(tert-Butyl)phenyl]methyl}-4-ethyl-3-{3-[4-(5-methoxy-6-{[(6-methoxy(3-pyridyl))sulfonyl]amino}(2-pyridyl))phenyl]propyl}-1,2,4-triazolin-5-one

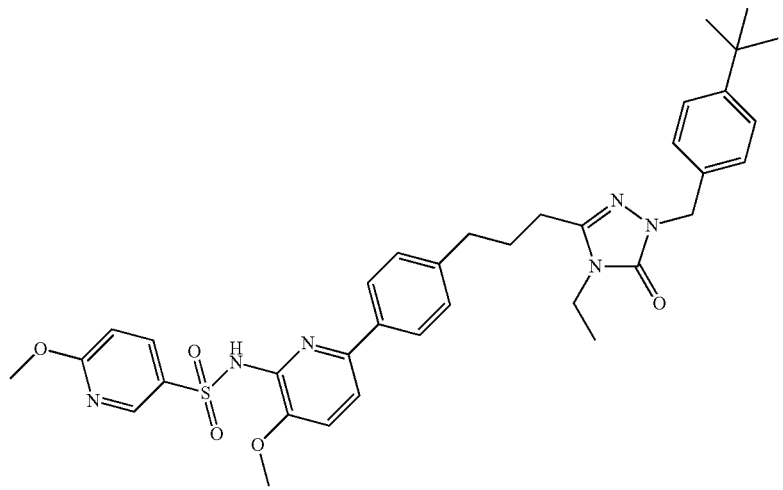 [SMILES: CCn1c(CCCc2ccc(-c3ccc(OC)c(NS(=O)(=O)c4ccc(OC)nc4)n3)cc2)nn(Cc2ccc(C(C)(C)C)cc2)c1=O]

Prepared in an analogous manner to example 59 using instead 6-methoxypyridine-3-sulfonyl chloride as the electrophile. LC-MS: 671 (M+H)+.

Example 115

2-(4'-(3-(1-(3-Methyl-4-(tert-butyl)benzyl)-4-ethyl-5-oxo-4,5-dihydro-1H-1,2,4-triazol-3-yl)propyl)-[1,1'-biphenyl]-3-yl) acetic acid

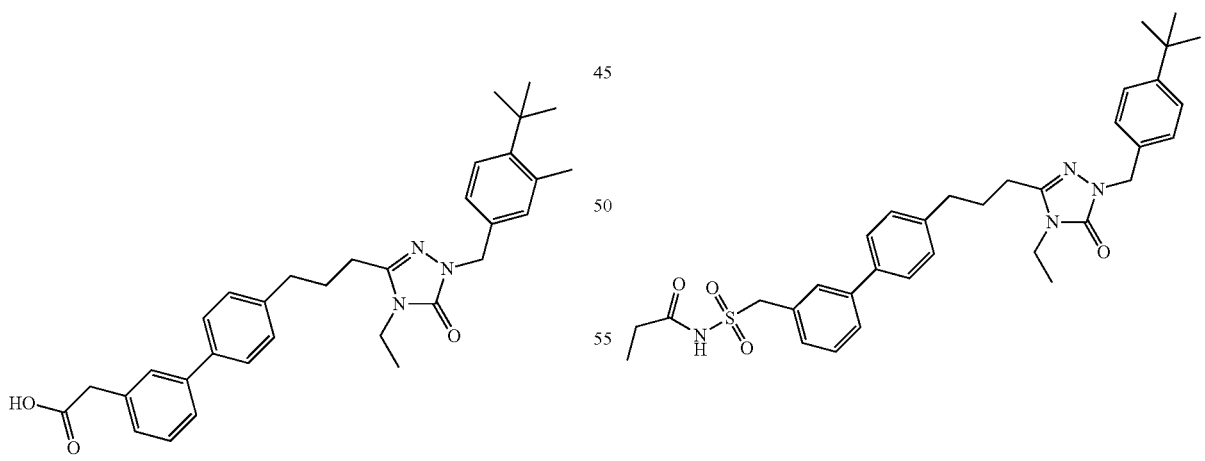

Prepared using the penultimate intermediate from example 67 and methylboronic acid using the coupling conditions described in example 22, step 3. Hydrolysis of the resulting ester was then carried out as in example 1, step 2 to deliver the title compound as a white foam. LC-MS: 526 (M+H)+.

Example 116

N-(((4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)methyl)sulfonyl)propionamide Prepared in an analogous manner to example 28 but omitting the first step and using instead N-((3-bromobenzyl)sulfonyl)propionamide as the coupling partner in step 2. LC-MS: 603 (M+H)+.

Example 117

N-(5-(4-(3-(1-(4-(tert-Butyl)benzyl)-4-ethyl-5-oxo-4,5-dihydro-1H-1,2,4-triazol-3-yl)propyl)phenyl)pyridin-3-yl)benzenesulfonamide

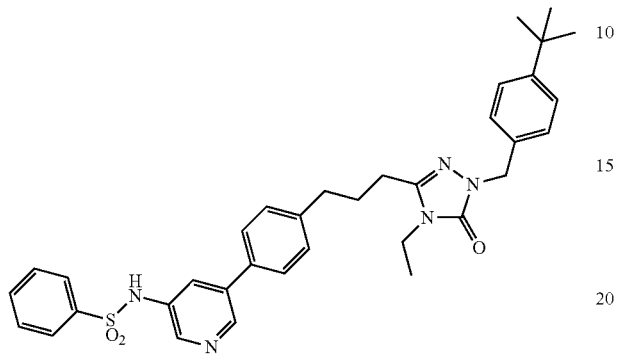

Prepared in an analogous manner to example 4 but using instead 3-(3-(4-(5-aminopyridin-3-yl)phenyl)propyl)-1-(4-(tert-butyl)benzyl)-4-ethyl-1H-1,2,4-triazol-5(4H)-one (example 109) as the nucleophile. LC-MS: 610 (M+H)⁺.

Example 118

N-(5-(4-(3-(1-(4-(tert-Butyl)benzyl)-4-ethyl-5-oxo-4,5-dihydro-1H-1,2,4-triazol-3-yl)propyl)phenyl)pyrazin-2-yl)benzenesulfonamide

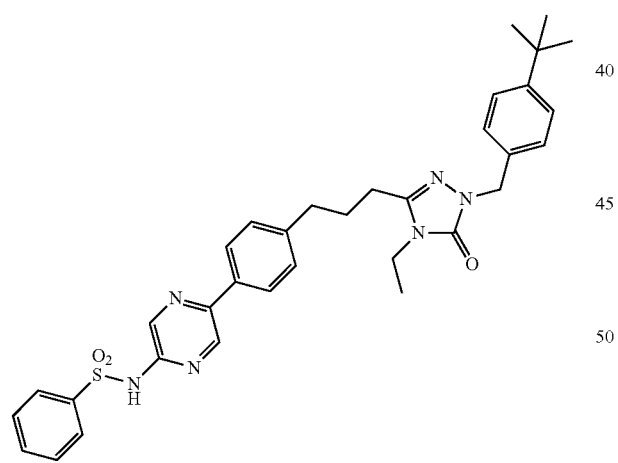

Step 1:
Carried out in an analogous manner to that detailed in example 3, using instead 5-chloropyrazin-2-amine as the coupling partner.

Step 2:
Carried out in an analogous manner to that detailed in example 4 using 5-(4-(3-(1-aminopyrazin-2-yl)phenyl)propyl)-1-(4-(tert-butyl)benzyl)-4-ethyl-1H-1,2,4-triazol-5(4H)-one from the previous step as the starting material. LC-MS: 611 (M+H)⁺.

Example 119

N-(5-(4-(3-(1-(4-(tert-Butyl)benzyl)-4-ethyl-5-oxo-4,5-dihydro-1H-1,2,4-triazol-3-yl)propyl)phenyl)pyrazin-2-yl)-1-phenylmethanesulfonamide Prepared in an analogous manner to example 118 but using instead phenylmethylsulfonyl chloride as the electrophile. LC-MS: 625 (M+H)⁺.

Example 120

1-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)cyclopropanecarbonitrile Carried out in an analogous manner as detailed in example 13, step 1, but using instead 1-(5-bromo-2-ethoxyphenyl)cyclopropanecarbonitrile as the coupling partner. LC-MS: 563 (M+H)⁺.

Example 121

4'-(3-(1-(4-(tert-Butyl)benzyl)-4-ethyl-5-oxo-4,5-dihydro-1H-1,2,4-triazol-3-yl)propyl)-4-(difluoromethoxy)-[1,1'-biphenyl]-3-carboxylic acid

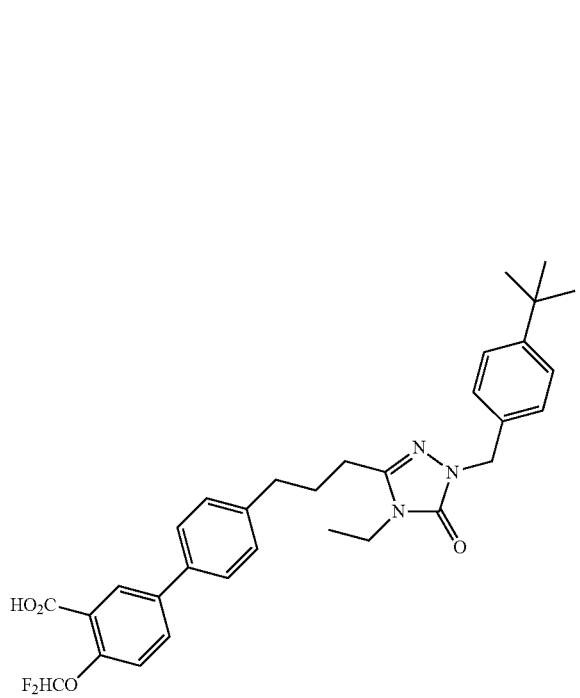 [SMILES: CCn1c(CCCc2ccc(-c3ccc(OC(F)F)c(C(=O)O)c3)cc2)nn(Cc2ccc(C(C)(C)C)cc2)c1=O]

Step 1;

To a solution of methyl 5-bromo-2-hydroxybenzoate (409 mg, 1.77 mmol) in DMF (5 mL) was added potassium carbonate (367 mg, 2.67 mmol) and ethyl 2-bromo-2,2-difluoroacetate (280 µL, 2.13 mmol). The resulting mixture was heated at 80° C. for 24 hrs. The resulting solution was cooled to RT, diluted with ether and washed sequentially with water, 10% aq. HCl, water and brine. The organic extract was then dried over Na$_2$SO$_4$, filtered and the filtrate concentrated in vacuo. Further purification by way of column chromatography (SiO$_2$, gradient elution, Hex to 2:1 (v/v) Hex: EtOAc) afforded methyl 5-bromo-2-(difluoromethoxy)benzoate as a yellow oil (250 mg, 50% yield).

Step 2;

Carried out in an analogous manner as detailed in example 13, step 1, but using instead methyl 5-bromo-2-(difluoromethoxy)benzoate as the coupling partner. Hydrolysis of the intermediate ester was carried out as in example 1, step 2. LC-MS: 564 (M+H)$^+$.

Example 122

1-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)cyclopropanecarboxylic acid

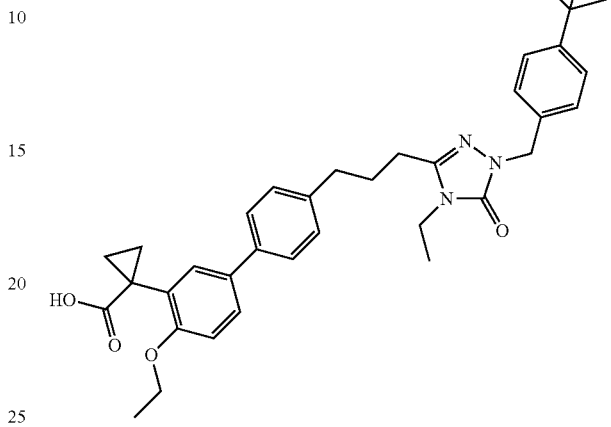

To a solution of 1-(4'-(3-(1-(4-(tert-butyl)benzyl)-4-ethyl-5-oxo-4,5-dihydro-1H-1,2,4-triazol-3-yl)propyl)-4-ethoxy-[1,1'-biphenyl]-3-yl)cyclopropanecarbonitrile (example 120; 120 mg, 0.21 mmol) in ethylene glycol (2 mL) and water (2 mL) was added potassium hydroxide (300 mg). The vessel was sealed and heated at 145° C. for 24 hrs. After cooling to RT, the reaction was quenched with 1 N aq. HCl and extracted with EtOAc. The combined organic extracts were washed further with water and brine, dried (MgSO$_4$), filtered and eand the filtrate concentrated in vacuo. Purification of the crude product thus obtained on silica gel eluting with a gradient of 0 to 6% MeOH in CHCl$_3$ afforded the title compound. LC-MS: 582 (M+H)$^+$.

Example 123

4'-(3-(1-(4-(tert-Butyl)benzyl)-4-ethyl-5-oxo-4,5-dihydro-1H-1,2,4-triazol-3-yl)propyl)-4-methoxy-N-(pyridin-2-yl)-[1,1'-biphenyl]-3-sulfonamide

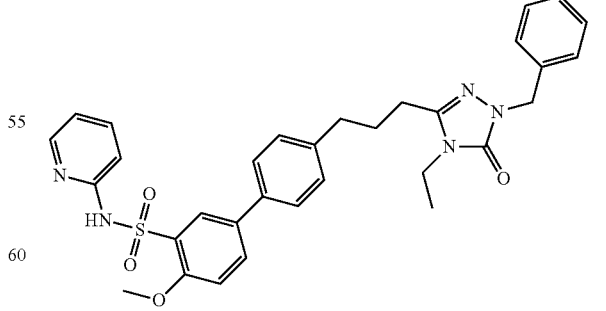

Prepared in an analogous manner to example 28 but omitting the first step and using instead 4-bromo-2-methoxy-N-(pyridin-2-yl)benzenesulfonamide as the coupling partner in step 2. LC-MS: 640 (M+H)$^+$.

Example 124

1-{[4-(tert-Butyl)phenyl]methyl}-4-ethyl-3-[3-(4-{6-methyl-5-[(phenylsulfonyl)amino](2-pyridyl)}phenyl)propyl]-1,2,4-triazolin-5-one

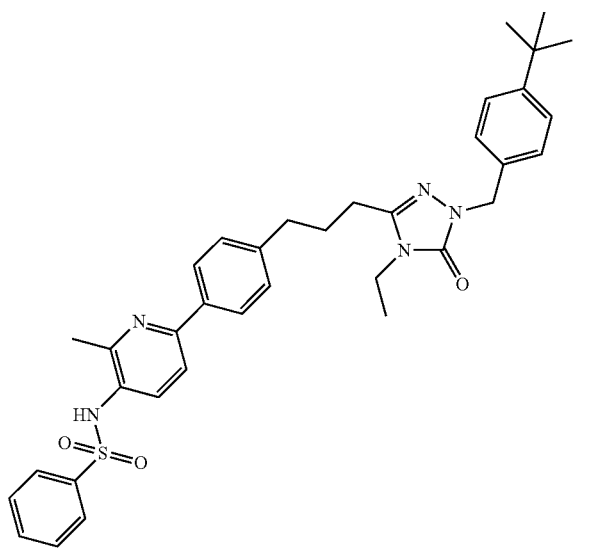 [SMILES: CCn1c(CCCc2ccc(-c3ccc(NS(=O)(=O)c4ccccc4)c(C)n3)cc2)nn(Cc2ccc(C(C)(C)C)cc2)c1=O]

Step 1 to 2;
Carried out in an analogous manner as detailed in step 3 to 4 of example 58, using instead 6-chloro-2-methyl-3-nitropyridine as the coupling partner in step 3.
Step 3:
Carried out in an analogous manner to example 59 using instead 3-(3-(4-(5-amino-6-methylpyridin-2-yl)phenyl)propyl)-1-(4-(tert-butyl)benzyl)-4-ethyl-1H-1,2,4-triazol-5(4H)-one prepared in the previous step as the nucleophile. LC-MS: 624 (M+H)⁺.

Example 125

1-{[4-(tert-Butyl)phenyl]methyl}-4-ethyl-3-{3-[4-(6-methyl-5-{[benzylsulfonyl]amino}(2-pyridyl))phenyl]propyl}-1,2,4-triazolin-5-one

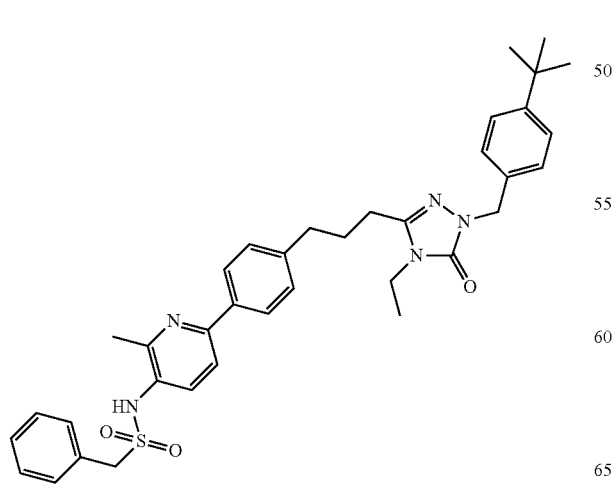

Prepared in an analogous manner to example 124 but using instead benzylsulfonyl chloride as the electrophile. LC-MS: 638 (M+H)⁺.

Example 126

1-{[4-(tert-Butyl)phenyl]methyl}-4-ethyl-3-[3-(4-{4-methyl-5-[(phenylsulfonyl)amino](2-pyridyl)}phenyl)propyl]-1,2,4-triazolin-5-one

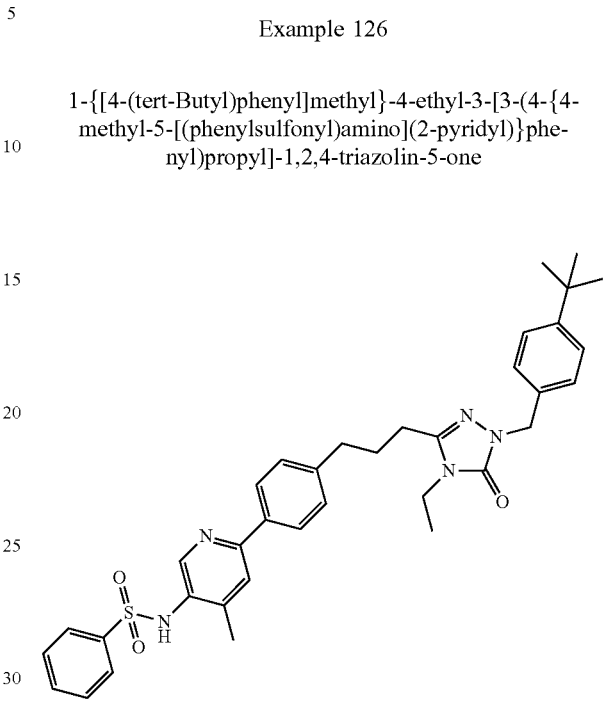

Prepared in an analogous manner to example 124 but using instead 2-chloro-4-methyl-5-nitropyridine as the coupling partner. LC-MS: 624 (M+H)⁺.

Example 127

1-{[4-(tert-Butyl)phenyl]methyl}-4-ethyl-3-{3-[4-(4-methyl-5-{[benzylsulfonyl]amino}(2-pyridyl))phenyl]propyl}-1,2,4-triazolin-5-one

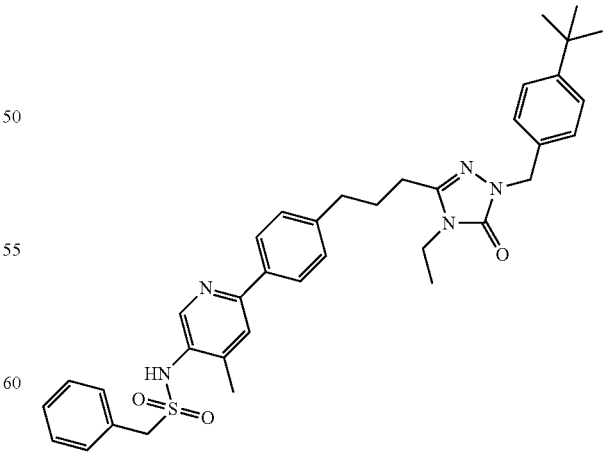

Prepared in an analogous manner to example 126 but using instead benzylsulfonyl chloride as the electrophile. LC-MS: 638 (M+H)⁺.

Example 128

1-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)cyclopropanecarboxylic acid

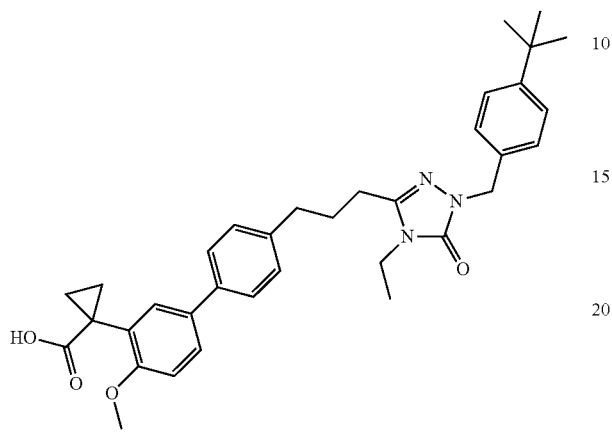

Step 1;
Carried out in analogous manner to example 120, step 1 using instead 1-(5-bromo-2-methoxyphenyl)cyclopropanecarbonitrile as the coupling partner.

Step 2:
The nitrile prepared from the previous step was combined with excess KOH in ethylene glycol and heated to 160° C. for 16 hrs. The resulting mixture was partitioned between EtOAc and 1 M aq. HCl. The organic phase was separated, washed further with water and brine, dried (MgSO$_4$), filtered, and concentrated in vacuo. The resulting residue was purified on reverse phase HPLC to afford the title compound. LC-MS: 568 (M+H)$^+$.

Example 129

N-(6-(4-(3-(1-(4-(tert-Butyl)benzyl)-4-ethyl-5-oxo-4,5-dihydro-1H-1,2,4-triazol-3-yl)propyl)phenyl)pyrazin-2-yl)benzenesulfonamide

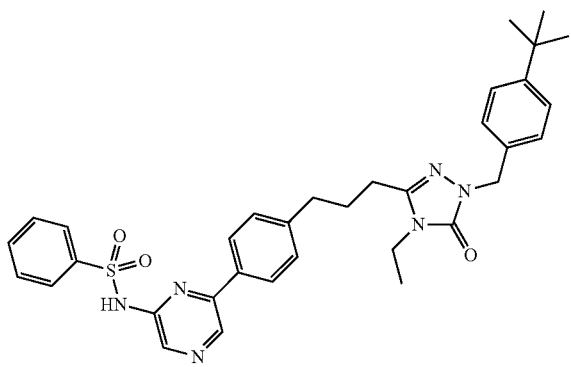 [SMILES: CCn1c(CCCc2ccc(-c3cncc(NS(=O)(=O)c4ccccc4)n3)cc2)nn(Cc2ccc(C(C)(C)C)cc2)c1=O]

Step 1:
Carried out in an analogous manner to that detailed in example 3, using 6-chloropyrazin-2-amine as the coupling partner.

Step 2:
Carried out in an analogous manner to that detailed in example 4 using 3-(3-(4-(6-aminopyrazin-2-yl)phenyl)propyl)-1-(4-(tert-butyl)benzyl)-4-ethyl-1H-1,2,4-triazol-5(4H)-one as the starting material. LC-MS: 611 (M+H)$^+$.

Example 130

2-(4'-(3-(1-(4-(tert-Butyl)benzyl)-4-ethyl-5-oxo-4,5-dihydro-1H-1,2,4-triazol-3-yl)propyl)-4-(trifluoromethoxy)-[1,1'-biphenyl]-3-yl)acetic acid

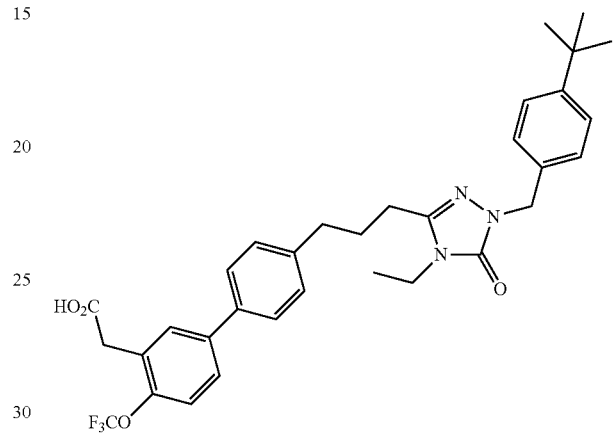

Step 1;
To a solution of 5-bromo-2-(trifluoromethoxy)benzoic acid (1.0 g, 3.5 mmol) in THF (20 mL) was added sequentially at −15° C. triethylamine (0.54 mL, 3.9 mmol) and ethyl chloroformate (0.37 mL, 3.9 mmol). The resulting white suspension was stirred at −5° C. for 3 hrs before anhydrous MeCN (20 mL) and trimethylsilyl diazomethane (5.5 mL, 10 mmol, 2 M solution in ether) were added, The now yellow solution was allowed to warm slowly to RT over 16 hrs. The reaction was carefully quenched with the addition of glacial acetic acid, followed by 10% aq. NaHCO$_3$. The aqueous layer was separated and back-extracted with ether. The combined organic extracts were then dried over Na$_2$SO$_4$, filtered and the filtrate concentrated in vacuo. Further purification by way of column chromatography (SiO$_2$, gradient elution, Hex to 2:1 (v/v) Hex: EtOAc) afforded 1-(5-bromo-2-(trifluoromethoxy)phenyl)-2-diazoethanone as a yellow oil (460 mg, 42% yield).

Step 2;
To a solution of 1-(5-bromo-2-(trifluoromethoxy)phenyl)-2-diazoethanone (460 mg, 1.5 mmol) in methanol (5 mL) was added, under gentle sonication, a triethylamine (1 mL) solution of silver benzoate (170 mg, 0.5 eq.) over a period of 5 min Following the completion of addition, the resulting brown suspension was sonicated for another 2 hrs. The volatiles were then removed in vacuo and the resulting residue was taken up in ether. The ether suspension thus obtained was washed sequentially with 10% aq. HCl, 1 N aq. NaOH, water and brine, dried over Na$_2$SO$_4$, filtered and the filtrate concentrated in vacuo. Further purification by way of column chromatography (SiO$_2$, gradient elution, Hex to 1:1 (v/v) Hex:EtOAc) afforded methyl 2-(5-bromo-2-(trifluoromethoxy)phenyl)acetate as a pale yellow oil (328 mg, 70% yield).

Step 3:
Carried out in an analogous manner to example 13, step 1 using methyl 2-(5-bromo-2-(trifluoromethoxy)phenyl)acetate as the coupling partner. Hydrolysis of the intermediate ester was carried out as in example 1, step 2. LC-MS: 596 (M+H)+.

Example 131

4'-(3-(1-(4-(tert-Butyl)benzyl)-4-ethyl-5-oxo-4,5-dihydro-1H-1,2,4-triazol-3-yl)propyl)-4-(trifluoromethoxy)-[1,1'-biphenyl]-3-carboxylic acid

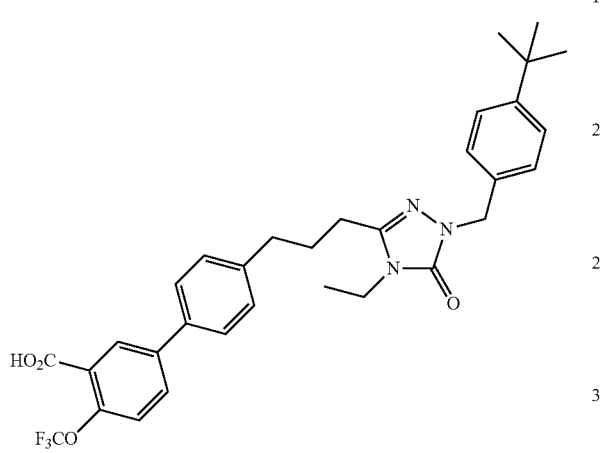

Prepared in an analogous manner to example 13, step 1 using methyl 5-bromo-2-(trifluoromethoxy)benzoate as the coupling partner. Hydrolysis of the intermediate ester was carried out as in example 1, step 2. LC-MS: 582 (M+H)+.

Example 132

4'-(3-(1-(4-(tert-Butyl)benzyl)-4-ethyl-5-oxo-4,5-dihydro-1H-1,2,4-triazol-3-yl)propyl)-4-methyl-[1,1'-biphenyl]-3-carboxylic acid

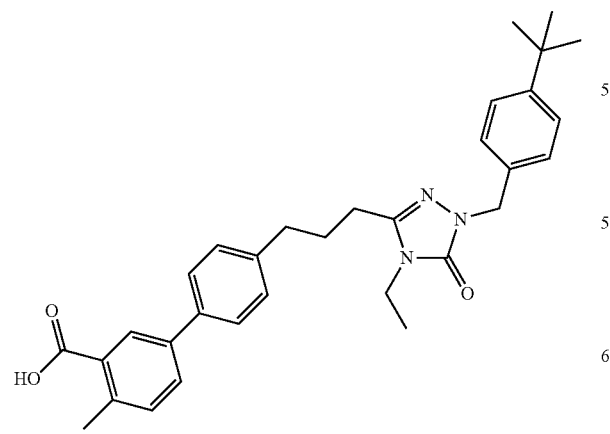

Prepared in an analogous manner to example 13, step 1 using methyl 5-bromo-2-methylbenzoate as the coupling partner. Hydrolysis of the intermediate ester was carried out at 65° C. under similar conditions to example 1, step 2 but using instead a mixture of 3 M aq. NaOH and solid KOH. LC-MS: 512 (M+H)+.

Example 133

1-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)cyclobutanecarboxylic acid

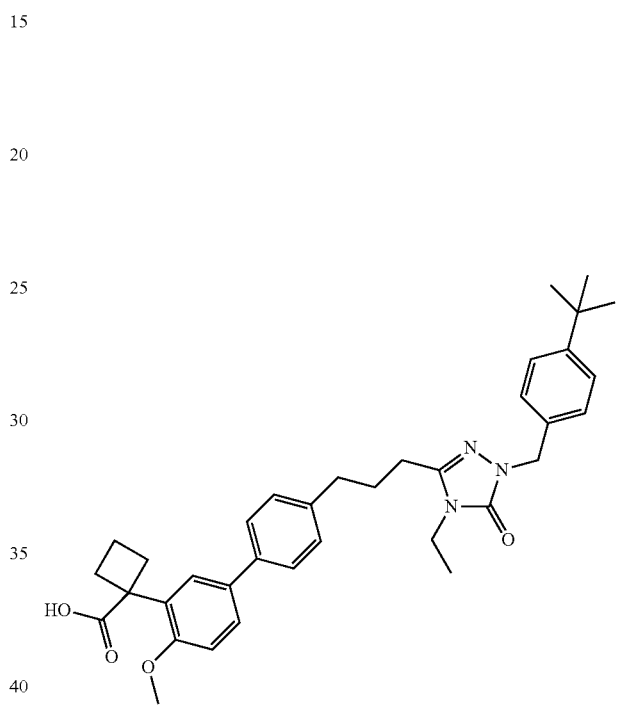

Step 1;
Carried out in analogous manner to example 13, step 1 using instead 1-(5-bromo-2-methoxyphenyl)cyclobutanecarbonitrile as the coupling partner.

Step 2:
The nitrile prepared from the previous step was combined with excess KOH in ethylene glycol and heated to 160° C. for 16 hrs. The resulting mixture was partitioned between EtOAc and 1 M aq. HCl. The organic phase was separated, washed further with water and brine, dried (MgSO4), filtered, and concentrated in vacuo. The resulting residue was purified on reverse phase HPLC to afford the title compound. LC-MS: 582 (M+H)+.

Example 134

4'-(3-(1-(4-(tert-Butyl)benzyl)-4-ethyl-5-oxo-4,5-dihydro-1H-1,2,4-triazol-3-yl)propyl)-4-(trifluoromethyl)-[1,1'-biphenyl]-3-carboxylic acid

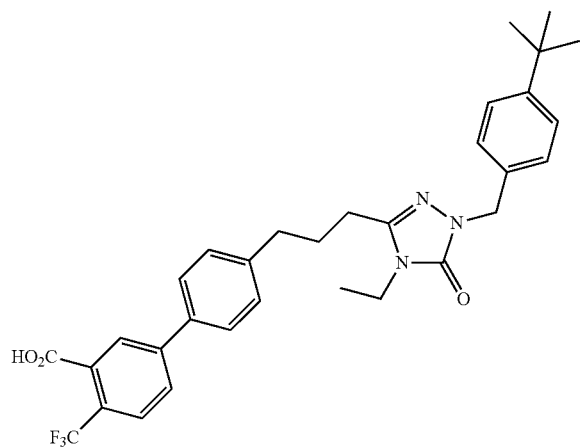 [SMILES: CCn1c(CCCc2ccc(-c3ccc(C(F)(F)F)c(C(=O)O)c3)cc2)nn(Cc2ccc(C(C)(C)C)cc2)c1=O]

Prepared in an analogous manner to example 13, step 1 using methyl 5-bromo-2-(trifluoromethyl)benzoate as the coupling partner. Hydrolysis of the intermediate ester was carried out as in example 1, step 2. LC-MS: 566 (M+H)$^+$.

Example 135

2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)-N-(methylsulfonyl)acetamide

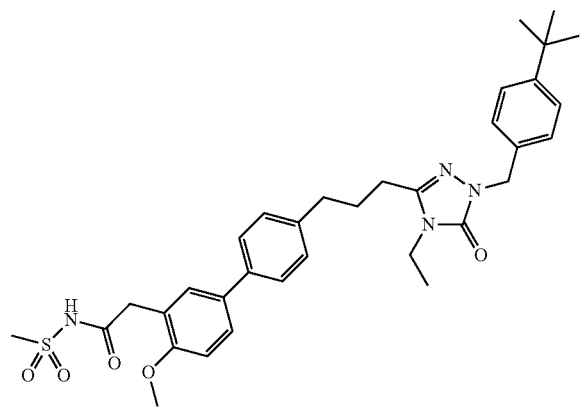 [SMILES: CCn1c(CCCc2ccc(-c3ccc(OC)c(CC(=O)NS(C)(=O)=O)c3)cc2)nn(Cc2ccc(C(C)(C)C)cc2)c1=O]

Step 1;

To a solution of sodium 2-(4'-(3-(1-(4-(tert-butyl)benzyl)-4-ethyl-5-oxo-4,5-dihydro-1H-1,2,4-triazol-3-yl)propyl)-4-methoxy-[1,1'-biphenyl]-3-yl)acetate (270 mg, 0.48 mmol, example 21) in CH$_2$Cl$_2$ (5 mL) at 0° C. was added catalytic amount of DMF, followed by oxalyl chloride (0.21 mL, 2.4 mmol). The reaction was stirred for 30 minutes and then concentrated in vacuo to afford the corresponding acid chloride. This was used without further purification.

Step 2;

To a stirred suspension of methansulfonamide (34 mg, 0.36 mmol) in CH$_2$Cl$_2$ (3 mL) was added diisopropylethylamine (0.15 mL, 0.84 mmol) and catalytic amount of 4-dimethylaminopyridine, and the mixture was allowed to stir at ambient temperature for 45 minutes. To the resulting solution was then added a suspension of the acid chloride from step 1 (0.24 mmol) in CH$_2$Cl$_2$ and the mixture was stirred for another 2 hrs. The reaction mixture was then partitioned between CH$_2$Cl$_2$ and water. The organic phase was separated, washed further with 1 N aq. HCl and water, dried (MgSO$_4$), filtered, and the filtrate concentrated in vacuo. The crude material thus obtained was purified using silica gel chromatography eluting with a gradient of 0 to 100% EtOAc in hexanes to afford the title compound. LC-MS: 619 (M+H)$^+$.

Example 136

2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)-N-(phenylsulfonyl)acetamide

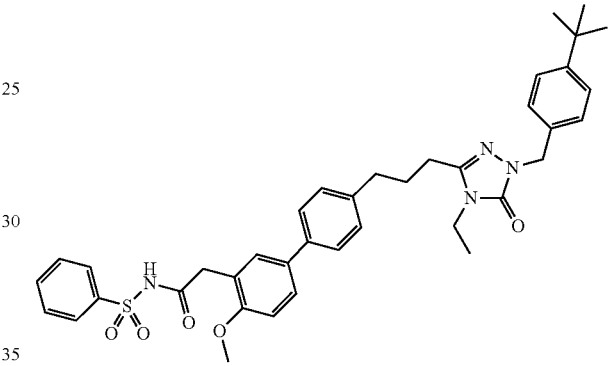

Prepared in an analogous manner to example 135 using instead benzensulfonamide as the coupling partner. LC-MS: 681 (M+H)$^+$.

Example 137

1-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)cyclopropanecarboxylic acid

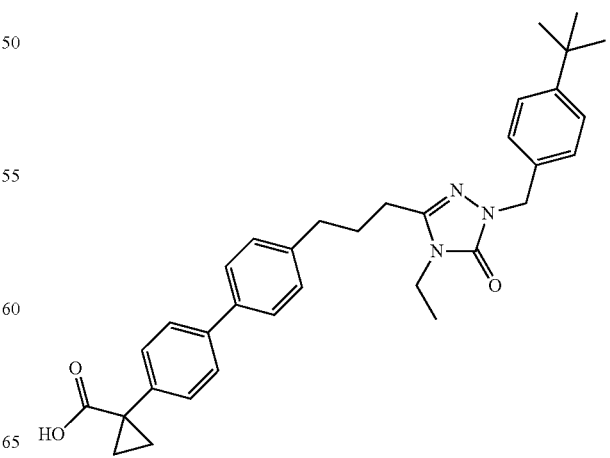

Prepared in an analogous manner to that detailed in example 1 using ethyl 1-(4-(4,4,5,5-tetramethyl-1,3,2-dioxaborolan-2-yl)phenyl)cyclopropanecarboxylate as the coupling partner in step 1. LC-MS: 538 (M+H)+.

Example 138

N-(4-(4-(3-(1-(4-(tert-Butyl)benzyl)-4-ethyl-5-oxo-4,5-dihydro-1H-1,2,4-triazol-3-yl)propyl)phenyl)pyrimidin-2-yl)benzenesulfonamide

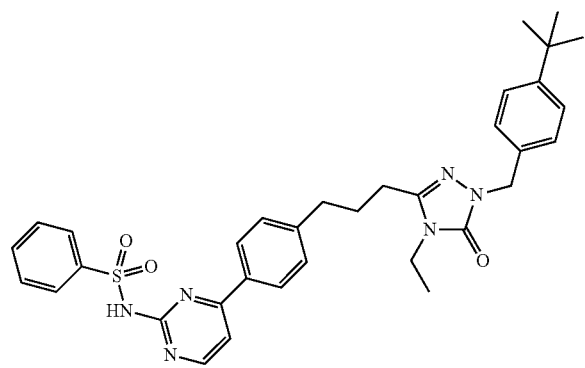 [SMILES: CCn1c(CCCc2ccc(-c3ccnc(NS(=O)(=O)c4ccccc4)n3)cc2)nn(Cc2ccc(C(C)(C)C)cc2)c1=O]

Step 1:
Carried out in an analogous manner to that detailed in example 3, using 2-chloropyrimidin-5-amine as the coupling partner.

Step 2:
Carried out in an analogous manner to that detailed in example 4 using 3-(3-(4-(2-aminopyrimidin-4-yl)phenyl)propyl)-1-(4-(tert-butyl)benzyl)-4-ethyl-1H-1,2,4-triazol-5(4H)-one as the starting material. LC-MS: 611 (M+H)+.

Example 139

6-(4-(3-(1-(4-(tert-Butyl)benzyl)-4-ethyl-5-oxo-4,5-dihydro-1H-1,2,4-triazol-3-yl)propyl)phenyl)-3-methoxypicolinic acid

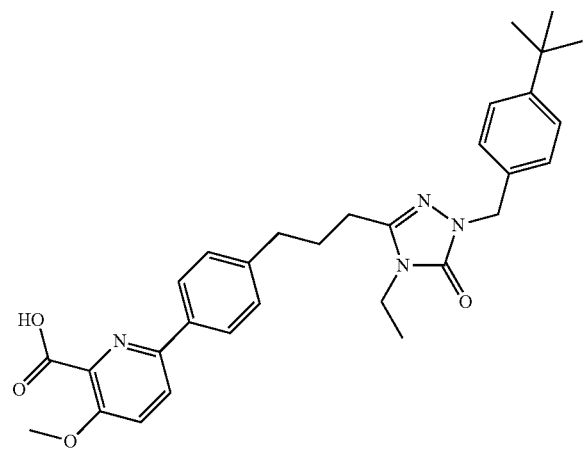 [SMILES: CCn1c(CCCc2ccc(-c3ccc(OC)c(C(=O)O)n3)cc2)nn(Cc2ccc(C(C)(C)C)cc2)c1=O]

Step 1;
To a solution of 2-methyl-3-hydroxypyridine (1.00 g, 9.16 mmol) in CH$_3$CN (25 mL) was added NBS (3.26 g, 18.33 mmol). The resulting mixture was heated at reflux for 1.5 hrs before the volatiles were removed in vacuo. The residue thus obtained was diluted with Et$_2$O and washed sequentially with water and brine. The organic extract was then dried over Na$_2$SO$_4$, filtered and the filtrate concentrated in vacuo. The crude product thus obtained was purified on silica gel eluting with a solvent gradient of 0 to 35% EtOAc in hexanes to afford 4,6-dibromo-2-methylpyridin-3-ol as a white solid.

Step 2;
4,6-Dibromo-2-methylpyridin-3-ol was converted into 6-bromo-2-methylpyridin-3-ol according to the published procedure found in Meana, A, et al., *Synlet,* 2003, 11, p. 1678-1682.

Step 3;
To a solution of 6-bromo-2-methylpyridin-3-ol (0.22 g, 1.2 mmol) in CH$_3$CN (5 mL) was added Cs$_2$CO$_3$ (1.14 g, 3.51 mmol) and iodomethane (0.080 mL, 1.3 mmol). The resulting mixture was then stirred at 50° C. for 16 hrs before the volatiles were removed in vacuo. The residue thus obtained was diluted with EtOAc and washed sequentially with water and brine. The organic extract was then dried over Na$_2$SO$_4$, filtered and the filtrate concentrated in vacuo. Crude 6-bromo-3-methoxy-2-methylpyridine thus obtained was used without further purification.

Step 4;
6-Bromo-3-methoxy-2-methylpyridine was converted into 6-bromo-3-methoxypicolinaldehyde in two steps according to the published procedures found in Mandal, A. B., et al., *Tetrahedron Letters* 2005, 46, p. 6033-6036.

Step 5;
To a solution of 6-bromo-3-methoxypicolinaldehyde (0.13 g, 0.60 mmol) in THF (6 mL) and tBuOH (6 mL) was added 2-methyl-2-butene (0.64 mL, 2.41 mmol), followed by an aqueous solution (2 mL) of sodium dihydrogen phosphate (0.29 mg, 2.4 mmol) and NaClO$_2$ (0.22 mg, 2.4 mol). The resulting mixture was stirred at RT for 16 hrs. The volatiles were then evaporated in vacuo and the residue thus obtained was purified on silica gel eluting with a solvent gradient of 0 to 10% MeOH in DCM (with 2% acetic acid as an additive in DCM) to afford 6-bromo-3-methoxypicolinic acid as a solid.

Step 6;
Carried out in an analogous manner to that detailed in step 2 of example 28, using instead 6-bromo-3-methoxypicolinic acid as the coupling partner. LC-MS: 529 (M+H)+.

Example 140

2-(4-(3-(1-(4-(tert-Butyl)benzyl)-4-ethyl-5-oxo-4,5-dihydro-1H-1,2,4-triazol-3-yl)propyl)phenyl)-5-methoxyisonicotinic acid

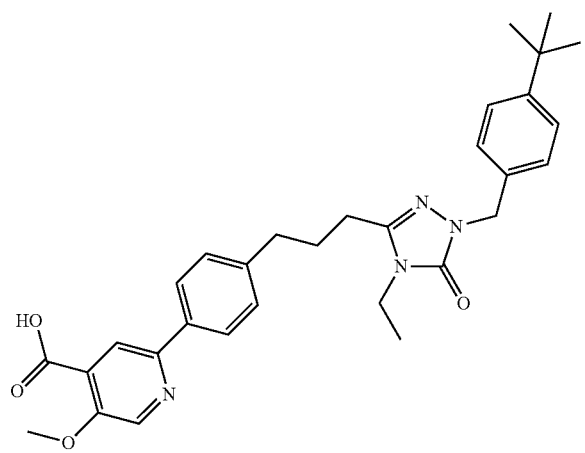 [SMILES: CCn1c(CCCc2ccc(-c3cc(C(=O)O)c(OC)cn3)cc2)nn(Cc2ccc(C(C)(C)C)cc2)c1=O]

Step 1 to 4:

Carried out in an analogous manner to that detailed in step 3 to 6 of example 139, but 2-chloro-5-hydroxy-4-methylpyridine as the starting material. LC-MS: 529 (M+H)+.

Example 141

(R)-2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)propanoic acid

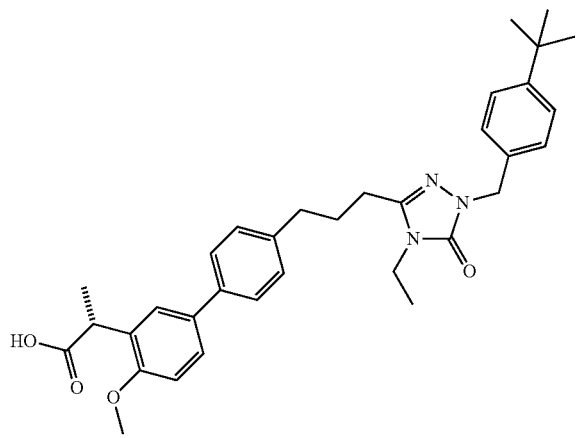 [SMILES: CCn1c(CCCc2ccc(-c3ccc(OC)c([C@@H](C)C(=O)O)c3)cc2)nn(Cc2ccc(C(C)(C)C)cc2)c1=O]

Step 1;

To a solution of 2-(5-bromo-2-methoxyphenyl)acetic acid (975 mg, 4.0 mmol) in CH$_3$CN (15 mL) was added 1,1'-carbonyldiimidazole (1.3 g, 8.0 mmol) and the resulting solution was heated to 70° C. After 1.5 hrs, (4R,5S)-4-methyl-5-phenyloxazolidin-2-one (1.4 g, 8.0 mmol) and triethylamine (1.1 mL, 8.0 mmol) were added, and stirring was continued at 70° C. for 2.5 hrs. The reaction mixture was then partitioned between EtOAc and 1 N aq. HCl. The organic phase was separated, washed further with water and brine, dried (Na$_2$SO$_4$), filtered and the filtrate concentrated in vacuo. The crude material thus obtained was purified using silica gel chromatography eluting with a gradient of 0 to 40% EtOAc in hexanes to deliver (4R,5S)-3-(2-(5-bromo-2-methoxyphenyl)acetyl)-4-methyl-5-phenyloxazolidin-2-one.

Step 2;

To a solution of (4R,5S)-3-(2-(5-bromo-2-methoxyphenyl)acetyl)-4-methyl-5-phenyloxazolidin-2-one from the previous step (300 mg, 0.74 mmol) in THF (3 mL) at −78° C. was added NaHMDS (1.0 M solution in THF, 0.82 mL, 0.82 mmol). After 20 minutes, iodomethane (51 μL, 0.82 mmol) was added neat, dropwise and the reaction was allowed to warm to room temperature over 2.5 hrs. The reaction was quenched by the addition of saturated, aqueous NH$_4$Cl and the resulting suspension was partitioned between EtOAc and 1 N aq. HCl. The organic phase was separated, washed further with water and brine, dried (MgSO$_4$), filtered and the filtrate concentrated in vacuo. The crude material thus obtained was purified further using silica gel chromatography eluting with a gradient of 0 to 30% EtOAc in hexanes to afford (4R,5S)-3-((R)-2-(5-bromo-2-methoxyphenyl)propanoyl)-4-methyl-5-phenyloxazolidin-2-one.

Step 3:

Carried out in an analogous manner to that detailed in example 13, step 1 but using (4R,5S)-3-((R)-2-(5-bromo-2-methoxyphenyl)propanoyl)-4-methyl-5-phenyloxazolidin-2-one as the aryl bromide coupling partner.

Step 4:

To a solution of (4R,5S)-3-((R)-2-(4'-(3-(1-(4-(tert-butyl)benzyl)-4-ethyl-5-oxo-4,5-dihydro-1H-1,2,4-triazol-3-yl)propyl)-4-methoxy-[1,1'-biphenyl]-3-yl)propanoyl)-4-methyl-5-phenyloxazolidin-2-one (71 mg, 0.10 mmol) from the previous step in THF (3 mL) and water (1 mL) was added H$_2$O$_2$ (56 μL, 0.50 mmol) and lithium hydroxide monohydrate (8.0 mg, 0.20 mmol) at 0° C. After 30 minutes the reaction was quenched by the addition of aqueous Na$_2$S$_2$O$_3$ and the resulting solution was partitioned between EtOAc and 1 N aq. HCl. The organic phase was separated, washed further with water and brine, dried (MgSO$_4$), filtered and the filtrate concentrated in vacuo. The crude material thus obtained was purified on reverse phase HPLC to afford the title compound as a white solid. LC-MS: 556 (M+H)+.

Example 142

(S)-2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)propanoic acid

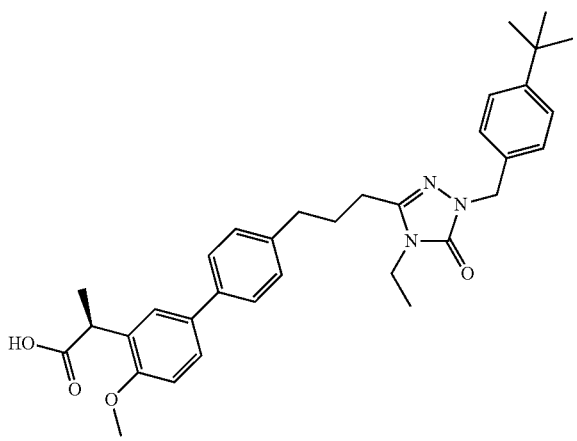 [SMILES: CCn1c(CCCc2ccc(-c3ccc(OC)c([C@H](C)C(=O)O)c3)cc2)nn(Cc2ccc(C(C)(C)C)cc2)c1=O]

Prepared in an analogous manner to example 142 using instead (4S,5R)-4-methyl-5-phenyloxazolidin-2-one as the chiral auxiliary in step 1. LC-MS: 556 (M+H)$^+$.

Example 143

1-(4-(tert-Butyl)benzyl)-4-ethyl-3-(3-(4%(3-fluorooxetan-3-yl)-[1,1'-biphenyl]-4-yl)propyl)-1H-1,2,4-triazol-5(4H)-one

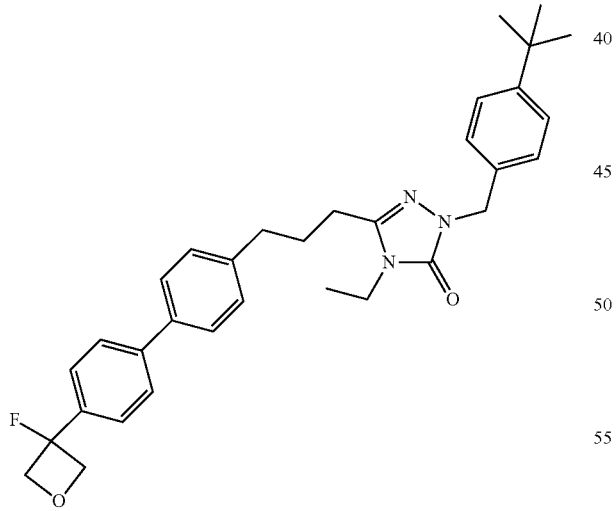

Step 1;

To a solution of 4-bromophenyl iodide (2.4 g, 8.5 mmol) and 3-oxetanone (220 μL, 3.8 mmol) in THF (50 mL) was added at −78° C. n-BuLi (1.5 mL, 3.8 mmol, 2.5 M solution in hexanes) dropwise over a period of 15 min. The resulting solution was allowed to warm slowly to RT of 3.5 hrs. The crude reaction mixture was then re-cooled to −78° C. and carefully quenched with MeOH. The volatiles were then removed in vacuo and the resulting residue was partitioned between ether and 10% aq. HCl. The organic extract was then separated, washed further with water, 1 N aq. NaOH, water and brine, dried over Na$_2$SO$_4$, filtered and the filtrate concentrated in vacuo. The crude product thus obtained can then be recrystallized from ether and hexanes to furnish 3-(4-bromophenyl)oxetan-3-ol as a white solid (730 mg, 80% yield).

Step 2;

To a solution of 3-(4-bromophenyl)oxetan-3-ol (730 mg, 3.2 mmol) in DCM (100 mL) was added at −78° C. neat diethylaminosulfur trifluoride (840 μL, 6.4 mmol) dropwise over 10 min. The resulting mixture was allowed to stir at −78° C. for 8 hrs before it was carefully quenched with sat. aq. NaHCO$_3$. The organic layer was separated, dried over Na$_2$SO$_4$, filtered and the filtrate concentrated in vacuo. Purification by way of column chromatography (SiO$_2$, gradient elution, Hex to 1:1 (v/v) Hex: EtOAc) afforded 3-(4-bromophenyl)-3-fluorooxetane as a volatile, colorless oil (370 mg, 50% yield).

Step 3:

Carried out in an analogous manner to example 13, step 1 using instead 3-(4-bromophenyl)-3-fluorooxeetane as the coupling partner. LC-MS: 528 (M+H)$^+$.

Example 144

2-(6-(4-(3-(1-(4-(tert-Butyl)benzyl)-4-ethyl-5-oxo-4,5-dihydro-1H-1,2,4-triazol-3-yl)propyl)phenyl)-3-methoxypyridin-2-yl)acetic acid

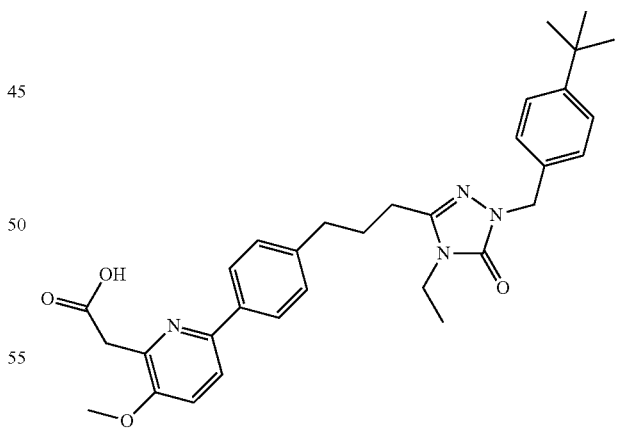

Prepared in an analogous manner to example 130 using instead 6-bromo-3-methoxypicolinic acid as the starting material. LC-MS: 543 (M+H)$^+$.

Example 145

2-(4'-(3-(1-(4-(tert-Butyl)benzyl)-4-ethyl-5-oxo-4,5-dihydro-1H-1,2,4-triazol-3-yl)propyl)-2'-hydroxy-4-methoxy-[1,1'-biphenyl]-3-yl) acetic acid

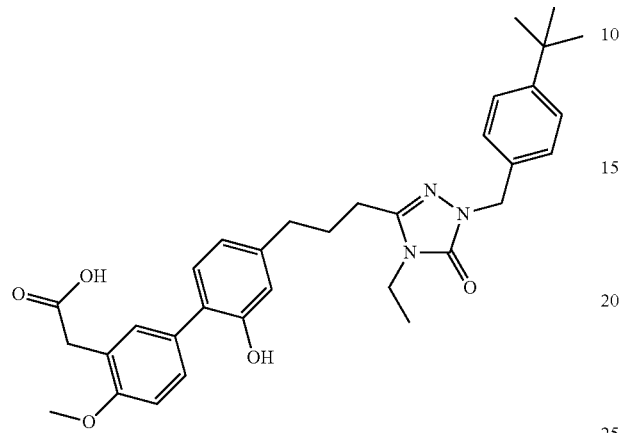

Prepared in an analogous manner to example 150 using 4-bromo-3-fluorobenzaldehyde as the reactant in step 1. LC-MS: 558 (M+H)+.

Example 146

2-(4'-(3-(1-(4-(tert-Butyl)benzyl)-4-ethyl-5-oxo-4,5-dihydro-1H-1,2,4-triazol-3-yl)propyl)-3'-hydroxy-4-methoxy-[1,1'-biphenyl]-3-yl) acetic acid

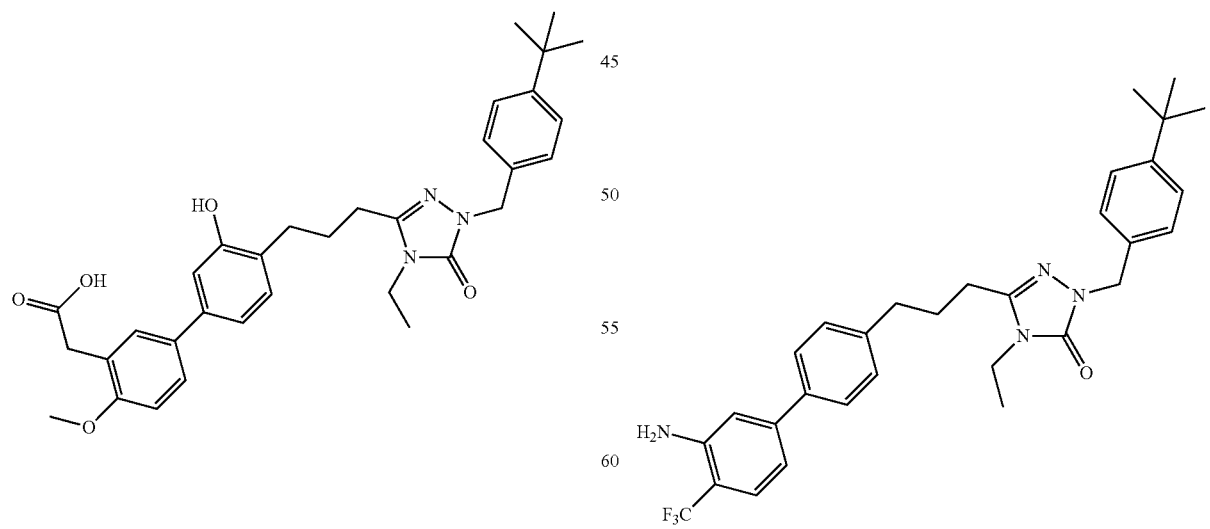

Prepared in an analogous manner to example 150 using 4-bromo-2-fluorobenzaldehyde as the reactant in step 1. LC-MS: 558 (M+H)+.

Example 147

3-(3-(3'-Amino-4'-methoxy-[1,1'-biphenyl]-4-yl)propyl)-1-(4-(tert-butyl)benzyl)-4-ethyl-1H-1,2,4-triazol-5(4H)-one

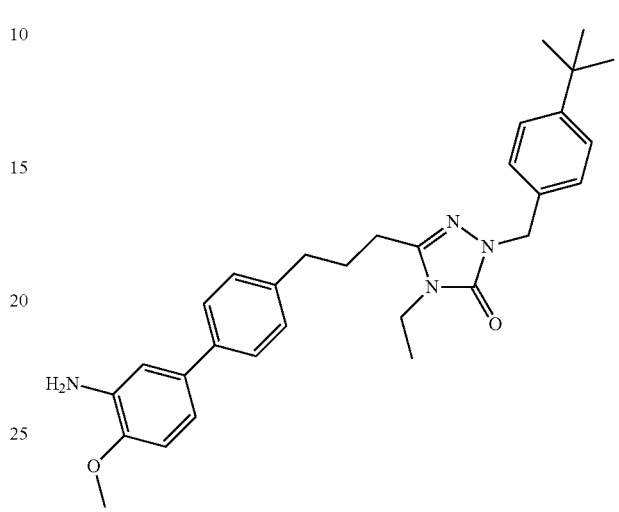

Prepared in an analogous manner to example 3 using 5-bromo-2-methoxyaniline as the coupling partner. LC-MS: 499 (M+H)+.

Example 148

3-(3-(3'-Amino-4'-(trifluoromethyl)-[1,1'-biphenyl]-4-yl)propyl)-1-(4-(tert-butyl)benzyl)-4-ethyl-1H-1,2,4-triazol-5(4H)-one Prepared in an analogous manner to example 3 using 5-bromo-2-(trifluoromethyl)aniline as the coupling partner. LC-MS: 537 (M+H)+.

Example 149

3-(3-(3'-Amino-4'-methyl-[1,1'-biphenyl]-4-yl)propyl)-1-(4-(tert-butyl)benzyl)-4-ethyl-1H-1,2,4-triazol-5(4H)-one

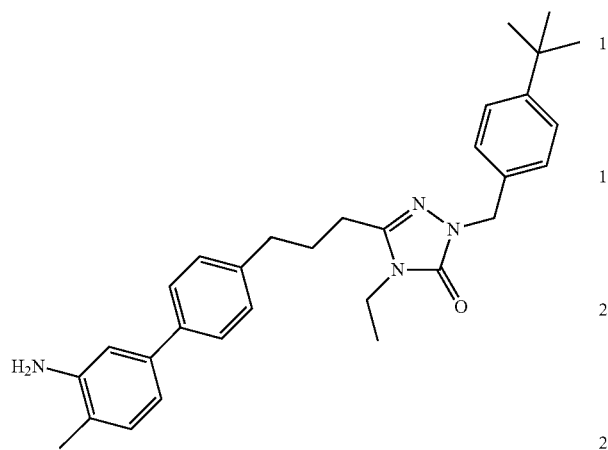

Prepared in an analogous manner to example 3 using 5-bromo-2-methylaniline as the coupling partner. LC-MS: 483 (M+H)$^+$.

Example 150

2-(4'-(3-(1-(4-(tert-Butyl)benzyl)-4-ethyl-5-oxo-4,5-dihydro-1H-1,2,4-triazol-3-yl)propyl)-4-methoxy-2'-(trifluoromethyl)-[1,1'-biphenyl]-3-yl) acetic acid

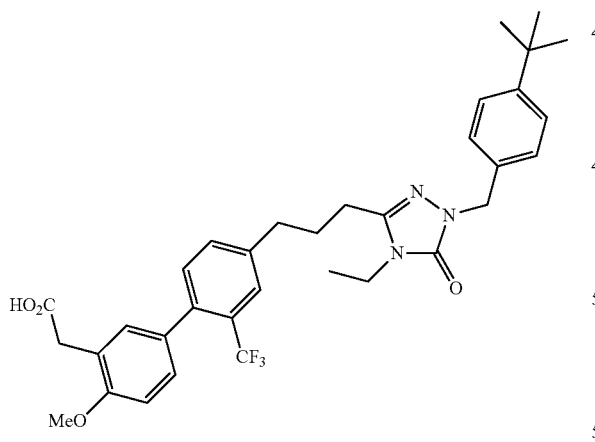

Step 1;

To a solution of 4-bromo-3-(trifluoromethyl)benzaldehyde (1.0 g, 4.0 mmol) in DMF (10 mL) was added sodium cyanide (48 mg, 1.0 mmol) in one rapid portion and the resulting dark red suspension was heated at 40° C. for 1 hr. Then, acrylonitrile (0.26 mL, 4 mmol) was added dropwise as a DMF solution (5 mL) to the now dark brown reaction suspension over a period of 15 min. The final reaction mixture was allowed to heat at 40° C. for 14 hrs. The crude reaction mixture was then cooled to RT, carefully quenched with glacial acetic acid and water, and extracted with methyl tert-butyl ether. The combined organic extracts were washed further with water and brine, dried over Na$_2$SO$_4$, filtered and the filtrate concentrated in vacuo to afford a dark red, viscous oil. Further purification by way of column chromatography (SiO$_2$, gradient elution, Hex→1:1 Hex:EtOAc) furnished 4-(4-bromo-3-(trifluoromethyl)phenyl)-4-oxobutanenitrile as an orange oil that solidified upon standing (880 mg, 73% yield).

Step 2;

To a solution 4-(4-bromo-3-(trifluoromethyl)phenyl)-4-oxobutanenitrile (880 mg, 2.9 mmol) and hydrazine hydrate (0.34 mL, 7 mmol) in ethylene glycol (5 mL) and water (0.15 mL) was added potassium hydroxide (850 mg, 15 mmol) portionwise over a period of 1.5 h. The resulting red solution was then heated at 195° C. for 16 hrs. The reaction mixture was then cooled to RT, diluted with water and carefully acidified with 2 N aq. HCl until an aqueous pH of ~2 was reached. The resulting suspension was then extracted with EtOAc. The combined organic extracts were washed further with water and brine, dried over Na$_2$SO$_4$, and filtered. Concentration of the filtrate concentrated in vacuo afforded crude 4-(4-bromo-3-(trifluoromethyl)phenylbutanoic acid as a beige solid.

Steps 3 to 6:

Carried out in an analogous manner as detailed in steps 3 to 6 of example 27, using instead 4-(4-bromo-3-(trifluoromethyl)phenylbutanoic acid as the acid coupling partner in step 3 and methyl 2-(2-methoxy-5-(4,4,5,5-tetramethyl-1,3,2-dioxaborolan-2-yl)phenyl)acetate as the boronate coupling partner in step 5. LC-MS: 610 (M+H)$^+$.

Example 151

1-{[4-(tert-Butyl)phenyl]methyl}-4-ethyl-3-[3-(4-{4-methoxy-3-[(phenylsulfonyl)amino]phenyl}phenyl)propyl]-1,2,4-triazolin-5-one

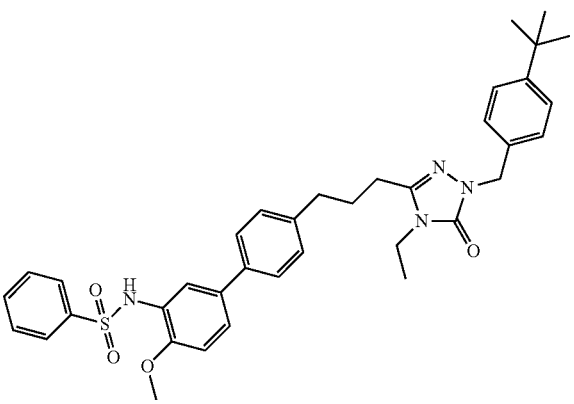 [SMILES: CCn1c(CCCc2ccc(-c3ccc(OC)c(NS(=O)(=O)c4ccccc4)c3)cc2)nn(Cc2ccc(C(C)(C)C)cc2)c1=O]

Prepared in an analogous manner to example 4 using 3-(3-(3'-amino-4'-methoxy-[1,1'-biphenyl]-4-yl)propyl)-1-(4-(tert-butyl)benzyl)-4-ethyl-1H-1,2,4-triazol-5(4H)-one (example 147) as the nucleophile. LC-MS: 639 (M+H)$^+$.

Example 152

1-{[4-(tert-Butyl)phenyl]methyl}-4-ethyl-3-[3-(4-{4-methyl-3-[(phenylsulfonyl)amino]phenyl}phenyl)propyl]-1,2,4-triazolin-5-one

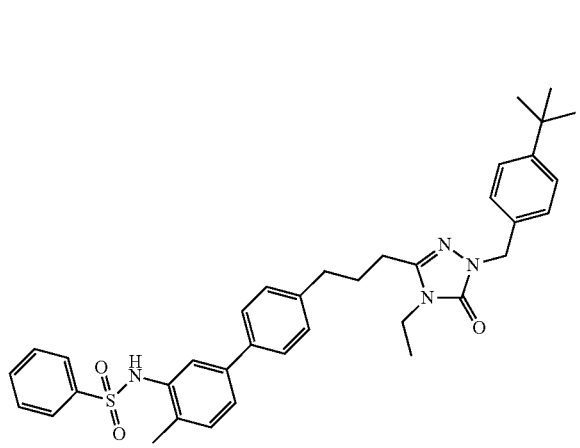 [SMILES: CCn1c(CCCc2ccc(-c3ccc(C)c(NS(=O)(=O)c4ccccc4)c3)cc2)nn(Cc2ccc(C(C)(C)C)cc2)c1=O]

Prepared in an analogous manner to example 4 using 3-(3-(3'-amino-4'-methyl-[1,1'-biphenyl]-4-yl)propyl)-1-(4-(tert-butyl)benzyl)-4-ethyl-1H-1,2,4-triazol-5(4H)-one (example 149) as the nucleophile. LC-MS: 623 (M+H)⁺.

Example 153

1-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)-3-phenylurea

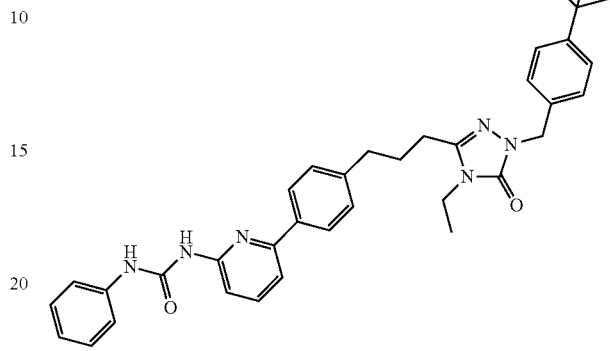

Prepared in an analogous manner to example 4 using instead phenyl isocyanate as the electrophile and THF as the solvent. LC-MS: 589 (M+H)⁺.

Example 154

N-((6-(4-(3-(1-(4-(tert-Butyl)benzyl)-4-ethyl-5-oxo-4,5-dihydro-1H-1,2,4-triazol-3-yl)propyl)phenyl)pyridin-2-yl)carbamoyl)benzenesulfonamide

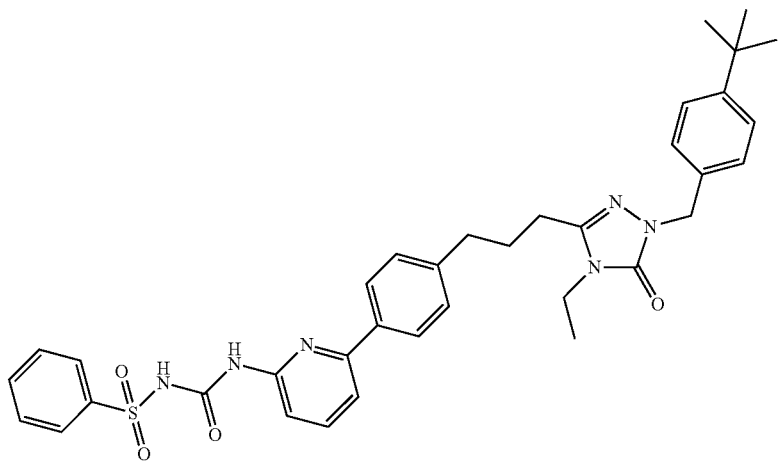 [SMILES: CCn1c(CCCc2ccc(-c3cccc(NC(=O)NS(=O)(=O)c4ccccc4)n3)cc2)nn(Cc2ccc(C(C)(C)C)cc2)c1=O]

Prepared in an analogous manner to example 4 using instead benzenesulfonyl isocyanate as the electrophile and THF as the solvent. LC-MS: 653 (M+H)⁺.

Example 155

1-Benzyl-3-(6-(4-(3-(1-(4-(tert-butyl)benzyl)-4-ethyl-5-oxo-4,5-dihydro-1H-1,2,4-triazol-3-yl)propyl)phenyl)pyridin-2yl)urea

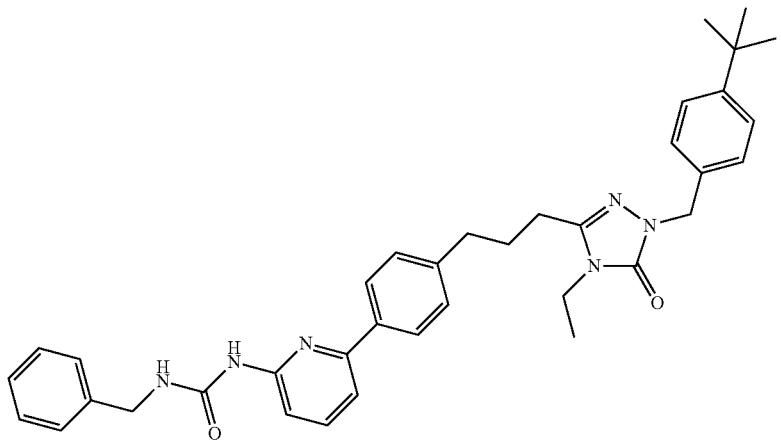 [SMILES: CCn1c(CCCc2ccc(-c3cccc(NC(=O)NCc4ccccc4)n3)cc2)nn(Cc2ccc(C(C)(C)C)cc2)c1=O]

Prepared in an analogous manner to example 4 using instead benzyl isocyanate as the electrophile and THF as the solvent. LC-MS: 603 (M+H)+.

Example 156

3-(3-{4-[5-Amino-3-(trifluoromethyl)(2-pyridyl)]phenyl}propyl)-1-{[4-(tert-butyl)phenyl]methyl}-4-ethyl-1,2,4-triazolin-5-one

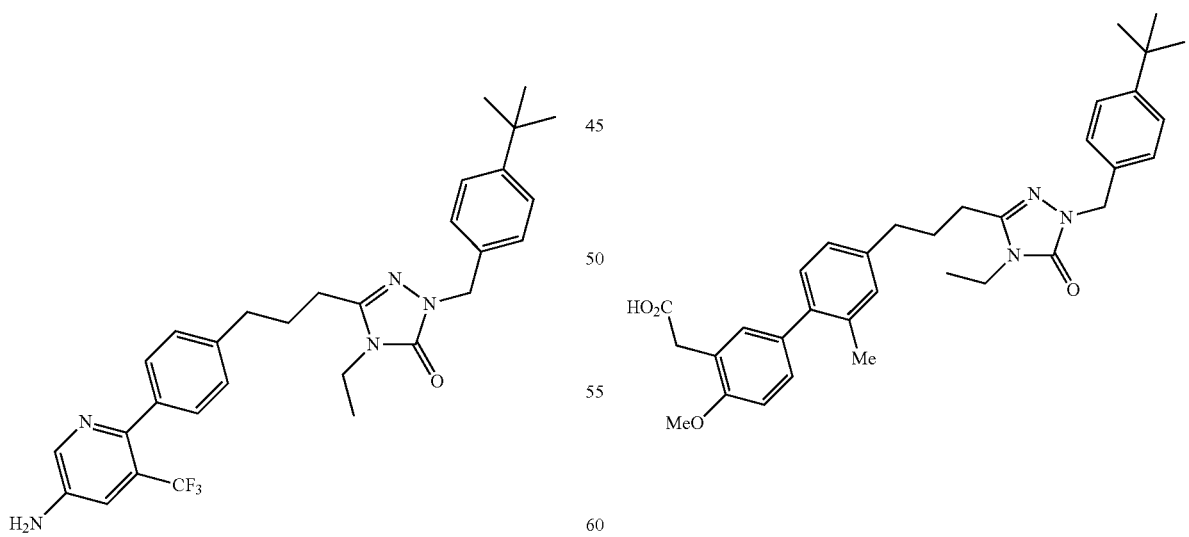

Prepared in an analogous manner to example 3 using instead 6-chloro-5-(trifluoromethyl)pyridin-2-amine (prepared according to the procedure found in Patent WO 2009/150240A1) as the aryl halide coupling partner. LC-MS: 538 (M+H)+.

Example 157

2-(4'-(3-(1-(4-(tert-Butyl)benzyl)-4-ethyl-5-oxo-4,5-dihydro-1H-1,2,4-triazol-3-yl)propyl)-4-methoxy-2'-methyl-[1,1'-biphenyl]-3-yl)acetic acid Prepared in an analogous manner to example 150 using instead 4-bromo-3-methylbenzaldehyde as the reactant in step 1. LC-MS: 556 (M+H)+.

Example 158

2-(4'-(3-(1-(4-(tert-Butyl)benzyl)-4-ethyl-5-oxo-4,5-dihydro-1H-1,2,4-triazol-3-yl)propyl)-3',4-dimethoxy-[1,1'-biphenyl]-3-yl)acetic acid

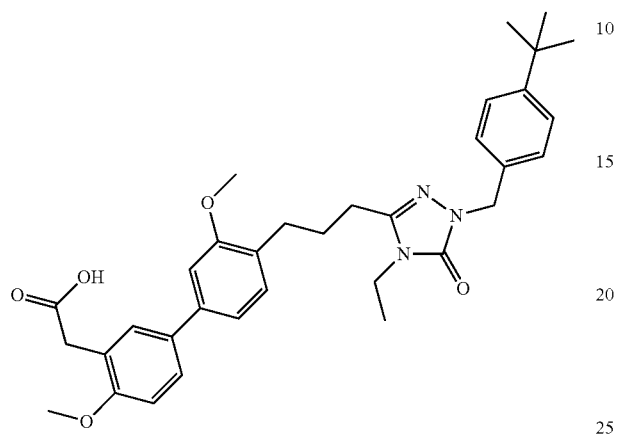

Steps 1 to 2:

Carried out in an analogous manner as detailed in steps 1 to 2 of example 150, using 4-bromo-2-fluorobenzaldehyde as the reactant in step 1.

Steps 3 to 5:

Carried out in an analogous manner as detailed in steps 3 to 5 of example 27, using instead 4-(4-bromo-2-hydroxyphenyl)butanoic acid as the acid coupling partner in step 3 and methyl 2-(2-methoxy-5-(4,4,5,5-tetramethyl-1,3,2-dioxaborolan-2-yl)phenyl)acetate as the boronate coupling partner in step 5.

Step 6:

To a solution of methyl 2-(4'-(3-(1-(4-(tert-butyl)benzyl)-4-ethyl-5-oxo-4,5-dihydro-1H-1,2,4-triazol-3-yl)propyl)-3'-hydroxy-4-methoxy-[1,1'-biphenyl]-3-yl)acetate (52 mg, 0.091 mmol) in acetone (1 mL) was added potassium carbonate (38 mg, 0.27 mmol, 3 eq) and dimethyl sulfate (10 µL, 0.11 mmol, 1.2 eq). The reaction vessel was heated to 40° C. for 24 hrs. Additional potassium carbonate (38 mg, 0.27 mmol, 3 eq) and dimethyl sulfate (10 µL, 0.11 mmol, 1.2 eq) were added and the reaction vessel was heated to 40° C. for an additional 24 hrs and then allowed to cool to RT. The reaction mixture was diluted with water (10 mL) and extracted with EtOAc (3×10 mL). The combined organic extracts were washed with brine, dried over MgSO$_4$, filtered and concentrated. The residue was purified by column chromatography (SiO$_2$, gradient elution, 9:1 (v/v) Hex: EtOAc to EtOAc) to afford methyl 2-(4'-(3-(1-(4-(tert-butyl)benzyl)-4-ethyl-5-oxo-4,5-dihydro-1H-1,2,4-triazol-3-yl)propyl)-3',4-dimethoxy-[1,1'-biphenyl]-3-yl)acetate as a colorless oil (23 mg, 43%).

Step 7:

Carried out in an analogous manner as detailed in step 2 of example 1. LC-MS: 572 (M+H)$^+$.

Example 159

2-(4'-(3-(1-(4-(tert-Butyl)benzyl)-4-ethyl-5-oxo-4,5-dihydro-1H-1,2,4-triazol-3-yl)propyl)-2',4-dimethoxy-[1,1'-biphenyl]-3-yl)acetic acid

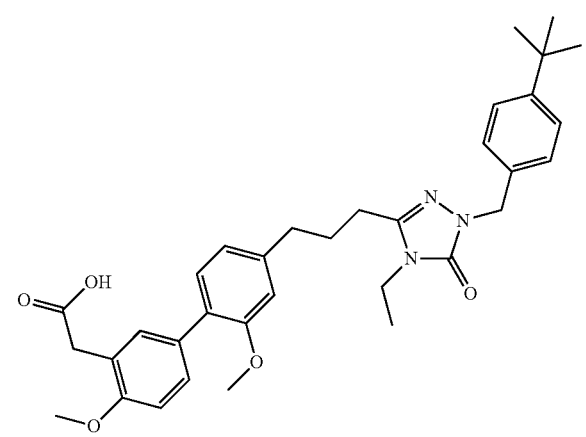 [SMILES: CCn1c(CCCc2ccc(-c3ccc(OC)c(CC(=O)O)c3)c(OC)c2)nn(Cc2ccc(C(C)(C)C)cc2)c1=O]

Steps 1 to 2:

Carried out in an analogous manner as detailed in steps 1 to 2 of example 150, using 4-bromo-3-fluorobenzaldehyde as the reactant in step 1.

Steps 3 to 4:

Carried out in an analogous manner as detailed in steps 3 to 4 of example 27, using instead 4-(4-bromo-3-hydroxyphenyl)butanoic acid as the acid coupling partner in step 3.

Step 5:

To a solution of 3-(3-(4-bromo-3-hydroxyphenyl)propyl)-1-(4-(tert-butyl)benzyl)-4-ethyl-1H-1,2,4-triazol-5(4H)-one (123 mg, 0.260 mmol) in acetone (3 mL) was added potassium carbonate (108 mg, 0.78 mmol, 3 eq) and dimethyl sulfate (30 µL, 0.312 mmol, 1.2 eq). The reaction vessel was heated to 40° C. for 48 hrs. The reaction mixture was diluted with water (20 mL) and extracted with EtOAc (3×10 mL). The combined organic extracts were washed with brine, dried over MgSO$_4$, filtered and concentrated. The residue was purified by column chromatography (SiO$_2$, gradient elution, 9:1 (v/v) Hex: EtOAc to EtOAc) to afford 3-(3-(4-bromo-3-methoxyphenyl)propyl)-1-(4-(tert-butyl)benzyl)-4-ethyl-1H-1,2,4-triazol-5(4H)-one as a colorless oil (125 mg, 99%).

Steps 6 to 7:

Carried out in an analogous manner as detailed in steps 5 to 6 of example 27, using instead methyl 2-(2-methoxy-5-(4,4,5,5-tetramethyl-1,3,2-dioxaborolan-2-yl)phenyl)acetate as the boronate coupling partner in step 6. LC-MS: 572 (M+H)$^+$.

Example 160

N-((6-(4-(3-(1-(4-(tert-Butyl)benzyl)-4-ethyl-5-oxo-4,5-dihydro-1H-1,2,4-triazol-3-yl)propyl)phenyl)pyridin-3-yl)carbamoyl)benzenesulfonamide

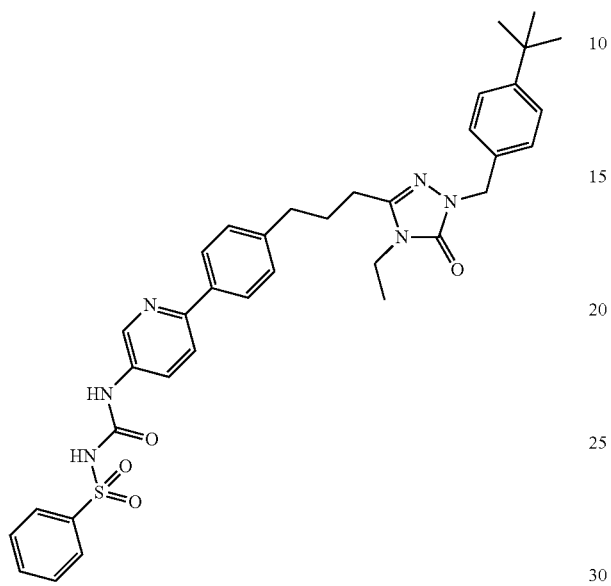

Prepared in an analogous manner to example 10 using instead benzenesulfonyl isocyanate as the electrophile and THF as the solvent. LC-MS: 653 (M+H)$^+$.

Example 161

3-(3-{4-[6-Amino-5-(trifluoromethyl)(2-pyridyl)]phenyl}propyl)-1-{[4-(tert-butyl)phenyl]methyl}-4-ethyl-1,2,4-triazolin-5-one

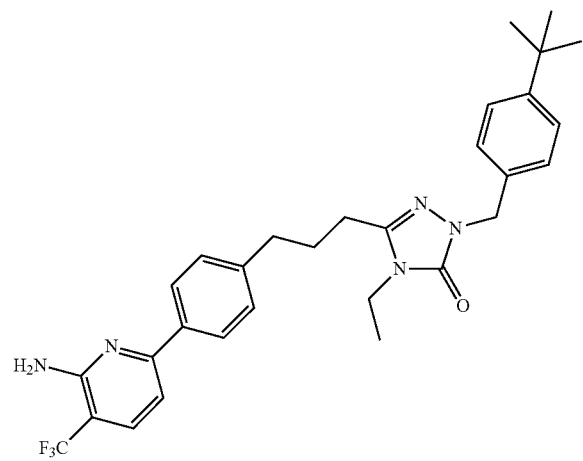 [SMILES: CCn1c(CCCc2ccc(-c3ccc(C(F)(F)F)c(N)n3)cc2)nn(Cc2ccc(C(C)(C)C)cc2)c1=O]

Prepared in an analogous manner to example 3 using instead 6-chloro-3-(trifluoromethyl)pyridin-2-amine (prepared according to the procedure found in Patent WO 2009/150240A1) as the aryl halide coupling partner. LC-MS: 538 (M+H)$^+$.

Example 162

6-(4-(3-(1-(4-(tert-Butyl)benzyl)-4-ethyl-5-oxo-4,5-dihydro-1H-1,2,4-triazol-3-yl)propyl)phenyl)-3-methoxypyrazine-2-carboxylic acid

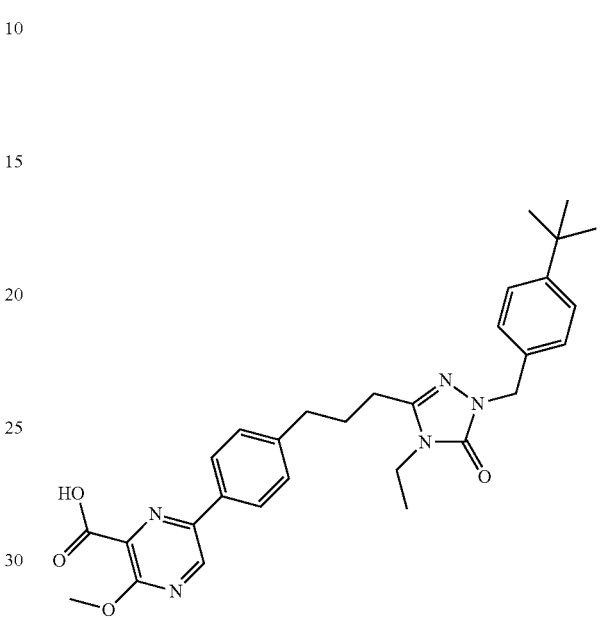

Step 1;

To a solution of methyl 3-amino-6-bromopyrazine-2-carboxylate (1.00 g, 4.31 mmol) in conc. H$_2$SO$_4$ (5.9 mL) at 0° C. was added NaNO$_2$ (0.60 g, 8.6 mmol) in one rapid portion. The resulting mixture was stirred at 0° C. for 30 minutes and then poured into 53 mL of MeOH. The combined mixture was then heated at reflux for 5 hrs. After cooling to RT and removal of the volatiles in vacuo, the resulting residue was taken up in ice-cold water and extracted with chloroform. The combined organic extracts were then washed sequentially with saturated aq. NaHCO$_3$ solution and water, dried over Na$_2$SO$_4$, filtered and the filtrate concentrated in vacuo. Further purification by way of column chromatography (SiO$_2$, gradient elution, Hex→1:1 Hex:EtOAc) furnished methyl 6-bromo-3-methoxypyrazine-2-carboxylate.

Step 2;

Carried out in an analogous manner to example 13 using methyl 6-bromo-3-methoxypyrazine-2-carboxylate from the previous step as the aryl halide coupling partner in step 1. Hydrolysis of the intermediate ester was carried out as in example 1, step 2 to obtain the title compound. LC-MS: 530 (M+H)$^+$.

Example 163

2-(4'-(3-(1-(4-(tert-Butyl)benzyl)-4-ethyl-5-oxo-4,5-dihydro-1H-1,2,4-triazol-3-yl)-1,1-difluoropropyl)-4-methoxy-[1,1'-biphenyl]-3-yl)acetic acid

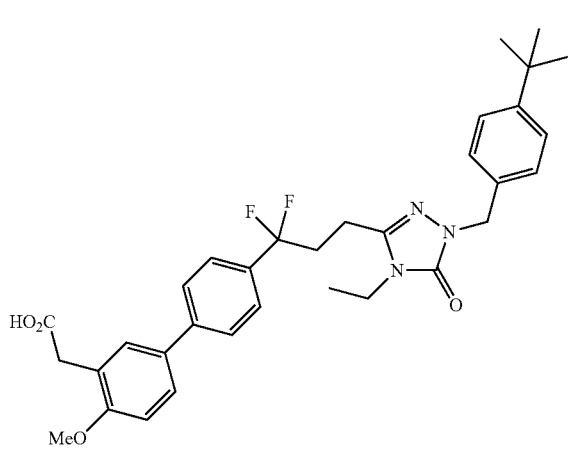 [SMILES: CCn1c(CCC(F)(F)c2ccc(-c3ccc(OC)c(CC(=O)O)c3)cc2)nn(Cc2ccc(C(C)(C)C)cc2)c1=O]

Step 1;

Carried in an analogous manner to example 150, step 1 using instead 4-bromobenzaldehyde as the reactant.

Step 2;

To a solution 4-(4-bromophenyl)-4-oxobutanenitrile (345 mg, 1.5 mmol) and Deoxyfluor (0.45 mL, 2.5 mmol) in toluene (3 mL) was added several drops of ethanol. The reaction vessel was then sealed and the mixture heated at 80° C. for 16 hrs. After cooling to RT, the reaction was quenched with the addition of 10% aq. NaHCO₃ and then extracted with ether. The combined organic extracts were washed further with 10% aq. HCl, water and brine, dried over Na₂SO₄, filtered and the filtrate concentrated in vacuo. Further purification by way of column chromatography (SiO₂, gradient elution, Hex→1:1 Hex:EtOAc) furnished 4-(4-bromophenyl)-4,4-difluorobutanenitrile as a pale yellow oil (260 mg, 74% yield).

Step 3;

To a solution of 4-(4-bromophenyl)-4,4-difluorobutanenitrile (400 mg, 1.5 mmol) in ethylene glycol (8 mL) and water (8 mL) was added potassium hydroxide (250 mg, 6.1 mmol). The resulting mixture was heated at 120° C. for 72 hrs until the reaction was deemed to be complete by LC-MS. After cooling to RT, the reaction was carefully quenched with 1 N aq. HCl and extracted with ether. The combined organic extracts were then washed further with water and brine, dried over Na₂SO₄, and filtered. Concentration of the filtrate in vacuo afforded 4-(4-bromophenyl)-4,4-difluorobutanoic acid as a pale yellow solid (354 mg, 83% yield).

Steps 4 to 7:

Carried out in an analogous manner as detailed in steps 3 to 6 of example 27, using instead 4-(4-bromophenyl)-4,4-difluorobutanoic acid as the acid coupling partner in step 3 and methyl 2-(2-methoxy-5-(4,4,5,5-tetramethyl-1,3,2-dioxaborolan-2-yl)phenyl)acetate as the boronate coupling partner in step 5. LC-MS: 578 (M+H)⁺.

Example 164

1-{[4-(tert-Butyl)phenyl]methyl}-4-ethyl-3-[3-(4-{6-[(phenylsulfonyl)amino]-5-(trifluoromethyl)(2-pyridyl)}phenyl)propyl]-1,2,4-triazolin-5-one

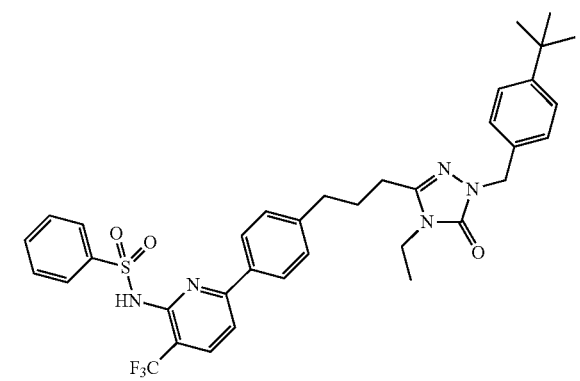 [SMILES: CCn1c(CCCc2ccc(-c3ccc(C(F)(F)F)c(NS(=O)(=O)c4ccccc4)n3)cc2)nn(Cc2ccc(C(C)(C)C)cc2)c1=O]

Prepared in an analogous manner to example 4 using instead 3-(3-{4-[6-amino-5-(trifluoromethyl)(2-pyridyl)]phenyl}propyl)-1-{[4-(tert-butyl)phenyl]methyl}-4-ethyl-1,2,4-triazolin-5-one (example 161) as the nucleophile, sodium hydride as the base and DMF as the solvent. LC-MS: 678 (M+H)⁺.

Example 165

6-(4-(3-(1-(4-(tert-Butyl)benzyl)-4-ethyl-5-oxo-4,5-dihydro-1H-1,2,4-triazol-3-yl)propyl)phenyl)-3-methylpicolinic acid

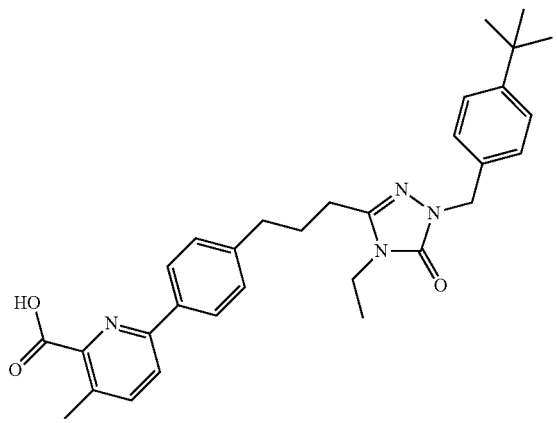 [SMILES: CCn1c(CCCc2ccc(-c3ccc(C)c(C(=O)O)n3)cc2)nn(Cc2ccc(C(C)(C)C)cc2)c1=O]

Prepared in an analogous manner to example 28 but omitting the first step and using instead 6-chloro-3-methylpicolinic acid as the coupling partner in step 2. LC-MS: 513 (M+H)⁺.

Example 166

1-(4-(tert-Butyl)benzyl)-4-ethyl-3-(3-(4-(6-(3-fluorooxetan-3-yl)pyridine-3-yl)phenyl)propyl)-1H-1,2,4-triazol-5(4H)-one

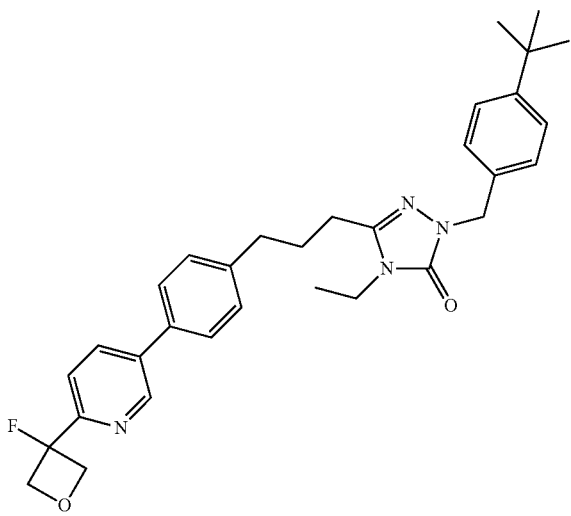 [SMILES: CCn1c(CCCc2ccc(-c3ccc(C4(F)COC4)nc3)cc2)nn(Cc2ccc(C(C)(C)C)cc2)c1=O]

Prepared in an analogous manner to example 143 using instead 2,5-dibromopyridine as the substrate in step 1. LC-MS: 529 (M+H)$^+$.

Example 167

1-(4-(tert-Butyl)benzyl)-3-(3-(4%(3-hydroxyoxetan-3-yl)-[1,1'-biphenyl]-4-yl)propyl)-1H-1,2,4-triazol-5(4H)-one

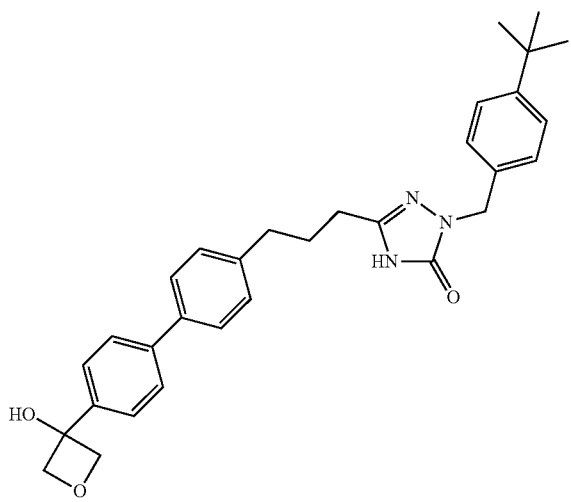 [SMILES: CC(C)(C)c1ccc(Cn2nc(CCCc3ccc(-c4ccc(C5(O)COC5)cc4)cc3)[nH]c2=O)cc1]

Step 1;

To a solution of 3-(4-bromophenyl)-3-fluorooxetane (344 mg, 1.49 mmol, Example 143, step 2) in p-dioxane (10 mL) was added potassium acetate (250 mg, 2.53 mmol), bis(pinacolato)diboron (454 mg, 1.79 mmol) and [1,1'-bis(diphenylphosphino)ferrocene]dichloropalladium(II) (55 mg, 0.07 mmol). The solution was degassed by sparging with nitrogen gas for 10 minutes and then heated at 80° C. under a nitrogen atmosphere for 16 hrs. The solvent was evaporated in vacuo and the residue thus obtained was partitioned between ether and water. The organic phase was then separated, washed with water and brine, dried (MgSO$_4$), filtered and the filtrate concentrated in vacuo. Further purification by way of column chromatography (SiO$_2$, gradient elution, Hex→1:1 Hex:EtOAc) afforded 2-(4-(3-fluorooxetan-3-yl)phenyl)-4,4,5,5-tetramethyl-1,3,2-dioxaborolane as an off-white solid.

Step 2;

To a solution of 3-(3-(4-bromophenyl)propyl)-1-(4-(tert-butyl)benzyl)-1H-1,2,4-triazol-5(4H)-one (77 mg, 0.18 mmol) in DME (3 mL) was added Pd$_2$dba$_3$ (5 mg, 0.005 mmol), dicyclohexyl(2',6'dimethoxybiphenyl-2-yl)phosphine (15 mg, 0.036 mmol), and 2-(4-(3-fluorooxetan-3-yl)phenyl)-4,4,5,5-tetramethyl-1,3,2-dioxaborolane (100 mg, 0.36 mmol) from the previous step. The resulting solution was sub-surface purged with nitrogen gas for 10 min before 0.4 M aq. potassium phosphate (1 mL) was added. The reaction vessel was sealed and heated at 110° C. for 18 hrs. The reaction mixture was then cooled to RT, quenched with 1N aq. HCl and extracted with ether. The combined organic extracts were washed further with 1N aq. HCl, water and finally brine. The organic extract was then dried over sodium sulfate, filtered and concentrated in vacuo. Purification by way of reverse-phase column chromatography (SiO$_2$, gradient elution, 4:1 Hex:EtOAc→EtOAc) afforded the title compound as a white solid (30 mg, 33% yield). LC-MS: 498 (M+H)$^+$.

Example 168

4'-(3-(1-(4-(tert-Butyl)benzyl)-4-ethyl-5-oxo-4,5-dihydro-1H-1,2,4-triazol-3-yl)propyl)-4-propoxy-[1,1'-biphenyl]-3-carboxylic acid

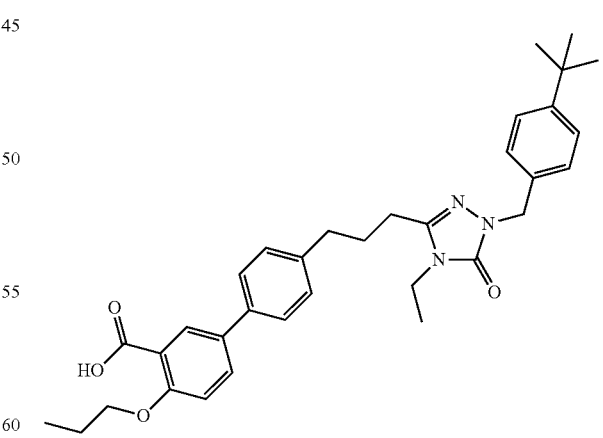

Prepared in an analogous manner to example 13 but using methyl 5-bromo-2-propoxybenzoate as the aryl halide coupling partner in step 1. Hydrolysis of the intermediate ester was carried out as in example 1, step 2 to obtain the title compound. LC-MS: 556 (M+H)$^+$.

Example 169

1-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)-3-ethylurea

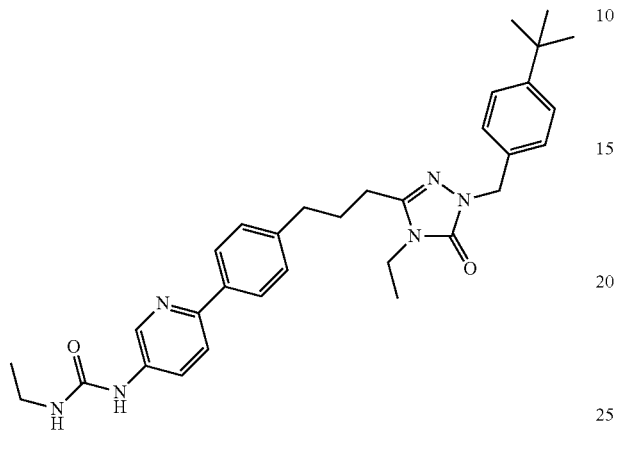

Prepared in an analogous manner to example 10 using instead ethyl isocyanate as the electrophile and THF as the solvent. LC-MS: 541 (M+H)+.

Example 170

1-(4-(tert-Butyl)benzyl)-4-ethyl-3-(3-(4-(2-(3-fluorooxetan-3-yl)pyrimidin-5-yl)phenyl)propyl)-1H-1,2,4-triazol-5(4H)-one

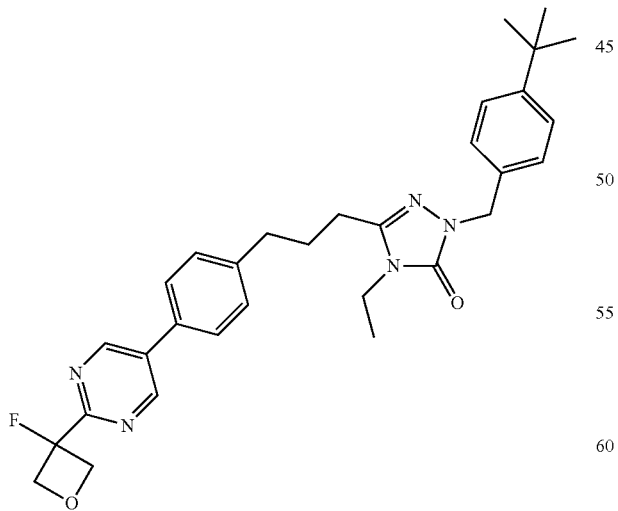

Prepared in an analogous manner to example 143 using instead 2,5-dibromopyrimidine as the substrate in step 1. LC-MS: 530 (M+H)+.

Example 171

1-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)-3-ethylurea

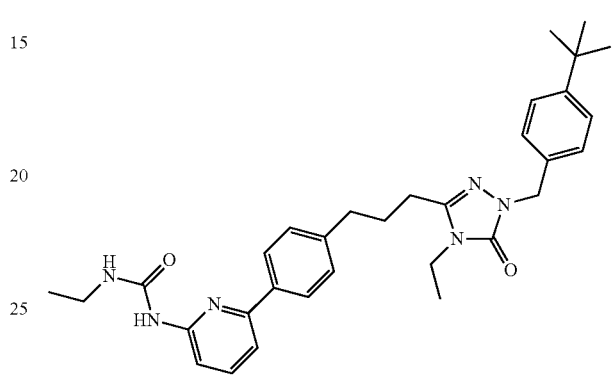

Prepared in an analogous manner to example 4 using instead ethyl isocyanate as the electrophile and THF as the solvent. LC-MS: 541 (M+H)+.

Example 172

3-(3-{4-[3-(Aminomethyl)phenyl]phenyl}propyl)-1-{[4-(tert-butyl)phenyl]methyl}-4-ethyl-1,2,4-triazolin-5-one

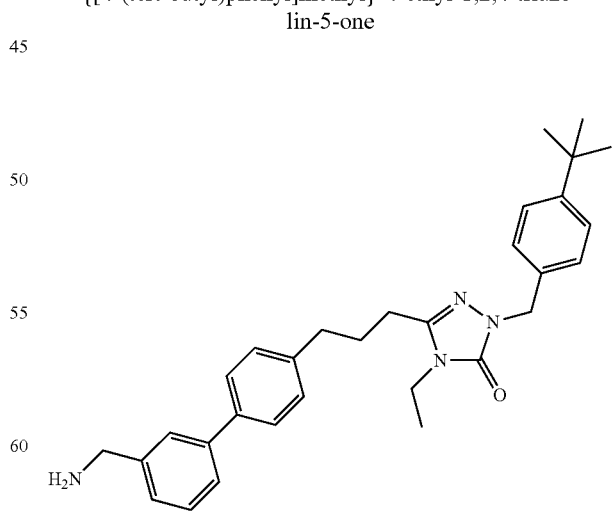

Prepared in an analogous manner to example 3 using instead 3-bromobenzyl amine as the aryl halide coupling partner. LC-MS: 484 (M+H)+.

Example 173

1-(4-(tert-Butyl)benzyl)-4-ethyl-3-(3-(4-(2-(3-hydroxyoxetan-3-yl)pyrimidin-5-yl)phenyl)propyl)-1H-1,2,4-triazol-5(4H)-one

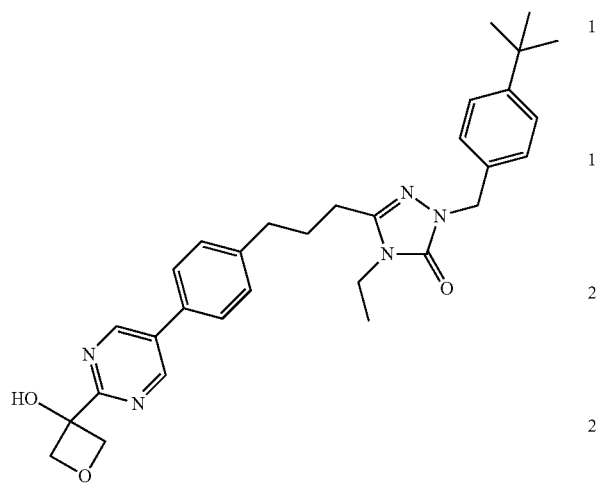

Prepared in an analogous manner to example 170 but omitting the deoxyfluorination step (i.e. step 2). LC-MS: 528 (M+H)+.

Example 174

1-(4-(tert-Butyl)benzyl)-4-ethyl-3-(3-(4'-(3-hydroxyoxetan-3-yl)-[1,1'-biphenyl]-4-yl)propyl)-1H-1,2,4-triazol-5(4H)-one

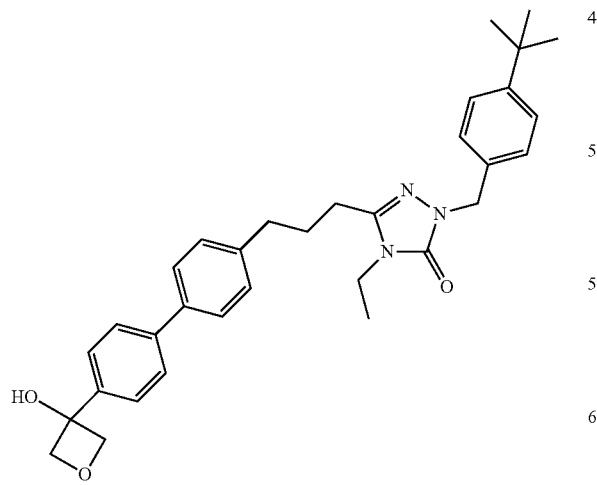

Prepared in an analogous manner to example 143 but omitting the deoxyfluorination step (i.e. step 2). LC-MS: 526 (M+H)+.

Example 176

1-(4-(tert-Butyl)benzyl)-4-ethyl-3-(3-(4'-(1-hydroxycyclobutyl)-[1,1'-biphenyl]-4-yl)propyl)-1H-1,2,4-triazol-5(4H)-one

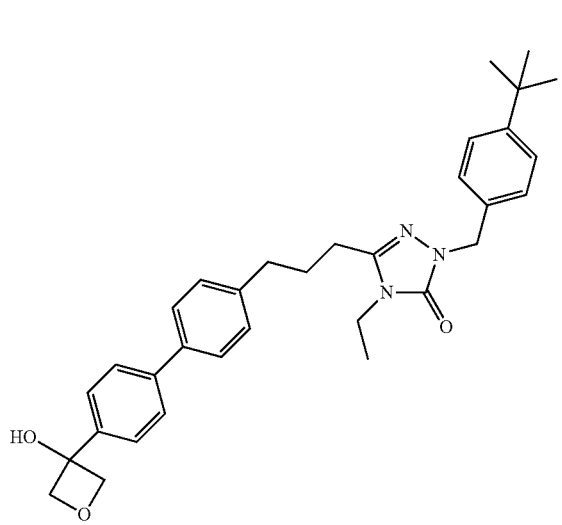 [SMILES: CCn1c(CCCc2ccc(-c3ccc(C4(O)COC4)cc3)cc2)nn(Cc2ccc(C(C)(C)C)cc2)c1=O]

Prepared in an analogous manner to example 143 using instead cyclobutanone as the substrate in step 1 and omitting the deoxyfluorination step (i.e. step 2). LC-MS: 524 (M+H)+.

Example 177

1-{[4-(tert-Butyl)phenyl]methyl}-4-ethyl-3-{3-[4-(3-{[(phenylsulfonyl)amino]methyl}phenyl)phenyl]propyl}-1,2,4-triazolin-5-one

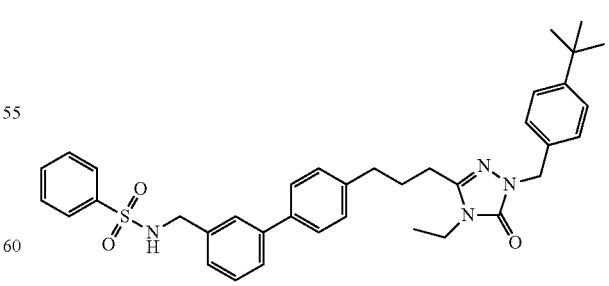

Prepared in an analogous manner to example 4 using instead 3-(3-{4-[3-(aminomethyl)phenyl]phenyl}propyl)-1-{[4-(tert-butyl)phenyl]methyl}-4-ethyl-1,2,4-triazolin-5-one (example 172) as the nucleophile. LC-MS: 624 (M+H)+.

Example 178

1-{[4-(tert-Butyl)phenyl]methyl}-4-ethyl-3-{3-[4-(3-{[(methylsulfonyl)amino]methyl}phenyl)phenyl]propyl}-1,2,4-triazolin-5-one

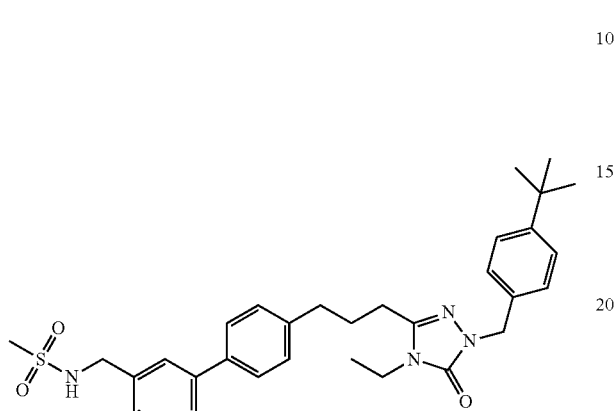

Prepared in an analogous manner to example 177 using instead methanesulfonyl chloride as the nucleophile. LC-MS: 562 (M+H)+.

Example 179

3-(5-{4-[3-(1-{[4-(tert-Butyl)phenyl]methyl}-4-ethyl-5-oxo(1,2,4-triazolin-3-yl))propyl]phenyl}-2-methoxyphenyl)propanoic acid Prepared in an analogous manner to example 28 but omitting the first step and using instead 3-(5-bromo-2-methoxyphenyl)propanoic acid as the coupling partner in step 2. LC-MS: 556 (M+H)+.

Example 180

1-{[4-(tert-Butyl)phenyl]methyl}-4-ethyl-3-[3-(4-{4-methoxy-3-[(methylamino)methyl]phenyl}phenyl)propyl]-1,2,4-triazolin-5-one Prepared in an analogous manner to example 3 using instead 5-bromo-2-methoxybenzylmethyl amine as the aryl halide coupling partner. LC-MS: 527 (M+H)+.

Example 181

2-(4-(3-(1-(4-(tert-Butyl)benzyl)-4-ethyl-5-oxo-4,5-dihydro-1H-1,2,4-triazol-3-yl)propyl)phenyl)-5-methoxypyrimidine-4-carboxylic acid

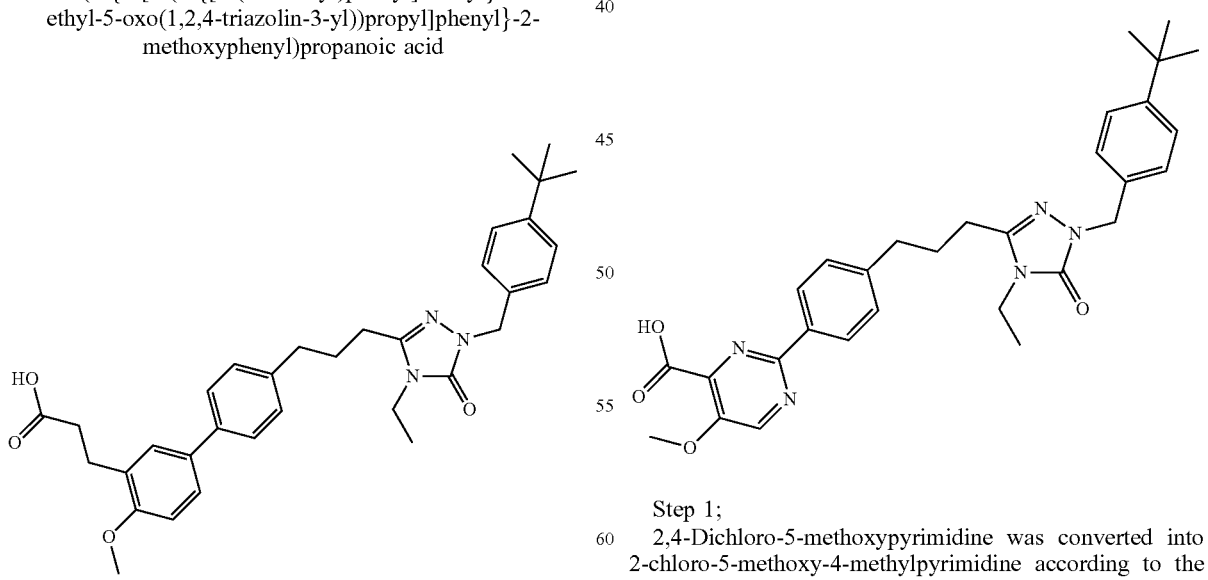

Step 1;
2,4-Dichloro-5-methoxypyrimidine was converted into 2-chloro-5-methoxy-4-methylpyrimidine according to the published procedure found in WO2010103334, p 21.

Step 2;
To a solution of 2-chloro-5-methoxy-4-methylpyrimidine (0.25 g, 1.58 mmol) in CCl4 (15 mL) was added NBS (0.337 g, 1.89 mmol) and AIBN (0.026 g, 0.16 mmol). The resulting mixture was heated at reflux for 4 hrs after which an additional amount of NBS (0.056 g, 0.32 mmol) and AIBN (0.013 g, 0.08 mmol) were added. After a further 16 hrs of reflux, the reaction mixture was cooled to RT, filtered through a Na$_2$SO$_4$/paper plug, and the filtrate concentrated in vacuo. The residue thus obtained was then re-suspended in Et$_2$O and re-filtered. Concentration of the resulting filtrate in vacuo afforded the crude 4-(bromomethyl)-2-chloro-5-methoxypyrimidine (slightly contaminated with the dibrominated byproduct) which was taken on to the next step.

Step 3;

To a solution of 4-(bromomethyl)-2-chloro-5-methoxypyrimidine from the previous step (0.19 g, 0.80 mmol) in MeCN (8 mL) was added sodium acetate (0.098 g, 0.80 mmol) and the resulting mixture was heated at 70° C. for 16 hrs. The volatiles were then removed in vacuo and the resulting residue was purified on silica gel, eluting with a solvent gradient of 0 to 50% EtOAc in hexanes, to afford (2-chloro-5-methoxypyrimidin-4-yl)methyl acetate as a solid.

Step 4;

Carried out in an analogous manner to example 13, step 1 using instead (2-chloro-5-methoxypyrimidin-4-yl)methyl acetate as the aryl halide coupling partner.

Step 5;

To a solution of (2-(4-(3-(1-(4-(tert-butyl)benzyl)-4-ethyl-5-oxo-4,5-dihydro-1H-1,2,4-triazol-3-yl)propyl)phenyl)-5-methoxypyrimidin-4-yl)methyl acetate from the previous step (0.17 g, 0.31 mmol) in water (2 mL) and MeOH (2 mL) was added K$_2$CO$_3$ (0.21 g, 1.52 mmol) in one rapid portion. The reaction mixture was stirred at RT for 16 hrs and then the volatiles were evaporated in vacuo. The resulting residue was diluted with water and extracted with dichloromethane. The combined organic extracts were washed further with brine, dried over Na$_2$SO$_4$, filtered and the filtrate concentrated in vacuo. Crude 1-(4-(tert-butyl)benzyl)-4-ethyl-3-(3-(4-(4-(hydroxymethyl)-5-methoxypyrimidin-2-yl)phenyl)propyl)-1H-1,2,4-triazol-5(4H)-one thus obtained was used without further purification.

Step 6;

To a solution of 1-(4-(tert-butyl)benzyl)-4-ethyl-3-(3-(4-(4-(hydroxymethyl)-5-methoxypyrimidin-2-yl)phenyl)propyl)-1H-1,2,4-triazol-5(4H)-one from the previous step (0.15 g, 0.29 mmol) in DCM (5 mL) was added sodium bicarbonate (0.036 mg, 0.49 mmol) and Dess-Martin periodinane (0.19 mg, 0.44 mmol). The resulting mixture was stirred at RT for 4 hrs after which the reaction was quenched with the addition of 1:1 (v/v) saturated aq. NaHCO$_3$ and 10% aq. Na$_2$S$_2$O$_3$ (aq.). The aqueous layer was separated and back-extracted with EtOAc. The combined organic extracts were then washed further with water and brine, dried over Na$_2$SO$_4$, filtered, and the filtrate concentrated in vacuo. Crude 2-(4-(3-(1-(4-(tert-butyl)benzyl)-4-ethyl-5-oxo-4,5-dihydro-1H-1,2,4-triazol-3-yl)propyl)phenyl)-5-methoxypyrimidine-4-carbaldehyde thus obtained was used without further purification.

Step 7;

To a solution of 2-(4-(3-(1-(4-(tert-butyl)benzyl)-4-ethyl-5-oxo-4,5-dihydro-1H-1,2,4-triazol-3-yl)propyl)phenyl)-5-methoxypyrimidine-4-carbaldehyde from the previous step (0.12 g, 0.23 mmol) in THF (1.5 mL) and t-BuOH (1.5 mL) was added 2-methyl-2-butene (0.25 mL, 2.33 mmol) followed by a premixed aqueous solution (0.5 mL) of sodium dihydrogen phosphate (0.11 mg, 0.94 mmol) and NaClO$_2$ (0.085 mg, 0.95 mol). The resulting mixture was stirred at RT for 16 hrs. The volatiles were then removed in vacuo and the resulting residue was suspended in MeOH. The suspension was then briefly sonicated, filtered and the filtrate concentrated in vacuo. This process was subsequently repeated using DCM as the suspending solvent. Further purification by way of reverse phase column chromatography (C$_{18}$-column, gradient elution, 5:1 (v/v) H$_2$O: MeCN+ 0.1% TFA to MeCN+0.1% TFA) afforded the title compound as a white solid. LC-MS: 530 (M+H)$^+$.

Example 182

1-{[4-(tert-Butyl)phenyl]methyl}-4-ethyl-3-{3-[4-(4-methoxy-3-{2-[(phenylsulfonyl)amino]ethyl}phenyl)phenyl]propyl}-1,2,4-triazolin-5-one

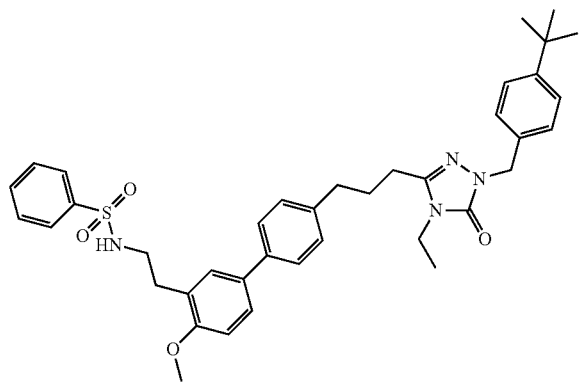 [SMILES: CCn1c(CCCc2ccc(-c3ccc(OC)c(CCNS(=O)(=O)c4ccccc4)c3)cc2)nn(Cc2ccc(C(C)(C)C)cc2)c1=O]

Step 1;

Carried out in an analogous manner to example 3 using instead 5-bromo-2-methoxyphenethylamine as the aryl halide coupling partner.

Step 2;

Carried out in an analogous manner to example 4 using the amine from the previous step as the nucleophile. LC-MS: 667 (M+H)$^+$.

Example 183

1-{[4-(tert-Butyl)phenyl]methyl}-4-ethyl-3-{3-[4-(4-methoxy-3-{2-[(methylsulfonyl)amino]ethyl}phenyl)phenyl]propyl}-1,2,4-triazolin-5-one

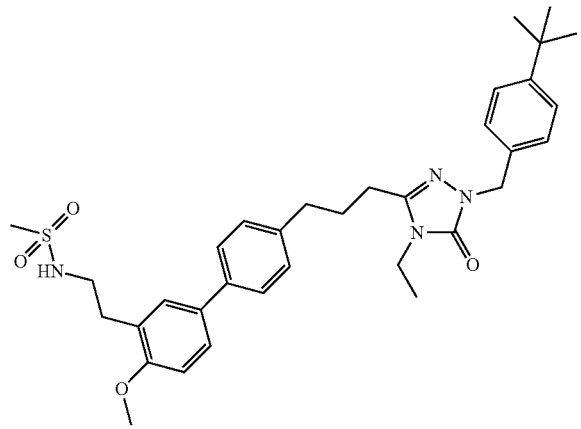 [SMILES: CCn1c(CCCc2ccc(-c3ccc(OC)c(CCNS(C)(=O)=O)c3)cc2)nn(Cc2ccc(C(C)(C)C)cc2)c1=O]

Step 1;
Carried out in an analogous manner to example 3 using instead 5-bromo-2-methoxyphenethylamine as the aryl halide coupling partner.
Step 2;
Carried out in an analogous manner to example 4 using the amine from the previous step as the nucleophile. LC-MS: 605 (M+H)+.

Example 184

3-(3-{4-[3-(Aminomethyl)-4-methoxyphenyl] phenyl}propyl)-1-{[4-(tert-butyl)phenyl]methyl}-4-ethyl-1,2,4-triazolin-5-one

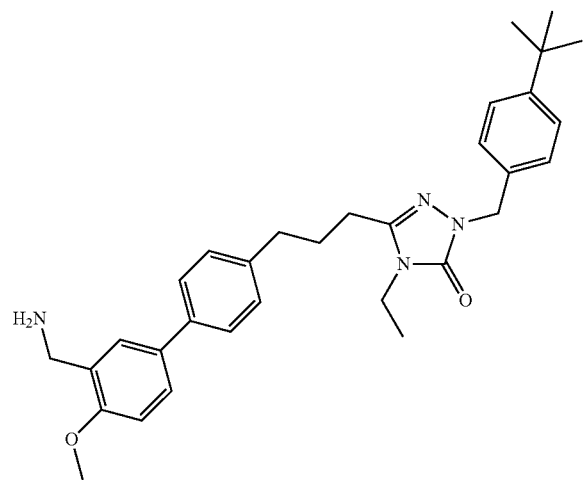 [SMILES: CCn1c(CCCc2ccc(-c3ccc(OC)c(CN)c3)cc2)nn(Cc2ccc(C(C)(C)C)cc2)c1=O]

Prepared in an analogous manner to example 3 using instead (5-bromo-2-methoxyphenyl)methanamine as the aryl halide coupling partner. LC-MS: 513 (M+H)+.

Example 185

1-{[4-(tert-Butyl)phenyl]methyl}-4-ethyl-3-{3-[4-(4-methoxy-3-{[(phenylsulfonyl)amino]methyl}phenyl) phenyl]propyl}-1,2,4-triazolin-5-one

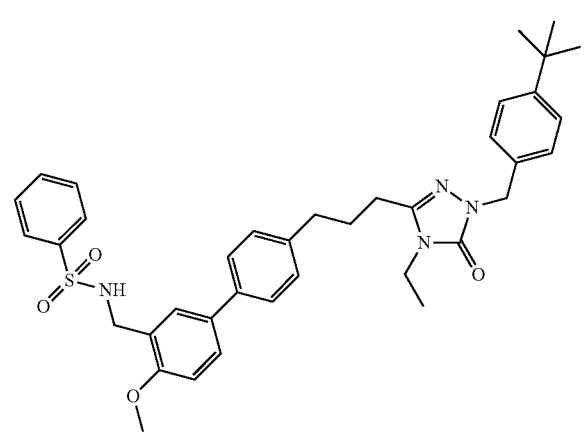 [SMILES: CCn1c(CCCc2ccc(-c3ccc(OC)c(CNS(=O)(=O)c4ccccc4)c3)cc2)nn(Cc2ccc(C(C)(C)C)cc2)c1=O]

Prepared in an analogous manner to example 4 using instead 3-(3-{4-[3-(aminomethyl)-4-methoxyphenyl] phenyl}propyl)-1-{[4-(tert-butyl)phenyl]methyl}-4-ethyl-1,2,4-triazolin-5-one (example 184) as the nucleophile. LC-MS: 653 (M+H)+.

Example 186

1-{[4-(tert-Butyl)phenyl]methyl}-4-ethyl-3-{3-[4-(4-methoxy-3-{[(methylsulfonyl)amino] methyl}phenyl)phenyl]propyl}-1,2,4-triazolin-5-one Prepared in an analogous manner to example 185 using instead methanesulfonyl chloride as the electrophile. LC-MS: 591 (M+H)+.

Example 187

1-(4-(tert-Butyl)benzyl)-4-ethyl-3-(3-(4'-(4-hydroxytetrahydro-2H-pyran-4-yl)-[1,1'-biphenyl]-4-yl)propyl)-1H-1,2,4-triazol-5(4H)-one Prepared in an analogous manner to example 143 using instead dihydro-2H-pyran-4(3H)-one as the substrate in step 1 and omitting the deoxyfluorination step (i.e. step 2). LC-MS: 554 (M+H)+.

Example 188

1-{[4-(tert-Butyl)phenyl]methyl}-4-ethyl-3-(3-{4-[4-methoxy-3-({[benzylsulfonyl]amino}methyl)phenyl]phenyl}propyl)-1,2,4-triazolin-5-one

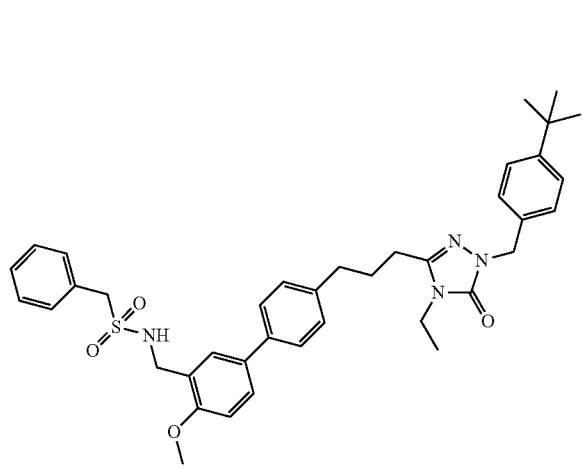 [SMILES: CCn1c(CCCc2ccc(-c3ccc(OC)c(CNS(=O)(=O)Cc4ccccc4)c3)cc2)nn(Cc2ccc(C(C)(C)C)cc2)c1=O]

Prepared in an analogous manner to example 185 using instead phenylmethanesulfonyl chloride as the electrophile. LC-MS: 667 (M+H)+.

Example 189

1-{[4-(tert-Butyl)phenyl]methyl}-4-ethyl-3-[3-(4-{6-[(ethylsulfonyl)amino]-5-methoxy(2-pyridyl)}phenyl)propyl]-1,2,4-triazolin-5-one

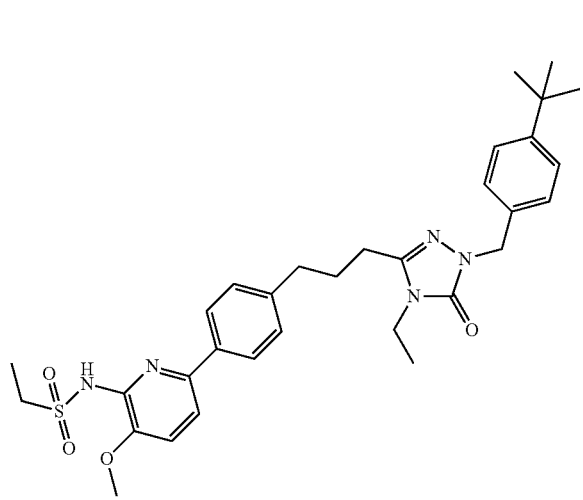 [SMILES: CCn1c(CCCc2ccc(-c3ccc(OC)c(NS(=O)(=O)CC)n3)cc2)nn(Cc2ccc(C(C)(C)C)cc2)c1=O]

Prepared in an analogous manner to example 59 using instead ethanesulfonyl chloride as the electrophile. LC-MS: 592 (M+H)+.

Example 190

1-{[4-(tert-Butyl)phenyl]methyl}-4-ethyl-3-[3-(4-{6-[(cyclopropylsulfonyl)amino]-5-methoxy(2-pyridyl)}phenyl)propyl]-1,2,4-triazolin-5-one

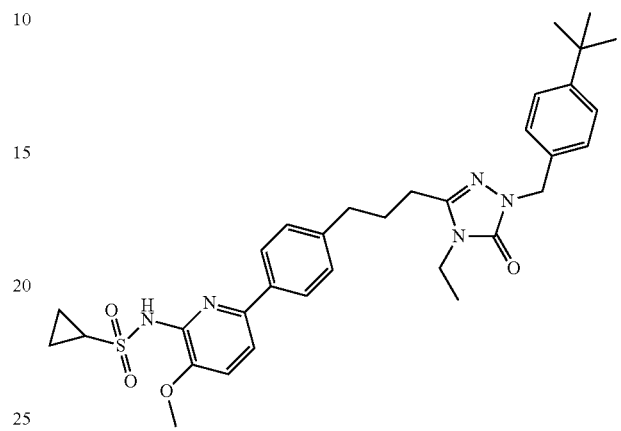

Prepared in an analogous manner to example 59 using instead cyclopropanesulfonyl chloride as the electrophile. LC-MS: 604 (M+H)+.

Example 191

1-(4-(tert-Butyl)benzyl)-4-ethyl-3-(3-(4-(5-(3-fluorooxetan-3-yl)pyridine-2-yl)phenyl)propyl)-1H-1,2,4-triazol-5(4H)-one

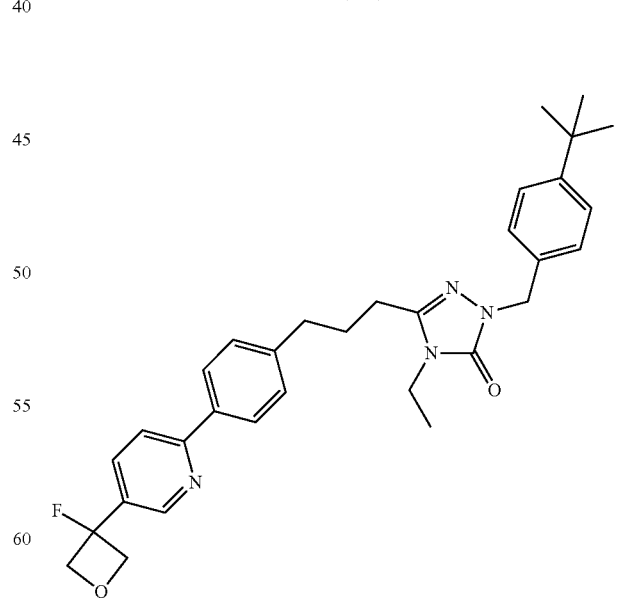

Prepared in an analogous manner to example 143 using instead 2-chloro-5-iodopyridine as the substrate in step 1. LC-MS: 529 (M+H)+.

Example 192

1-{[4-(tert-Butyl)phenyl]methyl}-4-ethyl-3-[3-(4-{6-[(cyclo hexylsulfonyl)amino]-5-methoxy(2-pyridyl)}phenyl)propyl]-1,2,4-triazolin-5-one

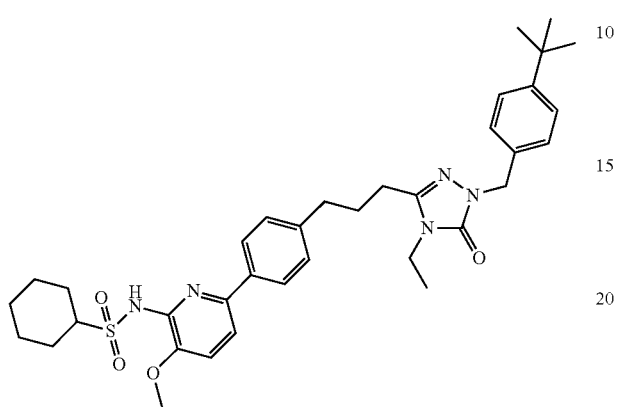

Prepared in an analogous manner to example 59 using instead cyclohexanesulfonyl chloride as the electrophile, benzene as the solvent and KHMDS as the base. LC-MS: 646 (M+H)+.

Example 193

3-{4-[3-(1-{[4-(tert-Butyl)phenyl]methyl}-4-ethyl-5-oxo(1,2,4-triazolin-3-yl))propyl]phenyl}-5-methoxy-benzoic acid

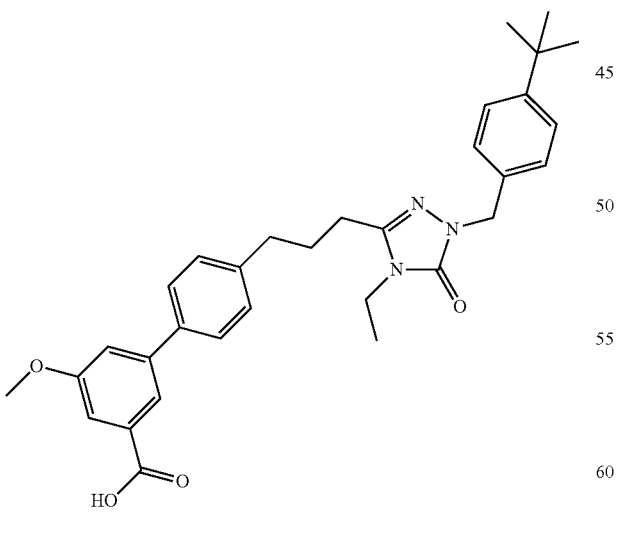

Prepared in an analogous manner to example 28 but omitting the first step and using instead 3-bromo-5-methoxybenzoic acid as the coupling partner in step 2. LC-MS: 528 (M+H)+.

Example 194

2-(3-{4-[3-(1-{[4-(tert-Butyl)phenyl]methyl}-4-ethyl-5-oxo(1,2,4-triazolin-3-yl))propyl]phenyl}-5-methoxyphenyl)acetic acid

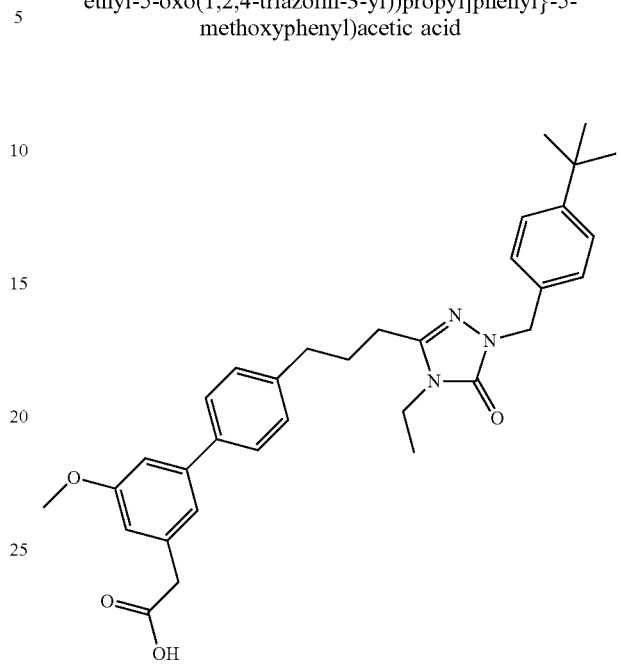

Prepared in an analogous manner to example 130 using instead 3-bromo-5-methoxybenzoic acid as the starting material. LC-MS: 542 (M+H)+.

Example 195

1-(4-(tert-Butyl)benzyl)-3-(3,3-difluoro-3-(4-(5-(3-fluorooxetan-3-yl)pyridine-2-yl)phenyl)propyl)-4-ethyl-1H-1,2,4-triazol-5(4H)-one

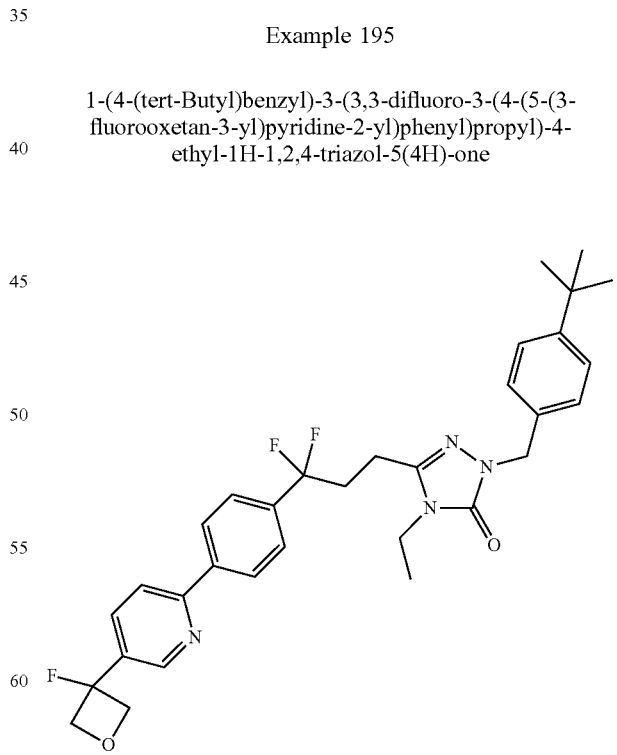

Prepared in an analogous manner to example 191 but using instead 3-(3-(4-bromophenyl)-3,3-difluoropropyl)-1-(4-tert-butyl)benzyl)-4-ethyl-1H-1,2,4-triazol-5(4H)-one (example 163, step 5) as the aryl bromide coupling partner in step 3. LC-MS: 563 (M+H)+.

Example 196

1-(4-(tert-Butyl)benzyl)-3-(3,3-difluoro-3-(4'-(3-hydroxyoxetan-3-yl)-[1,1'-biphenyl]-4-yl)propyl)-4-ethyl-1H-1,2,4-triazol-5(4H)-one

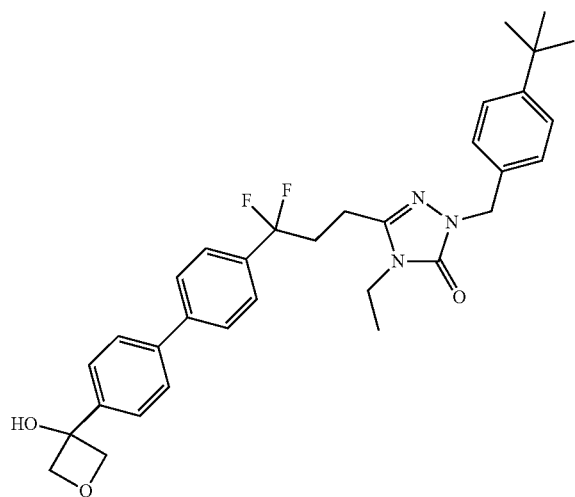 [SMILES: CCn1c(CCC(F)(F)c2ccc(-c3ccc(C4(O)COC4)cc3)cc2)nn(Cc2ccc(C(C)(C)C)cc2)c1=O]

Prepared in an analogous manner to example 174 but using instead 3-(3-(4-bromophenyl)-3,3-difluoropropyl)-1-(4-tert-butyl)benzyl)-4-ethyl-1H-1,2,4-triazol-5(4H)-one (example 163, step 5) as the aryl bromide coupling partner in step 3. LC-MS: 562 (M+H)+.

Example 197

1-(4-(tert-Butyl)benzyl)-4-ethyl-3-(3-(4-(5-(3-hydroxyoxetan-3-yl)pyridine-2-yl)phenyl)propyl)-1H-1,2,4-triazol-5(4H)-one

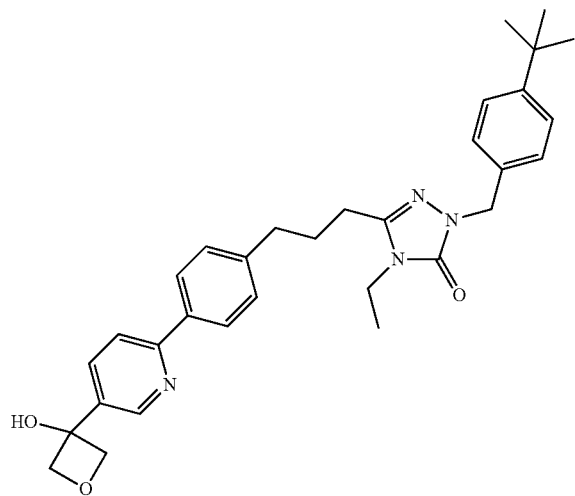 [SMILES: CCn1c(CCCc2ccc(-c3ccc(C4(O)COC4)cn3)cc2)nn(Cc2ccc(C(C)(C)C)cc2)c1=O]

Prepared in an analogous manner to example 191 but omitting the deoxyfluorination step (i.e. step 2). LC-MS: 527 (M+H)+.

Example 198

2-(5-(6-(3-(1-(4-(tert-Butyl)benzyl)-4-ethyl-5-oxo-4,5-dihydro-1H-1,2,4-triazol-3-yl)propyl)pyridin-3-yl)-2-methoxyphenyl)acetic acid Step 1:
To a degassed solution (via sub-surface purge with nitrogen) of 2,5-dibromopyridine (2.0 g, 8.44 mmol) in THF (60 mL) was added Pd(PPh3)4 (150 mg), followed by dropwise addition of 4-ethoxy-4-oxobutylzinc(II) bromide (0.5 M in THF, 16.9 mL, 8.45 mmol). After stirring at room temperature for 2 hrs, the reaction solution was poured into to a mixture of ice and 1 N aq. HCl. The organic layer was separated and the aqueous layer was back-extracted with EtOAc. The combined organic extracts were then dried over MgSO4, filtered and the filtrate concentrated in vacuo. Purification by way of column chromatography (SiO2, gradient elution, Hex→3:1 Hex:EtOAc) afforded ethyl 4-(5-bromopyridin-2-yl)butanoate.

Step 2:
To a solution of ethyl 4-(5-bromopyridin-2-yl)butanoate from the previous step (1.6 g, 5.9 mmol) in THF (20 mL), MeOH (5 mL) and water (5 mL) was added lithium hydroxide monohydrate (400 mg). When the hydrolysis was deemed to be complete by TLC analysis (~1 hr), the volatiles were removed in vacuo and the resulting aqueous suspension was acidified to pH of ~4 with the addition of solid citric acid. The resulting mixture was then extracted with EtOAc. The combined organic extracts were dried over MgSO4, filtered and the filtrate concentrated in vacuo. Crude 4-(5-bromopyridin-2-yl)butanoic acid was used without further purification.

Step 3:
To a solution of 4-(5-bromopyridin-2-yl)butanoic acid from the previous step (500 mg, 2.1 mmol) in DMF (10 mL) was added HATU (888 mg, 2.33 mmol), followed by diisopropylethylamine (1.1 mL, 6.14 mmol). After stirring at RT for 30 min, 1-(4-(tert-butyl)benzyl)-N-ethylhydrazinecarboxamide, monomethanesulfonate (743 mg, 2.15 mmol) was then added and the resulting golden yellow solution was allowed to stir at RT for another 16 hrs. After the coupling was deemed to be complete by LC-MS, the reaction mixture was diluted with EtOAc and washed further with water and brine. The organic phase thus obtained was then dried over MgSO$_4$, filtered and the filtrate concentrated in vacuo. The resulting residue was re-dissolved in EtOAc (20 mL) and added camphorsulfonic acid (476 mg, 2.05 mmol) added. After heating at reflux for 16 hrs, the reaction was quenched with the addition of saturated aq. NaHCO$_3$. The organic phase was then separated, dried (MgSO$_4$), filtered and the filtrate concentrated in vacuo. Further purification by way of column chromatography (SiO$_2$, gradient elution, Hex→3:1 Hex:EtOAc) afforded 3-(3-(5-bromopyridin-2-yl)propyl)-1-(4-(tert-butyl)benzyl)-4-ethyl-1H-1,2,4-triazol-5(4H)-one as a colorless solid.

Step 4:

Carried out as in example 1 using 3-(3-(5-bromopyridin-2-yl)propyl)-1-(4-(tert-butyl)benzyl)-4-ethyl-1H-1,2,4-triazol-5(4H)-one from the previous step and methyl 2-(2-methoxy-5-(4,4,5,5-tetramethyl-1,3,2-dioxaborolan-2-yl)phenyl)acetate as coupling partners. LC-MS: 543 (M+H)$^+$.

Example 199

2-(4'-(3-(1-(4-(tert-Butyl)benzyl)-4-ethyl-5-oxo-4,5-dihydro-1H-1,2,4-triazol-3-yl)propyl)-3-methoxy-[1,1'-biphenyl]-4-yl)acetic acid Example 200

2-(4'-(3-(1-(4-(tert-Butyl)benzyl)-4-ethyl-5-oxo-4,5-dihydro-1H-1,2,4-triazol-3-yl)propyl)-4-isopropoxy-[1,1'-biphenyl]-3-yl)acetic acid

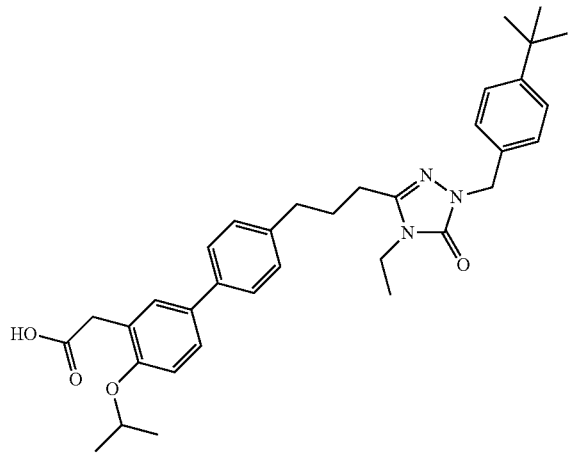 [SMILES: CCn1c(CCCc2ccc(-c3ccc(OC(C)C)c(CC(=O)O)c3)cc2)nn(Cc2ccc(C(C)(C)C)cc2)c1=O]

Prepared in an analogous manner to example 13 using instead 2-(5-bromo-2-isopropoxyphenyl)acetonitrile as the aryl halide coupling partner. LC-MS: 570 (M+H)$^+$.

Example 201

1-(4-(tert-Butyl)benzyl)-4-ethyl-3-(3-(4-(2-(3-fluorooxetan-3-yl)thiazol-4-yl)phenyl)propyl)-1H-1,2,4-triazol-5(4H)-one

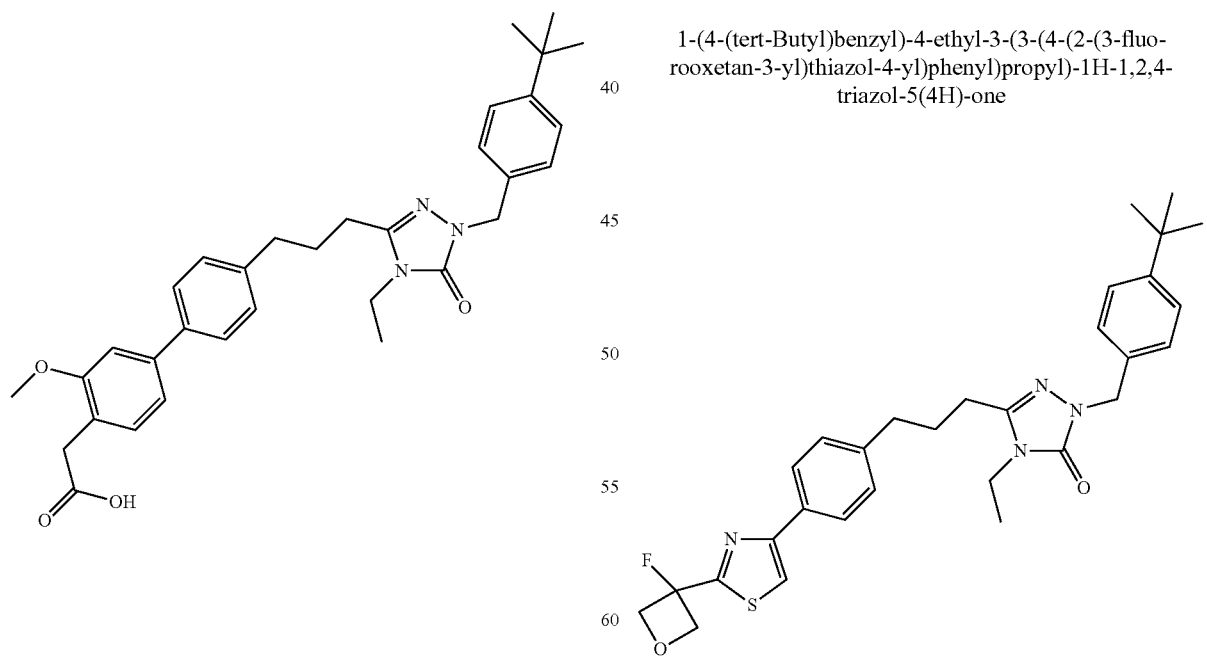

Prepared in an analogous manner to example 13 using instead 2-(4-bromo-2-methoxyphenyl)acetonitrile as the aryl halide coupling partner. LC-MS: 542 (M+H)$^+$.

Prepared in an analogous manner to example 143 using instead 2,4-dibromothiazole as the substrate. diethyl ether as the solvent and −100° C. as the reaction temperature in step 1. LC-MS: 535 (M+H)$^+$.

Example 202

1-(4-(tert-Butyl)benzyl)-4-ethyl-3-(3-(4-(2-(3-fluorooxetan-3-yl)thiazol-5-yl)phenyl)propyl)-1H-1,2,4-triazol-5(4H)-one

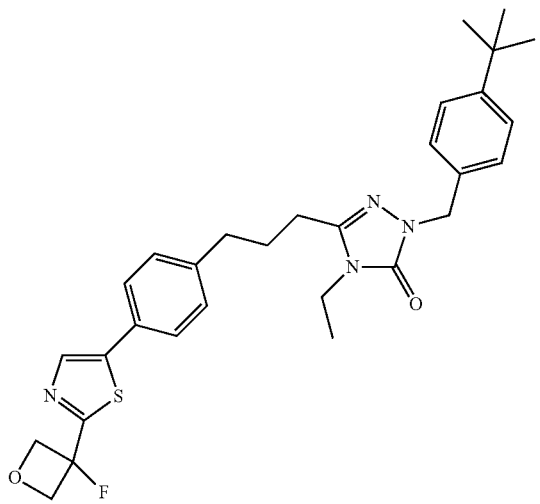 [SMILES: CCn1c(CCCc2ccc(-c3cnc(C4(F)COC4)s3)cc2)nn(Cc2ccc(C(C)(C)C)cc2)c1=O]

Prepared in an analogous manner to example 143 using instead 2,5-dibromothiazole as the substrate, diethyl ether as the solvent and −100° C. as the reaction temperature in step 1. LC-MS: 535 (M+H)$^+$.

Example 203

1-(4-(tert-Butyl)benzyl)-4-ethyl-3-(3-(4-(2-(3-hydroxyoxetan-3-yl)thiazol-4-yl)phenyl)propyl)-1H-1,2,4-triazol-5(4H)-one

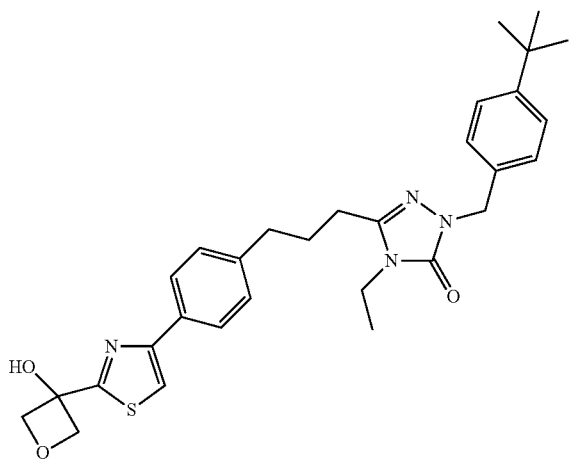 [SMILES: CCn1c(CCCc2ccc(-c3csc(C4(O)COC4)n3)cc2)nn(Cc2ccc(C(C)(C)C)cc2)c1=O]

Prepared in an analogous manner to example 201 but omitting the deoxygenation step (i.e. step 2). LC-MS: 533 (M+H)$^+$.

Example 204

1-(4-(tert-Butyl)benzyl)-4-ethyl-3-(3-(4-(2-(3-hydroxyoxetan-3-yl)thiazol-5-yl)phenyl)propyl)-1H-1,2,4-triazol-5(4H)-one

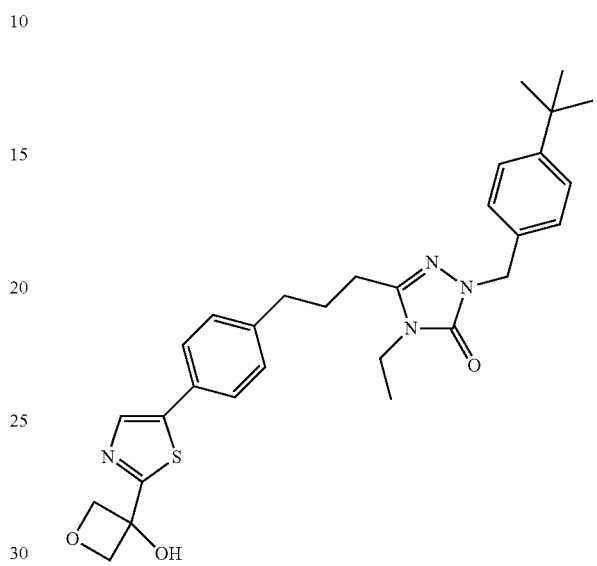

Prepared in an analogous manner to example 202 but omitting the deoxyfluorination step (i.e. step 2). LC-MS: 533 (M+H)$^+$ While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula I

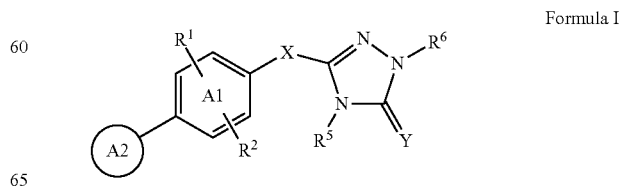

Formula I or a pharmaceutical acceptable salt thereof wherein:
A1 is phenyl or a 6 membered heteroaromatic ring having 1, 2 or 3 N in the heteroaromatic ring;
A2 is selected from A2a or A2b

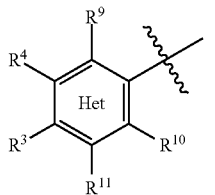

A2a or

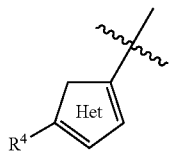

A2b wherein A2a phenyl or a 6-membered heteroaromatic ring having 1, 2 or 3 N in the heteroaromatic ring, and
A2b is a 5-membered heteroaromatic ring having 1, 2 or 3 heteroatoms independently selected from O, S and N;
X is —(CH$_2$)$_3$— optionally mono or di-substituted with halogen;
Y is O;
R$^1$ and R$^2$ are each independently selected from the group consisting of
  (a) hydrogen,
  (b) halogen,
  (c) CN,
  (d) —CF$_3$,
  (e) —C$_{1-6}$alkyl,
  (f) —C$_{1-6}$alkyl-C(=O)OH,
  (g) —O—(R$^7$),
  (h) —S(=O)$_o$R$^7$,
  (i) —N(R$^7$)(R$^8$),
  (j) —N(R$^7$)—C(=O)—(R$^8$),
  (k) —N(R$^7$)—C(=O)—O—(R$^8$),
  (l) —N(R$^7$)S(=O)$_2$(R$^8$),
  (m) —C$_{3-6}$cycloalkyl,
  (n) —C(=O)(R$^7$),
  (o) aryl,
  (p) heteroaryl,
  (q) —OC(=O)N(R$^7$)(R$^8$),
  (r) —S(=O)$_2$N(R$^7$)(R$^8$),
  (s) —C(=O)N(R$^7$)(R$^8$), and
  (t) —C(R$^7$)(R$^8$)OH,
wherein the alkyl portion of choices (e) and (f), and the cycloalkyl portion of choice (m) are optionally substituted with halogen, and
wherein the aryl of choice (o) and the heteroaryl of choice (p) are optionally mono- or di-substituted with substituents selected from the group consisting of halogen, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$ cycloalkyl), —N(C$_{1-6}$alkyl)$_2$, —N(C$_{3-6}$cycloalkyl)$_2$, —S(=O)$_o$C$_{1-6}$alkyl, —S(=O)$_o$C$_{3-6}$cycloalkyl and CN;
R$^3$ is selected from the group consisting of:
  (a) hydrogen,
  (b) halogen,
  (c) CN,
  (d) —CF$_3$,
  (e) —C$_{1-6}$alkyl,
  (f) —C$_{1-6}$alkyl-C(=O)OH,
  (g) —O—(R$^7$),
  (h) —S(=O)$_o$R$^7$,
  (i) —N(R$^7$)(R$^8$),
  (j) —N(R$^7$)—C(=O)—(R$^8$),
  (k) —N(R$^7$)—C(=O)—O—(R$^8$),
  (l) —N(R$^7$)S(=O)$_2$(R$^8$),
  (m) —C$_{3-6}$cycloalkyl,
  (n) —C(=O)(R$^7$),
  (o) aryl,
  (p) heteroaryl,
  (q) —OC(=O)N(R$^7$)(R$^8$),
  (r) —S(=O)$_2$N(R$^7$)(R$^8$),
  (s) —C(=O)N(R$^7$)(R$^8$),
  (t) —C(R$^7$)(R$^8$)OH,
  (u) —C$_{1-6}$alkyl-S(=O)$_2$N(R$^7$)(R$^8$),
  (v) —C$_{3-6}$cycloalkyl-S(=O)$_2$N(R$^7$)(R$^8$),
  (w) —C$_{3-6}$cycloalkyl-C(=O)OH,
  (x) heterocycle,
  (y) —C$_{1-6}$alkyl-C(=O)—N(R$^7$)(R$^8$),
  (z) —C$_{3-6}$cycloalkyl-C(=O)—N(R$^7$)(R$^8$),
  (aa) —C(=O)OH,
  (bb) —C$_{1-6}$alkyl-(R$^7$),
  (cc) —C$_{3-6}$cycloalkyl-(R$^7$),
  (dd) —N(R$^7$)—C(=O)—NH(R$^8$), and
  (ee) —N(R$^7$)—C(=O)N(R$^7$)—S(=O)$_2$(R$^8$),
wherein the alkyl portion of choices (e), (f), (u), (y) and (bb), and the cycloalkyl portion of choices (m), (v), (w), (z) and (cc), are optionally substituted with halogen, oxo or hydroxyl, and
wherein the aryl of choice (o), heteroaryl of choice (p), and the heterocycle of choice (x) are optionally mono- or di-substituted with substituents selected from the group consisting of halogen, nitro, C$_{1-6}$alkyl, C$_{1-6}$alkoxy, halo C$_{1-6}$alkyl, C$_{3-6}$cycloalkyl, C$_{3-6}$cycloalkoxy, —NH(C$_{1-6}$alkyl), —NH(C$_{3-6}$cycloalkyl), —N(C$_{1-6}$alkyl)$_2$, —N(C$_{3-6}$cycloalkyl)$_2$, —S(=O)$_o$C$_{1-6}$ alkyl, —S(=O)$_o$C$_{3-6}$cycloalkyl, hydroxyl and CN;
R$^4$ is selected from the group consisting of:
  (a) hydrogen,
  (b) —N(R$^7$)(R$^8$),
  (c) —N(R$^7$)S(=O)$_2$R$^8$,
  (d) —N(R$^7$)—C(=O)R$^8$,
  (e) —N(R$^7$)C(=O)OR$^8$,
  (f) —S(=O)$_o$R$_7$,
  (g) —S(=O)$_2$N(R$^7$)(R$^8$),
  (h) —C(=O)R$^7$,
  (i) —C(=O)N(R$^7$)(R$^8$),
  (j) —OC(=O)N(R$^7$)(R$^8$),
  (k) —O—R$^7$,
  (l) —C(R$^7$)(R$^8$)OH,
  (m) —C$_{1-4}$alkyl-C(=O)NHS(=O)$_2$R$^7$,
  (n) —C$_{1-4}$alkyl-S(=O)$_2$NHC(=O)R$^7$,
  (o) —C$_{1-4}$alkyl-C(=O)—N(R$^7$)(R$^8$),
  (p) —C$_{1-4}$alkyl-N(R$^7$)C(=O)(R$^8$),
  (q) —C$_{1-4}$alkyl-N(R$^7$)S(=O)$_2$(R$^8$),
  (r) —C$_{1-4}$alkyl-S(=O)$_2$N(R$^7$)(R$^8$),
  (s) —C$_{1-4}$alkyl-N(R$^7$)C(=O)O(R$^8$),
  (t) —C$_{1-4}$alkyl-O—C(=O)N(R$^7$)(R$^8$),
  (u) —C$_{1-4}$alkyl-C(=O)(R$^7$),
  (v) —C$_{1-4}$alkyl-C(R$^7$)(R$^8$)OH,
  (w) —C$_{1-4}$alkyl-O—(R$^7$),
  (x) —C$_{1-6}$alkyl-C(=O)OH,
  (y) —C$_{2-6}$alkenyl-C(=O)OH,
  (z) —C$_{3-6}$cycloalkyl-C(=O)OH,
  (aa) —C$_{3-6}$cycloalkyl-C(=O)NHS(=O)$_2$R$^7$,
  (bb) —C$_{3-6}$cycloalkyl-S(=O)$_2$NHC(=O)R$^7$, (cc) —$C_{3-6}$cycloalkyl-C(=O)—N($R^7$)($R^8$),
(dd) —$C_{3-6}$cycloalkyl-N($R^7$)C(=O)($R^8$),
(ee) —$C_{3-6}$cycloalkyl-N($R^7$)S(=O)$_2$($R^8$),
(ff) —$C_{3-6}$cycloalkyl-S(=O)$_2$N($R^7$)($R^8$),
(gg) —$C_{3-6}$cycloalkyl-N($R^7$)C(=O)O($R^8$),
(hh) —$C_{3-6}$cycloalkyl-O—C(=O)N($R^7$)($R^8$),
(ii) —$C_{3-6}$cycloalkyl-C(=O)($R^7$),
(jj) —$C_{3-6}$cycloalkyl-C($R^7$)($R^8$)OH,
(kk) —$C_{3-6}$cycloalkyl-O—($R^7$),
(ll) —C(=O)OH,
(mm) aryl,
(nn) heteroaryl,
(oo) —C(=O)N$R^7$S(=O)$_2$($R^8$),
(pp) —S(=O)$_2$N($R^7$)C(=O)($R^8$),
(qq) —$C_{1-4}$alkyl-$R^7$,
(rr) —$C_{3-6}$cycloalkyl-$R^7$
(ss) —N($R^7$)S(=O)$_2$N($R^8$)$_2$,
(tt) —N($R^7$)—C(=O)N($R^7$)—S(=O)$_2$($R^8$),
(uu) —N($R^7$)C(=O)NH($R^8$), and
(vv) heterocycle,
wherein the alkyl portion of choices (m), (n), (o), (p), (q), (r), (s); (t), (u), (v), (w), (x) and (qq), the alkenyl portion of choice (y), and the cycloalkyl portion of choices (z), (aa), (bb), (cc), (dd), (ee), (ff), (gg), (hh), (ii), (jj), (kk) and (rr), are optionally mono- or di-substituted with halogen, —$C_{1-6}$alkyl, —$C_{3-6}$cycloalkyl, —$C_{1-6}$alkoxy, —$C_{3-6}$cycloalkoxy, aryl, —$C_{1-6}$ alkylaryl, hydroxyl or oxo, and
wherein the aryl of choice (mm), the heteroaryl of choice (nn), and the heterocycle of choice (vv) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$ alkyl, —S(=O)$_o$$C_{3-6}$cycloalkyl, hydroxyl and CN, or
wherein $R^3$ and $R^4$ are joined together to form a 5- or 6-membered heterocyclic ring, said ring having one heteroatom selected from Q and N, wherein said ring is optionally substituted with —C(=O)OH or —$C_{1-6}$ alkyl-C(=O)OH, with the proviso that at least one of $R^3$ and $R^4$ is other than hydrogen;
$R^5$ is selected from the group consisting of:
(a) hydrogen,
(b) —$C_{1-6}$alkyl,
(c) —$C_{1-4}$alkyl($R^7$),
(d) —$C_{1-4}$alkylCN,
(e) —$C_{1-4}$alkyl-O—($R^7$),
(f) -aryl,
(g) -heteroaryl,
(h) —$C_{3-6}$cycloalkyl,
(i) —$C_{3-6}$cycloalkylCN,
(j) —$C_{3-6}$cycloalkyl($R^7$),
(k) —$C_{3-6}$cycloalkyl-O—($R^7$), and
(l) —$C_{2-6}$alkenyl,
wherein the alkyl portion of choices (b), (c), (d), and (e), the alkenyl of choice (l), and the cycloalkyl portion of choices (h), (i), (j) and (k), is optionally substituted with halogen or $C_{1-4}$alkyl, and
wherein the aryl of choice (0 and the heteroaryl of choice (g), are optionally mono- or di-substituted with substituents selected from the group consisting of halogen, nitro, $C_{1-6}$alkyl, $CF_3$, $C_{1-6}$alkoxy, halo $C_{1-6}$alkyl, aryl, heteroaryl, $C_{3-6}$cycloalkyl, $C_{3-6}$cycloalkoxy, and CN;
$R^6$ is selected from the group consisting of:
(a) hydrogen,
(b) —$C_{1-6}$alkyl,
(c) —$C_{1-6}$alkylaryl,
(d) —$C_{1-6}$alkylheteroaryl,
(e) —S(=O)$_o$$C_{1-6}$alkyl($R^7$),
(f) —C(=O)$C_{1-6}$alkyl($R^7$),
(g) —$C_{3-6}$cycloalkyl,
(h) aryl,
(i) heteroaryl,
(j) —C(=O)$C_{3-6}$cycloalkyl($R^7$),
(k) —S(=O)$_o$$C_{3-6}$cycloalkyl($R^7$),
(l) —$C_{1-6}$alkyl($R^7$),
wherein the alkyl portion of choices (b), (c), (d), (e), (f), and (l), and the cycloalkyl portion of choices (g), (j), and (k), are optionally substituted with halogen or $C_{1-4}$alkyl, and
wherein the aryl of choices (c) and (h), and the heteroaryl of choices (d) and (i), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl, (heterocyclyl optionally substituted with hydroxyl) or halogen, and CN;
$R^7$ and $R^8$ are each independently selected from the following:
(a) hydrogen,
(b) $C_{1-6}$alkyl,
(c) $C_{3-6}$cycloalkyl,
(d) aryl,
(e) heteroaryl,
(f) —$C_{1-6}$alkylaryl,
(g) —$C_{1-6}$alkylheteroaryl,
(h) cyano,
(i) -aryl-aryl,
(j) -aryl-heteroaryl,
(k) —$NH_2$,
(l) —NH($C_1$-$C_3$alkyl), and
(m) —N($C_1$-$C_3$alkyl)$_2$,
wherein the alkyl portion of choices (b), (f), (g), (l) and (m), and the cycloalkyl portion of choice (c), are each optionally mono-, di- or tri-substituted with halogen, hydroxyl, $C_{1-6}$alkyl, $C_{1-6}$alkoxy, $C_{3-6}$cycloalkyl or $C_{3-6}$cycloalkoxy, and
wherein the aryl portion of choices (d), (f), (i) and (j), and the heteroaryl portion of choices (e), (g) and (j), are each optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$ cycloalkyl), —N($C_{1-3}$alkyl)$_2$, —N($C_{3-6}$cycloalkyl)$_2$, —S(=O)$_o$$C_{1-4}$alkyl, —S(=O)$_o$$C_{3-6}$cycloalkyl, —C(=O)$C_{1-4}$alkyl, aryl, heteroaryl, —O-heteroaryl-$CF_3$, hydroxyl, CN, and —(C=O)OH;
$R^9$, $R^{10}$ and $R^{11}$ are each independently selected from the group consisting of:
(a) hydrogen,
(b) —$C_{1-6}$alkyl,
(c) —$C_{3-6}$cycloalkyl,
(d) halogen, and
(e) O—($R^7$),
wherein the alkyl of choice (b) and the cycloalkyl of choice (c), are each optionally mono-, di- or tri-substituted with halogen; and
o is 0, 1, or 2.

2. The compound according to claim 1, or a pharmaceutically acceptable salt thereof, wherein:
X is —$CH_2CH_2CH_2$—.

3. The compound according to claim 1, or a pharmaceutically acceptable salt thereof, wherein:
A1 is a substituted phenyl or substituted pyridine.

4. The compound according to claim 1, or a pharmaceutically acceptable salt thereof, wherein:
A2 is A2a.

5. The compound according to claim 4, or a pharmaceutically acceptable salt thereof, wherein:
A2a is a substituted phenyl or substituted pyridine.

6. The compound according to claim 1, or a pharmaceutically acceptable salt thereof, wherein:
$R^1$ and $R^2$ are each independently selected from the group consisting of:
  (a) hydrogen,
  (b) halogen,
  (c) CN,
  (d) $CF_3$,
  (e) $C_{1-6}$alkyl,
  (f) —O—$(R^7)$, and
  (g) —N$(R^7)(R^8)$,
wherein the alkyl portion of choice (e), is optionally substituted with halogen.

7. The compound according to claim 6, or a pharmaceutically acceptable salt thereof, wherein:
$R^1$ and $R^2$ are each hydrogen.

8. A compound according to claim 1, or a pharmaceutically acceptable salt thereof, wherein:
$R^3$ is selected from the group consisting of:
  (a) —O—$(R^7)$,
  (b) —N$(R^7)$—C(=O)—O—$(R^8)$,
  (c) —N$(R^7)$S(=O)$_2(R^8)$,
  (d) —C(=O)$(R^7)$,
  (e) aryl,
  (f) heteroaryl,
  (g) —OC(=O)N$(R^7)(R^8)$,
  (h) —C$(R^7)(R^8)$OH, and
  (i) hydrogen,
wherein the aryl of choice (e) and the heteroaryl of choice (f) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$ cycloalkyl), —N($C_{1-6}$alkyl)$_2$, —N($C_{3-6}$cycloalkyl)$_2$, —S(=O)$_o C_{1-6}$alkyl, —S(=O)$_o C_{3-6}$cycloalkyl and CN.

9. The compound according to claim 7, or a Pharmaceutically acceptable salt thereof, wherein:
$R^3$ is selected from the group consisting of:
  (a) hydrogen,
  (b) —O—$(R^7)$, and
  (c) —N$(R^7)$S(=O)$_2(R^8)$.

10. The compound according to claim 1, or a pharmaceutically acceptable salt thereof, wherein:
$R^4$ is selected from the group consisting of:
  (a) hydrogen,
  (b) —N$(R^7)(R^8)$,
  (c) —N$(R^7)$S(=O)$_2 R^8$,
  (d) —S(=O)$_2$N$(R^7)(R^8)$,
  (e) —C(=O)N$(R^7)(R^8)$,
  (f) —$C_{1-4}$alkyl-C(=O)NHS(=O)$_2 R^7$,
  (g) —$C_{1-4}$alkyl-S(=O)$_2$NHC(=O)$R^7$,
  (h) —$C_{1-4}$alkyl-C(=O)—N$(R^7)(R^8)$,
  (i) —$C_{1-4}$alkyl-N$(R^7)$S(=O)$_2(R^8)$,
  (j) —$C_{1-4}$alkyl-S(=O)$_2$N$(R^7)(R^8)$,
  (k) —$C_{1-4}$alkyl-C(=O)OH,
  (l) —$C_{3-6}$cycloalkyl-C(=O)OH,
  (m) —$C_{3-6}$cycloalkyl-C(=O)NHS(=O)$_2 R^7$,
  (n) —$C_{3-6}$cycloalkyl-S(=O)$_2$NHC(=O)$R^7$,
  (o) —$C_{3-6}$cycloalkyl-C(=O)—N$(R^7)(R^8)$,
  (p) —$C_{3-6}$cycloalkyl-N$(R^7)$C(=O)$(R^8)$,
  (q) —$C_{3-6}$cycloalkyl-N$(R^7)$S(=O)$_2(R^8)$,
  (r) —$C_{3-6}$cycloalkyl-S(=O)$_2$N$(R^7)(R^8)$,
  (s) —C(=O)OH,
  (t) —C(=O)N$R^7$S(=O)$_2(R^8)$,
  (u) —$C_{1-4}$alkyl-N$(R^7)$—C(=O)$R^8$, and
  (v) —S(=O)$_2$N$(R^7)$C(=O)$R^8$,
wherein the alkyl portion of choices (f), (g), (h), (i), (j), (k) and (u), and the cycloalkyl portion of choices (l), (m), (n), (o), (p), (q) and (r), are optionally mono- or di-substituted with halogen, $C_{1-6}$alkyl, $C_{3-6}$cycloalkyl, $C_{1-6}$alkoxy, or $C_{3-6}$cycloalkoxy.

11. The compound according to claim 1, or a pharmaceutically acceptable salt thereof, wherein:
$R^5$ is $C_{1-6}$alkyl, optionally substituted with halogen or $C_{1-4}$alkyl.

12. The compound according to claim 1, or a pharmaceutically acceptable salt thereof, wherein:
$R^6$ is selected from the group consisting of:
  (a) —$C_{1-6}$alkylaryl,
  (b) —$C_{1-6}$alkylheteroaryl, and
  (c) —$C_{3-6}$cycloalkyl,
wherein the alkyl portion of choices (a) and (b), and the cycloalkyl portion of choice (c), are optionally substituted with halogen or $C_{1-4}$alkyl, and the aryl portion of choice (a) and the heteroaryl portion of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o C_{1-6}$alkyl, —S(=O)$_o C_{3-6}$cycloalkyl and CN.

13. The compound according to claim 1, or a pharmaceutically acceptable salt thereof, wherein:
$R^7$ is selected from hydrogen and $C_{1-4}$alkyl optionally substituted with halo;
$R^8$ is selected from hydrogen, $C_{1-4}$alkyl optionally substituted with halo, and aryl optionally mono or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), NH($C_{3-6}$cycloalkyl), —N($C_{1-3}$alkyl)$_2$, —N($C_{3-6}$cycloalkyl)$_2$, —S(=O)$_o C_{1-4}$alkyl, S(=O)$_o C_{3-6}$cycloalkyl, aryl, heteroaryl, hydroxyl and CN.

14. The compound according to claim 1, or a pharmaceutically acceptable salt thereof, wherein:
$R^9$ and $R^{10}$ are each independently hydrogen or F.

15. The compound according to claim 1, or a pharmaceutically acceptable salt thereof, wherein:
X is —$(CH_2)_3$;
A1 is a substituted phenyl or pyridine;
A2 is A2a;
$R^1$ and $R^2$ are each independently selected from the group consisting of:
  (a) hydrogen,
  (b) halogen,
  (c) CN,
  (d) $CF_3$,
  (e) —$C_{1-6}$alkyl,
  (f) —O—$(R^7)$, and
  (g) —N$(R^7)(R^8)$,
wherein the alkyl portion of choice (e) is optionally substituted with halogen;

$R^3$ is selected from the group consisting of:
(a) —O—($R^7$),
(b) —N($R^7$)—C(=O)—O—($R^8$),
(c) —N($R^7$)S(=O)$_2$($R^8$),
(d) —C(=O)($R^7$),
(e) aryl,
(f) heteroaryl,
(g) —OC(=O)N($R^7$)($R^8$),
(h) —C($R^7$)($R^8$)OH, and
(i) hydrogen,
wherein aryl of choice (e) and heteroaryl of choice (f) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN;

$R^4$ is selected from the group consisting of:
(a) hydrogen,
(b) —N($R^7$)($R^8$),
(c) —N($R^7$)S(=O)$_2$$R^8$,
(d) —S(=O)$_2$N($R^7$)($R^8$),
(e) —C(=O)N($R^7$)($R^8$),
(f) —$C_{1-4}$alkyl-C(=O)NHS(=O)$_2$$R^7$,
(g) —$C_{1-4}$alkyl-S(=O)$_2$NHC(=O)$R^7$,
(h) —$C_{1-4}$alkyl-C(=O)—N($R^7$)($R^8$),
(i) —$C_{1-4}$alkyl-N($R^7$)S(=O)$_2$($R^8$),
(j) —$C_{1-4}$alkyl-S(=O)$_2$N($R^7$)($R^8$),
(k) —$C_{1-6}$alkyl-C(=O)OH,
(l) —$C_{3-6}$cycloalkyl-C(=O)OH,
(m) —$C_{3-6}$cycloalkyl-C(=O)NHS(=O)$_2$$R^7$,
(n) —$C_{3-6}$cycloalkyl-S(=O)$_2$NHC(=O)$R^7$,
(o) —$C_{3-6}$cycloalkyl-C(=O)—N($R^7$)($R^8$),
(p) —$C_{3-6}$cycloalkyl-N($R^7$)C(=O)($R^8$)
(q) —$C_{3-6}$cycloalkyl-N($R^7$)S(=O)$_2$($R^8$),
(r) —$C_{3-6}$cycloalkyl-S(=O)$_2$N($R^7$)($R^8$),
(s) —C(=O)OH,
(t) —C(=O)N$R^7$S(=O)$_2$($R^8$),
(u) —$C_{1-4}$alkyl-N($R^7$)—C(=O)$R^8$, and
(v) —S(=O)$_2$N($R^7$)C(=O)$R^8$,
wherein the alkyl portion of choices (f), (g), (h), (i), (j), (k) and (u), and the cycloalkyl portion of choices (l), (m), (n), (o), (p), (q) and (r), are optionally mono- or di-substituted with halogen, $C_{1-6}$alkyl, $C_{3-6}$cycloalkyl, $C_{1-6}$alkoxy, or $C_{3-6}$cycloalkoxy;

$R^5$ is $C_{1-6}$alkyl, optionally substituted with halogen or $C_{1-4}$alkyl;

$R^6$ is selected from the group consisting of:
(a) —$C_{1-6}$alkylaryl,
(b) —$C_{1-6}$alkylheteroaryl, and
(c) —$C_{3-6}$cycloalkyl,
wherein the alkyl portion of choices (a) and (b), and the cycloalkyl portion of choice (c), are optionally substituted with halogen or $C_{1-4}$alkyl, and the aryl portion of choice (a) and the heteroaryl portion of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN;

$R^7$ is selected from the group consisting of hydrogen and $C_{1-4}$alkyl optionally substituted with halogen;

$R^8$ is selected from the group consisting of hydrogen, $C_{1-4}$alkyl optionally substituted with halogen, and aryl optionally mono- or di-substituted with substituents selected from halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o$$C_{1-4}$alkyl, —S(=O)$_o$$C_{3-6}$cycloalkyl, aryl, heteroaryl, hydroxyl and CN; and $R^9$ and $R^{10}$ are each independently hydrogen or F.

16. The compound according to claim 15, or a pharmaceutically acceptable salt thereof, wherein:

A1 is a substituted phenyl or substituted pyridine;

A2 is A2a, and A2a is a substituted phenyl or substituted pyridine;

$R^1$ and $R^2$ are each hydrogen;

$R^3$ is selected from the group consisting of:
(a) hydrogen,
(b) —O—($R^7$), and
(c) —N($R^7$)S(=O)$_2$($R^8$);

$R^4$ is selected from the group consisting of:
(a) hydrogen,
(b) —N($R^7$)S(=O)$_2$$R^8$,
(c) —$C_{1-6}$alkyl-C(=O)OH,
(d) —$C_{3-6}$cycloalkyl-C(=O)OH,
(e) —C(=O)OH,
(f) —C(=O)N($R^7$)S(=O)$_2$($R^8$), and
(g) —S(=O)$_2$N($R^7$)C(=O)$R^8$,
wherein the alkyl portion of choice (c) and the cycloalkyl portion of choices (d), are optionally mono- or di-substituted with halogen, $C_{1-6}$alkyl, $C_{3-6}$cycloalkyl, $C_{1-6}$alkoxy, or $C_{3-6}$cycloalkoxy;

$R^5$ is $C_{1-6}$alkyl, optionally substituted with halogen or $C_{1-4}$alkyl;

$R^6$ is selected from the group consisting of:
(a) —$C_{1-6}$alkylaryl, and
(b) —$C_{1-6}$alkylheteroaryl,
wherein the alkyl portion of choices (a) and (b), are optionally substituted with halogen or $C_{1-4}$alkyl, and the aryl portion of choice (a) and the heteroaryl portion of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$ alkyl, —S(=O)$_o$$C_{3-6}$cycloalkyl and CN;

$R^7$ is selected from hydrogen and $C_{1-4}$alkyl optionally substituted with halogen;

$R^8$ is selected from hydrogen, $C_{1-4}$alkyl optionally substituted with halogen, and aryl optionally mono- or di-substituted with substituents selected from halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH ($C_{3-6}$ cycloalkyl), —N($C_{1-3}$alkyl)$_2$, —N($C_{3-6}$cycloalkyl)$_2$, —S(=O)$_o$$C_{1-4}$alkyl, —S(=O)$_o$$C_{3-6}$ cycloalkyl, aryl, heteroaryl, hydroxyl and CN; and $R^9$ and $R^{10}$ are each independently hydrogen or F.

17. The compound according to claim 1, wherein the compound has a structure selected from the group consisting of Formula 1a, Formula 1b, or Formula 1c:

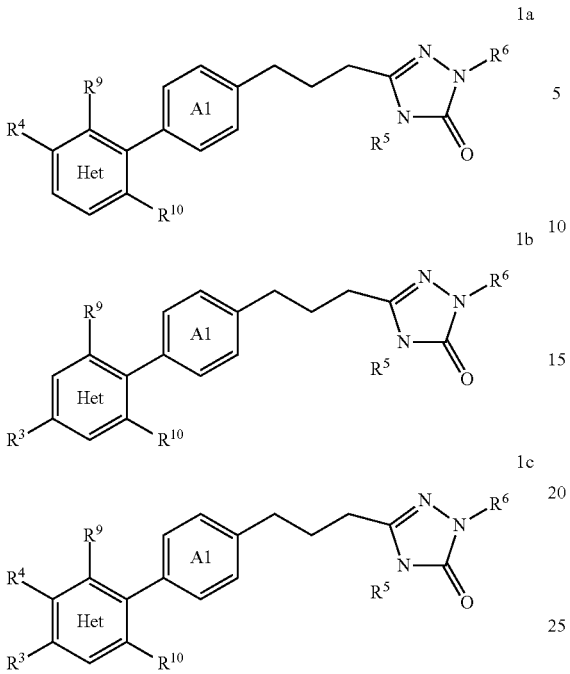

or a pharmaceutically acceptable salt thereof.

18. The compound according to claim 17, or a pharmaceutically acceptable salt thereof, wherein:

A1 is a phenyl or pyridine;
Het is A2a, where A2a is substituted phenyl, or substituted pyridine;
$R^3$ is selected from the group consisting of:
  (a) —O—($R^7$),
  (b) —N($R^7$)—C(=O)—O—($R^8$),
  (c) —N($R^7$)S(=O)$_2$($R^8$),
  (d) —C(=O)($R^7$),
  (e) aryl,
  (f) heteroaryl,
  (g) —OC(=O)N($R^7$)($R^8$),
  (h) —C($R^7$)($R^8$)OH, and
  (i) hydrogen,
wherein aryl of choice (e) and heteroaryl of choice (f) are optionally mono- or di-substituted with substituents selected from the group consisting of halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN;
$R^4$ is selected from the group consisting of:
  (a) hydrogen,
  (b) —N($R^7$)($R^8$),
  (c) N($R^7$)S(=O)$_2$$R^8$,
  (d) —S(=O)$_2$N($R^7$)($R^8$),
  (e) —C(=O)N($R^7$)($R^8$),
  (f) —$C_{1-4}$alkyl-C(=O)NHS(=O)$_2$$R^7$,
  (g) —$C_{1-4}$alkyl-S(=O)$_2$NHC(=O)$R^7$,
  (h) —$C_{1-4}$alkyl-C(=O)—N($R^7$)($R^8$),
  (i) —$C_{1-4}$alkyl-N($R^7$)—C(=O)$R^8$,
  (j) —$C_{1-4}$alkyl-N($R^7$)S(=O)$_2$($R^8$),
  (k) —$C_{1-4}$alkyl-S(=O)$_2$N($R^7$)($R^8$),
  (l) —$C_{1-6}$alkyl-C(=O)OH,
  (m) —$C_{3-6}$cycloalkyl-C(=O)OH,
  (n) —$C_{3-6}$cycloalkyl-C(=O)NHS(=O)$_2$$R^7$,
  (o) —$C_{3-6}$cycloalkyl-S(=O)$_2$NHC(=O)$R^7$,
  (p) —$C_{3-6}$cycloalkyl-C(=O)—N($R^7$)($R^8$),
  (q) —$C_{3-6}$cycloalkyl-N($R^7$)C(=O)($R^8$),
  (r) —$C_{3-6}$cycloalkyl-N($R^7$)S(=O)$_2$($R^8$),
  (s) —$C_{3-6}$cycloalkyl-S(=O)$_2$N($R^7$)($R^8$),
  (t) —C(=O)OH,
  (u) —C(=O)N($R^7$)S(=O)$_2$($R^8$), and
  (v) —S(=O)$_2$N($R^7$)C(=O)$R^8$,
wherein the alkyl portion of choices (f), (g), (h), (i), (j), (k) and (l), and the cycloalkyl portion of choices (m), (n), (o), (p), (q), (r) and (s), are optionally mono- or di-substituted with halogen, $C_{1-6}$alkyl, $C_{3-6}$cycloalkyl, $C_{1-6}$alkoxy, or $C_{3-6}$cycloalkoxy;
$R_5$ is $C_{1-6}$alkyl, optionally substituted with halogen or $C_{1-4}$alkyl;
$R_6$ is selected from the group consisting of:
  (a) —$C_{1-6}$alkylaryl,
  (b) —$C_{1-6}$alkylheteroaryl, and
  (c) —$C_{3-6}$cycloalkyl,
wherein the alkyl portion of choices (a) and (b), and the cycloalkyl portion of choice (c), are optionally substituted with halogen or $C_{1-4}$alkyl, and the aryl portion of choice (a) and the heteroaryl portion of choice (b), are optionally mono- or di-substituted with substituents selected from the group consisting of halogen, nitro, —CF$_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$$C_{1-6}$alkyl, —S(=O)$_o$$C_{3-6}$cycloalkyl and CN;
$R^7$ is selected from hydrogen and $C_{1-4}$alkyl optionally substituted with halogen;
$R^8$ is selected from hydrogen, $C_{1-4}$alkyl optionally substituted with halogen, and aryl optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{3-6}$cycloalkyl), —N($C_{1-3}$alkyl)$_2$, —N($C_{3-6}$cycloalkyl)$_2$, —S(=O)$_o$$C_{1-4}$alkyl, —S(=O)$_o$$C_{3-6}$cycloalkyl, aryl, heteroaryl, hydroxyl and CN;
and
$R^9$ and $R^{10}$ are each independently hydrogen or F.

19. The compound according to claim 18, or a pharmaceutically acceptable salt thereof, wherein:
A1 is a phenyl or pyridine;
Het is A2a, and A2a is a substituted phenyl, substituted pyridine;
$R^3$ is selected from the group consisting of:
  (a) hydrogen,
  (b) —O—($R^7$), and
  (c) —N($R^7$)S(=O)$_2$($R^8$);
$R^4$ is selected from the group consisting of
  (a) hydrogen,
  (b) N($R^7$)S(=O)$_2$$R^8$,
  (c) —$C_{1-6}$alkyl-C(=O)OH,
  (d) —$C_{3-6}$cycloalkyl-C(=O)OH,
  (e) —C(=O)OH,
  (f) —C(=O)N($R^7$)S(=O)$_2$($R^8$), and
  (g) —S(=O)$_2$N($R^7$)C(=O)$R^8$,
wherein the alkyl portion of choice (c) and the cycloalkyl portion of choice (d), are optionally mono- or di-substituted with halogen, $C_{1-6}$alkyl, $C_{3-6}$cycloalkyl, $C_{1-6}$alkoxy, or $C_{3-6}$cycloalkoxy,
$R^5$ is $C_{1-6}$alkyl, optionally substituted with halogen or $C_{1-4}$alkyl;

$R^6$ is selected from the group consisting of:
(a) —$C_{1-6}$alkylaryl, and
(b) —$C_{1-6}$alkylheteroaryl,
wherein the alkyl portion of choices (a) and (b) are optionally substituted with halogen or $C_{1-4}$alkyl, and the aryl portion of choice (a) and the heteroaryl portion of choice (b), are optionally mono- or di-substituted with substituents selected from the group consisting of halogen, nitro, $CF_3$, $C_{1-6}$alkyl, $C_{1-6}$alkoxy, halo $C_{1-6}$alkyl, $C_{3-6}$cycloalkyl, $C_{3-6}$cycloalkoxy, aryl, heteroaryl, —NH($C_{1-6}$alkyl), —NH($C_{3-6}$cycloalkyl), —N($C_{1-6}$alkyl)$_2$, —N($C_{3-6}$cycloalkyl)$_2$, —S(=O)$_o$ $C_{1-6}$ alkyl, —S(=O)$_o$$C_{3-6}$cycloalkyl and CN;
$R^7$ is selected from hydrogen and $C_{1-4}$alkyl optionally substituted with halogen;
$R^8$ is selected from hydrogen, $C_{1-4}$alkyl optionally substituted with halogen, and aryl optionally mono- or di-substituted with substituents selected from the group consisting of halogen, nitro, $C_{1-6}$alkyl, $C_{1-6}$alkoxy, halo$C_{1-6}$alkyl, $C_{3-6}$cycloalkyl, $C_{3-6}$cycloalkoxy, —NH($C_{1-3}$alkyl), —NH($C_{3-6}$cycloalkyl), —N($C_{1-3}$alkyl)$_2$, —N($C_{3-6}$cycloalkyl)$_2$, —S(=O)$_o$$C_{1-4}$alkyl, —S(=O)$_o$ $C_{3-6}$cycloalkyl, aryl, heteroaryl, hydroxyl and CN; and
$R^9$ and $R^{10}$ are each independently hydrogen or F.

20. The compound according to claim 1 selected from the group consisting of:
2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)acetic acid;
4'-(3-(1-(4-(tert-Butyl)benzyl)-4-ethyl-5-oxo-4,5-dihydro-1H-1,2,4-triazol-3-yl)propyl)-[1,1'-biphenyl]-3-carboxylic acid;
3-(3-(4-(6-Aminopyridin-2-yl)phenyl)propyl)-1-(4-(tert-butyl)benzyl)-4-ethyl-1H-1,2,4-triazol-5(4H)-one;
N-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)benzenesulfonamide;
3-(3-(4-(5-Aminopyridin-2-yl)phenyl)propyl)-1-(4-(tert-butyl)benzyl)-4-ethyl-1H-1,2,4-triazol-5(4H)-one;
3-(3-(3'-Amino-[1,1'-biphenyl]-4-yl)propyl)-1-(4-(tert-butyl)benzyl)-4-ethyl-1H-1,2,4-triazol-5(4H)-one;
N-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-4-methylbenzenesulfonamide;
2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-(phenylsulfonyl)acetamide;
4'-(3-(1-(4-(tert-Butyl)benzyl)-4-ethyl-5-oxo-4,5-dihydro-1H-1,2,4-triazol-3-yl)propyl)-N-(phenylsulfonyl)-[1,1'-biphenyl]-3-carboxamide;
N-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)benzenesulfonamide;
3-(3-(4-(4-Aminopyridin-2-yl)phenyl)propyl)-1-(4-(tert-butyl)benzyl)-4-ethyl-1H-1,2,4-triazol-5(4H)-one;
N-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)methanesulfonamide;
1-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)cyclopropanecarboxylic acid;
1-(4'-(3-(1-(4-(tert-butyl)benzyl)-4-ethyl-5-oxo-4,5-dihydro-1H-1,2,4-triazol-3-yl)propyl)-[1,1'-biphenyl]-3-yl)cyclopropanecarboxamide;
2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-2-methylpropanamide;
N-(2-(4-(3-(1-(4-(tert-Butyl)benzyl)-4-ethyl-5-oxo-4,5-dihydro-1H-1,2,4-triazol-3-yl)propyl)phenyl)pyridin-4-yl)benzenesulfonamide;
N-(6-(4-(3-(1-(4-(tert-Butyl)benzyl)-4-ethyl-5-oxo-4,5-dihydro-1H-1,2,4-triazol-3-yl)propyl)phenyl)pyridin-4-yl)methanesulfonamide;
2-(4'-(3-(1-(4-(tert-Butyl)benzyl)-4-ethyl-5-oxo-4,5-dihydro-1H-1,2,4-triazol-3-yl)propyl)-2-fluoro-[1,1'-biphenyl]-3-yl)acetic acid;
2-(4'-(3-(1-(4-(tert-Butyl)benzyl)-4-ethyl-5-oxo-4,5-dihydro-1H-1,2,4-triazol-3-yl)propyl)-6-fluoro-[1,1'-biphenyl]-3-yl)acetic acid;
2-(4'-(3-(1-(4-(tert-Butyl)benzyl)-4-ethyl-5-oxo-4,5-dihydro-1H-1,2,4-triazol-3-yl)propyl)-6-methoxy-[1,1'-biphenyl]-3-yl)acetic acid;
2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)acetic acid;
2-(4'-(3-(1-(4-Cyclopropylbenzyl)-4-ethyl-5-oxo-4,5-dihydro-1H-1,2,4-triazol-3-yl)propyl)-[1,1'-biphenyl]-3-yl)acetic acid;
2-(4'-(3-(1-Benzyl-4-ethyl-5-oxo-4,5-dihydro-1H-1,2,4-triazol-3-yl)propyl)-[1,1'-biphenyl]-3-yl)acetic acid;
2-(4'-(3-(4-Ethyl-5-oxo-1-(4-(trifluoromethyl)benzyl)-4,5-dihydro-1H-1,2,4-triazol-3-yl)propyl)-[1,1'-biphenyl]-3-yl)acetic acid;
tert-Butyl(2-(4-(3-(1-(4-(tert-butyl)benzyl)-4-ethyl-5-oxo-4,5-dihydro-1H-1,2,4-triazol-3-yl)propyl)phenyl)oxazol-4-yl)carbamate;
2-(4'-(3-(1-(4-Cyclohexylbenzyl)-4-ethyl-5-oxo-4,5-dihydro-1H-1,2,4-triazol-3-yl)propyl)-[1,1'-biphenyl]-3-yl)acetic acid;
2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-2,2-difluoroacetic acid;
3-(3-(3'-(1H-Tetrazol-5-yl)-[1,1'-biphenyl]-4-yl)propyl)-1-(4-(tert-butyl)benzyl)-4-ethyl-1H-1,2,4-triazol-5 (4H)-one;
2-(4'-(3-(1-(4-(tert-Butyl)benzyl)-4-isopropyl-5-oxo-4,5-dihydro-1H-1,2,4-triazol-3-yl)propyl)-[1,1'-biphenyl]-3-yl)acetic acid;
2-(4'-(3-(1-(4-(tert-Butyl)benzyl)-5-oxo-4-phenyl-4,5-dihydro-1H-1,2,4-triazol-3-yl)propyl)-[1,1'-biphenyl]-3-yl)acetic acid;
2-(4'-(3-(1-(4-(tert-Butyl)benzyl)-4-ethyl-5-oxo-4,5-dihydro-1H-1,2,4-triazol-3-yl)propyl)-4-fluoro-[1,1'-biphenyl]-3-yl)acetic acid;
3-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)acrylic-3-yl)acrylic acid;
2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)cyclopropanecarboxylic acid;
3-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)propanoic acid;
2-(4'-(3-(1-(4-Bromobenzyl)-4-ethyl-5-oxo-4,5-dihydro-1H-1,2,4-triazol-3-yl)propyl)-[1,1'-biphenyl]-3-yl)acetic acid;
2-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)acetic acid;

2-(4-(4-(3-(1-(4-(tert-Butyl)benzyl)-4-ethyl-5-oxo-4,5-dihydro-1H-1,2,4-triazol-3-yl)propyl)phenyl)thiophen-2-yl)acetic acid;

1-{[4-(tert-Butyl)phenyl]methyl}-4-ethyl-3-[3-(4-{4-[(methylsulfonyl)amino](2-pyridyl)}phenyl)propyl]-1,2,4-triazolin-5-one;

4'-(3-(1-(4-(tert-Butyl)benzyl)-4-ethyl-5-oxo-4,5-dihydro-1H-1,2,4-triazol-3-yl)propyl)-5-(trifluoromethyl)-[1,1'-biphenyl]-3-carboxylic acid;

1-{[4-(tert-Butyl)phenyl]methyl}-3-[3-(4-{6-[(cyclopropylsulfonyl)amino](2-pyridyl)}phenyl)propyl]-4-ethyl-1,2,4-triazolin-5-one;

2-(5-{4-[3-(1-{[4-(tert-Butyl)phenyl]methyl}-4-ethyl-5-oxo-1,2,4-triazolin-3-yl)propyl]phenyl}-2-pyridyl)acetic acid;

2-(3-{4-[3-(1-{[4-(tert-Butyl)phenyl]methyl}-4-ethyl-5-oxo-1,2,4-triazolin-3-yl)propyl]phenyl}phenyl)propanoic acid;

2-(2{4-[3-(1-{[4-(tert-Butyl)phenyl]methyl}-4-ethyl-5-oxo-1,2,4-triazolin-3-yl)propyl]phenyl}-4-pyridyl)acetic acid;

2-(3-{4-[3-(1-{[4-(tert-Butyl)phenyl]methyl}-4-ethyl-5-oxo-1,2,4-triazolin-3-yl)propyl]phenyl}phenyl)butanoic acid;

2-(3-{4-[3-(1-{[4-(tert-Butyl)phenyl]methyl}-4-ethyl-5-oxo(1,2,4-triazolin-3-yl))propyl]phenyl}phenyl)-3-phenylpropanoic acid;

2-(6-{4-[3-(1-{[4-(tert-Butyl)phenyl]methyl}-4-ethyl-5-oxo(1,2,4-triazolin-3-yl))propyl]phenyl}-4-(trifluoromethyl)-2-pyridyl)acetic acid;

2-(4'-(3-(1-(4-(tert-Butyl)benzyl)-4-ethyl-5-oxo-4,5-dihydro-1H-1,2,4-triazol-3-yl)propyl)-4-(cyclopropylmethoxy)-[1,1'-biphenyl]-3-yl)acetic acid;

2-(6-{4-[3-(1-{[4-(tert-Butyl)phenyl]methyl}-4-ethyl-5-oxo-1,2,4-triazolin-3-yl)propyl]phenyl}-2-pyridyl)acetic acid;

2-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)-N-cyclopropyl-2-hydroxyacetamide;

2-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)-N-cyclopropyl-2-oxoacetamide;

2-(4'-(3-(1-(4-(tert-Butyl)benzyl)-4-(cyclopropylmethyl)-5-oxo-4,5-dihydro-1H-1,2,4-triazol-3-yl)propyl)-[1,1'-biphenyl]-3-yl)acetic acid;

2-(4'-(3-(1-((5-(tert-Butyl)thiophen-2-yl)methyl)-4-ethyl-5-oxo-4,5-dihydro-1H-1,2,4-triazol-3-yl)propyl)-[1,1'-biphenyl]-3-yl)acetic acid;

2-(4'-(3-(1-(4-(tert-Butyl)benzyl)-5-oxo-4-(2,2,2-trifluoroethyl)-4,5-dihydro-1H-1,2,4-triazol-3-yl)propyl)-4-methoxy-[1,1'-biphenyl]-3-yl)acetic acid;

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-cyclopropyl-2-hydroxyacetamide;

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)-N-cyclopropyl-2-oxoacetamide;

3-{3-[4-(6-Amino-5-methoxy(2-pyridyl))phenyl]propyl}-1-{[4-(tert-butyl)phenyl]methyl}-4-ethyl-1,2,4-triazolin-5-one;

1-{[4-(tert-Butyl)phenyl]methyl}-4-ethyl-3-[3-(4-{5-methoxy-6-[(phenylsulfonyl)amino](2-pyridyl)}phenyl)propyl]-1,2,4-triazolin-5-one;

3-{3-[4-(6-Amino-5-ethoxy(2-pyridyl))phenyl]propyl}-1-{[4-(tert-butyl)phenyl]methyl}-4-ethyl-1,2,4-triazolin-5-one;

2-(5-{4-[3-(1-{[4-(tert-Butyl)phenyl]methyl}-4-ethyl-5-oxo(1,2,4-triazolin-3-yl))propyl]phenyl}-2-ethylthiophenyl)acetic acid;

1-{[4-(tert-Butyl)phenyl]methyl}-3-[3-(4-{5-ethoxy-6-[(phenylsulfonyl)amino](2-pyridyl)}phenyl)propyl]-4-ethyl-1,2,4-triazolin-5-one;

2-(4'-(3-(4-Ethyl-1-(4-(3-fluorooxetan-3-yl)benzyl)-5-oxo-4,5-dihydro-1H-1,2,4-triazol-3-yl)propyl)-[1,1'-biphenyl]-3-yl)acetic acid;

2-(5-{4-[3-(1-{[4-(tert-Butyl)phenyl]methyl}-4-ethyl-5-oxo(1,2,4-triazolin-3-yl))propyl]phenyl}-2-methylthiophenyl)acetic acid;

4'-(3-(1-(4-(tert-Butyl)benzyl)-4-ethyl-5-oxo-4,5-dihydro-1H-1,2,4-triazol-3-yl)propyl)-4-methoxyl-[1,1'-biphenyl]-3-carboxylic acid;

4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-carboxylic acid;

2-(4'-(3-(1-(3-Bromo-4-(tert-butyl)benzyl)-4-ethyl-5-oxo-4,5-dihydro-1H-1,2,4-triazol-3-yl)propyl)-[1,1'-biphenyl]-3-yl)acetic acid;

2-(4'-(3-(1-(4-(tert-Butyl)benzyl)-5-oxo-4-propyl-4,5-dihydro-1H-1,2,4-triazol-3-yl)propyl)-4-ethoxy-[1,1'-biphenyl]-3-yl)acetic acid;

2-(4'-(3-(4-Butyl-1-(4-(tert-butyl)benzyl)-5-oxo-4,5-dihydro-1H-1,2,4-triazol-3-yl)propyl)-4-ethoxy-[1,1'-biphenyl]-3-yl)acetic acid;

5-(4-(3-(1-(4-(tert-Butyl)benzyl)-4-ethyl-5-oxo-4,5-dihydro-1H-1,2,4-triazol-3-yl)propyl)phenyl)-1H-indole-3-carboxylic acid;

1-{[4-(tert-Butyl)phenyl]methyl}-4-ethyl-3-{3-[4-(5-{[(4-propylphenyl)sulfonyl]amino}(2-pyridyl))phenyl]propyl}-1,2,4-triazolin-5-one;

1-{[4-(tert-Butyl)phenyl]methyl}-4-ethyl-3-{3-[4-(6-{[(4-propylphenyl)sulfonyl]amino}(2-pyridyl))phenyl]propyl}-1,2,4-triazolin-5-one;

1-{[4-(tert-Butyl)phenyl]methyl}-4-ethyl-3-(3-{4-[6-({[4-(4-methylphenyl)phenyl]sulfonyl}amino)(2-pyridyl)]phenyl}propyl)-1,2,4-triazolin-5-one;

1-{[4-(tert-Butyl)phenyl]methyl}-4-ethyl-3-(3-{4-[6-({[4-(4-methoxyphenyl)phenyl]sulfonyl}amino)(2-pyridyl)]phenyl}propyl)-1,2,4-triazolin-5-one;

1-Acetyl-5-{[(6-{4-[3-(1-{[4-(tert-butyl)phenyl]methyl}-4-ethyl-5-oxo(1,2,4-triazolin-3-yl))propyl]phenyl}(3-pyridyl))amino]sulfonyl}indoline;

2-(4'-(3-(4-Allyl-1-(4-(tert-butyl)benzyl)-5-oxo-4,5-dihydro-1H-1,2,4-triazol-3-yl)propyl)-4-methoxy-[1,1'-biphenyl]-3-yl)acetic acid;

1-{[4-(tert-Butyl)phenyl]methyl}-4-ethyl-3-[3-(4-{5-[({4-[5-(trifluoromethyl)(2-pyridyloxy)]phenyl}sulfonyl)amino](2-pyridyl)}phenyl)propyl]-1,2,4-triazolin-5-one;

1-{[4-(tert-Butyl)phenyl]methyl}-4-ethyl-3-{3-[4-(6-{[benzylsulfonyl]amino}(2-pyridyl))phenyl]propyl}-1,2,4-triazolin-5-one;

1-{[4-(tert-Butyl)phenyl]methyl}-4-ethyl-3-{3-[4-(5-{[benzylsulfonyl]amino}(2-pyridyl))phenyl]propyl}-1,2,4-triazolin-5-one;

2-(4'-(3-(1-(4-(tert-Butyl)benzyl)-5-oxo-4-propyl-4,5-dihydro-1H-1,2,4-triazol-3-yl)propyl)-4-methoxy-[1,1'-biphenyl]-3-yl)acetic acid;

N-(2-(4-(3-(1-(4-(tert-Butyl)benzyl)-4-ethyl-5-oxo-4,5-dihydro-1H-1,2,4-triazol-3-yl)propyl)phenyl)pyrimidin-4-yl)benzenesulfonamide;

1-{[4-(tert-Butyl)phenyl]methyl}-4-ethyl-3-(3-{4-[6-({[4-(trifluoromethyl)phenyl]sulfonyl}amino)(2-pyridyl)]phenyl}propyl)-1,2,4-triazolin-5-one;

1-{[4-(tert-Butyl)phenyl]methyl}-3-{3-[4-(6-{[(4-chlorophenyl)sulfonyl]amino}(2-pyridyl))phenyl]propyl}-4-ethyl-1,2,4-triazolin-5-one;

1-{[4-(tert-Butyl)phenyl]methyl}-4-ethyl-3-{3-[4-(6-{[(4-methoxyphenyl)sulfonyl]amino}(2-pyridyl))phenyl]propyl}-1,2,4-triazolin-5-one;

2-(4'-(3-(1-(3-Cyclopropyl-4-(tert-butyl)benzyl)-4-ethyl-5-oxo-4,5-dihydro-1H-1,2,4-triazol-3-yl)propyl)-[1,1'-biphenyl]-3-yl)acetic acid;

1-{[4-(tert-Butyl)phenyl]methyl}-4-ethyl-3-(3-{4-[5-({[4-(trifluoromethyl)phenyl]sulfonyl}amino)(2-pyridyl)]phenyl}propyl)-1,2,4-triazolin-5-one;

1-{[4-(tert-Butyl)phenyl]methyl}-4-ethyl-3-{3-[4-(5-methoxy-6-{[benzylsulfonyl]amino}(2-pyridyl))phenyl]propyl}-1,2,4-triazolin-5-one;

1-{[4-(tert-Butyl)phenyl]methyl}-4-ethyl-3-(3-{4-[5-methoxy-6-({[4-(trifluoromethyl)phenyl]sulfonyl}amino)(2-pyridyl)]phenyl}propyl)-1,2,4-triazolin-5-one;

5-(4-(3-(1-(4-(tert-Butyl)benzyl)-4-ethyl-5-oxo-4,5-dihydro-1H-1,2,4-triazol-3-yl)propyl)phenyl)benzofuran-3-carboxylic acid;

1-{[4-(tert-Butyl)phenyl]methyl}-3-{3-[4-(5-{[(4-chlorophenyl)sulfonyl]amino}(2-pyridyl))phenyl]propyl}-4-ethyl-1,2,4-triazolin-5-one;

1-{[4-(tert-Butyl)phenyl]methyl}-4-ethyl-3-{3-[4-(5-{[(4-methoxyphenyl)sulfonyl]amino}(2-pyridyl))phenyl]propyl}-1,2,4-triazolin-5-one;

1-{[4-(tert-Butyl)phenyl]methyl}-3-{3-[4-(6-{[(4-chlorophenyl)sulfonyl]amino}-5-methoxy(2-pyridyl))phenyl]propyl}-4-ethyl-1,2,4-triazolin-5-one;

1-{[4-(tert-Butyl)phenyl]methyl}-4-ethyl-3-{3-[4-(5-methoxy-6-{[(4-methoxyphenyl)sulfonyl]amino}(2-pyridyl))phenyl]propyl}-1,2,4-triazolin-5-one;

2-(4'-(3-(1-(4-(tert-Butyl)benzyl)-4-ethyl-5-oxo-4,5-dihydro-1H-1,2,4-triazol-3-yl)propyl)-4-propoxy-[1,1'-biphenyl]-3-yl)acetic acid;

2-(4'-(3-(1-(4-(tert-Butyl)benzyl)-4-methyl-5-oxo-4,5-dihydro-1H-1,2,4-triazol-3-yl)propyl)-4-ethoxy-[1,1'-biphenyl]-3-yl)acetic acid;

(rac)-5-(4-(3-(1-(4-(tert-Butyl)benzyl)-4-ethyl-5-oxo-4,5-dihydro-1H-1,2,4-triazol-3-yl)propyl)phenyl)-2,3-dihydrobenzofuran-3-carboxylic acid;

N-(6-{4-[3-(1-{[4-(tert-Butyl)phenyl]methyl}-4-ethyl-5-oxo(1,2,4-triazolin-3-yl))propyl]phenyl}(2-pyridyl))benzamide;

1-{[4-(tert-Butyl)phenyl]methyl}-4-ethyl-3-[3-(4-{6-methoxy-5-[(phenylsulfonyl)amino](2-pyridyl)}phenyl)propyl]-1,2,4-triazolin-5-one;

N-benzyl-4'-(3-(1-(4-(tert-butyl)benzyl)-4-ethyl-5-oxo-4,5-dihydro-1H-1,2,4-triazol-3-yl)propyl)-[1,1'-biphenyl]-4-sulfonamide;

N-(6-{4-[3-(1-{[4-(tert-Butyl)phenyl]methyl}-4-ethyl-5-oxo-1,2,4-triazolin-3-yl)propyl]phenyl}-2-pyridyl)butanamide;

N-(6-{4-[3-(1-{[4-(tert-Butyl)phenyl]methyl}-4-ethyl-5-oxo(1,2,4-triazolin-3-yl))propyl]phenyl}(2-pyridyl))-2-phenylacetamide;

N-(6-{4-[3-(1-{[4-(tert-Butyl)phenyl]methyl}-4-ethyl-5-oxo(1,2,4-triazolin-3-yl))propyl]phenyl}(2-pyridyl))cyclopropylcarboxamide;

N-((4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)sulfonyl)propionamide;

N-Benzyl-1-(4'-(3-(1-(4-(tert-butyl)benzyl)-4-ethyl-5-oxo-4,5-dihydro-1H-1,2,4-triazol-3-yl)propyl)-[1,1'-biphenyl]-4-yl)methanesulfonamide;

N-Benzyl-1-(1-(4-(tert-butyl)benzyl)-4-ethyl-5-oxo-4,5-dihydro-1H-1,2,4-triazol-3-yl)propyl)-[1,1'-biphenyl]-3-yl)methanesulfonamide;

2-(4'-(3-(1-(4-(tert-Butyl)benzyl)-4-methyl-5-oxo-4,5-dihydro-1H-1,2,4-triazol-3-yl)propyl)-4-methoxy-[1,1'-biphenyl]-3-yl)acetic acid;

3-{3-[4-(3-{[(Dimethylamino)sulfonyl]amino}phenyl)phenyl]propyl}-1-{[4-(tert-butyl)phenyl]methyl}-4-ethyl-1,2,4-triazolin-5-one;

N-(2-(4-(3-(1-(4-(tert-Butyl)benzyl)-4-ethyl-5-oxo-4,5-dihydro-1H-1,2,4-triazol-3-yl)propyl)phenyl)pyrimidin-5-yl)benzenesulfonamide;

3-(3-(4-(5-Aminopyridin-3-yl)phenyl)propyl)-1-(4-(tert-butyl)benzyl)-4-ethyl-1H-1,2,4-triazol-5(4H)-one;

1-{[4-(tert-Butyl)phenyl]methyl}-4-ethyl-3-[3-(4-{5-methoxy-6-[N-methyl(phenylsulfonyl)amino](2-pyridyl)}phenyl)propyl]-1,2,4-triazolin-5-one;

3-{3-[4-(5-Amino-4-methoxy(2-pyridyl))phenyl]propyl}-1-{[4-(tert-butyl)phenyl]methyl}-4-ethyl-1,2,4-triazolin-5-one;

1-{[4-(tert-Butyl)phenyl]methyl}-4-ethyl-3-[3-(4-{4-methoxy-5-[(phenylsulfonyl)amino](2-pyridyl)}phenyl)propyl]-1,2,4-triazolin-5-one;

1-{[4-(tert-Butyl)phenyl]methyl}-3-{3-[4-(6-{[(6-chloro(3-pyridyl))sulfonyl]amino}-5-methoxy(2-pyridyl))phenyl]propyl}-4-ethyl-1,2,4-triazolin-5-one;

1-{[4-(tert-Butyl)phenyl]methyl}-4-ethyl-3-{3-[4-(5-methoxy-6-{[(6-methoxy(3-pyridyl))sulfonyl]amino}(2-pyridyl))phenyl]propyl}-1,2,4-triazolin-5-one;

2-(4'-(3-(1-(3-Methyl-4-(tert-butyl)benzyl)-4-ethyl-5-oxo-4,5-dihydro-1H-1,2,4-triazol-3-yl)propyl)-[1,1'-biphenyl]-3-yl)acetic acid;

N-(((4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)methyl)sulfonyl)propionamide;

N-(5-(4-(3-(1-(4-(tert-Butyl)benzyl)-4-ethyl-5-oxo-4,5-dihydro-1H-1,2,4-triazol-3-yl)propyl)phenyl)pyridin-3-yl)benzenesulfonamide;

N-(5-(4-(3-(1-(4-(tert-Butyl)benzyl)-4-ethyl-5-oxo-4,5-dihydro-1H-1,2,4-triazol-3-yl)propyl)phenyl)pyrazin-2-yl)benzenesulfonamide;

N-(5-(4-(3-(1-(4-(tert-Butyl)benzyl)-4-ethyl-5-oxo-4,5-dihydro-1H-1,2,4-triazol-3-yl)propyl)phenyl)pyrazin-2-yl)-1-phenylmethanesulfonamide;

1-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)cyclopropanecarbonitrile;

4'-(3-(1-(4-(tert-Butyl)benzyl)-4-ethyl-5-oxo-4,5-dihydro-1H-1,2,4-triazol-3-yl)propyl)-4-(difluoromethoxy)-[1,1'-biphenyl]-3-carboxylic acid;

1-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)cyclopropanecarboxylic acid;

4'-(3-(1-(4-(tert-Butyl)benzyl)-4-ethyl-5-oxo-4,5-dihydro-1H-1,2,4-triazol-3-yl)propyl)-4-methoxy-N-(pyridin-2-yl)-[1,1'-biphenyl]-3-sulfonamide;

1-{[4-(tert-Butyl)phenyl]methyl}-4-ethyl-3-[3-(4-{6-methyl-5-[(phenylsulfonyl)amino](2-pyridyl)}phenyl)propyl]-1,2,4-triazolin-5-one;

1-{[4-(tert-Butyl)phenyl]methyl}-4-ethyl-3-{3-[4-(6-methyl-5-{[benzylsulfonyl]amino}(2-pyridyl))phenyl]propyl}-1,2,4-triazolin-5-one;

1-{[4-(tert-Butyl)phenyl]methyl}-4-ethyl-3-[3-(4-{4-methyl-5-[(phenylsulfonyl)amino](2-pyridyl)}phenyl)propyl]-1,2,4-triazolin-5-one;

1-{[4-(tert-Butyl)phenyl]methyl}-4-ethyl-3-{3-[4-(4-methyl-5-{[benzylsulfonyl]amino}(2-pyridyl))phenyl]propyl}-1,2,4-triazolin-5-one;
1-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)cyclopropanecarboxylic acid;
N-(6-(4-(3-(1-(4-(tert-Butyl)benzyl)-4-ethyl-5-oxo-4,5-dihydro-1H-1,2,4-triazol-3-yl)propyl)phenyl)pyrazin-2-yl)benzenesulfonamide;
2-(4'-(3-(1-(4-(tert-Butyl)benzyl)-4-ethyl-5-oxo-4,5-dihydro-1H-1,2,4-triazol-3-yl)propyl)-4-(trifluoromethoxy)-[1,1'-biphenyl]-3-yl)acetic acid;
4'-(3-(1-(4-(tert-Butyl)benzyl)-4-ethyl-5-oxo-4,5-dihydro-1H-1,2,4-triazol-3-yl)propyl)-4-(trifluoromethoxy)-[1,1'-biphenyl]-3-carboxylic acid;
4'-(3-(1-(4-(tert-Butyl)benzyl)-4-ethyl-5-oxo-4,5-dihydro-1H-1,2,4-triazol-3-yl)propyl)-4-methyl-[1,1'-biphenyl]-3-carboxylic acid;
1-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)cyclobutanecarboxylic acid;
4'-(3-(1-(4-(tert-Butyl)benzyl)-4-ethyl-5-oxo-4,5-dihydro-1H-1,2,4-triazol-3-yl)propyl)-4-(trifluoromethyl)-[1,1'-biphenyl]-3-carboxylic acid;
2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)-N-(methylsulfonyl)acetamide;
2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)-N-(phenylsulfonyl)acetamide;
1-(4'-(3-(1-(4-(tert-Butyl)benzyl)-4-ethyl-5-oxo-4,5-dihydro-1H-1,2,4-triazol-3-yl)propyl)-[1,1'-biphenyl]-4-yl)cyclopropanecarboxylic acid;
N-(4-(4-(3-(1-(4-(tert-Butyl)benzyl)-4-ethyl-5-oxo-4,5-dihydro-1H-1,2,4-triazol-3-yl)propyl)phenyl)pyrimidin-2-yl)benzenesulfonamide;
6-(4-(3-(1-(4-(tert-Butyl)benzyl)-4-ethyl-5-oxo-4,5-dihydro-1H-1,2,4-triazol-3-yl)propyl)phenyl)-3-methoxypicolinic acid;
2-(4-(3-(1-(4-(tert-Butyl)benzyl)-4-ethyl-5-oxo-4,5-dihydro-1H-1,2,4-triazol-3-yl)propyl)phenyl)-5-methoxyisonicotinic acid;
(R)-2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)propanoic acid;
(S)-2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)propanoic acid;
1-(4-(tert-Butyl)benzyl)-4-ethyl-3-(3-(4'-(3-fluorooxetan-3-yl)-[1,1'-biphenyl]-4-yl)propyl)-1H-1,2,4-triazol-5(4H)-one;
2-(6-(4-(3-(1-(4-(tert-Butyl)benzyl)-4-ethyl-5-oxo-4,5-dihydro-1H-1,2,4-triazol-3-yl)propyl)phenyl)-3-methoxypyridin-2-yl)acetic acid;
2-(4'-(3-(1-(4-(tert-Butyl)benzyl)-4-ethyl-5-oxo-4,5-dihydro-1H-1,2,4-triazol-3-yl)propyl)-2'-hydroxy-4-methoxy-[1,1'-biphenyl]-3-yl)acetic acid;
2-(4'-(3-(1-(4-(tert-Butyl)benzyl)-4-ethyl-5-oxo-4,5-dihydro-1H-1,2,4-triazol-3-yl)propyl)-3'-hydroxy-4-methoxy-[1,1'-biphenyl]-3-yl)acetic acid;
3-(3'-Amino-4'-methoxy-[1,1'-biphenyl]-4-yl)propyl)-1-(4-(tert-butyl)benzyl)-4-ethyl-1H-1,2,4-triazol-5(4H)-one;
3-(3-(3'-Amino-4'-(trifluoromethyl)-[1,1'-biphenyl]-4-yl)propyl)-1-(4-(tert-butyl)benzyl)-4-ethyl-4H-1,2,4-triazol-5(4H)-one;
3-(3-(3'-Amino-4'-methyl-[1,1'-biphenyl]-4-yl)propyl)-1-(4-(tert-butyl)benzyl)-4-ethyl-1H-1,2,4-triazol-5(4H)-one;
2-(4'-(3-(1-(4-(tert-Butyl)benzyl)-4-ethyl-5-oxo-4,5-dihydro-1H-1,2,4-triazol-3-yl)propyl)-4-methoxy-2'-(trifluoromethyl)-[1,1'-biphenyl]-3-yl)acetic acid;
1-{[4-(tert-Butyl)phenyl]methyl}-4-ethyl-3-[3-(4-{4-methoxy-3-[(phenylsulfonyl)amino]phenyl}phenyl)propyl]-1,2,4-triazolin-5-one;
1-{[4-(tert-Butyl)phenyl]methyl}-4-ethyl-3-[3-(4-{4-methyl-3-[(phenylsulfonyl)amino]phenyl}phenyl)propyl]-1,2,4-triazolin-5-one;
1-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)-3-phenylurea;
N-((6-(4-(3-(1-(4-(tert-Butyl)benzyl)-4-ethyl-5-oxo-4,5-dihydro-1H-1,2,4-triazol-3-yl)propyl)phenyl)pyridin-2-yl)carbamoyl)benzenesulfonamide;
1-Benzyl-3-(6-(4-(3-(1-(4-(tert-butyl)benzyl)-4-ethyl-5-oxo-4,5-dihydro-1H-1,2,4-triazol-3-yl)propyl)phenyl)pyridin-2yl)urea;
3-(3-{4-[5-Amino-3-(trifluoromethyl)(2-pyridyl)]phenyl}propyl)-1-{[4-(tert-butyl)phenyl]methyl}-4-ethyl-1,2,4-triazolin-5-one;
2(4'(3-(1-(4-(tert-Butyl)benzyl)-4-ethyl-5-oxo-4,5-dihydro-1H-1,2,4-triazol-3-yl)propyl)-4-methoxy-2'-methyl-[1,1'-biphenyl]-3-yl)acetic acid;
2-(4'-(3-(1-(4-(tert-Butyl)benzyl)-4-ethyl-5-oxo-4,5-dihydro-1H-1,2,4-triazol-3-yl)propyl)-3',4-dimethoxy-[1,1'-biphenyl]-3-yl)acetic acid;
2-(4'-(3(1-(4-(tert-Butyl)benzyl)-4-ethyl-5-oxo-4,5-dihydro-1H-1,2,4-triazol-3-yl)propyl)-2',4-dimethoxy-[1,1'-biphenyl]-3-yl)acetic acid;
N-((6-(4-(3 (1(4-(tert-Butyl)benzyl)-4-ethyl-5-oxo-4,5-dihydro-1H-1,2,4-triazol-3-yl)propyl)phenyl)pyridin-3-yl)carbamoyl)benzenesulfonamide;
3-(3-{4-[6-Amino-5-(trifluoromethyl)(2-pyridyl)]phenyl}propyl)-1-{[4-(tert-butyl)phenyl]methyl}-4-ethyl-1,2,4-triazolin-5-one;
6-(4-(3-(1(4-(tert-Butyl)benzyl)-4-ethyl-5-oxo-4,5-dihydro-1H-1,2,4-triazol-3-yl)propyl)phenyl)-3-methoxypyrazine-2-carboxylic acid;
2-(4'-(3-(1-(4-(tert-Butyl)benzyl)-4-ethyl-5-oxo-4,5-dihydro-1H-1,2,4-triazol-3-yl)-1,1-difluoropropyl)-4-methoxy-[1,1'-biphenyl]-3-yl)acetic acid;
1-{[4-(tert-Butyl)phenyl]methyl}-4-ethyl-3-[3-(4-{6-[(phenylsulfonyl)amino]-5-(trifluoromethyl)(2-pyridyl)}phenyl)propyl]-1,2,4-triazolin-5-one;
6-(4-(3-(1-(4-(tert-Butyl)benzyl)-4-ethyl-5-oxo-4,5-dihydro-1H-1,2,4-triazol-3-yl)propyl)phenyl)-3-methylpicolinic acid;
1-(4-(tert-Butyl)benzyl)-4-ethyl-3-(3-(4-(6-(3-fluorooxetan-3-yl)pyridine-3-yl)phenyl)propyl)-1H-1,2,4-triazol-5(4H)-one;
1-(4-(tert-Butyl)benzyl)-3-(3-(4'-(3-hydroxyoxetan-3-yl)-[1,1'-biphenyl]-4-yl)propyl)-1H-1,2,4-triazol-5(4H)-one;
4'-(3-(1-(4-(tert-Butyl)benzyl)-4-ethyl-5-oxo-4,5-dihydro-1H-1,2,4-triazol-3-yl)propyl)-4-propoxy-[1,1'-biphenyl]-3-carboxylic acid;
1-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)-3-ethylurea;
1-(4-(tert-Butyl)benzyl)-4-ethyl-3-(3-(4-(2-(3-fluorooxetan-3-yl)pyrimidin-5-yl)phenyl)propyl)-1H-1,2,4-triazol-5(4H)-one;

1-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)-3-ethylurea;

3-(3-{4-[3-(Aminomethyl)phenyl]phenyl}propyl)-1-{[4-(tert-butyl)phenyl]methyl}-4-ethyl-1,2,4-triazolin-5-one;

1-(4-(tert-Butyl)benzyl)-4-ethyl-3-(3-(4-(2-(3-hydroxyoxetan-3-yl)pyrimidin-5-yl)phenyl)propyl)-1H-1,2,4-triazol-5(4H)-one;

1-(4-(tert-Butyl)benzyl)-4-ethyl-3-(3-(4'-(3-hydroxyoxetan-3-yl)-[1,1'-biphenyl]-4-yl)propyl)-1H-1,2,4-triazol-5(4H)-one;

1-(4-(tert-Butyl)benzyl)-4-ethyl-3-(3-(4'-(1-hydroxycyclobutyl)-[1,1'-biphenyl]-4-yl)propyl)-1H-1,2,4-triazol-5(4H)-one;

1-{[4-(tert-Butyl)phenyl]methyl}-4-ethyl-3-{3-[4-(3-{[(phenylsulfonyl)amino]methyl}phenyl)phenyl]propyl}-1,2,4-triazolin-5-one;

1-{[4-(tert-Butyl)phenyl]methyl}-4-ethyl-3-{3-[4-(3-{[(methylsulfonyl)amino]methyl}phenyl)phenyl]propyl}-1,2,4-triazolin-5-one;

3-(5-{4-[3-(1-{[4-(tert-Butyl)phenyl]methyl}-4-ethyl-5-oxo(1,2,4-triazolin-3-yl))propyl]phenyl}-2-methoxyphenyl)propanoic acid;

1-{[4-(tert-Butyl)phenyl]methyl}-4-ethyl-3-[3-(4-{4-methoxy-3-[(methylamino)methyl]phenyl}phenyl)propyl]-1,2,4-triazolin-5-one;

2-(4-(3-(1-(4-(tert-Butyl)benzyl)-4-ethyl-5-oxo-4,5-dihydro-1H-1,2,4-triazol-3-yl)propyl)phenyl)-5-methoxypyrimidine-4-carboxylic acid;

1-{[4-(tert-Butyl)phenyl]methyl}-4-ethyl-3-{3-[4-(4-methoxy-3-{2-[(phenylsulfonyl)amino]ethyl}phenyl)phenyl]propyl}-1,2,4-triazolin-5-one;

1-{[4-(tert-Butyl)phenyl]methyl}-4-ethyl-3-{3-[4-(4-methoxy-3-{2-[(methylsulfonyl)amino]ethyl}phenyl)phenyl]propyl}-1,2,4-triazolin-5-one;

3-(3-{4-[3-(Aminomethyl)-4-methoxyphenyl]phenyl}propyl)-1-{[4-(tert-butyl)phenyl]methyl}-4-ethyl-1,2,4-triazolin-5-one;

1-{[4-(tert-Butyl)phenyl]methyl}-4-ethyl-3-{3-[4-(4-methoxy-3-{[(phenylsulfonyl)amino]methyl}phenyl)phenyl]propyl}-1,2,4-triazolin-5-one;

1-{[4-(tert-Butyl)phenyl]methyl}-4-ethyl-3-{3-[4-(4-methoxy-3-{[(methylsulfonyl)amino]methyl}phenyl)phenyl]propyl}-1,2,4-triazolin-5-one;

1-(4-(tert-Butyl)benzyl)-4-ethyl-3-(3-(4'-(4-hydroxytetrahydro-2H-pyran-4-yl)-[1,1'-biphenyl]-4-yl)propyl)-1H-1,2,4-triazol-5(4H)-one;

1-{[4-(tert-Butyl)phenyl]methyl}-4-ethyl-3-(3-{4-[4-methoxy-3-({[benzylsulfonyl]amino}methyl)phenyl]phenyl}propyl)-1,2,4-triazolin-5-one;

1-{[4-(tert-Butyl)phenyl]methyl}-4-ethyl-3-[3-(4-{6-[(ethylsulfonyl)amino]-5-methoxy(2-pyridyl)}phenyl)propyl]-1,2,4-triazolin-5-one;

1-{[4-(tert-Butyl)phenyl]methyl}-4-ethyl-3-[3-(4-{6-[(cyclopropylsulfonyl)amino]-5-methoxy(2-pyridyl)}phenyl)propyl]-1,2,4-triazolin-5-one;

1-(4-(tert-Butyl)benzyl)-4-ethyl-3-(3-(4-(5-(3-fluorooxetan-3-yl)pyridine-2-yl)phenyl)propyl)-1H-1,2,4-triazol-5(4H)-one;

1-{[4-(tert-Butyl)phenyl]methyl}-4-ethyl-3-[3-(4-{6-[(cyclohexylsulfonyl)amino]-5-methoxy(2-pyridyl)}phenyl)propyl]-1,2,4-triazolin-5-one;

3-{4-[3-(1-{[4-(tert-Butyl)phenyl]methyl}-4-ethyl-5-oxo(1,2,4-triazolin-3-yl))propyl]phenyl}-5-methoxybenzoic acid;

2-(3-{4-[3-(1-{[4-(tert-Butyl)phenyl]methyl}-4-ethyl-5-oxo(1,2,4-triazolin-3-yl))propyl]phenyl}-5-methoxyphenyl)acetic acid;

1(4-(tert-Butyl)benzyl)-3-(3,3-difluoro-3-(4-(5-(3-fluorooxetan-3-yl)pyridine-2-yl)phenyl)propyl)-4-ethyl-1H-1,2,4-triazol-5(4H)-one;

1-(4-(tert-Butyl)benzyl)-3-(3,3-difluoro-3-(4'-(3-hydroxyoxetan-3-yl)-[1,1'-biphenyl]-4-yl)propyl)-4-ethyl-1H-1,2,4-triazol-5(4H)-one;

1-(4-(tert-Butyl)benzyl)-4-ethyl-3-(3-(4-(5-(3-hydroxyoxetan-3-yl)pyridine-2-yl)phenyl)propyl)-1H-1,2,4-triazol-5(4H)-one;

2-(5-(6-(3-(1-(4-(tert-Butyl)benzyl)-4-ethyl-5-oxo-4,5-dihydro-1H-1,2,4-triazol-3-yl)propyl)pyridin-3-yl)-2-methoxyphenyl)acetic acid;

2-(4'-(3-(1-(4-(tert-Butyl)benzyl)-4-ethyl-5-oxo-4,5-dihydro-1H-1,2,4-triazol-3-yl)propyl)-3-methoxy-[1,1'-biphenyl]-4-yl)acetic acid;

2-(4'-(3-(1-(4-(tert-Butyl)benzyl)-4-ethyl-5-oxo-4,5-dihydro-1H-1,2,4-triazol-3-yl)propyl)-4-isopropoxy-[1,1'-biphenyl]-3-yl)acetic acid;

1-(4-(tert-Butyl)benzyl)-4-ethyl-3-(3-(4-(2-(3-fluorooxetan-3-yl)thiazol-4-yl)phenyl)propyl)-1H-1,2,4-triazol-5(4H)-one;

1-(4-(tert-Butyl)benzyl)-4-ethyl-3-(3-(4-(2-(3-fluorooxetan-3-yl)thiazol-5-yl)phenyl)propyl)-1H-1,2,4-triazol-5(4H)-one;

1-(4-(tert-Butyl)benzyl)-4-ethyl-3-(3-(4-(2-(3-hydroxyoxetan-3-yl)thiazol-4-yl)phenyl)propyl)-1H-1,2,4-triazol-5(4H)-one; and 1-(4-(tert-Butyl)benzyl)-4-ethyl-3-(3-(4-(2-(3-hydroxyoxetan-3-yl)thiazol-5-yl)phenyl)propyl)-1H-1,2,4-triazol-5(4H)-one;

or a pharmaceutically acceptable salt thereof.

21. A pharmaceutical composition comprising a compound according to claim 1, or a pharmaceutically acceptable salt thereof, and at least one pharmaceutically acceptable carrier.

22. A method of treating a cancer in a mammal comprising the administration of a therapeutically effective amount of a compound of claim 1, or a pharmaceutically acceptable salt thereof, to the mammal in need thereof, wherein the cancer is selected from the group consisting of prostate cancer, breast cancer, colon cancer, pancreatic cancer, ovarian cancer, liver cancer, kidney cancer, human chronic lymphocytic leukemia, and melanoma.

23. The method of claim 22, wherein the cancer is negatively impacted by diminution in its metabolism of fatty acid oxidation.

24. A compound selected from 2-(4'(((1-(4-(tert-Butyl)benzyl)-4-ethyl-5-oxo-4,5-dihydro-1H-1,2,4-triazol-3-yl)methoxy)methyl)-[1,1'-biphenyl]-3-yl)acetic acid and 2-(4'-(2-((1-(4-(tert-butyl)benzyl)-4-ethyl-5-oxo-4,5-dihydro-1H-1,2,4-triazol-3-yl)methyl)cyclopropyl)-[1,1'-biphenyl]-3-yl) acetic acid, or a pharmaceutical acceptable salt thereof.

25. A compound of claim 20 selected from the group consisting of:

2-(4'-(3-(1-(4-(tert-Butyl)benzyl)-4-ethyl-5-oxo-4,5-dihydro-1H-1,2,4-triazol-3-yl)propyl)-[1,1'-biphenyl]-3-yl)acetic acid;

N-(6-(4-(3-(1-(4-(tert-Butyl)benzyl)-4-ethyl-5-oxo-4,5-dihydro-1H-1,2,4-triazol-3-yl)propyl)phenyl)pyridin-2-yl)benzenesulfonamide;

N-(6-(4-(3-(1-(4-(tert-Butyl)benzyl)-4-ethyl-5-oxo-4,5-dihydro-1H-1,2,4-triazol-3-yl)propyl)phenyl)pyridin-3-yl)benzenesulfonamide;

2-(4'-(3-(1-(4-(tert-Butyl)benzyl)-4-ethyl-5-oxo-4,5-dihydro-1H-1,2,4-triazol-3-yl)propyl)-4-methoxy-[1,1'-biphenyl]-3-yl)acetic acid;

2-(4'-(3-(1-(4-(tert-Butyl)benzyl)-4-ethyl-5-oxo-4,5-dihydro-1H-1,2,4-triazol-3-yl)propyl)-4-ethoxy-[1,1'-biphenyl]-3-yl)acetic acid;

1-{[4-(tert-Butyl)phenyl]methyl}-4-ethyl-3-[3-(4-{5-methoxy-6-[(phenylsulfonyl)amino](2-pyridyl)}phenyl)propyl]-1,2,4-triazolin-5-one; and 1-{[4-(tert-Butyl)phenyl]methyl}-3-[3-(4-{5-ethoxy-6-[(phenylsulfonyl)amino](2-pyridyl)}phenyl)propyl]-4-ethyl-1,2,4-triazolin-5-one; or a pharmaceutically acceptable salt thereof.

* * * * *